(12) United States Patent
Schiemann et al.

(10) Patent No.: US 9,493,444 B2
(45) Date of Patent: Nov. 15, 2016

(54) AZAHETEROCYCLIC COMPOUNDS

(71) Applicants: Merck Patent GmbH, Darmstadt (DE);
Cancer Research Technology Limited, London (GB)

(72) Inventors: Kai Schiemann, Seeheim-Jugenheim (DE); Frank Stieber, Einhausen (DE); Christina Esdar, Mainz (DE)

(73) Assignees: Merck Patent GmbH, Darmstadt (DE); Cancer Research Technology Limited, London (GB)

( * ) Notice: Subject to any disclaimer, the term of this patent is extended or adjusted under 35 U.S.C. 154(b) by 0 days.

(21) Appl. No.: 14/375,072

(22) PCT Filed: Jan. 10, 2013

(86) PCT No.: PCT/EP2013/000050
§ 371 (c)(1),
(2) Date: Jul. 28, 2014

(87) PCT Pub. No.: WO2013/110433
PCT Pub. Date: Aug. 1, 2013

(65) Prior Publication Data
US 2015/0005294 A1    Jan. 1, 2015

(30) Foreign Application Priority Data
Jan. 28, 2012 (EP) .................... 12000559

(51) Int. Cl.
| | | |
|---|---|---|
| *A61K 31/497* | (2006.01) | |
| *C07D 401/12* | (2006.01) | |
| *C07D 401/14* | (2006.01) | |
| *C07D 403/12* | (2006.01) | |
| *C07D 413/14* | (2006.01) | |
| *C07D 487/04* | (2006.01) | |
| *C07D 409/12* | (2006.01) | |
| *C07D 403/14* | (2006.01) | |
| *C07D 405/12* | (2006.01) | |
| *C07D 413/12* | (2006.01) | |
| *C07D 241/20* | (2006.01) | |
| *C07D 417/12* | (2006.01) | |
| *C07D 495/04* | (2006.01) | |
| *A61K 31/4965* | (2006.01) | |
| *A61K 31/501* | (2006.01) | |
| *A61K 31/506* | (2006.01) | |
| *A61K 31/5377* | (2006.01) | |
| *A61K 31/5415* | (2006.01) | |

(52) U.S. Cl.
CPC .......... *C07D 409/12* (2013.01); *A61K 31/497* (2013.01); *A61K 31/4965* (2013.01); *A61K 31/501* (2013.01); *A61K 31/506* (2013.01); *A61K 31/5377* (2013.01); *A61K 31/5415* (2013.01); *C07D 241/20* (2013.01); *C07D 401/12* (2013.01); *C07D 401/14* (2013.01); *C07D 403/12* (2013.01); *C07D 403/14* (2013.01); *C07D 405/12* (2013.01); *C07D 413/12* (2013.01); *C07D 417/12* (2013.01); *C07D 495/04* (2013.01)

(58) Field of Classification Search
CPC ............... C07D 401/12; C07D 401/14; C07D 403/12; C07D 413/14; C07D 487/04
See application file for complete search history.

(56) References Cited

U.S. PATENT DOCUMENTS

| | | |
|---|---|---|
| 8,778,925 B2 | 7/2014 | McDonald et al. |
| 2011/0190297 A1 | 8/2011 | McDonald et al. |

FOREIGN PATENT DOCUMENTS

| | | | |
|---|---|---|---|
| WO | 2010041054 A1 | 4/2010 | |

OTHER PUBLICATIONS

International Search Report for PCT/EP2013/000050 dated Apr. 8, 2013.
Qiao, K. et al., "A fungal nonribosomal peptide synthetase module that can synthesize thiopyrazines," Organic Letters, Apr. 1, 2011, vol. 13, No. 7, pp. 1758-1761.
Gong, Young-Dae et al., "A novel 3-arylethynyl-substituted pyrido[2,3,-b]pyrazine derivatives and pharmacophore model as Wnt2/beta-catenin pathway inhibitors in non-small-cell lung cancer cell lines," Bioorganic & Medicinial Chemistry, Jul. 13, 2011, vol. 19, No. 18, pp. 5639-5647.
Moore, W. J. et al., "Modulation of Wnt signaling through inhibition of secreted frizzled-related protein I (sFRP-1) with N-substituted piperidyinyl diphenylsulfonyl sulfonamides: Part II," Bioorganic & Medicinal Chemistry, Jan. 1, 2010, vol. 18, No. 1, pp. 190-201.

*Primary Examiner* — Brian McDowell
(74) *Attorney, Agent, or Firm* — Millen White Zelano & Branigan, P.C.

(57) ABSTRACT

22 Claims, No Drawings

AZAHETEROCYCLIC COMPOUNDS

FIELD OF THE INVENTION

The invention relates to a series of novel substituted azaheterocyclic compounds that are useful in the treatment of hyperproliferative diseases such as cancer, as well as inflammatory or degenerative diseases, in mammals. Also encompassed by the present invention is the use of such compounds in the treatment of hyperproliferative, inflammatory or degenerative diseases in mammals, especially humans, and pharmaceutical compositions containing such compounds.

SUMMARY OF THE RELATED ART

Wnt proteins comprise a large family of cysteine-rich secreted ligands that are highly conserved among species. Currently, three different pathways are believed to be activated by Wnt signaling: the canonical Wnt/β-catenin cascade, the noncanonical planar cell polarity pathway, and the Wnt/Ca2+ pathway. Of these three, the canonical pathway is best understood and has the highest incidence for cancer relevance.

Therefore, this project is focusing on canonical Wnt/β-catenin signaling. In the canonical pathway, β-catenin is the key mediator of Wnt signaling. In the absence of Wnt ligands, a protein complex, that contains Axin, adenomatous polyposis coli (APC), glycogen synthase kinase 3β (GSK3β) and casein kinase 1 (CK1), functions in phosphorylating β-catenin and thereby marking it for destruction via ubiquitination and degradation by the proteasome. Following Wnt binding to a receptor complex composed of members of the Frizzled (Fz) family of seven transmembrane, serpentine receptors and low density lipoprotein receptor-related proteins 5/6 (LRP5/6), Disheveled (Dsh) and Axin are recruited to the plasma membrane. Subsequently, the Axin-APC-GSK3β complex is inhibited, non-phosphorylated β-catenin accumulates in the cytoplasm and then translocates into the nucleus where it regulates target gene expression in combination with members of the DNA-binding T cell factor/lymphoid enhancer factor (TCF/LEF) family. Many different target genes of canonical Wnt/β-catenin signaling have been described (e.g. c-Myc, Cyclin D1, VEGF, survivin) which are involved in cell growth, migration and survival (Logan & Nusse, Annu Rev Cell Dev Biol. 2004; 20:781-810).

The Wnt/β-catenin signaling cascade is frequently over-activated in different tumor types and several proteins of the pathway act as oncogenes or tumor suppressors (Giles et al., Biochim Biophys Acta. 2003 Jun. 5; 1653(1):1-24, van Es et al., Curr Opin Genet Dev. 2003 February; 13(1):28-33).

Most prominently, the tumor suppressor APC is mutated in nearly 60% of all colon cancers. In addition, many colon cancers express mutated β-catenin which cannot be phosphorylated and is therefore stabilized. Furthermore, loss of function mutations of the tumor suppressor axin have been detected in hepatocellular, lung and colon cancers Thus, interference with Wnt/β-catenin signaling is a conceivable strategy for the treatment of cancer (reviewed in Dihlmann & von Knebel Doeberitz, Int. J. Cancer: 113, 515-524 (2005), Luu et al., Curr Cancer Drug Targets. 2004 December; 4(8):653-71).

WO 2010/041054 discloses a series of chemical compounds which act on the Wnt pathway.

However, as a therapeutic directed to this pathway has yet to be commercialized, a significant unmet medical need still exists, so that further promising Wnt pathway inhibitors have to be identified and developed.

DESCRIPTION OF THE INVENTION

It is the object of the present invention to provide novel Wnt pathway inhibitors useful in the treatment of inflammatory or hyperproliferative diseases, such as cancer in mammals, with superior pharmacological properties both with respect to their activities as well as their solubility, metabolic clearance and bioavailability characteristics.

As a result, this invention provides novel substituted azaheterocyclic compounds or their stereoisomers or tautomers, or pharmaceutically acceptable salts, that are Wnt pathway inhibitors and useful as medicaments, especially in the treatment of the diseases mentioned above and below.

The compounds are defined by Formula (I):

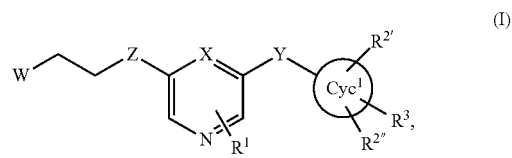

wherein:
$R^1$ is H, LA, Hal, OH, CN, $NO_2$, $NH_2$, O(LA), NH(LA), $N(LA)_2$,
$R^{2'}$, $R^{2''}$ are independently H, Hal, OH, CN, LA, O(LA),
$R^3$ is H, LA, Hal, OH, SH, S(LA), CN, $NO_2$, $NH_2$, O(LA), (LA)OCO(LA), (LA)COO(LA), NH(LA), NHCOO(LA), $N(LA)_2$, (LA)$NH_2$, (LA)NH(LA), $SO_2NH_2$, $SO_2$(LA), or L-$Cyc^2$,
$R^4$ is H, LA, (LA)OH, (LA)NH($R^2$), O(LA), $Cyc^3$,
$R^5$ is H, LA,
$R^4$, $R^5$ together with the atoms they are attached to, can form a 4, 5, 6 or 7 membered heterocycle, having 1 or 2 heteroatoms, which is optionally substituted by $R^6$,
$R^6$ is H, LA, Hal, OH, CN, $NO_2$, $NH_2$, O(LA), NH(LA), $N(LA)_2$,
W is —$NR^5COR^4$ or —CON($R^4$)($R^5$),
X is N or CH,
Y is O or $CH_2$,
Z is NH, N(LA), S, $CH_2$, CH(LA), C(LA)$_2$,
$Cyc^1$ is a mono- or binuclear, aliphatic or aromatic, 4, 5, 6, 7, 8, 9 or 10 membered homo- or heterocycle, having 0, 1, 2, 3 or 4 N, O and/or S atoms, which may be substituted by one or two oxo groups, and in which one N atom may be replaced by a $N^+$—$O^-$ group,
$Cyc^2$ is a mono- or binuclear, aliphatic or aromatic, 4, 5, 6, 7, 8, 9 or 10 membered homo- or heterocycle, having 0, 1, 2, 3 or 4 N, O and/or S atoms, which may be mono-substituted by an oxo group, S(LA), $SO_2$(LA), $N_3$, NHCOH, NHCO(LA), NHCOO(LA), $NHSO_2$(LA), COO(LA), $CONH_2$, (LA)$CONH_2$, CONH(LA), L-$Cyc^3$ or A, or independently mono-, di-, tri- or tetra-substituted by LA, Hal, OH, CN, $NO_2$, $NH_2$, O(LA), NH(LA), $N(LA)_2$, CO(LA), and in which one N atom may be replaced by a $N^+$—$O^-$ group,
$Cyc^3$ is a monocyclic, aliphatic or aromatic homo- or heterocycle having 0, 1, 2 or 3 N, $N^+$—$O^-$, O and/or S atoms and 5 or 6 skeleton atoms, which may be mono- or di-substituted by LA, Hal, OH, CN, $NO_2$, $NH_2$, O(LA), S(LA), NH(LA), $N(LA)_2$, and in which one N atom may be replaced by a $N^+$—$O^-$ group, L is a bond, or a unbranched alkyl or alkenyl linker, having 1, 2 or 3 carbon atoms, in which one $CH_2$ group may be replaced by a carbonyl group, LA is unbranched or branched alkyl, alkenyl or alkynyl, having 1, 2, 3, 4 or 5 carbon atoms, wherein one, two or three H atoms may be replaced by Hal, A is a unbranched or branched alkyl or alkenyl chain having up to 25 non-hydrogen atoms, wherein 1, 2, 3, 4, 5 or 6 $CH_2$ groups may be replaced by O, S, NH, CO, N(LA), $SO_2$, and 1-7H atoms may be replaced by Hal, and one $CH_3$ group may be replaced by OH, $NH_2$ or $Cyc^1$, Hal is F, Cl, Br or I.

In general, all residues which occur more than once may be identical or different, i.e. are independent of one another. Above and below, the residues and parameters have the meanings indicated for the Formula (I), unless expressly indicated otherwise. Accordingly, the invention relates, in particular, to the compounds of the Formula (I) in which at least one of the said residues has one of the preferred meanings indicated below.

Hal denotes fluorine, chlorine, bromine or iodine, in particular fluorine, chlorine or bromine.

"A" denotes an alkyl or alkenyl chain, for example, methyl, furthermore ethyl, propyl, isopropyl, butyl, isobutyl, sec-butyl or tert-butyl, furthermore also pentyl, 1-, 2- or 3-methyl-butyl, 1,1-, 1,2- or 2,2-dimethylpropyl, or 1-ethylpropyl.

"A" further denotes an alkyl or alkenyl chain as defined above, in which 1, 2, 3, 4, 5 or 6 $CH_2$ groups may be replaced by O, S, NH, CO, N(LA), $SO_2$, and 1-7H atoms may be replaced by Hal, and in which one $CH_3$ group may be replaced by $Cyc^1$, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy, N,N'-dimethylaminoalkyl, 2-aminoethyl, 3-aminopropyl, 4-aminobutyl, 5-aminopentyl, 3-aminomethylcyclobutyl or 6-[5-(2-Oxo-hexahydro-thieno[3,4-d]imidazol-6-yl)-pentanoylamino]-hexanoyl.

"LA" denotes unbranched or branched, linear alkyl, alkenyl or alkynyl, having 1, 2, 3, 4 or 5 C atoms, wherein 1, 2 or 3H atoms may be replaced by Hal, e.g. methyl, ethyl, trifluoromethyl, difluoromethyl, 1,1,1-trifluoroethyl, propyl, isopropyl, butyl, isobutyl, sec-butyl, tert-butyl, sec-pentyl, iso-pentyl or neopentyl.

"$Cyc^1$" and "$Cyc^2$" denote, for example, cyclobutyl, cyclopentyl, cyclohexyl, azetidine-1-, 2- or 3-yl, oxazolidine-2-, 3-, 4- or 5-yl, isoxazolidine-2-, 3-, 4- or 5-yl, 2,3-dihydro-2-, -3-, -4- or -5-furyl, 2,5-dihydro-2-, -3-, -4- or -5-furyl, tetrahydro-2- or -3-furyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3-, 1-, 5- or 6-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, phenyl, 2- or 3-furyl, 2- or 3-thienyl, 1-, 2- or 3-pyrrolyl, 1-, 2- or 3-pyrrolidinyl, 1-, 2, 4- or 5-imidazolyl, 1-, 3-, 4- or 5-pyrazolyl, 2-, 3- or 4-pyridyl, 2-, 4-, 5- or 6-pyrimidinyl, pyrazin-2- or 3-yl, pyridazin-3- or 4-yl, 1,2,3-triazol-1-, -4- or -5-yl, 1,2,4-triazol-1-, -3- or 5-yl, 1- or 5-tetrazolyl, 1-, 2-, 3-, 4-, 5-, 6- or 7-indolyl, 2-, 3-, 4-, 5-, 6- or 7-indazolyl, 2-, 3-, 4- or 5-isoindolyl, 2, 6, - or 8-purinyl, 1-, 2-, 4- or 5-benzimidazolyl, 1-, 3-, 4-, 5-, 6- or 7-benzopyrazolyl, 2-, 4-, 5- or 6-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, 1,3-benzodioxol-2-, 4- or 5-yl, indan-1-, 2-, 4- or 5-yl, 2-oxo-1,2-dihydrothiazolo[5,4-b]pyridin-5, 6, or 7-yl, 7H-pyrrolo[2,3-d]pyrimidin-2, 3, 4 or 6-yl, 1H-pyrrolo[2,3-c]pyridin-2, 3, 4, 5 or 7-yl.

"$Cyc^3$" denotes, for example, cyclopentyl, cyclohexyl, oxazolidine-2-, 3-, 4- or 5-yl, isoxazolidine-2-, 3-, 4- or 5-yl, 2,3-dihydro-2-, -3-, -4- or -5-furyl, 2,5-dihydro-2-, -3-, -4- or -5-furyl, tetrahydro-2- or -3-furyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3-, 1-, 5- or 6-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, phenyl, 2- or 3-furyl, 2- or 3-thienyl, 1-, 2- or 3-pyrrolyl, 1-, 2- or 3-pyrrolidinyl, 1-, 2, 4- or 5-imidazolyl, 1-, 3-, 4- or 5-pyrazolyl, 2-, 3- or 4-pyridyl, 2-, 4-, 5- or 6-pyrimidinyl, pyrazin-2- or 3-yl, pyridazin-3- or 4-yl, 1,2,3-triazol-1-, -4- or -5-yl, 1,2,4-triazol-1-, -3- or 5-yl, 1- or 5-tetrazolyl.

In a preferred embodiment the compounds of the invention conform to Subformulae 1 to 22 of Formulae (I), wherein in Subformula 1
Z is H, $NCH_3$, $CH_2$,
in Subformula 2
W is $—NR^5COR^4$,
in Subformula 3
W is $—CON(R^4)(R^5)$,
in Subformula 4
Y is O,
in Subformula 5
Z is H, $NCH_3$, $CH_2$,
$R^4$, $R^5$ are methyl,
in Subformula 6
W is $—NR^6COR^4$,
$R^4$, $R^5$ together with the atoms they are attached to, form piperidin-2-one or pyrrolidin-2-one,
$R^6$ is H,
in Subformula 7
W is $—CON(R^4)(R^5)$,
$R^4$ is methyl,
$R^5$ is H,
in Subformula 8
X is N,
in Subformula 9
W is $—NR^6COR^4$,
$R^4$ is methyl, hydroxymethyl, tert-butyloxy, neopentyl,
$R^5$ is H, methyl, ethyl, isopropyl, fluoromethyl,
in Subformula 10
W is $—NR^6COR^4$,
$R^4$, $R^5$ are methyl,
in Subformula 11
X is N,
$R^1$ is H,
in Subformula 12
$Cyc^1$ is indanyl, indolyl, isoquinolinyl, benzoisoxazolyl,
in Subformula 13
$Cyc^1$ is phenyl, which is independently mono-, di- or tri-substituted by F, Br, CN, O(LA), LA, in Subformula 14
Cyc$^1$ is phenyl, which is substituted in 4-position by L-Cyc$^2$,
in Subformula 15
Cyc$^1$ is phenyl, which is substituted in 4-position by L-Cyc$^2$,
   and in 1- and/or 2-position by F,
in Subformula 16
X is N,
Y is O,
Z is H, NCH$_3$, CH$_2$,
in Subformula 17
X is N,
Y is O,
Z is NCH$_3$, CH$_2$,
R$^1$ is H,
in Subformula 18
W is —NR$^5$COR$^4$,
X is N,
Y is O,
Z is NCH$_3$, CH$_2$,
R$^1$ is H,
Cyc$^1$ is phenyl, which is independently mono-, di- or tri-substituted by F,
Br, CN, O(LA), LA,
in Subformula 19
W is —NR$^5$COR$^4$,
X is N,
Y is O,
Z is NCH$_3$, CH$_2$,
R$^1$ is H,
Cyc$^1$ is phenyl, which is substituted in 4-position by L-Cyc$^2$
   and, optionally, in 1- and/or 2-position by F,
in Subformula 20
W is —NR$^5$COR$^4$,
X is N,
Y is O,
Z is NCH$_3$, CH$_2$,
R$^1$ is H,
Cyc$^1$ is phenyl, which is substituted in 4-position by L-Cyc$^2$
   and, optionally, in 1- and/or 2-position by F,
in Subformula 21
X is N,
Y is O,
Z is NCH$_3$, CH$_2$, S,
R$^4$ is methyl,
R$^5$ is methyl, ethyl, isopropyl,
R$^1$ is H,
Cyc$^1$ is phenyl, which is substituted in 4-position by L-Cyc$^2$
   and, optionally, in 1- and/or 2-position by F,
Cyc$^2$ is pyridin-2, 3, or 4-yl, or pyrazin-2-yl, each of which
   is unsubstituted or substituted by HO(LA), LA, NH$_2$, CN,
in Subformula 22
W is —NR$^5$COR$^4$,
X is N,
Y is O,
Z is NCH$_3$, CH$_2$, S,
R$^4$, R$^5$ together with the atoms they are attached to, form
   piperidin-2-one
R$^1$ is H,
Cyc$^1$ is phenyl, which is substituted in 4-position by L-Cyc$^2$
   and, optionally, in 1- and/or 2-position by F,
Cyc$^2$ is pyridin-2, 3, or 4-yl, or pyrazin-2-yl, each of which
   is unsubstituted or substituted by HO(LA), LA, NH$_2$, CN,
and the remaining residues have the meaning as indicated
for Formula (I).

The compounds of the Formula (I) may have one or more centres of chirality. They may accordingly occur in various enantiomeric forms and be in racemic or optically active form. The invention, therefore, also relates to the optically active forms, enantiomers, racemates, diastereomers, collectively: stereoisomers, of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

It is well known that atoms may have atomic masses or mass numbers which differ from the atomic masses or mass numbers of the atoms which usually occur naturally. Examples of isotopes which are readily commercially available and which can be incorporated into a compound of the present invention by well-known methods include isotopes of hydrogen, carbon, nitrogen, oxygen, phosphorus, fluorine and chlorine, for example $^2$H, $^3$H, $^{13}$O, $^{14}$O, $^{15}$N, $^{18}$O, $^{17}$O, $^{31}$F, $^{32}$P, $^{35}$S, $^{18}$F and $^{36}$Cl, respectively.

Incorporation of heavier isotopes, especially deuterium ($^2$H), into a compound of the invention has therapeutic advantages owing to the higher metabolic stability of this isotope-labelled compound. Higher metabolic stability translates directly into an increased in vivo half-life or lower dosages. Therefore, these isotopes are included in the definition of atoms H, C, N etc., as used in the chemical compounds of this invention.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable solvates" means addition forms with pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

Therefore, the following items are also in accordance with the invention:
a) all stereoisomers or tautomers of the compounds, including mixtures thereof in all ratios,
b) prodrugs of the compounds, or stereoisomers or tautomers of these prodrugs,
c) pharmaceutically acceptable salts of the compounds and of the items mentioned under (a) and (b),
d) pharmaceutically acceptable solvates of the compounds and of the items mentioned under (a), (b) and (c).

It should be understood that all references to compounds above and below are meant to include these items, in particular pharmaceutically acceptable solvates of the compounds, or pharmaceutically acceptable solvates of their pharmaceutically acceptable salts.

Furthermore, the present invention relates to pharmaceutical compositions comprising a compound of the present invention, or its stereoisomers or tautomers, or pharmaceutically acceptable salts of each of the foregoing, including mixtures thereof in all ratios, as active ingredient, together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or other Wnt pathway inhibitors. The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head & neck, renal, kidney, liver, ovarian, prostate, uterine, oesophageal, testicular, gynecological, thyroid cancer, melanoma, as well as hematologic malignancies such as acute myelogenous leukemia, multiple myeloma, chronic myelogneous leukemia, myeloid cell leukemia, Kaposi's sarcoma, or any other type of solid or liquid tumors. Preferably, the cancer to be treated is chosen from colon, lung, breast and hematological tumor types.

In addition, said compounds and pharmaceutical composition are for the treatment of inflammatory diseases such as multiple sclerosis, rheumatoid arthritis, systemic lupus, inflammatory bowel diseases or degenerative diseases such as osteoarthritis and Alzheimer's disease.

This invention also relates to a compound or pharmaceutical composition for inhibiting abnormal cell growth in a mammal which comprises an amount of a compound of the present invention, in combination with an amount of another anti-cancer therapeutic, wherein the amounts of the compound, and of the other anti-cancer therapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, cell cycle inhibitors, topoisomerase inhibitors, or a biological response modifiers, such as anti-hormones, angiogenesis inhibitors, integrin antagonists, such as cilengitide, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of a protein kinase, such as Akt, Axl, Aurora A, Aurora B, c-Met, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, p70S6K, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention or pharmaceutical composition, in combination with radiation therapy, wherein the amounts of the compound or pharmaceutical composition, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention, or pharmaceutical composition, in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutical composition, which amount is effective in sensitizing abnormal cells to treatment with radiation. The amount of the compound in this method can be determined according to the means for ascertaining effective amounts of such compounds described herein.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin.

When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating inflammatory, degenerative or hyperproliferative diseases for which compounds of the present invention are indicated, generally satisfactory results are obtained when the compounds of the present invention are administered at a daily dosage of from about 0.01 milligram to about 100 milligram per kilogram of body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of a) an effective amount of a compound according to the invention or its stereoisomers or tautomers, or pharmaceutically acceptable salts of each of the foregoing, including mixtures thereof in all ratios, and b) an effective amount of a further medicament active ingredient.

The set comprises suitable containers, such as boxes, individual bottles, bags or ampoules.

By way of example, the set may comprise separate ampoules, each containing an effective amount of a compound according to the invention, and an effective amount of a further medicament active ingredient in dissolved or lyophilised form.

Experimental Section

Some abbreviations that may appear in this application are as follows:

Abbreviations

| Designation | |
|---|---|
| ATP | Adenosine triphosphate |
| b | Broad peak |
| d | Doublet |
| DMF | Dimethylformamide |
| h | Hour |
| HBBS | Hank's Balanced Salt Solution |
| HPLC | High Pressure Liquid Chromatography |
| LC/MS | Liquid Chromatography coupled to Mass Spectrometry |
| m | Multiplet |
| m/z | Mass-to-charge ratio |
| min | Minute |
| MS | Mass spectrometry |
| N | Normal (unit of concentration) |
| NMR | Nuclear Magnetic Resonance |
| q | Quartette (or quartet) |
| Rf | Retention factor |
| RT | Room temperature |
| Rt. | Retention time |
| s | Singlet |
| Tert | Tertiary |
| THF | Tetrahydrofuran |
| UV | Ultraviolet |
| VIS | Visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at room temperature. Compounds were purified by either silica chromatography or preparative HPLC.

The present invention relates also to a process for the manufacture of compounds of Formula (I), wherein a compound of Formula (V)

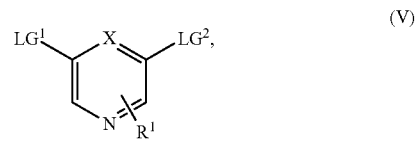

is reacted with a compound of Formula (IV)

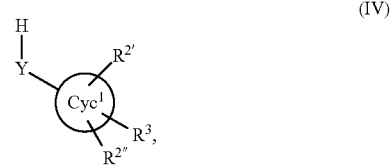

to yield a compound of Formula (III)

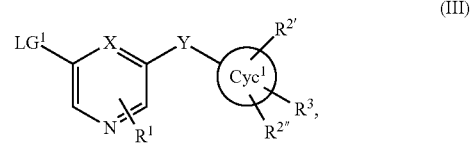

which is then further reacted with a compound of Formula (II)

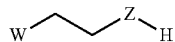

to yield a compound of Formula (I).

LG$^1$ and LG$^2$ are leaving groups typically used in nucleophilic substitutions, preferably Hal, such as Cl or Br.

EXAMPLES

HPLC Method (Polar)

Solvent A: water+0.05% formic acid

Solvent B: acetonitril+0.04% formic acid

Flow: 2.4 ml/min, wave length: 220 nm

Gradient: 0.0 min 4% B 2.8 min 100% B 3.3 min 100% B 3.4 min 4% B

Column: Chromolith Speed ROD RP-18e 50-4.6 mm (Merck KGaA)

The working examples presented below are intended to illustrate particular embodiments of the invention, and are not intended to limit the scope of the specification or the claims in any way.

Chemical Synthesis

In this section experimental details are provided for a number of Example compounds according to Formula (I), and synthesis intermediates thereof.

N-(2-{[6-(4-Fluoro-phenoxy)-pyrazin-2-yl]-methyl-amino}-ethyl)-N-methyl-acetamide (4)

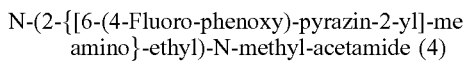

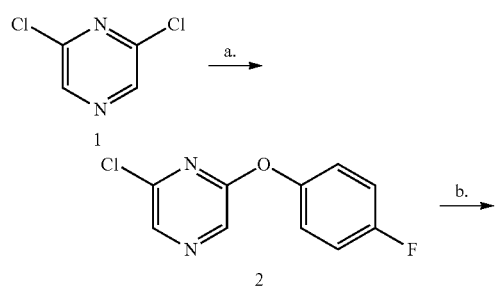

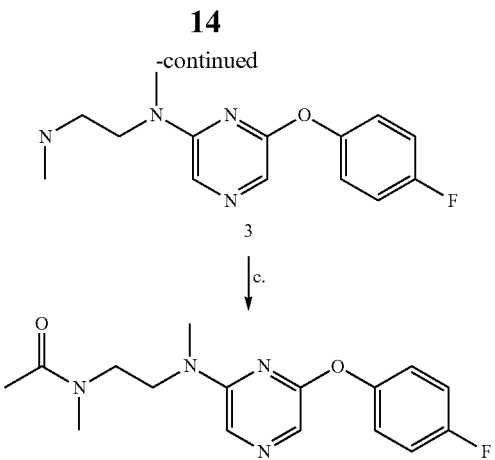

a. 2,6-Dichloropyrazine (98%, 1.00 g, 6.58 mmol) and 4-Fluorophenol (98%, 0.83 g, 7.26 mmol) were dissolved in dioxan (2 mL), To this solution sodium hydride (60% in paraffin oil, 0.29, 7.25 mmol) were added at RT in small portions and stirring continued under inert atmosphere (N$_2$) 18 h at RT. Since the reaction was not completed the mixture was stirred at 100° C. for 30 min. After cooling water was added and the aqueous layer was extracted with ethyl acetate. The organic layer was washed with water twice, dried over sodium sulfate, filtered and the solvent was evaporated under reduced pressure. The residue was purified by chromatography (heptane/ethyl acetate) to yield in a colorless solid, which was characterized as compound 2 (1.38 g, 6.14 mmol, 93%).

b. Compound 2 (600 mg, 2.67 mmol) and N,N'-dimethylethylenediamine (1.20 mL, 11.1 mmol) was dissolved in dimethylsulfoxide (10 mL), cesium fluoride (1.30 g, 8.56 mmol) was added at RT and stirring was continued at 120° C. for 12 h. After cooling the solvent was evaporated under reduced pressure and the residue purified directly by chromatography (dichloromethane/methanol) to yield in a colorless solid identified as compound 3 (668 mg, 2.42 mmol, 91%).

c. Compound 3 (100 mg, 0.36 mmol) was dissolved dichloromethane (2 mL), triethyl amine (0.05 mL, 0.36 mmol) at RT followed by acetic anhydride (0.04 mL, 0.42 mmol) dropwise at RT. The mixture was stirred for 15 h at RT. Water was added and the aqueous layer was extracted with ethyl acetate. The organic layer was washed with water twice, dried over sodium sulfate, filtered and the solvent was evaporated under reduced pressure. The residue was purified by chromatography (dichloromethane/methanol) to yield in a colorless solid, which was characterized as compound 4 (113 mg, 0.35 mmol, 98%).

N-[2-({6-[4-(6-Hydroxymethyl-pyridin-3-yl)-phenoxy]-pyrazin-2-yl}-methyl-amino)-ethyl]-N-methyl-acetamide (8)

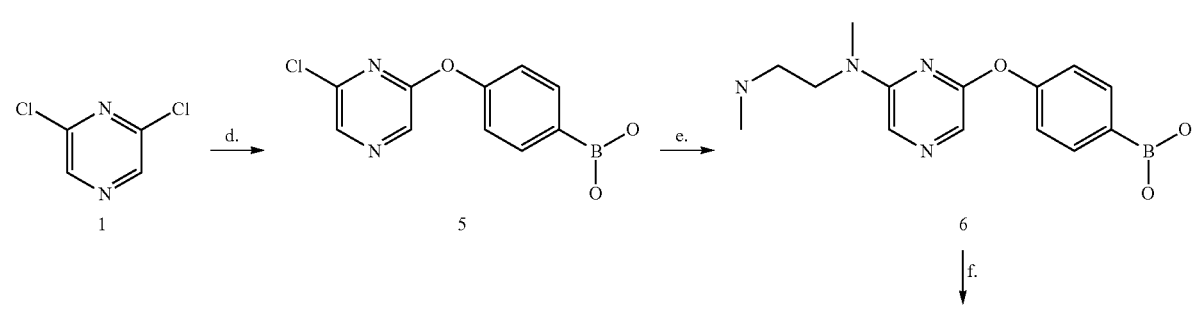

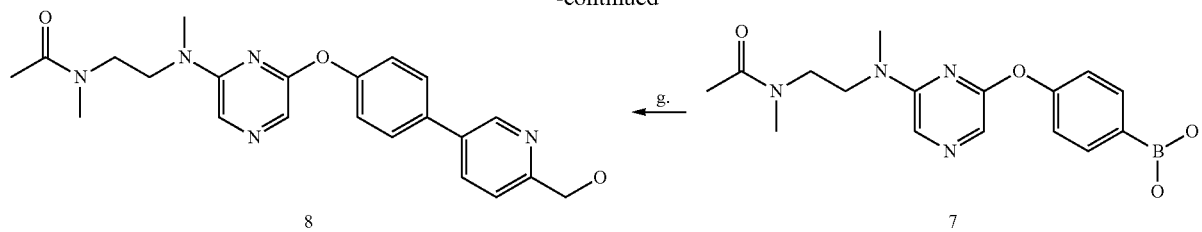

d. 2,6-Dichloropyrazine (98%, 5.00 g, 32.9 mmol) and 4-Hydroxyphenyl boronic acid (98%, 5.00 g, 36.2 mmol) were dissolved in dimethyl sulfoxide (70 mL). To this solution sodium hydride (60% in paraffin oil, 1.58, 39.5 mmol) were added at RT in small portions and stirring continued under inert atmosphere (N2) 3 h at 100° C. After cooling water was added and the aqueous layer was extracted with ethyl acetate. The aqueous layer was slightly acidified with diluted HCl and extracted with ethyl acetate. The combined organic layers were washed with water and saturated NaCl-solution, dried over sodium sulfate, filtered and the solvent was evaporated under reduced pressure. The dark residue was crystallized from acetonitrile resulting in a colorless solid, which was characterized as compound 5 (6.05 g, 24.2 mmol, 73%).

e. Compound 5 (4.30 g, 17.3 mmol) and N,N'-dimethylethylenediamine (4.70 mL, 43.3 mmol) was dissolved in dimethyl sulfoxide (10 mL), cesium fluoride (6.60 g, 43.3 mmol) was added at RT and stirring was continued at 120° C. for 15 h. After cooling the solvent was evaporated under reduced pressure and the residue purified by crystallization (dichloromethane/methanol) to yield in a colorless solid identified as compound 6 (4.18 mg, 13.8 mmol, 80%).

f. Compound 6 (1.40 g, 4.63 mmol) was dissolved in dimethyl sulfoxide (6 mL), triethyl amine (0.65 mL, 4.63 mmol) at RT followed by acetic anhydride (0.53 mL, 5.55 mmol) dropwise at RT. The mixture was stirred for 15 h at RT and the solvent evaporated under reduced pressure to dryness. The residue was redissolved in ethyl acetate and washed with water. The aqueous layer was acidified with diluted HCl to pH 6 and extracted with Ethyl acetate twice. The combined organic layers were dried over sodium sulfate, filtered and the solvent was evaporated under reduced pressure. The residue was purified by chromatography (dichloromethane/methanol) to yield in colorless solid, which was characterized as compound 7 (980 mg, 2.85 mmol, 61%) was obtained and used without further purification.

g. Compound 7 (252 mg, 0.73 mmol) and 5-Bromo-2hydroxymethylpyridine (138 mg, 0.73 mmol) was suspended in dioxane/water (4 mL, 3:1) and flushed with argon. To this suspension potassium carbonate (203 mg, 1.47 mmol) and Dichloro[1,1'-bis(diphenylphosphino)ferrocene] palladium(11) dichloromethane adduct (88.6 mg, 0.11 mmol) were added at RT under Argon atmosphere. The mixture was stirred for 15 h at 120° C. The recooled mixture was filtered and ethyl acetate was added to the filtrate. The organic layer was washed with sodium hydrogen carbonate solution, water and saturated NaCl solution. It was filtered and the solvent was evaporated under reduced pressure to dryness. The residue was purified by chromatography (dichloromethane/methanol) to yield in colorless solid, which was characterized as compound 8 (153 mg, 0.38 mmol, 61%).

Other phenols with boronic acids/esters functionality reacted in a similar matter are:

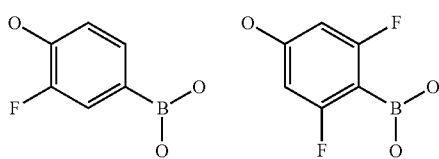 [SMILES: OB(O)c1ccc(O)c(F)c1 ; OB(O)c1c(F)cc(O)cc1F]

N-Methyl-N-[2-(6-(4-[6-(4-methyl-piperazin-1-yl)-pyridin-2-yl]-phenoxyl-pyrazin-2-ylamino)-ethyl]-acetamide (12)

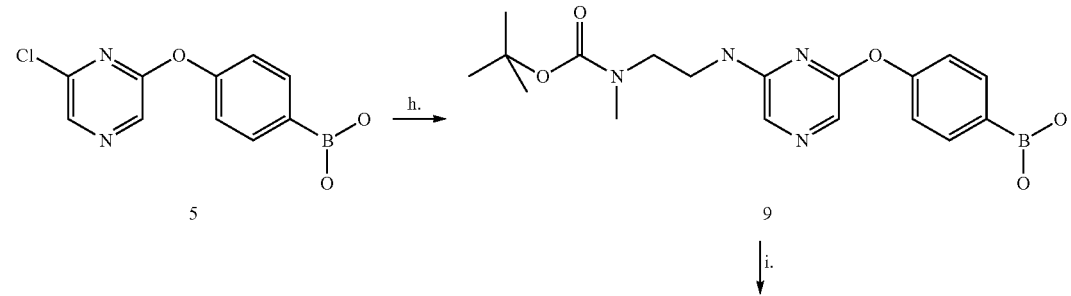

-continued

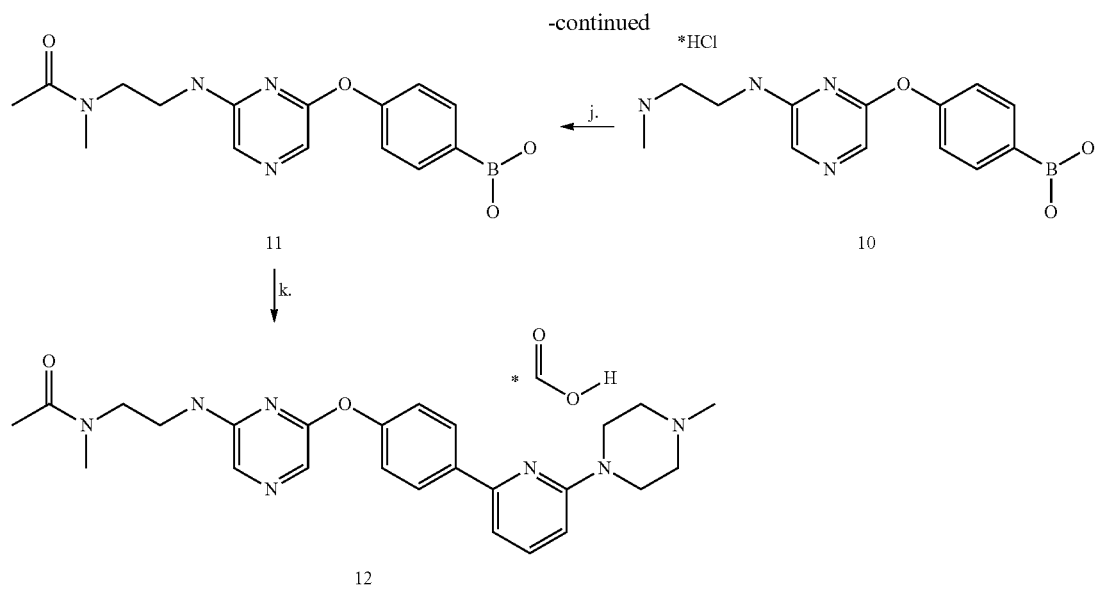

h. Compound 5 (3.89 g, 15.5 mmol) and (2-Amino-ethyl) methyl-carbamic acid tert.-butyl ester (3.25 g, 18.7 mmol) was dissolved in dimethyl sulfoxide (50 mL), cesium fluoride (2.83 g, 18.7 mmol) was added at RT and stirring was continued at 120° C. for 4 days. After cooling the solvent was evaporated under reduced pressure and the residue was redissolved in ethyl acetate and washed with water and saturated NaCl solution. It was dried over sodium sulfate, filtered and evaporated to dryness under reduced pressure. The crude solid was purified by chromatography (dichloromethane/methanol) to yield in a colorless solid identified as compound 9 (3.72 g, 8.62 mmol, 56%).

i. Compound 9 (3.72 g, 8.62 mmol) was dissolved 2-propanole (50 mL). To this solution 6N HCl solution in 2-propanole (25 mL) was added dropwise at RT and stirring was continued for 48 h at RT. The solvent was evaporated to dryness and the residue crystallized from 2-propanole/diethylether to result in the hydrochloride salt 10 as a colorless solid (2.99 g, 9.20 mmol, 96%).

j. Compound 10 (2.99 g, 9.20 mmol) was dissolved in acetonitrile/dimethyl formamide (75 mL, 2:1), triethyl amine (3.97 mL, 28.7 mmol) at RT followed by acetic anhydride (0.95 mL, 10.0 mmol) dropwise at RT. The mixture was stirred for 2 h and the solvent evaporated under reduced pressure to dryness. The residue was directly purified by chromatography (dichloromethane/methanol) to yield in light yellow solid, which was characterized as compound 11 (1.90 g, 5.76 mmol, 63%).

k. Compound 11 (80.0 mg, 0.24 mmol) and 1-(6-Bromo-pyridin-2-yl)-4-methyl-piperazine (68.3 mg, 0.27 mmol) was suspended in dioxane/water (10 mL, 7:3) and flushed with argon. To this suspension potassium carbonate (67.0 mg, 0.49 mmol) and Dichloro[1,1'-bis(diphenylphosphino) ferrocene]palladium(11) dichloromethane adduct (9.90 mg, 0.012 mmol) were added at RT under Argon atmosphere. The mixture was stirred for 120 min at 120° C. in the microwave. The solvent was removed under reduced pressure, the residue redissolved in ethyl acetate, filtered and the filter residue washed with ethyl acetate. The solvent was evaporated under reduced pressure to dryness. The residue was purified directly by preparative HPLC (Agilent Technologies, 1200 series, acetonitrile/water, gradient), to yield in colorless solid, which was characterized as the formic acid salt 12 (65.0 mg, 0.12 mmol, 50%).

N-Ethyl-N-(2-{6-[4-(5-methyl-pyridin-2-yl)-phenoxy]-pyrazin-2-ylsulfanyl}-ethyl)-acetamide (17)

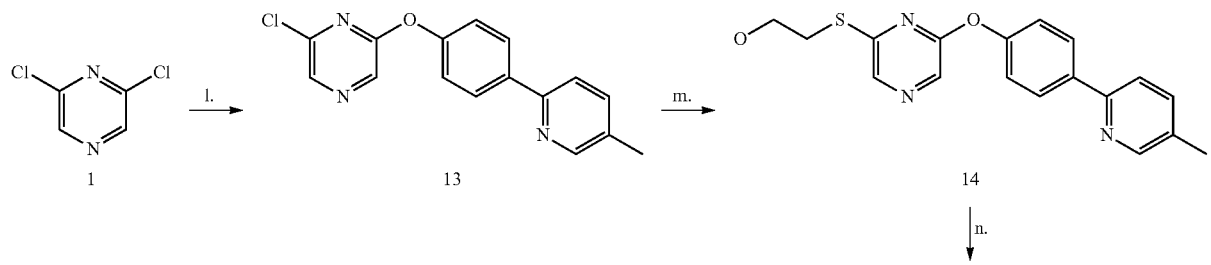

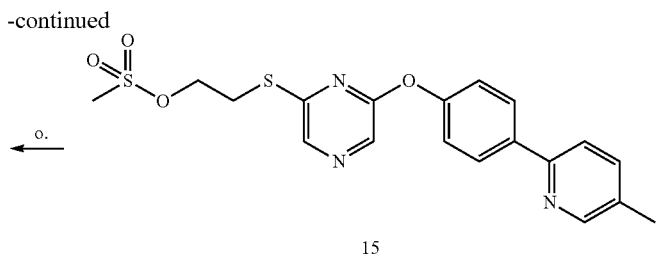

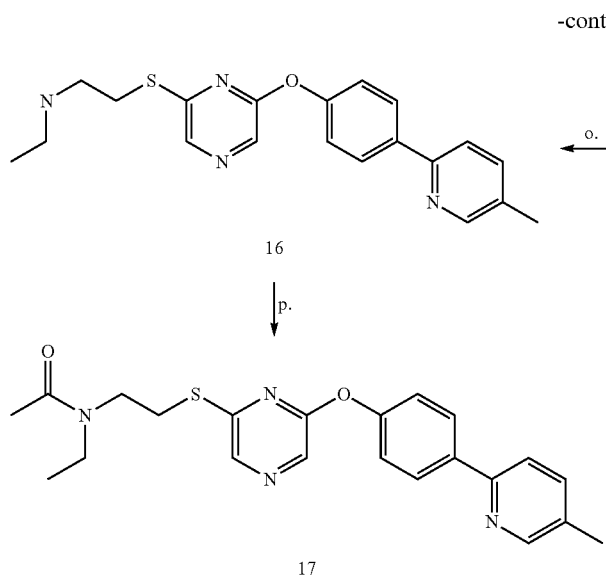

l. 2,6-Dichloropyrazine (3.86 g, 25.9 mmol) and 4-(5-methyl-pyridin-2-yl)-phenol (4.00 g, 21.6 mmol) were dissolved in dioxane (80 mL). To this solution sodium hydride (60% in paraffin oil, 1.04, 25.9 mmol) were added at RT in small portions and stirring continued under inert atmosphere (N2) for 15 h at 120° C. After cooling water and ethyl acetate were added, the aqueous layer slightly basified with sodium hydroxide solution (1 N) to pH 8 and the aqueous layer was extracted with the organic solvent mixture, followed by ethyl acetate twice. The combined organic layers were washed with water and saturated NaCl-solution, dried over sodium sulfate, filtered and the solvent was evaporated under reduced pressure. The residue was purified by chromatography (ethyl acetate/cyclohexane) to yield in a colorless solid, which was characterized as compound 13 (4.50 g, 15.1 mmol, 70%).

m. Compound 13 (1.50 g, 5.04 mmol) and 2-mercaptoethanol (0.43 g, 5.54 mmol) was dissolved in acetonitrile (8 mL) and stirred at 60° C. for 14 h and additional 4 h at 80° C. After cooling the solvent was evaporated under reduced pressure and the residue was redissolved in ethyl acetate and washed with water and saturated NaCl solution. It was dried over sodium sulfate, filtered and evaporated to dryness under reduced pressure. The crude solid was purified by chromatography (ethyl acetate/cyclohexane) to yield in a colorless solid identified as compound 14 (1.32 g, 3.89 mmol, 77%).

n. Compound 14 (1.13 g, 3.33 mmol) was dissolved in acetonitrile (20 mL), triethyl amine (0.69 mL, 4.99 mmol) at RT followed by metyhanesulfonyl chloride (0.39 mL, 4.99 mmol) dropwise at RT. The mixture was stirred for 15 h at RT. Additional 0.39 mL (4.99 mmol) metyhanesulfonyl chloride were added at RT and stirring continued for 2 h at RT. The solvent was evaporated under reduced pressure to dryness. The residue was redissolved in ethyl acetate, water wad added and the organic layer separated. The aqueous layer was extracted twice with ethyl acetate. The combined organic layers were washed with water and saturated NaCl-solution, dried over sodium sulfate, filtered and the solvent was evaporated under reduced pressure. The residue (15, 90% purity, 1.50 g, 3.23 mmol, 97%) was used without further purification.

o. Compound 15 (90% purity, 400 mg, 0.86 mmol) was dissolved in acetonitrile (5 mL), ethyl amine (2M solution in THF, 1.73 mL, 3.45 mmol) was added at RT dropwise and the mixture stirred for 15 h at 90° C. The solvent was evaporated under reduced pressure to dryness. The residue was redissolved in ethyl acetate, water wad added and the organic layer separated. The aqueous layer was extracted twice with ethyl acetate. The combined organic layers were washed with water and saturated NaCl-solution, dried over sodium sulfate, filtered and the solvent was evaporated under reduced pressure. The crude solid was purified by chromatography (dichloromethane/methanol) to yield in a colorless solid identified as compound 16 (160 mg, 0.44 mmol, 51%).

p. Compound 16 (40.3 mg, 0.11 mmol) was dissolved in dichloromethane (2 mL) and triethyl amine (20 μL, 0.14 mmol) was added at RT followed by acetic anhydride (11 μL, 0.12 mmol) at RT. The mixture was stirred for 15 h at RT and the solvent evaporated under reduced pressure to dryness. The residue was directly purified by chromatography (dichloromethane/methanol) to yield in colorless solid, which was characterized as compound 17 (33.0 g, 0.08 mmol, 73%).

N-Methyl-N-(2-{6-[4-(5-methyl-pyridin-2-yl)-phenoxy]-pyrazin-2-ylamino}-ethyl)-acetamide (19)

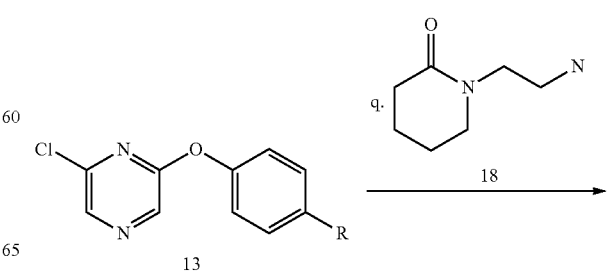

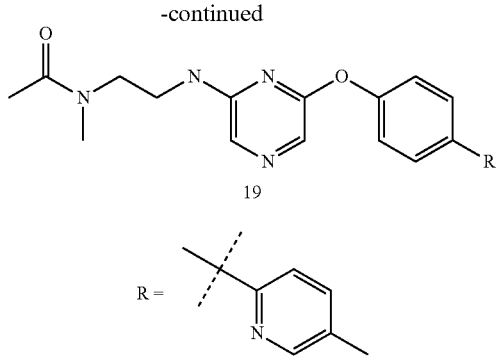

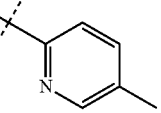

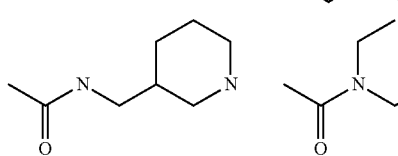

q. Compound 13 (100 mg, 0.34 mmol) and 1-(2-amino-ethyl)-2-piperidinone 18 (143 mg, 1.01 mmol) were dissolved in dimethyl sulfoxide (5 mL), cesium fluoride (153 mg, 1.01 mmol) was added at RT and stirring was continued at 120° C. for 15 h. After cooling the solvent was evaporated under reduced pressure and the residue was redissolved in ethyl acetate and washed with water and saturated NaCl solution. It was dried over sodium sulfate, filtered and evaporated to dryness under reduced pressure. The crude solid was purified by chromatography (dichloromethane/methanol) to yield in a colorless solid identified as compound 19 (52.2 mg, 0.13 mmol, 38%).

In addition to 18 the following amines were reacted as well:

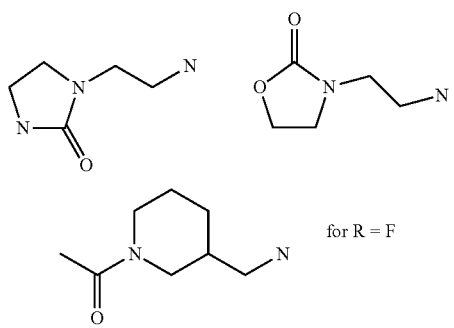

These compounds can also be synthesized as outlined before, reacting the dichloropyrazine first with the phenol, and in the second step with the amines shown above with improved overall yield.

1-(3-{6-[4-(6-Morpholin-4-yl-pyridin-3-yl)-phenoxy]-pyrazin-2-yl}-propyl)-piperidin-2-one (25)

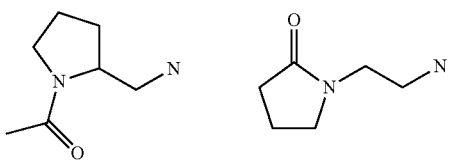

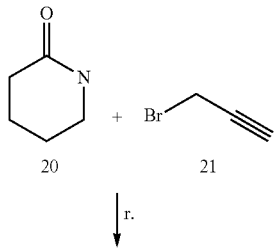

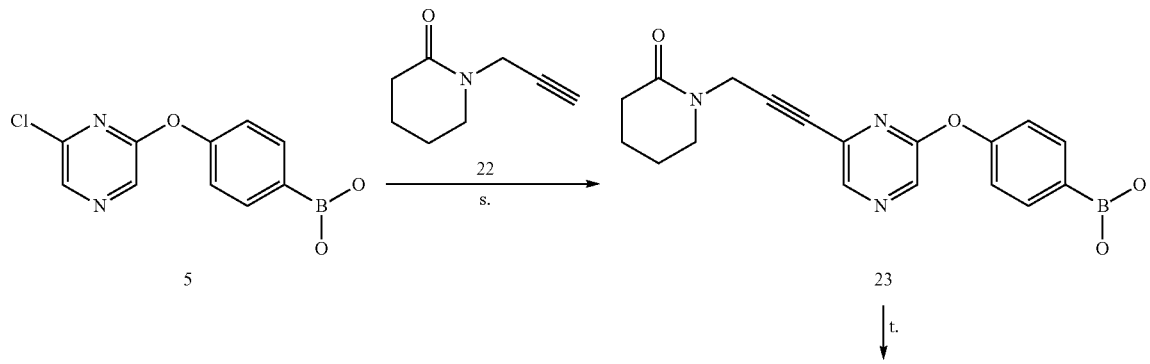

-continued

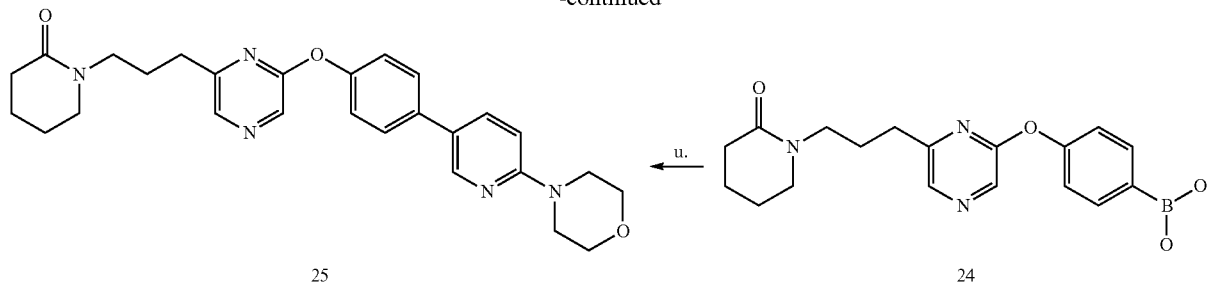

r. 2-piperidinone 20 (0.50 g, 5.04 mmol) was dissolved in tetrahydrofuran (5 mL) and NaH (60% in mineral oil, 242 mg, 6.05 mmol) was added in small portion at RT under inert atmosphere. To this suspension additional 40 mL of tetrahydrofuran and 10 mL dimethyl formamide were added, followed dropwise by a solution of propargyl bromide 21 (80%, 1.38 g, 7.57 mmol) in THF (10 mL9 over a period of 10 min at RT. The mixture was stirred at RT for 12 h. The residue was redissolved in ethyl acetate, water wad added and the organic layer separated. The aqueous layer was extracted twice with ethyl acetate. The combined organic layers were washed with water and saturated NaCl-solution, dried over sodium sulfate, filtered and the solvent was evaporated under reduced pressure. The crude yellow oil (22, 80% purity, 0.62 g, 3.62 mmol, 72%) was used without further purification.

s. Compound 22 (80% purity, 616 mg, 3.59 mmol) was dissolved in acetonitrile (5 mL) and consecutively triethyl amine (0.55 mL, 3.99 mmol), copper(I)iodide (38.0 mg, 0.20 mmol) and compound 5 (500 mg, 2.00 mmol) were added and the vessel was flushed with argon. To this suspension bis-(triphenylphosphino)palladium(II)-chloride were added at RT under Argon atmosphere. The mixture was stirred for 3 h at 50° C. and additional 4 h at 70° C. The solvent was removed under reduced pressure, the residue redissolved in ethyl acetate, filtered, washed with water and saturated sodium chloride. The organic layer was dried over sodium sulfate, filtered and the solvent was evaporated under reduced pressure to dryness. The residue was purified by chromatography (dichloromethane/methanol) to yield in yellowish solid, which was characterized as 23 (400 mg, 1.14 mmol, 57%).

t. Boronic acid 23 (323 mg, 0.91 mmol) was dissolved in tetrahydrofuran (10 mL), Pd/C (5%, 0.40 g, 54% water) and stirred over hydrogen atmosphere at RT and 1 atm for 15 h. Additional 0.40 g Pd/C (5%, 54% water) was added and stirring under hydrogen atmosphere for additional 18 h continued. The mixture was filtered, the residue washed with tetrahydrofuran and the solvent was evaporated to dryness under reduced pressure. The residue was purified by chromatography (dichloromethane/methanol) to yield in colorless solid, which was characterized as compound 24 (180 mg, 0.51 mmol, 56%).

u. Boronic acid 24 (67.5 mg, 0.19 mmol) and 4-(5-Bromo-pyridin-2-yl)-morpholine (50.8 mg, 0.21 mmol) was suspended in acetonitrile/water (10 mL, 7:3) and flushed with argon. To this suspension potassium carbonate (52.5 mg, 0.38 mmol) and Dichloro[1,1'-bis(diphenylphosphino)ferrocene]palladium(11) dichloromethane adduct (7.80 mg, 0.01 mmol) were added at RT under Argon atmosphere. The mixture was stirred for 20 min at 120° C. in the microwave. The solvent was removed under reduced pressure, the residue resuspended in ethyl acetate, filtered and the filter residue washed with ethyl acetate. The filtrate was evaporated under reduced pressure to dryness. The residue was purified directly by preparative HPLC (Agilent Technologies, 1200 series, acetonitrile/water, gradient), to yield in colorless solid, which was characterized as 25 (62.3 mg, 0.13 mmol, 69%).

According to the conditions described in r. the following lactams were reacted to its N-alkylated alkynes and transferred to the corresponding final products as described in (s.), (t.) and (u.).

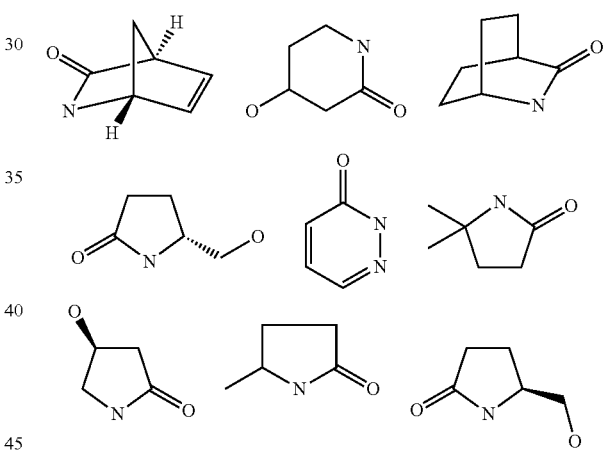

3-([6-(4-Fluoro-phenoxy)-pyrazin-2-yl]-methyl-amino]-N-methyl-propionamide (29)

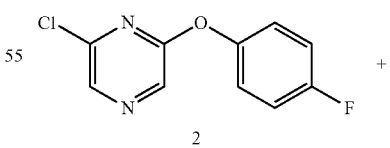

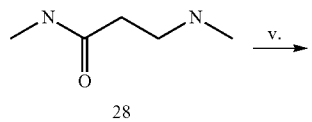

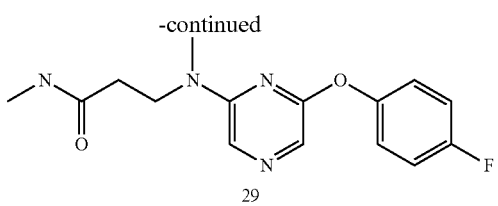

v. Compound 2 (150 mg, 0.67 mmol) and N-methyl-3-(methyl amino)propanamide) 28 (240 mg, 2.06 mmol) were dissolved in dimethyl sulfoxide (5 mL), cesium fluoride (314 mg, 2.06 mmol) was added at RT and stirring was continued at 120° C. for 15 h. After cooling the solvent was evaporated under reduced pressure and the residue was redissolved in ethyl acetate and washed with water and saturated NaCl solution. It was dried over sodium sulfate, filtered and evaporated to dryness under reduced pressure. The crude solid was purified by chromatography (dichloromethane/methanol) to yield in a colorless solid identified as compound 29 (96.0 mg, 0.31 mmol, 47%).

Instead of compound 2 also compound 5 can be used in this reaction, resulting in a boronic acid, which then can be reacted under Suzuki conditions as described in (g.), (k.) or (u.) to the final compounds 298-301 when 28 was also changed.

N-{3-[5-(4-Fluoro-phenoxy)-pyridin-3-yl]-propyl}-N-methyl-acetamide (31)

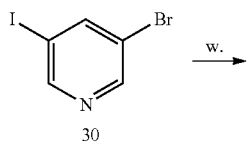

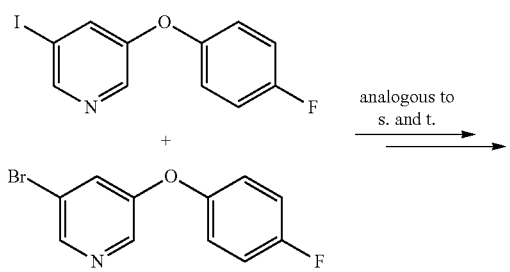

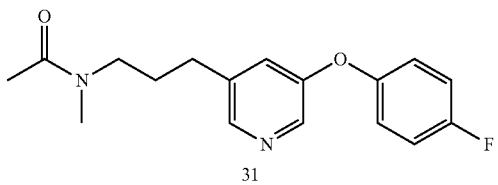

w. 4-Fluorophenol (98%, 2.37 g, 21.1 mmol) was dissolved in DMF (50 mL), NaH (60% in paraffin oil, 0.89 g, 22.2 mmol) was added at RT in small portions and stirred for 1 h at RT. To this suspension 3-Bromo-5-iodopyridine (3.00 g, 10.6 mmol) was added at RT and stirring was continued for 2 h at 90° C. After cooling the solvent was removed under reduced pressure. The residue was redissolved in ethyl acetate, washed with diluted sodium hydroxide solution, water and saturated NaCl solution. It was dried over sodium sulfate, filtered and the solvent was evaporated under reduced pressure. The residue containing of a 1:1 mixture of the bromo- and iodo-intermediate was used without further purification.

According to the procedures (s.) and (t.) compound 31 was obtained in 52% yield over 2 steps. As an alternative, instead of pyridine, 3-5-dibromopyridine-N-oxide was reacted as described in (a.), (s.) and (t.) to obtain compound 31. The reduction of the N-oxide to the pyridine under the condition described in (t.) required an extended reaction time of 37 h.

Biological Activity

1. Cellular Assay for Wnt Pathway Activity

Compounds were tested for their Wnt pathway inhibitory activities using a luciferase reporter cell based assay. A HEK293 luciferase reporter cell line was used which contained an Estrogen Receptor-Dishevelled (ER-DSH) construct and a T-Cell Factor (TCF) dependent gene promoter luciferase construct.

Compounds, in concentrations from 30 µM down to 1 nM, were incubated for 24 hours on the cells, which were induced for TCF-dependent transcription by the addition of estrogen (10). Luciferase activities were determined using the ONE GLO Luciferase Assay System (Promega) and the ENVISION microplate reader (Perkin Elmer). For analysis, the obtained data were normalized against the untreated vehicle control and fitted for determination of the $IC_{50}$ values using the Assay Explorer software (Accelrys).

An additional test was run to confirm the specificifity of the compounds on the Wnt pathway: Compounds were tested in HEK293 cells, containing the TCF-dependent gene promoter, for inhibition of cellular viabilities using an ATP quantification readout. The compounds of the present invention were inactive in this test, pointing to Wnt pathway specific activity.

To assess the inhibitory potential of the compounds on the Wnt pathway, $IC_{50}$-values were determined, as shown in Table 1 below, whereby the following classification is used:

| | |
|---|---|
| $IC_{50} < 0.2$ µM | "A" |
| $0.2$ µM $\leq IC_{50} < 1$ µM | "B" |
| $1$ µM $\leq IC_{50} < 10$ µM | "C" |
| $10$ µM $\leq IC_{50}$ | "D" |

TABLE 1

| No | Chemical Structure | IC$_{50}$ | HPLC/MS Rt [Min] | Chemical Name | NMR data |
|---|---|---|---|---|---|
| 4 | 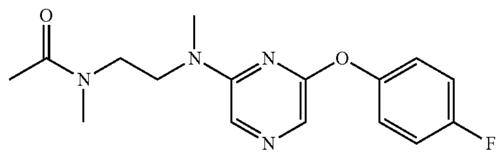 [SMILES: CC(=O)N(C)CCN(C)c1cncc(Oc2ccc(F)cc2)n1] | B | 2.05 | N-(2-{[6-(4-Fluoro-phenoxy)-pyrazin-2-yl]-methyl-amino}-ethyl)-N-methyl-acetamide | 1H NMR (400 MHz, DMSO-d6) ppm = 7.81 (s, 1H), 7.55 (s, 1H), 7.29-7.17 (m, 4H), 3.49-3.37 (m, 2H), 3.28-3.22 (m, 2H), 2.93 (s, 3H), 2.73 (s, 3H), 1.85 (s, 3H). |
| 7 | 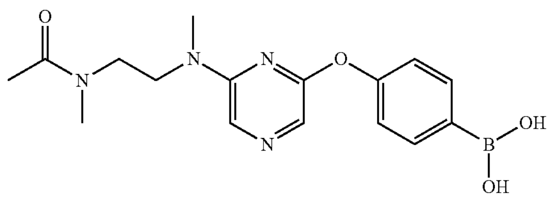 [SMILES: CC(=O)N(C)CCN(C)c1cncc(Oc2ccc(B(O)O)cc2)n1] | B | 1.56 | 4-(6-{[2-(Acetyl-methyl-amino)-ethyl]-methyl-amino}-pyrazin-2-yloxy)-boronic acid | 1H NMR (400 MHz, DMSO-d6) ppm = 8.02 (s, 2H), 7.84-7.79 (m, 3H), 7.54 (s, 1H), 7.12 (d, J = 8.5, 2H), 3.53-3.42 (m, 2H), 3.31-3.20 (m, 2H), 2.94 (s, 3H), 2.69 (s, 3H), 1.84 (s, 3H). |
| 8 | 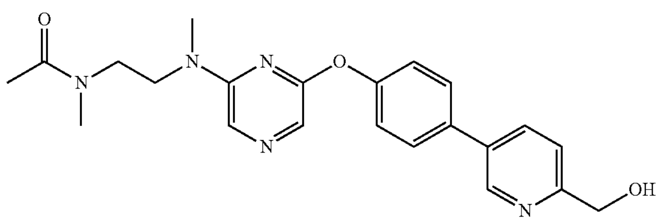 [SMILES: CC(=O)N(C)CCN(C)c1cncc(Oc2ccc(-c3ccc(CO)nc3)cc2)n1] | A | 1.51 | N-[2-({6-[4-(6-Hydroxy-methyl-pyridin-3-yl)-phenoxy]-pyrazin-2-yl}-methyl-amino)-ethyl]-N-methyl-acetamide | 1H NMR (500 MHz, DMSO-d6) ppm = 8.79 (d, J = 2.5, 1H), 8.09 (dd, J = 8.1, 2.5, 1H), 7.84 (s, 1H), 7.78 (d, J = 8.6, 2H), 7.60 (s, 1H), 7.56 (d, J = 8.1, 1H), 7.31 (d, J = 8.6, 2H), 3.52-3.45 (m, 2H), 3.29-3.21 (m, 2H), 2.97 (s, 3H), 2.70 (s, 3H), 1.84 (s, 3H). |
| 12 | 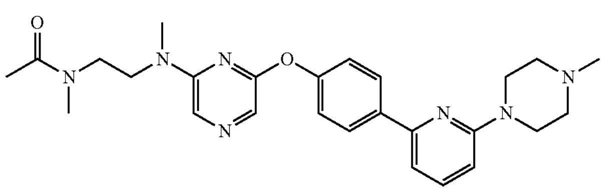 [SMILES: CC(=O)N(C)CCN(C)c1cncc(Oc2ccc(-c3cccc(N4CCN(C)CC4)n3)cc2)n1] | A | 1.59 | N-Methyl-N-{2-[methyl-(6-{4-[6-(4-methyl-piperazin-1-yl)-pyridin-2-yl]-phenoxy}-pyrazin-2-yl)-amino]-ethyl}-acetamide | 1H NMR (500 MHz, DMSO-d6) ppm = 8.08 (d, J = 8.6, 2H), 7.83 (s, 1H), 7.62 (d, J = 8.5, 1H), 7.59 (s, 1H), 7.25 (d, J = 8.7, 1H), 7.22 (d, J = 8.6, 2H), 6.79 (d, J = 8.5, 1H), 3.69-3.52 (m, 4H), 3.51-3.40 (m, 2H), 3.28-3.24 (m, 2H), 2.95 (s, 3H), 2.55 (s, 3H), 2.47-2.40 (m, 4H), 2.24 (s, 3H), 1.83 (s, 3H). |
| 17 | 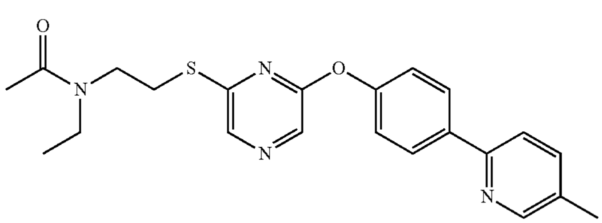 [SMILES: CCN(CCSc1cncc(Oc2ccc(-c3ccc(C)cn3)cc2)n1)C(C)=O] | A | 1.93 | N-Ethyl-N-(2-{6-[4-(5-methyl-pyridin-2-yl)-phenoxy]-pyrazin-2-ylsulfanyl}-ethyl)-acetamide | 1H NMR (400 MHz, DMSO-d6) ppm = 8.50 (s, 1H), 8.38 (s, 1H), 8.23 (s, 1H), 8.14 (d, J = 8.8, 2H), 7.88 (d, J = 8.1, 1H), 7.70 (dd, J = 8.1, 1.8, 1H), 7.34 (d, J = 8.7, 2H), 3.28-3.23 (m, 2H), 3.06-2.97 (m, 2H), 2.89 (q, J = 7.0, 2H), 2.34 (s, 3H), 1.89 (s, 3H), 0.88 (t, J = 7.1, 3H). |

TABLE 1-continued

| No | Chemical Structure | IC$_{50}$ | HPLC/MS Rt [Min] | Chemical Name | NMR data |
|---|---|---|---|---|---|
| 19 | 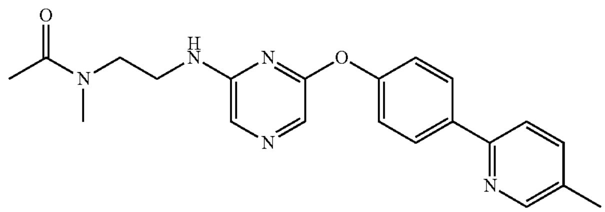 [SMILES: CC(=O)N(C)CCNc1cncc(Oc2ccc(-c3ccc(C)cn3)cc2)n1] | A | 1.61 | N-Methyl-N-(2-{6-[4-(5-methyl-pyridin-2-yl)-phenoxy]-pyrazin-2-ylamino}-ethyl)-acetamide | 1H NMR (400 MHz, DMSO-d6) ppm = 8.49 (d, J = 1.8, 1H), 8.09 (d, J = 8.7, 2H), 7.95-7.76 (m, 2H), 7.69 (dd, J = 8.1, 1.8, 1H), 7.54 (s, 1H), 7.25 (d, J = 8.7, 2H), 3.51-3.06 (m, 4H), 2.95 (s, 3H), 2.33 (s, 3H), 1.74 (s, 3H). |
| 25 | 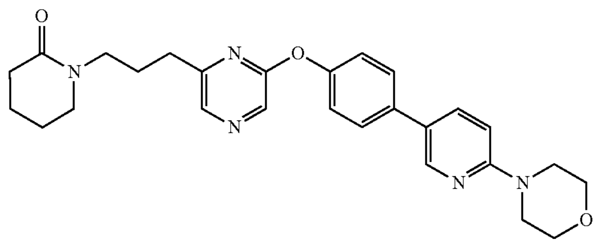 [SMILES: O=C1CCCCN1CCCc1cncc(Oc2ccc(-c3ccc(N4CCOCC4)nc3)cc2)n1] | A | 1.82 | 1-(3-{6-[4-(6-Morpholin-4-yl-pyridin-3-yl)-phenoxy]-pyrazin-2-yl}-propyl)-piperidin-2-one | 1H NMR (400 MHz, DMSO-d6) ppm = 8.49 (d, J = 2.5, 1H), 8.33 (s, 1H), 8.30 (s, 1H), 7.91 (dd, J = 8.9, 2.6, 1H), 7.69 (d, J = 8.7, 2H), 7.27 (d, J = 8.7, 2H), 6.93 (d, J = 8.9, 1H), 3.73 (dd, J = 5.7, 4.0, 4H), 3.50 (dd, J = 5.8, 4.1, 4H), 3.25 (dd, J = 7.9, 6.5, 2H), 3.12 (q, J = 2.3, 2H), 2.62 (t, J = 7.4, 2H), 2.14 (h, J = 2.7, 2.1, 2H), 1.78 (p, J = 7.4, 2H), 1.61 (dq, J = 6.6, 3.1, 4H). |
| 29 | 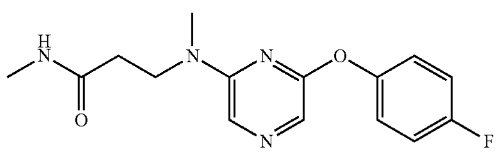 [SMILES: CNC(=O)CCN(C)c1cncc(Oc2ccc(F)cc2)n1] | B | 1.85 | 3-{[6-(4-Fluoro-phenoxy)-pyrazin-2-yl]-methyl-amino}-N-methyl-propionamide | 1H NMR (400 MHz, DMSO-d6) ppm = 7.80 (s, 1H), 7.73 (s, 1H), 7.51 (s, 1H), 7.22 (d, J = 6.6, 4H), 3.54 (t, J = 7.0, 2H), 2.90 (s, 3H), 2.54 (d, J = 4.6, 3H), 2.23 (t, J = 6.9, 2H). |
| 30 | 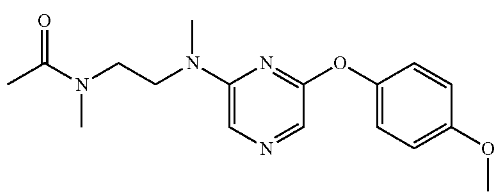 [SMILES: COc1ccc(Oc2cncc(N(C)CCN(C)C(C)=O)n2)cc1] | B | 2.00 | N-(2-{[6-(4-Methoxy-phenoxy)-pyrazin-2-yl]-methyl-amino}-ethyl)-N-methyl-acetamide | 1H NMR (400 MHz, DMSO-d6) ppm = 7.75 (s, 1H), 7.48 (s, 1H), 7.08 (d, J = 9.0, 2H), 6.96 (d, J = 9.0, 2H), 3.76 (s, 3H), 3.49-3.39 (m, 2H), 3.36-3.23 (m, 2H), 2.93 (s, 3H), 2.72 (s, 3H), 1.85 (s, 3H). |
| 31 | 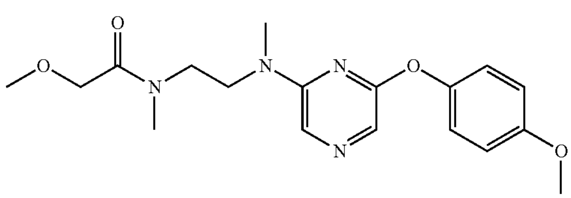 | C | 1.96 | 2-Methoxy-N-(2-{[6-(4-methoxy-phenoxy)-pyrazin-2-yl]-methyl-amino}-ethyl)-N-methyl-acetamide | 1H NMR (400 MHz, DMSO-d6) ppm = 7.74 (s, 1H), 7.48 (s, 1H), 7.11 (d, J = 9.0, 2H), 6.96 (d, J = 8.9, 2H), 3.90 (s, 2H), 3.75 (s, 3H), 3.55-3.38 (m, 2H), 3.29-3.21 (m, 2H), 3.17 (s, 3H), 2.94 (s, 3H), 2.66 (s, 3H). |
| 32 | 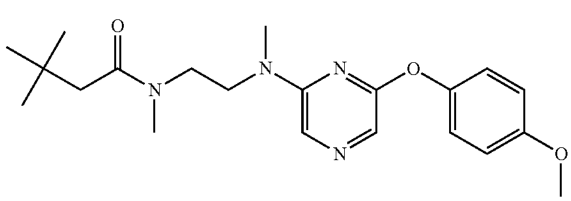 [SMILES: COc1ccc(Oc2cncc(N(C)CCN(C)C(=O)CC(C)(C)C)n2)cc1] | C | 2.35 | N-(2-{[6-(4-Methoxy-phenoxy)-pyrazin-2-yl]-methyl-amino}-ethyl)-3,3-N-trimethyl-butyramide | 1H NMR (400 MHz, DMSO-d6) ppm = 7.74 (s, 1H), 7.46 (s, 1H), 7.16-7.02 (m, 2H), 7.02-6.92 (m, 2H), 3.75 (s, 3H), 3.51-3.38 (m, 2H), 3.38-3.32 (m, 2H), 2.94 (s, 3H), 2.72 (s, 3H), 2.05 (s, 2H), 0.89 (s, 9H). |

TABLE 1-continued

| No | Chemical Structure | IC$_{50}$ | HPLC/MS Rt [Min] | Chemical Name | NMR data |
|---|---|---|---|---|---|
| 33 | 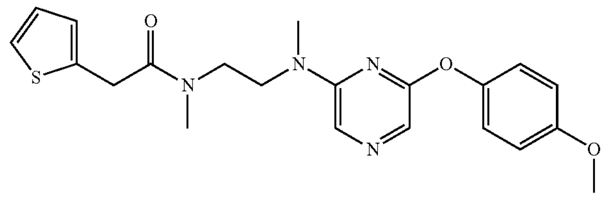 [SMILES: COc1ccc(Oc2cncc(N(C)CCN(C)C(=O)Cc3cccs3)n2)cc1] | C | 2.24 | N-(2-{[6-(4-Methoxy-phenoxy)-pyrazin-2-yl]-methyl-amino}-ethyl)-N-methyl-2-thiophen-2-yl-acetamide | 1H NMR (400 MHz, DMSO-d6) ppm = 7.73 (s, 1H), 7.48 (s, 1H), 7.33 (d, J = 5.0, 1H), 7.08 (d, J = 9.0, 2H), 6.97-6.87 (m, 3H), 6.82-6.74 (m, 1H), 3.75 (s, 3H), 3.74 (s, 2H), 3.50-3.34 (m, 4H), 2.91 (s, 3H), 2.77 (s, 3H). |
| 34 | 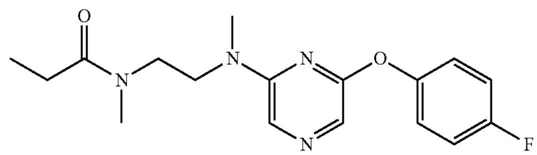 [SMILES: CCC(=O)N(C)CCN(C)c1cncc(Oc2ccc(F)cc2)n1] | C | 2.13 | N-(2-{[6-(4-Fluoro-phenoxy)pyrazin-2-yl]-methyl-amino}-ethyl)-N-methyl-propionamide | 1H NMR (400 MHz, DMSO-d6) ppm = 7.78 (s, 1H), 7.53 (s, 1H), 7.31-7.13 (m, 4H), 3.58-3.41 (m, 2H), 3.30-3.23 (m, 2H), 2.93 (s, 3H), 2.71 (s, 3H), 2.13 (q, J = 7.4, 2H), 0.86 (t, J = 7.4, 3H). |
| 35 | 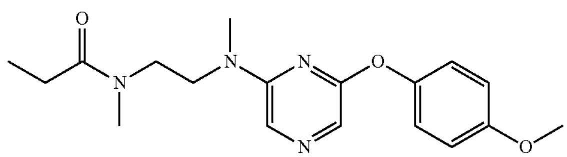 [SMILES: CCC(=O)N(C)CCN(C)c1cncc(Oc2ccc(OC)cc2)n1] | C | 2.08 | N-(2-{[6-(4-Methoxy-phenoxy)-pyrazin-2-yl]-methyl-amino}-ethyl)-N-methyl-propionamide | 1H NMR (400 MHz, DMSO-d6) ppm = 7.74 (s, 1H), 7.47 (s, 1H), 7.11 (d, J = 9.1, 2H), 6.96 (d, J = 9.0, 2H), 3.76 (s, 3H), 3.43 (t, J = 6.7, 2H), 3.37-3.22 (m, 2H), 2.93 (s, 3H), 2.70 (s, 3H), 2.13 (q, J = 7.4, 2H), 0.86 (t, J = 7.4, 3H). |
| 36 | 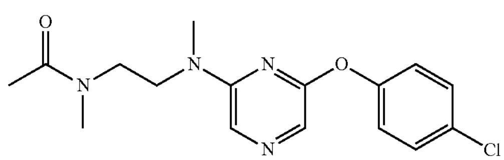 [SMILES: CC(=O)N(C)CCN(C)c1cncc(Oc2ccc(Cl)cc2)n1] | B | 2.20 | N-(2-{[6-(4-Chloro-phenoxy)-pyrazin-2-yl]-methyl-amino}-ethyl)-N-methyl-acetamide | 1H NMR (400 MHz, DMSO-d6) ppm = 7.82 (s, 1H), 7.57 (s, 1H), 7.46 (d, J = 8.8, 2H), 7.22 (d, J = 8.9, 2H), 3.54-3.38 (m, 2H), 3.38-3.20 (m, 2H), 2.94 (s, 3H), 2.73 (s, 3H), 1.85 (s, 3H). |
| 37 | 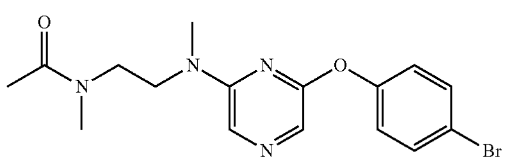 [SMILES: CC(=O)N(C)CCN(C)c1cncc(Oc2ccc(Br)cc2)n1] | A | 2.23 | N-(2-{[6-(4-Bromo-phenoxy)-pyrazin-2-yl]-methyl-amino}-ethyl)-N-methyl-acetamide | 1H NMR (400 MHz, DMSO-d6) ppm = 7.83 (s, 1H), 7.66-7.54 (m, 3H), 7.16 (d, J = 8.9, 2H), 3.52-3.38 (m, 2H), 3.35-3.20 (m, 2H), 2.94 (s, 3H), 2.73 (s, 3H), 1.85 (s, 3H). |
| 38 | 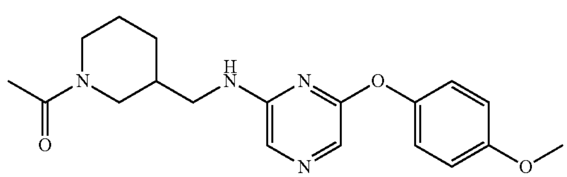 [SMILES: COc1ccc(Oc2cncc(NCC3CCCN(C(C)=O)C3)n2)cc1] | C | 2.04 | 1-(3-{[6-(4-Methoxy-phenoxy)-pyrazin-2-ylamino]-methyl}-piperidin-1-yl)-ethanone | 1H NMR (400 MHz, DMSO-d6) ppm = 7.94 (s, 1H), 7.42 (s, 1H), 7.07 (d, J = 9.0, 2H), 6.96 (d, J = 9.1, 2H), 4.32-3.85 (m, 2H), 3.76 (s, 3H), 3.11-2.69 (m, 2H), 1.79 (s, 3H), 1.74-0.90 (m, 8H). |
| 39 | 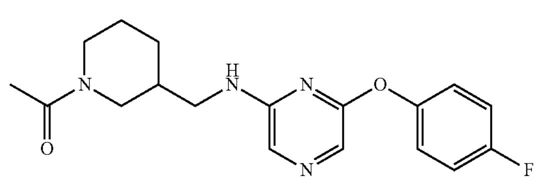 [SMILES: CC(=O)N1CCCC(CNc2cncc(Oc3ccc(F)cc3)n2)C1] | C | 2.10 | 1-(3-{[6-(4-Fluoro-phenoxy)-pyrazin-2-ylamino]-methyl}-piperidin-1-yl)-ethanone | |

TABLE 1-continued

| No | Chemical Structure | IC$_{50}$ | HPLC/MS Rt [Min] | Chemical Name | NMR data |
|---|---|---|---|---|---|
| 40 | 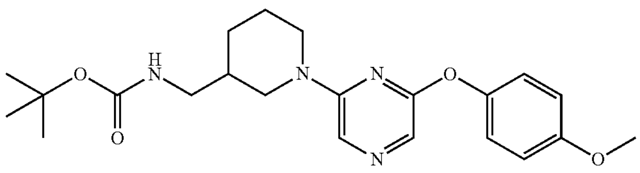 [SMILES: COc1ccc(Oc2cncc(N3CCCC(CNC(=O)OC(C)(C)C)C3)n2)cc1] | C | 2.59 | {1-[6-(4-Methoxy-phenoxy)-pyrazin-2-yl]-piperidin-3-ylmethyl}-carbamic acid tert-butyl ester | 1H NMR (400 MHz, DMSO-d6) ppm = 7.92 (s, 1H), 7.40 (s, 1H), 7.10 (d, J = 9.0, 2H), 6.97 (d, J = 9.1, 2H), 6.86 (t, J = 4.9, 1H), 4.08-3.86 (m, 2H), 3.76 (s, 3H), 2.90-2.82 (m, 2H), 2.81-2.58 (m, 2H), 1.85-1.68 (m, 1H), 1.68-1.49 (m, 2H), 1.38 (s, 9H), 1.35-1.08 (m, 2H). |
| 41 | 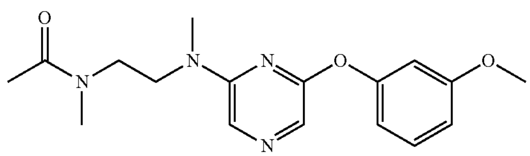 [SMILES: COc1cccc(Oc2cncc(N(C)CCN(C)C(C)=O)n2)c1] | C | 2.02 | N-(2-{[6-(3-Methoxy-phenoxy)-pyrazin-2-yl]-methyl-amino}-ethyl)-N-methyl-acetamide | 1H NMR (400 MHz, DMSO-d6) ppm = 7.79 (d, J = 8.1, 1H), 7.52 (s, 1H), 7.30 (t, J = 8.1, 1H), 6.82-6.66 (m, 3H), 3.75 (s, 3H), 3.54-3.39 (m, 2H), 3.37-3.31 (m, 2H), 2.95 (s, 3H), 2.73 (s, 3H), 1.85 (s, 3H). |
| 43 | 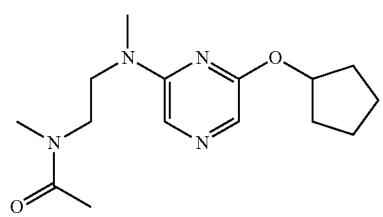 [SMILES: CC(=O)N(C)CCN(C)c1cncc(OC2CCCC2)n1] | C | 2.05 | N-{2-[(6-Cyclopentyloxy-pyrazin-2-yl)-methyl-amino]-ethyl}-N-methyl-acetamide | 1H NMR (400 MHz, DMSO-d6) ppm = 7.57 (s, 1H), 7.33 (s, 1H), 5.36-5.24 (m, 1H), 3.61 (t, J = 6.5, 2H), 3.46 (t, J = 6.3, 2H), 3.01 (s, 3H), 2.94 (s, 3H), 2.03-1.92 (m, 2H), 1.90 (s, 3H), 1.77-1.63 (m, 4H), 1.63-1.53 (m, 2H). |
| 44 | 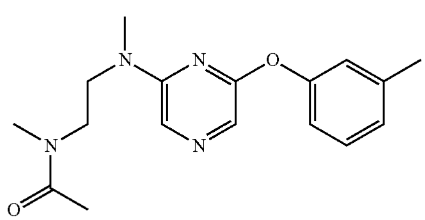 | C | 2.12 | N-Methyl-N-{2-[methyl-(6-m-tolyloxy-pyrazin-2-yl)-amino]-ethyl}-acetamide | 1H NMR (400 MHz, DMSO-d6) ppm = 7.78 (s, 1H), 7.50 (s, 1H), 7.29 (t, J = 7.8, 1H), 7.07-6.89 (m, 3H), 3.54-3.20 (m, 4H), 2.94 (s, 3H), 2.71 (s, 3H), 2.31 (s, 3H), 1.85 (s, 3H). |
| 45 | 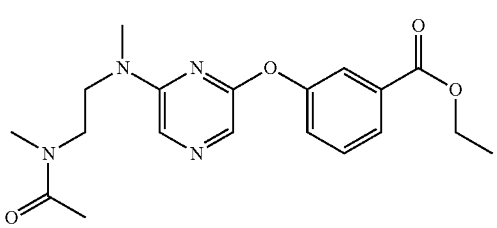 [SMILES: CCOC(=O)c1cccc(Oc2cncc(N(C)CCN(C)C(C)=O)n2)c1] | C | 2.14 | 3-(6-{[2-(Acetyl-methyl-amino)-ethyl]-methyl-amino}-pyrazin-2-yloxy)-benzoic acid ethyl ester | 1H NMR (400 MHz, DMSO-d6) ppm = 7.83 (s, 1H), 7.81 (d, J = 7.7, 1H), 7.74-7.66 (m, 1H), 7.61 (s, 1H), 7.58 (t, J = 7.9, 1H), 7.54-7.36 (m, 1H), 4.32 (q, J = 7.1, 2H), 3.49-3.41 (m, 2H), 3.30-3.20 (m, 2H), 2.93 (s, 3H), 2.69 (s, 3H), 1.84 (s, 3H), 1.31 (t, J = 7.1, 3H). |

TABLE 1-continued

| No | Chemical Structure | IC$_{50}$ | HPLC/MS Rt [Min] | Chemical Name | NMR data |
|---|---|---|---|---|---|
| 46 | 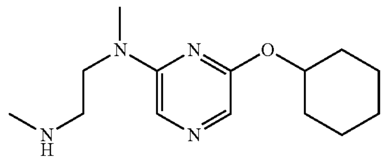 [SMILES: CNCCN(C)c1cncc(OC2CCCCC2)n1] | B | 1.52 | N-(6-Cyclo-hexyloxy-pyrazin-2-yl)-N,N'-dimethyl-ethane-1,2-diamine | 1H NMR (400 MHz, DMSO-d6) ppm = 7.56 (s, 1H), 7.30 (s, 1H), 4.88 (tt, J = 9.0, 3.8, 1H), 3.53 (t, J = 6.8, 2H), 3.28 (s, 1H), 3.02 (s, 3H), 2.66 (t, J = 6.8, 2H), 2.30 (s, 3H), 2.04-1.84 (m, 2H), 1.78-1.65 (m, 2H), 1.62-1.14 (m, 6H). |
| 47 | 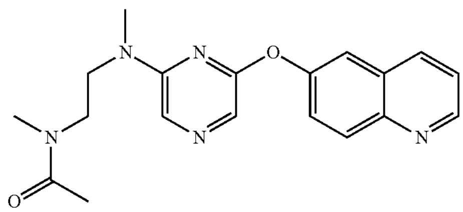 [SMILES: CC(=O)N(C)CCN(C)c1cncc(Oc2ccc3ncccc3c2)n1] | C | 1.65 | N-Methyl-N-(2-{methyl-[6-(quinolin-6-yloxy)-pyrazin-2-yl]-amino}-ethyl)-acetamide | 1H NMR (400 MHz, DMSO-d6) ppm = 8.93-8.81 (m, 1H), 8.39-8.29 (m, 1H), 8.06 (d, J = 9.1, 1H), 7.87 (s, 1H), 7.79-7.69 (m, 1H), 7.66 (s, 1H), 7.65-7.57 (m, 1H), 7.57-7.50 (m, 1H), 3.62-3.14 (m, 4H), 2.93 (s, 3H), 2.37 (s, 3H), 1.80 (s, 3H). |
| 48 | 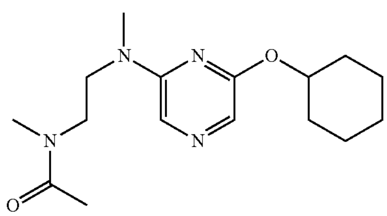 [SMILES: CC(=O)N(C)CCN(C)c1cncc(OC2CCCCC2)n1] | C | 2.20 | N-{2-[(6-Cyclo-hexyloxy-pyrazin-2-yl)-methyl-amino]-ethyl}-N-methyl-acetamide | 1H NMR (500 MHz, DMSO-d6) ppm = 7.56 (s, 1H), 7.33 (s, 1H), 5.00-4.84 (m, 1H), 3.60 (t, J = 6.5, 2H), 3.45 (t, J = 6.5, 2H), 3.00 (s, 3H), 2.95 (s, 3H), 2.03-1.84 (m, 5H), 1.80-1.63 (m, 2H), 1.61-1.17 (m, 6H). |
| 49 | 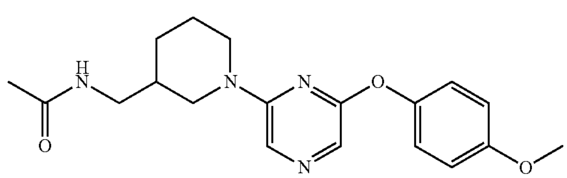 [SMILES: COc1ccc(Oc2cncc(N3CCCC(CNC(C)=O)C3)n2)cc1] | C | 2.02 | N-{1-[6-(4-Methoxy-phenoxy)-pyrazin-2-yl]-piperidin-3-ylmethyl}-acetamide | 1H NMR (400 MHz, DMSO-d6) ppm = 7.93 (s, 1H), 7.79 (t, J = 5.4, 1H), 7.42 (s, 1H), 7.10 (d, J = 9.0, 2H), 6.96 (d, J = 9.0, 2H), 4.10-3.85 (m, 2H), 3.76 (s, 3H), 2.93 (t, J = 6.3, 2H), 2.90-2.79 (m, 1H), 2.60 (dd, J = 13.0, 10.4, 1H), 1.79 (s, 3H), 1.77-1.68 (m, 1H), 1.68-1.48 (m, 2H), 1.44-1.28 (m, 1H), 1.26-1.10 (m, 1H). |
| 50 | 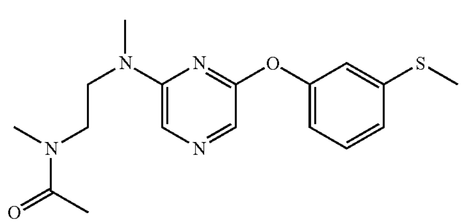 | B | 2.16 | N-Methyl-N-(2-{methyl-[6-(3-methyl-sulfanyl-phenoxy)-pyrazin-2-yl]-amino}-ethyl)-acetamide | 1H NMR (400 MHz, DMSO-d6) ppm = 7.80 (s, 1H), 7.54 (s, 1H), 7.34 (t, J = 8.0, 1H), 7.09 (d, J = 8.0, 1H), 7.06 (t, J = 1.9, 1H), 6.94 (dd, J = 8.1, 1.8, 1H), 3.59-3.39 (m, 2H), 3.30-3.18 (m, 2H), 2.95 (s, 3H), 2.59 (s, 3H), 2.47 (s, 3H), 1.85 (s, 3H). |

TABLE 1-continued

| No | Chemical Structure | IC$_{50}$ | HPLC/MS Rt [Min] | Chemical Name | NMR data |
|---|---|---|---|---|---|
| 51 | 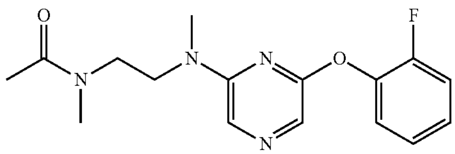 [SMILES: CC(=O)N(C)CCN(C)c1cncc(Oc2ccccc2F)n1] | B | 2.04 | N-(2-{[6-(2-Fluoro-phenoxy)-pyrazin-2-yl]-methyl-amino}-ethyl)-N-methyl-acetamide | 1H NMR (400 MHz, DMSO-d6) ppm = 7.82 (s, 1H), 7.63 (s, 1H), 7.43-7.18 (m, 4H), 3.50-3.38 (m, 2H), 3.27-3.18 (m, 2H), 2.90 (s, 3H), 2.65 (s, 3H), 1.83 (s, 3H). |
| 52 | 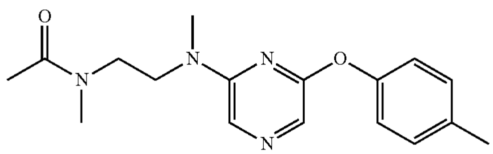 [SMILES: CC(=O)N(C)CCN(C)c1cncc(Oc2ccc(C)cc2)n1] | A | 2.16 | N-Methyl-N-{2-[methyl-(6-p-tolyloxy-pyrazin-2-yl)-amino]-ethyl}-acetamide | 1H NMR (400 MHz, DMSO-d6) ppm = 7.78 (s, 1H), 7.49 (s, 1H), 7.21 (d, J = 8.2, 2H), 7.05 (d, J = 8.4, 2H), 3.50-3.38 (m, 2H), 3.33-3.20 (m, 2H), 2.94 (s, 3H), 2.70 (s, 3H), 2.30 (s, 3H), 1.85 (s, 3H). |
| 53 | 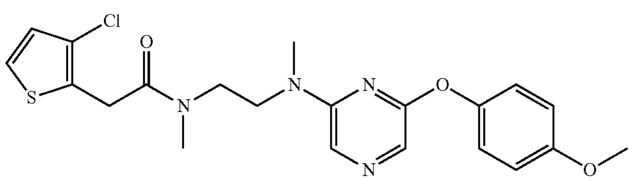 [SMILES: COc1ccc(Oc2cncc(N(C)CCN(C)C(=O)Cc3sccc3Cl)n2)cc1] | C | 2.39 | 2-(3-Chloro-thiophen-2-yl)-N-(2-{[6-(4-methoxy-phenoxy)-pyrazin-2-yl]-methyl-amino}-ethyl)-N-methyl-acetamide | 1H NMR (400 MHz, DMSO-d6) ppm = 7.72 (s, 1H), 7.56-7.44 (m, 2H), 7.09 (d, J = 9.1, 2H), 7.02-6.88 (m, 3H), 3.78-3.62 (m, 5H), 3.55-3.36 (m, 4H), 2.93 (s, 3H), 2.80 (s, 3H). |
| 54 | 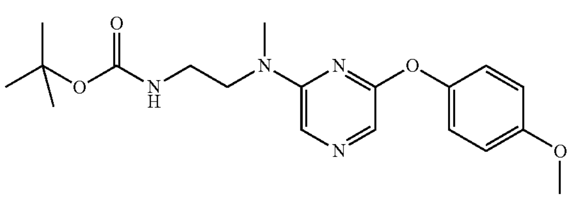 [SMILES: COc1ccc(Oc2cncc(N(C)CCNC(=O)OC(C)(C)C)n2)cc1] | C | 2.32 | (2-{[6-(4-Methoxy-phenoxy)-pyrazin-2-yl]-methyl-amino}-ethyl)-carbamic acid tert-butyl ester | 1H NMR (400 MHz, DMSO-d6) ppm = 7.78 (s, 1H), 7.39 (s, 1H), 7.10 (d, J = 8.9, 2H), 6.96 (d, J = 9.0, 2H), 6.72 (t, J = 5.5, 1H), 3.76 (s, 3H), 3.38-3.31 (m, 2H), 3.13-2.99 (m, 2H), 2.92 (s, 3H), 1.32 (s, 9H). |
| 55 | 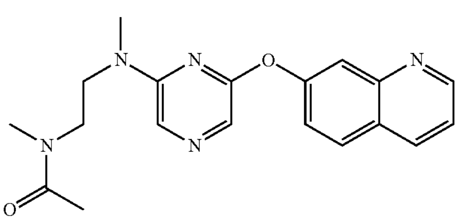 [SMILES: CC(=O)N(C)CCN(C)c1cncc(Oc2ccc3cccnc3c2)n1] | C | 1.62 | N-Methyl-N-(2-{methyl-[6-(quinolin-7-yloxy)-pyrazin-2-yl]-amino}-ethyl)-acetamide | 1H NMR (400 MHz, DMSO-d6) ppm = 8.90 (d, J = 1.6, 1H), 8.40 (d, J = 8.1, 1H), 8.05 (d, J = 8.9, 1H), 7.88 (s, 1H), 7.76-7.64 (m, 2H), 7.58-7.42 (m, 2H), 3.57-3.37 (m, 2H), 3.30-3.13 (m, 2H), 2.94 (s, 3H), 2.39 (s, 3H), 1.80 (s, 3H). |
| 56 | 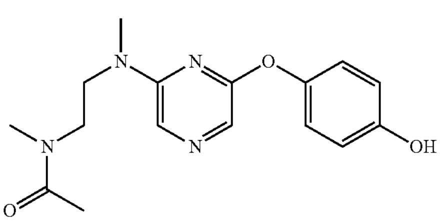 [SMILES: CC(=O)N(C)CCN(C)c1cncc(Oc2ccc(O)cc2)n1] | B | 1.73 | N-(2-{[6-(4-Hydroxy-phenoxy)-pyrazin-2-yl]-methyl-amino}-ethyl)-N-methyl-acetamide | 1H NMR (400 MHz, DMSO-d6) ppm = 9.32 (s, 1H), 7.73 (s, 1H), 7.44 (s, 1H), 6.97 (d, J = 8.9, 2H), 6.77 (d, J = 8.8, 2H), 3.56-3.37 (m, 2H), 3.37-3.16 (m, 2H), 2.93 (s, 3H), 2.74 (s, 3H), 1.85 (s, 3H). |

TABLE 1-continued

| No | Chemical Structure | IC$_{50}$ | HPLC/ MS Rt [Min] | Chemical Name | NMR data |
|---|---|---|---|---|---|
| 57 | 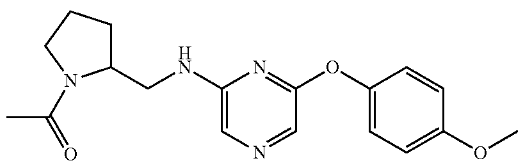 [SMILES: COc1ccc(Oc2cncc(NCC3CCCN3C(C)=O)n2)cc1] | C | 2.04 | 1-(2-{[6-(4-Methoxy-phenoxy)-pyrazin-2-ylamino]-methyl}-pyrrolidin-1-yl)-ethanone | 1H NMR (400 MHz, DMSO-d6) ppm = 7.61 (s, 1H), 7.32 (s, 1H), 7.71 (t, J = 4.7, 1H), 7.11-6.99 (m, 2H), 6.99-6.89 (m, 2H), 4.05-3.79 (m, 1H), 3.75 (d, J = 1.4, 3H), 3.29-2.90 (m, 4H), 2.01-1.60 (m, 7H). |
| 58 | 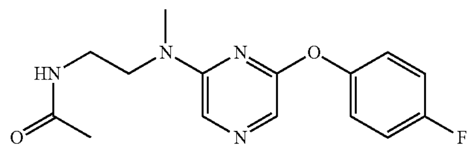 [SMILES: CC(=O)NCCN(C)c1cncc(Oc2ccc(F)cc2)n1] | C | 1.94 | N-(2-{[6-(4-Fluoro-phenoxy)-pyrazin-2-yl]-methyl-amino}-ethyl)-acetamide | 1H NMR (400 MHz, DMSO-d6) ppm = 7.85 (t, J = 5.2, 1H), 7.82 (s, 1H), 7.49 (s, 1H), 7.27-7.17 (m, 4H), 3.44-3.37 (m, 2H), 3.14 (q, J = 6.2, 2H), 2.93 (s, 3H), 1.75 (s, 3H). |
| 59 | 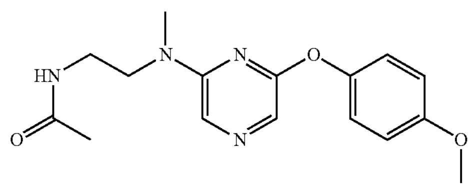 [SMILES: COc1ccc(Oc2cncc(N(C)CCNC(C)=O)n2)cc1] | B | 1.90 | N-(2-{[6-(4-Methoxy-phenoxy)-pyrazin-2-yl]-methyl-amino}-ethyl)-acetamide | 1H NMR (400 MHz, DMSO-d6) ppm = 7.84 (t, J = 5.8, 1H), 7.79 (s, 1H), 7.41 (s, 1H), 7.10 (d, J = 9.0, 2H), 6.96 (d, J = 9.0, 2H), 3.76 (s, 3H), 3.42 (t, J = 6.4, 2H), 3.15 (q, J = 6.2, 2H), 2.93 (s, 3H), 1.75 (s, 3H). |
| 60 | 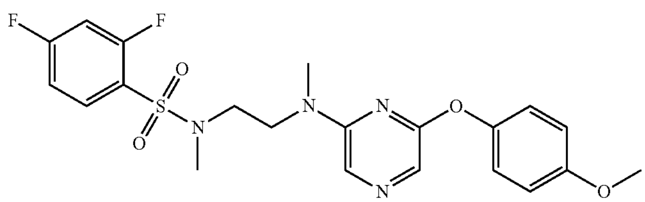 [SMILES: COc1ccc(Oc2cncc(N(C)CCN(C)S(=O)(=O)c3ccc(F)cc3F)n2)cc1] | C | 2.40 | 2,4-Difluoro-N-(2-{[6-(4-methoxy-phenoxy)-pyrazin-2-yl]-methyl-amino}-ethyl)-N-methyl-benzene-sulfonamide | 1H NMR (500 MHz, DMSO-d6) ppm = 7.77 (td, J = 8.6, 6.3, 1H), 7.67 (s, 1H), 7.52 (s, 1H), 7.48 (ddd, J = 10.7, 9.2, 2.5, 1H), 7.23 (td, J = 8.6, 2.5, 1H), 7.08 (d, J = 9.0, 2H), 6.92 (d, J = 9.0, 2H), 3.74 (s, 3H), 3.47 (t, J = 6.1, 2H), 3.16 (t, J = 6.1, 2H), 2.93 (s, 3H), 2.57 (s, 3H). |
| 61 | 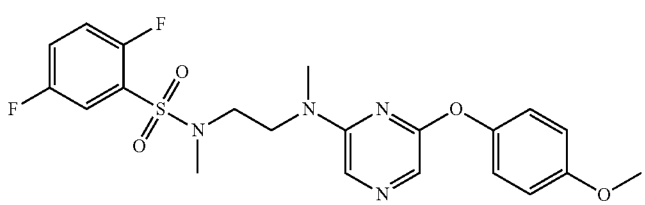 [SMILES: COc1ccc(Oc2cncc(N(C)CCN(C)S(=O)(=O)c3cc(F)ccc3F)n2)cc1] | C | 2.40 | 2,5-Difluoro-N-(2-{[6-(4-methoxy-phenoxy)-pyrazin-2-yl]-methyl-amino}-ethyl)-N-methyl-benzene-sulfonamide | 1H NMR (500 MHz, DMSO-d6) ppm = 7.68 (s, 1H), 7.60-7.52 (m, 1H), 7.52 (s, 1H), 7.51-7.43 (m, 2H), 7.07 (d, J = 9.0, 2H), 6.92 (d, J = 9.0, 2H), 3.74 (s, 3H), 3.48 (t, J = 6.1, 2H), 3.19 (t, J = 6.0, 2H), 2.94 (s, 3H), 2.60 (s, 3H). |
| 62 | 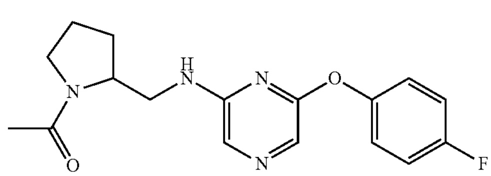 [SMILES: CC(=O)N1CCCC1CNc1cncc(Oc2ccc(F)cc2)n1] | C | 2.09 | 1-(2-{[6-(4-Fluoro-phenoxy)-pyrazin-2-ylamino]-methyl}-pyrrolidin-1-yl)-ethanone | |

TABLE 1-continued

| No | Chemical Structure | IC$_{50}$ | HPLC/MS Rt [Min] | Chemical Name | NMR data |
|---|---|---|---|---|---|
| 63 | 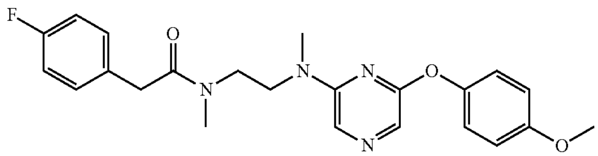 [SMILES: COc1ccc(Oc2cncc(N(C)CCN(C)C(=O)Cc3ccc(F)cc3)n2)cc1] | C | 2.28 | 2-(4-Fluoro-phenyl)-N-(2-{[6-(4-methoxy-phenoxy)-pyrazin-2-yl]-methyl-amino}-ethyl)-N-methyl-acetamide | 1H NMR (400 MHz, DMSO-d6) ppm = 7.72 (s, 1H), 7.48 (s, 1H), 7.13-7.00 (m, 6H), 6.98-6.90 (m, 2H), 3.74 (s, 3H), 3.53 (s, 2H), 3.43 (t, J = 6.5, 2H), 3.36 (t, J = 6.3, 2H), 2.90 (s, 3H), 2.73 (s, 3H). |
| 64 | 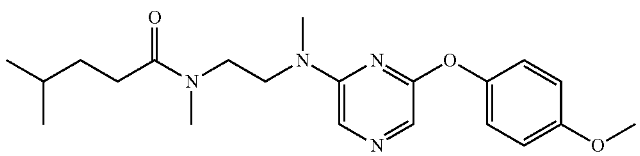 [SMILES: COc1ccc(Oc2cncc(N(C)CCN(C)C(=O)CCC(C)C)n2)cc1] | C | 2.36 | 4-Methyl-pentanoic acid (2-{[6-(4-methoxy-phenoxy)-pyrazin-2-yl]-methyl-amino}-ethyl)-methyl-amide | 1H NMR (400 MHz, DMSO-d6) ppm = 7.72 (s, 1H), 7.46 (s, 1H), 7.10 (d, J = 9.0, 2H), 6.96 (d, J = 9.0, 2H), 3.76 (s, 3H), 3.54-3.39 (m, 2H), 3.33 (dd, J = 11.4, 5.8, 2H), 2.92 (s, 3H), 2.70 (s, 3H), 2.14-2.05 (m, 2H), 1.40 (ddt, J = 20.6, 13.5, 6.7, 1H), 1.30-1.13 (m, 2H), 0.80 (d, J = 6.6, 6H). |
| 65 | 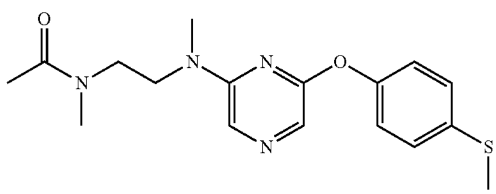 [SMILES: CSc1ccc(Oc2cncc(N(C)CCN(C)C(C)=O)n2)cc1] | A | 2.15 | N-Methyl-N-(2-{methyl-[6-(4-methyl-sulfanyl-phenoxy)-pyrazin-2-yl]-amino}-ethyl)-acetamide | 1H NMR (400 MHz, DMSO-d6) ppm = 7.80 (s, 1H), 3.24-3.17 (m, 0H), 7.60 (s, 1H), 7.31 (d, J = 8.7, 2H), 7.14 (d, J = 12.2, 2H), 3.47-3.42 (m, 2H), 3.32-3.25 (m, 1H), 3.00 (s, 3H), 2.72 (s, 3H), 2.48 (s, 3H), 1.85 (s, 3H), 3.27-3.24 (m, 1H). |
| 66 | 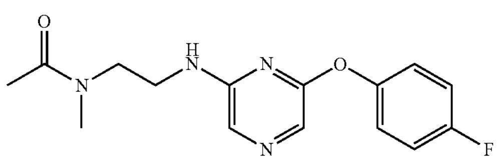 | C | 1.97 | N-{2-[6-(4-Fluoro-phenoxy)-pyrazin-2-ylamino]-ethyl}-N-methyl-acetamide | 1H NMR (400 MHz, DMSO-d6) ppm = 7.65 (s, 1H), 7.45 (s, 1H), 7.34 (s, 1H), 7.24-7.14 (m, 4H), 3.27-3.18 (m, 3H), 3.18-3.10 (m, 1H), 2.63 (s, 3H), 1.76 (s, 3H). |
| 67 | 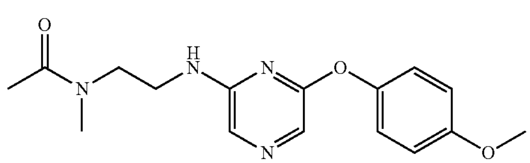 [SMILES: COc1ccc(Oc2cncc(NCCN(C)C(C)=O)n2)cc1] | C | 1.92 | N-{2-[6-(4-Methoxy-phenoxy)-pyrazin-2-ylamino]-ethyl}-N-methyl-acetamide | 1H NMR (400 MHz, DMSO-d6) ppm = 7.61 (s, 1H), 7.38 (s, 1H), 7.18 (t, J = 5.6, 1H), 7.07 (d, J = 9.1, 2H), 6.95 (d, J = 9.0, 2H), 3.75 (s, 3H), 3.29-3.09 (m, 4H), 2.63 (s, 3H), 1.77 (s, 3H). |
| 69 | 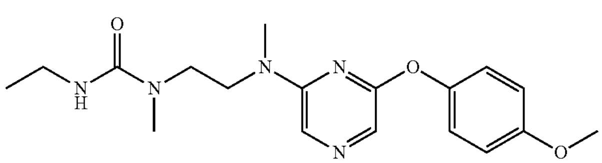 [SMILES: CCNC(=O)N(C)CCN(C)c1cncc(Oc2ccc(OC)cc2)n1] | C | 2.05 | 3-Ethyl-1-(2-{[6-(4-methoxy-phenoxy)-pyrazin-2-yl]-methyl-amino}-ethyl)-1-methyl-urea | 1H NMR (400 MHz, DMSO-d6) ppm = 7.75 (s, 1H), 7.46 (s, 1H), 7.10 (d, J = 9.0, 2H), 6.95 (d, J = 9.0, 2H), 6.11 (t, J = 5.5, 1H), 3.39 (dd, J = 7.5, 5.9, 2H), 3.22 (dd, J = 7.5, 5.8, 2H), 2.99 (qd, J = 7.1, 5.3, 2H), 2.56 (s, 3H), 0.95 (t, J = 7.1, 3H). |

TABLE 1-continued

| No | Chemical Structure | IC$_{50}$ | HPLC/MS Rt [Min] | Chemical Name | NMR data |
|---|---|---|---|---|---|
| 70 | 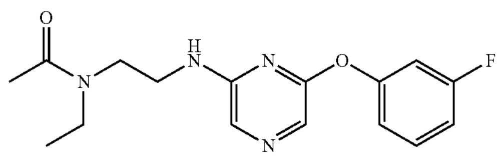 [SMILES: CCN(CCNc1cncc(Oc2cccc(F)c2)n1)C(C)=O] | C | 2.08 | N-Ethyl-N-{2-[6-(3-fluoro-phenoxy)-pyrazin-2-ylamino]-ethyl}-acetamide | 1H NMR (400 MHz, DMSO-d6) ppm = 7.66 (s, 1H), 7.47 (s, 1H), 7.46-7.41 (m, 1H), 7.33 (d, J = 4.9, 1H), 7.14-6.95 (m, 3H), 3.26-3.12 (m, 4H), 3.07 (q, J = 7.1, 2H), 1.94 (s, 3H), 0.89 (t, J = 7.1, 3H). |
| 71 | 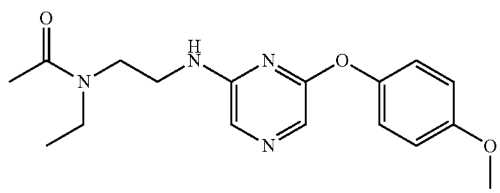 [SMILES: CCN(CCNc1cncc(Oc2ccc(OC)cc2)n1)C(C)=O] | B | 2.02 | N-Ethyl-N-{2-[6-(4-methoxy-phenoxy)-pyrazin-2-ylamino]-ethyl}-acetamide | 1H NMR (400 MHz, DMSO-d6) ppm = 7.61 (s, 1H), 7.39 (s, 1H), 7.22 (t, J = 4.7, 1H), 7.09 (d, J = 8.8, 2H), 6.95 (d, J = 9.0, 2H), 3.76 (s, 3H), 3.25-3.11 (m, 4H), 3.06 (q, J = 7.0, 2H), 1.79 (s, 3H), 0.89 (t, J = 7.1, 3H). |
| 72 | 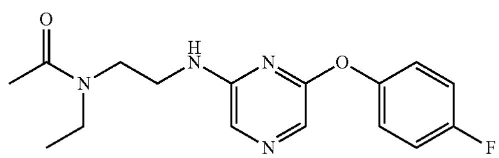 [SMILES: CCN(CCNc1cncc(Oc2ccc(F)cc2)n1)C(C)=O] | C | 2.07 | N-Ethyl-N-{2-[6-(4-fluoro-phenoxy)-pyrazin-2-ylamino]-ethyl}-acetamide | 1H NMR (400 MHz, DMSO-d6) ppm = 7.65 (s, 1H), 7.46 (s, 1H), 7.39-7.12 (m, 5H), 3.31-3.10 (m, 4H), 3.06 (q, J = 6.9, 2H), 1.94 (s, 3H), 0.89 (t, J = 7.1, 3H). |
| 73 | 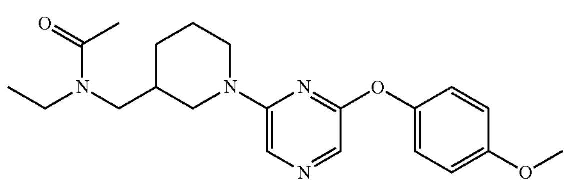 [SMILES: CCN(CC1CCCN(c2cncc(Oc3ccc(OC)cc3)n2)C1)C(C)=O] | C | 2.22 | N-Ethyl-N-{1-[6-(4-methoxy-phenoxy)-pyrazin-2-yl]-piperidin-3-ylmethyl}-acetamide | |
| 74 | 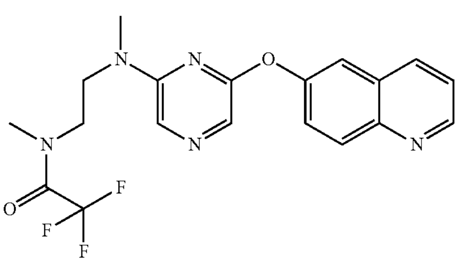 [SMILES: CN(CCN(C)c1cncc(Oc2ccc3ncccc3c2)n1)C(=O)C(F)(F)F] | C | 1.95 | 2,2,2-Trifluoro-N-methyl-N-(2-{methyl-[6-(quinolin-6-yloxy)-pyrazin-2-yl]-amino}-ethyl)-acetamide | 1H NMR (500 MHz, DMSO-d6) ppm = 8.88 (dd, J = 4.3, 1.6, 1H), 8.37-8.30 (m, 1H), 8.06 (dd, J = 9.1, 3.6, 1H), 7.83 (s, 1H), 7.76-7.72 (m, 1H), 7.68 (s, 1H), 7.60 (td, J = 9.5, 2.7, 1H), 7.54 (dd, J = 8.3, 4.2, 1H), 3.57-3.40 (m, 3H), 3.36-3.30 (m, 1H), 2.95 (s, 3H), 2.67 (s, 3H). |
| 75 | 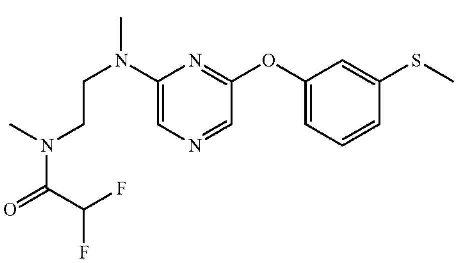 | C | 2.25 | 2,2-Difluoro-N-methyl-N-(2-{methyl-[6-(3-methyl-sulfanyl-phenoxy)-pyrazin-2-yl]-amino}-ethyl)-acetamide | 1H NMR (400 MHz, DMSO-d6) ppm = 7.79 (s, 1H), 7.56 (s, 1H), 7.34 (t, J = 9.0, 1H), 7.10 (dd, J = 7.9, 1.7, 1H), 7.06 (t, J = 1.9, 1H), 6.96-6.88 (m, 1H), 6.56 (t, J = 52.7, 1H), 3.56-3.46 (m, 2H), 3.46-3.35 (m, 2H), 2.96 (s, 3H), 2.80 (s, 3H), 2.47 (s, 3H). |

TABLE 1-continued

| No | Chemical Structure | IC$_{50}$ | HPLC/MS Rt [Min] | Chemical Name | NMR data |
|---|---|---|---|---|---|
| 76 | 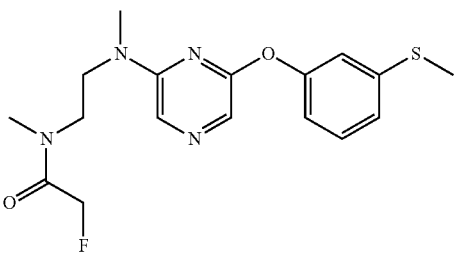 | B | 2.14 | 2-Fluoro-N-methyl-N-(2-{methyl-[6-(3-methyl-sulfanyl-phenoxy)-pyrazin-2-yl]-amino}-ethyl)-acetamide | 1H NMR (400 MHz, DMSO-d6) ppm = 7.81 (s, 1H), 7.56 (s, 1H), 7.38-7.29 (m, 1H), 7.15-7.01 (m, 2H), 7.01-6.80 (m, 1H), 4.96 (d, J = 46.7, 2H), 3.50-3.13 (m, 4H), 2.96 (s, 3H), 2.62 (s, 3H), 2.47 (s, 3H). |
| 77 | 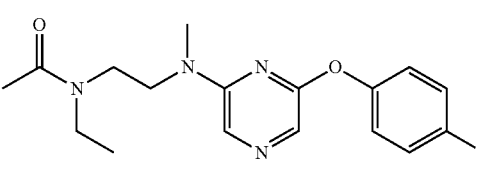 | A | 2.11 | N-Ethyl-N-(2-{[6-(4-methoxy-phenoxy)-pyrazin-2-yl]-methyl-amino}-ethyl)-acetamide | 1H NMR (400 MHz, DMSO-d6) ppm = 7.77 (s, 1H), 7.49 (s, 1H), 7.10 (d, J = 9.1, 2H), 6.96 (d, J = 7.4, 2H), 3.75 (d, J = 3.8, 3H), 3.53-3.32 (m, 3H), 3.27-3.14 (m, 2H), 3.08-2.88 (m, 4H), 1.89 (s, 3H), 0.94 (t, J = 7.1, 3H). |
| 78 | 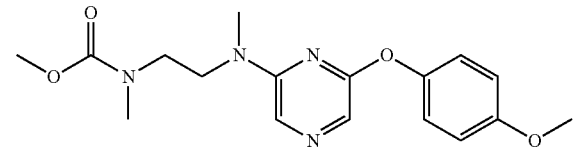 | C | 2.18 | (2-{[6-(4-Methoxy-phenoxy)-pyrazin-2-yl]-methyl-amino}-ethyl)-methyl-carbamic acid methyl ester | 1H NMR (400 MHz, DMSO-d6) ppm = 7.73 (s, 1H), 7.48 (s, 1H), 7.09 (d, J = 8.9, 2H), 6.95 (d, J = 9.0, 2H), 3.75 (s, 3H), 3.54-3.39 (m, 5H), 3.25 (t, J = 6.4, 2H), 2.94 (s, 3H), 2.60 (s, 3H). |
| 79 | 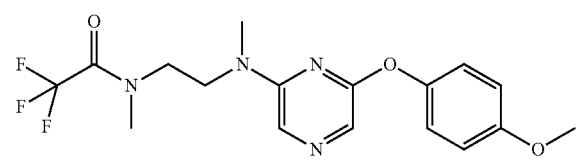 [SMILES: COc1ccc(Oc2cncc(N(C)CCN(C)C(=O)C(F)(F)F)n2)cc1] | C | 2.30 | 2,2,2-Trifluoro-N-(2-{[6-(4-methoxy-phenoxy)-pyrazin-2-yl]-methyl-amino}-ethyl)-N-methyl-acetamide | 1H NMR (400 MHz, DMSO-d6) ppm = 7.71 (s, 1H), 7.50 (s, 1H), 7.15-7.04 (m, 2H), 7.04-6.82 (m, 2H), 3.75 (s, 3H), 3.62-3.51 (m, 2H), 3.52-3.38 (m, 2H), 2.95 (s, 3H), 2.85-2.67 (m, 3H). |
| 80 | 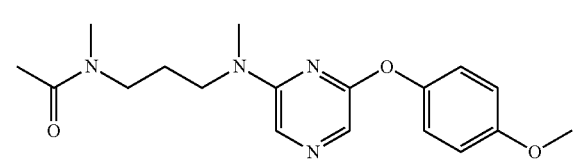 [SMILES: COc1ccc(Oc2cncc(N(C)CCCN(C)C(C)=O)n2)cc1] | C | 2.03 | N-(3-{[6-(4-Methoxy-phenoxy)-pyrazin-2-yl]-methyl-amino}-propyl)-N-methyl-acetamide | 1H NMR (400 MHz, DMSO-d6) ppm = 7.74 (s, 1H), 7.45 (s, 1H), 7.10 (d, J = 9.0, 2H), 6.96 (d, J = 9.0, 2H), 3.76 (s, 3H), 3.29-3.22 (m, 2H), 3.14 (t, J = 7.3, 2H), 2.93 (s, 3H), 2.83 (s, 3H), 1.92 (s, 3H), 1.58 (p, J = 7.4, 2H). |
| 81 | 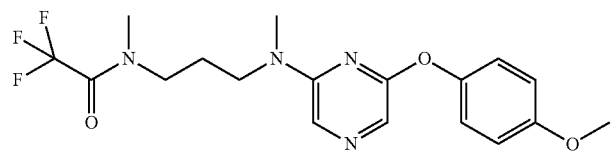 [SMILES: COc1ccc(Oc2cncc(N(C)CCCN(C)C(=O)C(F)(F)F)n2)cc1] | C | 2.43 | 2,2,2-Trifluoro-N-(3-{[6-(4-methoxy-phenoxy)-pyrazin-2-yl]-methyl-amino}-propyl)-N-methyl-acetamide | 1H NMR (400 MHz, DMSO-d6) ppm = 7.76 (s, 1H), 7.48 (s, 1H), 7.15-7.04 (m, 2H), 6.99-6.90 (m, 2H), 3.75 (s, 3H), 3.28-3.15 (m, 4H), 2.99 (s, 3H), 2.86 (s, 3H), 1.80-1.62 (m, 2H). |

TABLE 1-continued

| No | Chemical Structure | IC$_{50}$ | HPLC/MS Rt [Min] | Chemical Name | NMR data |
|---|---|---|---|---|---|
| 82 | 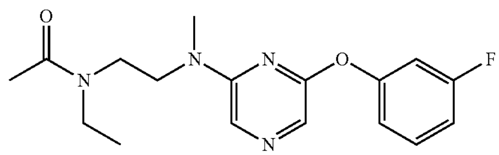 [SMILES: CCN(CCN(C)c1cncc(Oc2cccc(F)c2)n1)C(C)=O] | B | 2.18 | N-Ethyl-N-(2-{[6-(3-fluoro-phenoxy)-pyrazin-2-yl]-methyl-amino}-ethyl)-acetamide | 1H NMR (400 MHz, DMSO-d6) ppm = 7.86 (s, 1H), 7.59 (s, 1H), 7.43 (d, J = 8.1, 1H), 7.14-6.97 (m, 3H), 3.49-3.38 (m, 2H), 3.28-3.20 (m, 2H), 3.08-2.93 (m, 5H), 1.90 (s, 3H), 0.87 (t, J = 7.0, 3H). |
| 83 | 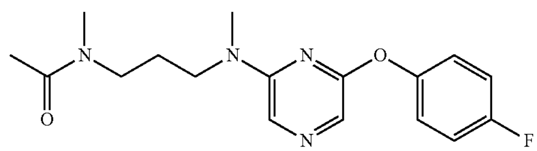 [SMILES: CC(=O)N(C)CCCN(C)c1cncc(Oc2ccc(F)cc2)n1] | C | 2.09 | N-(3-{[6-(4-Fluoro-phenoxy)-pyrazin-2-yl]-methyl-amino}-propyl)-N-methyl-acetamide | 1H NMR (400 MHz, DMSO-d6) ppm = 7.78 (s, 1H), 7.52 (s, 1H), 7.34-7.16 (m, 4H), 3.29-3.21 (m, 2H), 3.13 (t, J = 7.3, 2H), 2.93 (s, 3H), 2.83 (s, 3H), 1.92 (s, 3H), 1.58 (p, J = 7.3, 2H). |
| 84 | 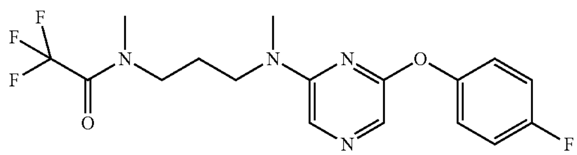 [SMILES: CN(CCCN(C)c1cncc(Oc2ccc(F)cc2)n1)C(=O)C(F)(F)F] | C | 2.48 | 2,2,2-Trifluoro-N-(3-{[6-(4-fluoro-phenoxy)-pyrazin-2-yl]-methyl-amino}-propyl)-N-methyl-acetamide | 1H NMR (400 MHz, DMSO-d6) ppm = 7.80 (s, 1H), 7.55 (s, 1H), 7.30-7.11 (m, 4H), 3.27-3.15 (m, 4H), 2.95 (s, 6H), 1.79-1.60 (m, 2H). |
| 85 | 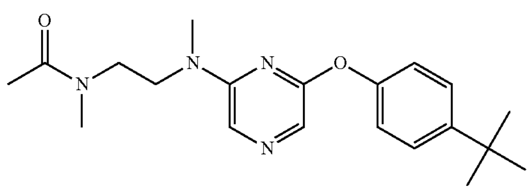 [SMILES: CC(=O)N(C)CCN(C)c1cncc(Oc2ccc(C(C)(C)C)cc2)n1] | A | 2.53 | N-(2-{[6-(4-tert-Butyl-phenoxy)-pyrazin-2-yl]-methyl-amino}-ethyl)-N-methyl-acetamide | 1H NMR (500 MHz, DMSO-d6) ppm = 7.80 (s, 1H), 7.52 (s, 1H), 7.43 (d, J = 8.8, 2H), 7.08 (d, J = 8.7, 2H), 3.53-3.37 (m, 2H), 3.31-3.17 (m, 2H), 2.96 (s, 3H), 2.54 (s, 3H), 1.84 (s, 3H), 1.30 (s, 9H). |
| 86 | 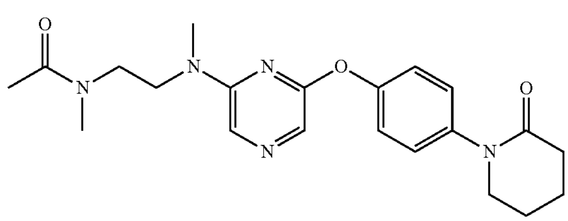 [SMILES: CC(=O)N(C)CCN(C)c1cncc(Oc2ccc(N3CCCCC3=O)cc2)n1] | B | 1.77 | N-Methyl-N-[2-(methyl-{6-[4-(2-oxo-piperidin-1-yl)-phenoxy]-pyrazin-2-yl}-amino)-ethyl]-acetamide | 1H NMR (500 MHz, DMSO-d6) ppm = 7.80 (s, 1H), 7.54 (s, 1H), 7.30 (d, J = 8.7, 2H), 7.17 (d, J = 8.8, 2H), 3.64-3.56 (m, 2H), 3.51-3.41 (m, 2H), 3.36-3.29 (m, 2H), 2.96 (s, 3H), 2.71 (s, 3H), 2.39 (t, J = 6.4, 2H), 1.88-1.73 (m, 7H). |
| 87 | 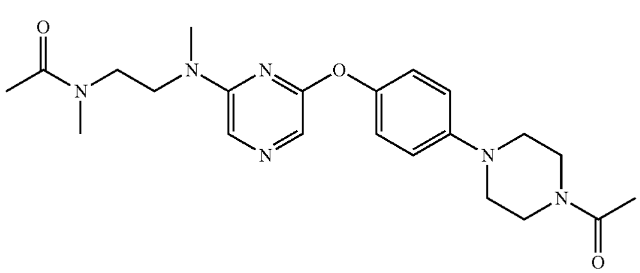 [SMILES: CC(=O)N(C)CCN(C)c1cncc(Oc2ccc(N3CCN(C(C)=O)CC3)cc2)n1] | B | 1.76 | N-[2-({6-[4-(4-Acetyl-piperazin-1-yl)-phenoxy]-pyrazin-2-yl}-methyl-amino)-ethyl]-N-methyl-acetamide | 1H NMR (500 MHz, DMSO-d6) ppm = 7.76 (s, 1H), 7.46 (s, 1H), 7.03 (d, J = 9.2, 2H), 6.98 (d, J = 9.3, 2H), 3.58 (dd, J = 4.9, 4H), 3.44 (dt, J = 16.7, 6.6 2H), 3.30 (dt, 2H), 3.15-3.08 (m, 2H), 3.07-3.02 (m, 2H), 2.94 (s, 3H), 2.58 (s, 3H), 2.04 (s, 3H), 1.85 (s, 3H). |

TABLE 1-continued

| No | Chemical Structure | IC$_{50}$ | HPLC/MS Rt [Min] | Chemical Name | NMR data |
|---|---|---|---|---|---|
| 88 | 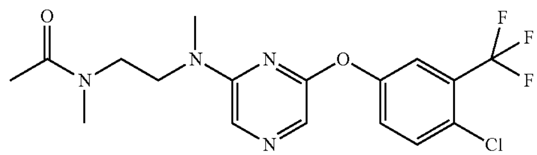 [SMILES: CC(=O)N(C)CCN(C)c1cncc(Oc2ccc(Cl)c(C(F)(F)F)c2)n1] | C | 2.40 | N-(2-{[6-(4-Chloro-3-trifluoro-methyl-phenoxy)-pyrazin-2-yl]-methyl-amino}-ethyl)-N-methyl-acetamide | 1H NMR (400 MHz, DMSO-d6) ppm = 7.87 (s, 1H), 7.80-7.71 (m, 2H), 7.71 (d, J = 2.4, 1H), 7.56 (dd, J = 8.9, 2.8, 1H), 3.49-3.35 (m, 2H), 3.29-3.21 (m, 2H), 2.93 (s, 3H), 2.72 (s, 3H), 1.85 (s, 3H). |
| 89 | 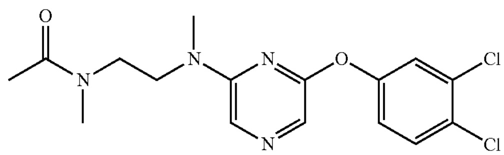 [SMILES: CC(=O)N(C)CCN(C)c1cncc(Oc2ccc(Cl)c(Cl)c2)n1] | B | 2.38 | N-(2-{[6-(3,4-Dichloro-phenoxy)-pyrazin-2-yl]-methyl-amino}-ethyl)-N-methyl-acetamide | 1H NMR (400 MHz, DMSO-d6) ppm = 7.87 (s, 1H), 7.72-7.59 (m, 2H), 7.57 (d, J = 2.7, 1H), 7.20 (dd, J = 9.0, 2.9, 1H), 3.52-3.40 (m, 2H), 3.31-3.21 (m, 2H), 2.95 (s, 3H), 2.75 (s, 3H), 1.86 (s, 3H). |
| 90 | 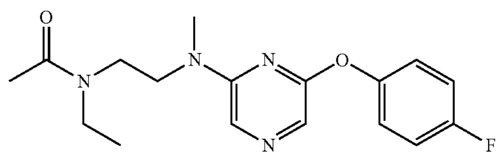 [SMILES: CCN(CCN(C)c1cncc(Oc2ccc(F)cc2)n1)C(C)=O] | A | 2.16 | N-Ethyl-N-(2-{[6-(4-fluoro-phenoxy)-pyrazin-2-yl]-methyl-amino}-ethyl)-acetamide | 1H NMR (500 MHz, DMSO-d6) ppm = 8.08 (d, J = 8.8, 2H), 7.87 (s, 2H), 7.62 (d, J = 8.2, 1H), 7.53 (s, 1H), 7.28-7.16 (m, 3H), 6.79 (d, J = 8.5, 1H), 3.61-3.56 (m, 4H), 3.46-3.42 (m, 2H), 3.19-3.13 (m, 2H), 2.95 (s, 3H), 2.49-2.44 (m, 4H), 2.26 (s, 3H), 2.07 (s, 3H). |
| 91 | 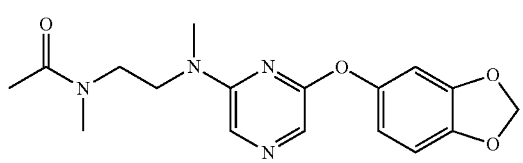 [SMILES: CC(=O)N(C)CCN(C)c1cncc(Oc2ccc3c(c2)OCO3)n1] | B | 1.91 | N-(2-{[6-(Benzo[1,3]dioxol-5-yloxy)-pyrazin-2-yl]-methyl-amino}-ethyl)-N-methyl-acetamide | 1H NMR (400 MHz, DMSO-d6) ppm = 7.77 (s, 1H), 7.49 (s, 1H), 6.92 (d, J = 8.4, 1H), 6.84 (d, J = 2.4, 1H), 6.61 (dd, J = 8.5, 2.4, 1H), 6.05 (s, 2H), 3.53-3.41 (m, 2H), 3.37-3.32 (m, 2H), 2.96 (s, 3H), 2.78 (s, 3H), 1.87 (s, 3H). |
| 92 | 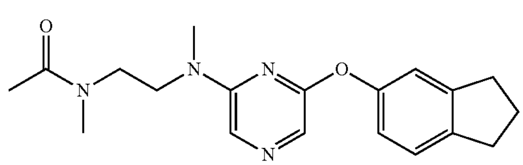 [SMILES: CC(=O)N(C)CCN(C)c1cncc(Oc2ccc3c(c2)CCC3)n1] | A | 2.31 | N-(2-{[6-(Indan-5-yloxy)-pyrazin-2-yl]-methyl-amino}-ethyl)-N-methyl-acetamide | 1H NMR (400 MHz, DMSO-d6) ppm = 7.77 (s, 1H), 7.49 (s, 1H), 7.24 (d, J = 8.1, 1H), 7.00 (d, J = 1.7, 1H), 6.88 (dd, J = 8.2, 2.3, 1H), 3.50-3.40 (m, 2H), 3.30-3.22 (m, 2H), 2.96 (s, 3H), 2.90-2.82 (m, 4H), 2.71 (s, 3H), 2.12-1.98 (m, 2H), 1.86 (s, 3H). |

TABLE 1-continued

| No | Chemical Structure | IC$_{50}$ | HPLC/MS Rt [Min] | Chemical Name | NMR data |
|---|---|---|---|---|---|
| 93 | 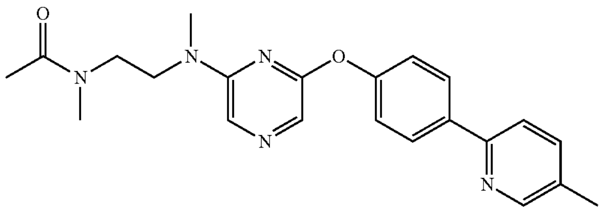 [SMILES: CC(=O)N(C)CCN(C)c1cncc(Oc2ccc(-c3ccc(C)cn3)cc2)n1] | A | 1.78 | N-Methyl-N-[2-(methyl-{6-[4-(5-methyl-pyridin-2-yl)-phenoxy]-pyrazin-2-yl}-amino)-ethyl]-acetamide | 1H NMR (400 MHz, DMSO-d6) ppm = 8.52-8.47 (m, 1H), 8.10 (d, J = 8.6, 2H), 7.89-7.80 (m, 2H), 7.69 (dd, J = 8.1, 1.9, 1H), 7.59 (s, 1H), 7.26 (d, J = 8.7, 2H), 3.53-3.40 (m, 2H), 3.38-3.30 (m, 2H), 2.95 (s, 3H), 2.70 (s, 3H), 2.34 (s, 3H), 1.82 (s, 3H). |
| 94 | 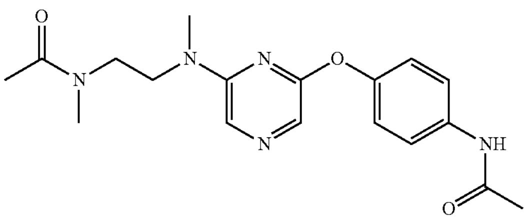 [SMILES: CC(=O)Nc1ccc(Oc2cncc(N(C)CCN(C)C(C)=O)n2)cc1] | B | 1.65 | N-(2-{[6-(4-Acetylamino-phenoxy)-pyrazin-2-yl]-methyl-amino}-ethyl)-N-methyl-acetamide | 1H NMR (400 MHz, DMSO-d6) ppm = 9.93 (s, 1H), 7.78 (s, 1H), 7.59 (d, J = 8.9, 2H), 7.50 (s, 1H), 7.10 (d, J = 8.9, 2H), 3.43 (t, J = 6.4, 2H), 3.37-3.19 (m, 2H), 2.97 (s, 3H), 2.72 (s, 3H), 2.04 (s, 3H), 1.84 (s, 3H). |
| 95 | 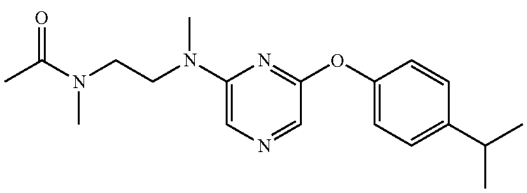 [SMILES: CC(=O)N(C)CCN(C)c1cncc(Oc2ccc(C(C)C)cc2)n1] | A | 2.46 | N-(2-{[6-(4-Isopropyl-phenoxy)-pyrazin-2-yl]-methyl-amino}-ethyl)-N-methyl-acetamide | 1H NMR (400 MHz, DMSO-d6) ppm = 7.79 (s, 1H), 7.50 (s, 1H), 7.27 (d, J = 8.5, 2H), 7.09 (d, J = 8.6, 2H), 3.52-3.36 (m, 2H), 3.35-3.18 (m, 2H), 2.95 (s, 3H), 2.93-2.82 (m, 1H), 2.67 (s, 3H), 1.78 (d, J = 42.7, 3H), 1.21 (d, J = 6.9, 6H). |
| 96 | 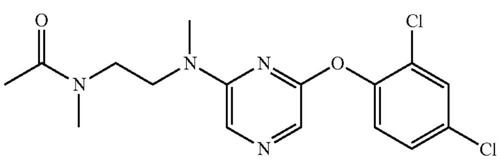 [SMILES: CC(=O)N(C)CCN(C)c1cncc(Oc2ccc(Cl)cc2Cl)n1] | B | 2.36 | N-(2-{[6-(2,4-Dichloro-phenoxy)-pyrazin-2-yl]-methyl-amino}-ethyl)-N-methyl-acetamide | 1H NMR (400 MHz, DMSO-d6) ppm = 7.83 (s, 1H), 7.79-7.74 (m, 1H), 7.65 (s, 1H), 7.52-7.45 (m, 1H), 7.43-7.34 (m, 1H), 3.43-3.32 (m, 2H), 3.22 (t, J = 6.7, 2H), 2.94 (s, 3H), 2.69 (s, 3H), 1.85 (s, 3H). |
| 97 | 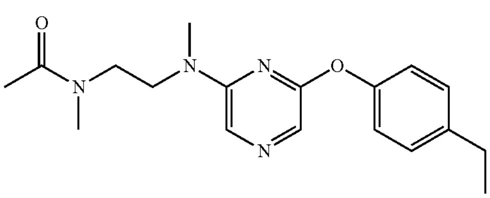 [SMILES: CCc1ccc(Oc2cncc(N(C)CCN(C)C(C)=O)n2)cc1] | A | 2.34 | N-(2-{[6-(4-Ethyl-phenoxy)-pyrazin-2-yl]-methyl-amino}-ethyl)-N-methyl-acetamide | 1H NMR (400 MHz, DMSO-d6) ppm = 7.79 (s, 1H), 7.50 (s, 1H), 7.24 (d, 2H), 7.12-6.99 (m, 2H), 3.54-3.39 (m, 2H), 3.29-3.19 (m, 2H), 2.94 (s, 3H), 2.68 (s, 3H), 2.61 (q, J = 7.6, 2H), 1.84 (s, 3H), 1.19 (t, J = 7.6, 3H). |
| 98 | 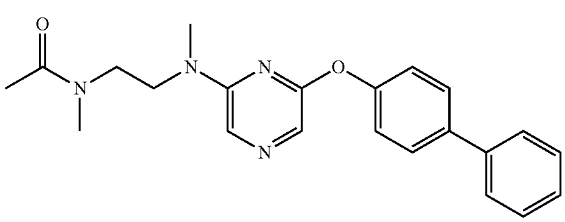 [SMILES: CC(=O)N(C)CCN(C)c1cncc(Oc2ccc(-c3ccccc3)cc2)n1] | A | 2.48 | N-(2-{[6-(Biphenyl-4-yloxy)-pyrazin-2-yl]-methyl-amino}-ethyl)-N-methyl-acetamide | 1H NMR (400 MHz, DMSO-d6) ppm = 7.83 (s, 1H), 7.78-7.54 (m, 5H), 7.47 (t, J = 7.6, 2H), 7.36 (t, J = 7.3, 1H), 7.27 (d, J = 8.6, 2H), 3.56-3.36 (m, 2H), 3.36-3.17 (m, 2H), 2.96 (s, 3H), 2.70 (s, 3H), 1.83 (s, 3H). |

| No | Chemical Structure | IC$_{50}$ | HPLC/MS Rt [Min] | Chemical Name | NMR data |
|----|---|---|---|---|---|
| 99 | 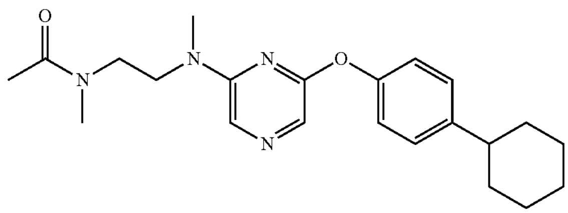 [SMILES: CC(=O)N(C)CCN(C)c1cncc(Oc2ccc(C3CCCCC3)cc2)n1] | C | 2.83 | N-(2-{[6-(4-Cyclohexyl-phenoxy)-pyrazin-2-yl]-methyl-amino}-ethyl)-N-methyl-acetamide | 1H NMR (400 MHz, DMSO-d6) ppm = 7.78 (s, 1H), 7.50 (s, 1H), 7.24 (d, J = 8.4, 2H), 7.07 (d, J = 8.6, 2H), 3.50-3.37 (m, 2H), 3.28-3.22 (m, 2H), 2.94 (s, 3H), 2.70-2.52 (m, 4H), 1.88-1.66 (m, 8H), 1.47-1.06 (m, 5H). |
| 100 | 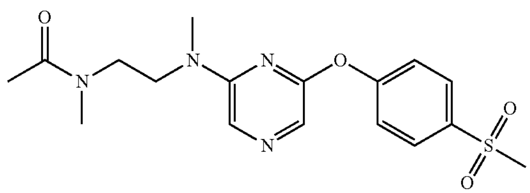 [SMILES: CC(=O)N(C)CCN(C)c1cncc(Oc2ccc(S(C)(=O)=O)cc2)n1] | B | 1.69 | N-(2-{[6-(4-Methane-sulfonyl-phenoxy)-pyrazin-2-yl]-methyl-amino}-ethyl)-N-methyl-acetamide | 1H NMR (400 MHz, DMSO-d6) ppm = 8.05-7.85 (m, 3H), 7.65 (s, 1H), 7.42 (d, J = 12.2, 2H), 3.45 (t, J = 6.5, 2H), 3.33 (t, J = 6.5, 2H), 3.23 (s, 3H), 3.00 (s, 3H), 2.65 (s, 3H), 1.85 (s, 3H). |
| 101 | 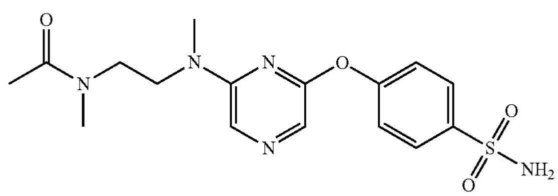 [SMILES: CC(=O)N(C)CCN(C)c1cncc(Oc2ccc(S(N)(=O)=O)cc2)n1] | B | 1.57 | N-Methyl-N-(2-[methyl-[6-(4-sulfamoyl-phenoxy)-pyrazin-2-yl]-amino}-ethyl)-acetamide | 1H NMR (400 MHz, DMSO-d6) ppm = 7.88 (s, 1H), 7.85 (d, J = 8.7, 2H), 7.63 (s, 1H), 7.34 (s, 2H), 7.32 (d, J = 8.7, 2H), 3.51-3.25 (m, 4H), 2.96 (s, 3H), 2.71 (s, 3H), 1.85 (s, 3H). |
| 102 | 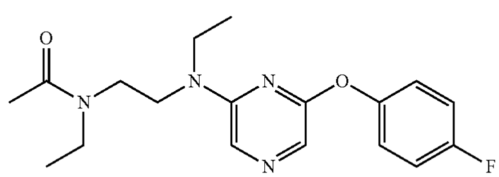 [SMILES: CCN(CCN(CC)c1cncc(Oc2ccc(F)cc2)n1)C(C)=O] | B | 2.21 | N-Ethyl-N-(2-{ethyl-[6-(4-fluoro-phenoxy)-pyrazin-2-yl]-amino}-ethyl)-acetamide | 1H NMR (400 MHz, DMSO-d6) ppm = 7.87 (s, 1H), 7.55 (s, 1H), 7.33-7.06 (m, 4H), 3.47-3.30 (m, 4H), 3.25-3.11 (m, 2H), 3.06 (q, J = 7.2, 2H), 1.94 (s, 3H), 1.02 (t, J = 7.0, 3H), 0.95 (t, J = 7.1, 3H). |
| 103 | 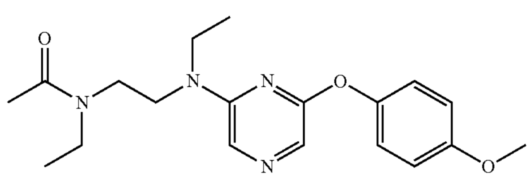 [SMILES: CCN(CCN(CC)c1cncc(Oc2ccc(OC)cc2)n1)C(C)=O] | B | 2.19 | N-Ethyl-N-(2-{ethyl-[6-(4-methoxy-phenoxy)-pyrazin-2-yl]-amino}-ethyl)-acetamide | 1H NMR (500 MHz, DMSO-d6) ppm = 7.82 (s, 1H), 7.49 (s, 1H), 7.09 (d, J = 9.0, 2H), 6.96 (d, J = 9.0, 2H), 3.76 (s, 3H), 3.45-3.30 (m, 4H), 3.23-3.16 (m, 2H), 2.99 (q, J = 7.0 2H), 1.94 (s, 3H), 1.03 (t, J = 7.0, 3H), 0.95 (t, J = 7.1, 3H). |
| 104 | 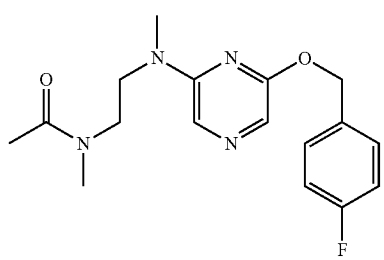 [SMILES: CC(=O)N(C)CCN(C)c1cncc(OCc2ccc(F)cc2)n1] | C | 2.03 | N-(2-{[6-(4-Fluoro-benzyloxy)-pyrazin-2-yl]-methyl-amino}-ethyl)-N-methyl-acetamide | 1H NMR (400 MHz, DMSO-d6) ppm = 7.62 (s, 1H), 7.53-7.41 (m, 3H), 7.24-7.15 (m, 2H), 5.32 (s, 2H), 3.76-3.59 (m, 2H), 3.49-3.40 (m, 2H), 3.02 (s, 3H), 2.91 (s, 3H), 1.89 (s, 3H). |

TABLE 1-continued

| No | Chemical Structure | IC$_{50}$ | HPLC/MS Rt [Min] | Chemical Name | NMR data |
|---|---|---|---|---|---|
| 105 | 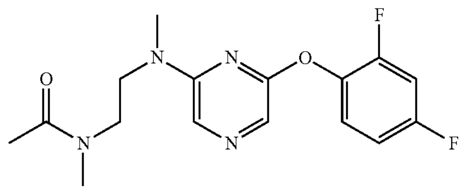 [SMILES: CC(=O)N(C)CCN(C)c1cncc(Oc2ccc(F)cc2F)n1] | B | 2.03 | N-(2-{[6-(2,4-Difluoro-phenoxy)-pyrazin-2-yl]-methyl-amino}-ethyl)-N-methyl-acetamide | 1H NMR (400 MHz, DMSO-d6) ppm = 7.80 (s, 1H), 7.64 (s, 1H), 7.53-7.28 (m, 2H), 7.25-6.95 (m, 1H), 3.52-3.34 (m, 2H), 3.34-3.18 (m, 2H), 2.91 (s, 3H), 2.70 (s, 3H), 1.84 (s, 3H). |
| 106 | 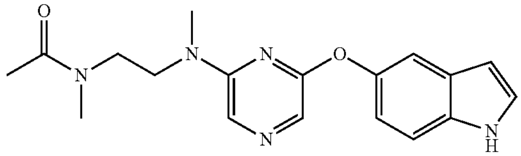 [SMILES: CC(=O)N(C)CCN(C)c1cncc(Oc2ccc3[nH]ccc3c2)n1] | B | 1.84 | N-(2-{[6-(1H-Indol-5-yloxy)-pyrazin-2-yl]-methyl-amino}-ethyl)-N-methyl-acetamide | 1H NMR (500 MHz, DMSO-d6) ppm = 11.12 (s, 1H), 7.74 (s, 1H), 7.54-7.33 (m, 3H), 7.30 (d, J = 1.8, 1H), 6.86 (dd, J = 8.7, 2.1, 1H), 6.41 (s, 1H), 3.46-3.37 (m, 2H), 3.29-3.10 (m, 2H), 2.93 (s, 3H), 2.44 (s, 3H), 1.82 (s, 3H). |
| 107 | 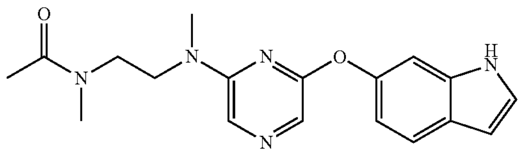 [SMILES: CC(=O)N(C)CCN(C)c1cncc(Oc2ccc3cc[nH]c3c2)n1] | A | 1.91 | N-(2-{[6-(1H-Indol-5-yloxy)-pyrazin-2-yl]-methyl-amino}-ethyl)-N-methyl-acetamide | 1H NMR (500 MHz, DMSO-d6) ppm = 11.06 (s, 1H), 7.76 (s, 1H), 7.57-7.44 (m, 2H), 7.33 (s, 1H), 7.18 (d, J = 1.7, 1H), 6.81 (dd, J = 8.5, 2.1, 1H), 6.43 (s, 1H), 3.45-3.38 (m, 2H), 3.29-3.19 (m, 2H), 2.94 (s, 3H), 2.58 (s, 3H), 1.82 (s, 3H). |
| 108 | 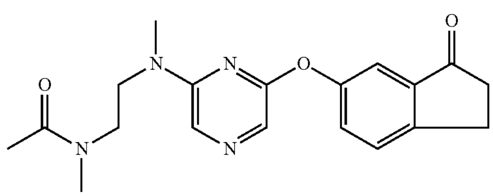 [SMILES: CC(=O)N(C)CCN(C)c1cncc(Oc2ccc3c(c2)C(=O)CC3)n1] | C | 1.79 | N-Methyl-N-(2-{methyl-[6-(3-oxo-indan-5-yloxy)-pyrazin-2-yl]-amino}-ethyl)-acetamide | 1H NMR (400 MHz, DMSO-d6) ppm = 7.83 (s, 1H), 7.67-7.58 (m, 2H), 7.50 (dd, J = 8.8, 1.9, 1H), 7.33 (d, J = 2.3, 1H), 3.51-3.34 (m, 2H), 3.29-3.20 (m, 2H), 3.15-3.06 (m, 2H), 2.93 (s, 3H), 2.75-2.54 (m, 5H), 1.84 (s, 3H). |
| 109 | 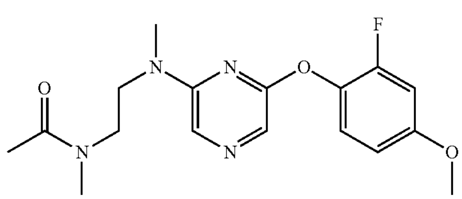 [SMILES: COc1ccc(Oc2cncc(N(C)CCN(C)C(C)=O)n2)c(F)c1] | B | 2.01 | N-(2-{[6-(2-Fluoro-4-methoxy-phenoxy)-pyrazin-2-yl]-methyl-amino}-ethyl)-N-methyl-acetamide | 1H NMR (400 MHz, DMSO-d6) ppm = 7.76 (s, 1H), 7.59 (s, 1H), 7.30-7.20 (m, 1H), 7.04-6.96 (m, 1H), 6.83-6.77 (m, 1H), 3.77 (s, 3H), 3.46-3.34 (m, 2H), 3.28-3.14 (m, 2H), 2.91 (s, 3H), 2.69 (s, 3H), 1.84 (s, 3H). |
| 110 | 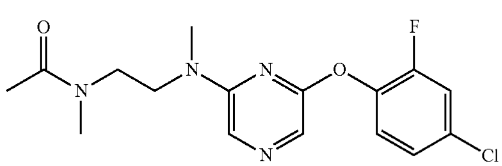 [SMILES: CC(=O)N(C)CCN(C)c1cncc(Oc2ccc(Cl)cc2F)n1] | B | 2.24 | N-(2-{[6-(4-Chloro-2-fluoro-phenoxy)-pyrazin-2-yl]-methyl-amino}-ethyl)-N-methyl-acetamide | 1H NMR (400 MHz, DMSO-d6) ppm = 7.82 (s, 1H), 7.66 (s, 1H), 7.65-7.58 (m, 1H), 7.48-7.23 (m, 2H), 3.48-3.34 (m, 2H), 3.28-3.17 (m, 2H), 2.91 (s, 3H), 2.70 (s, 3H), 1.85 (s, 3H). |

TABLE 1-continued

| No | Chemical Structure | IC$_{50}$ | HPLC/MS Rt [Min] | Chemical Name | NMR data |
|---|---|---|---|---|---|
| 111 | 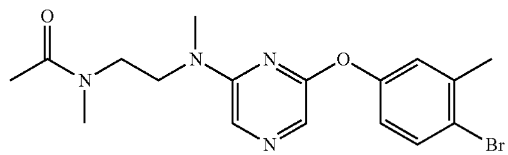 [SMILES: CC(=O)N(C)CCN(C)c1cncc(Oc2ccc(Br)c(C)c2)n1] | B | 2.40 | N-(2-{[6-(4-Bromo-3-methyl-phenoxy)-pyrazin-2-yl]-methyl-amino}-ethyl)-N-methyl-acetamide | 1H NMR (400 MHz, DMSO-d6) ppm = 7.83 (s, 1H), 7.61 (d, J = 8.8, 1H), 7.55 (s, 1H), 7.18 (d, J = 2.7, 1H), 6.94 (dd, J = 8.9, 3.0, 1H), 3.52-3.35 (m, 2H), 3.31-3.32 (m, 2H), 2.95 (s, 3H), 2.72 (s, 3H), 2.34 (s, 3H), 1.85 (s, 3H). |
| 112 | 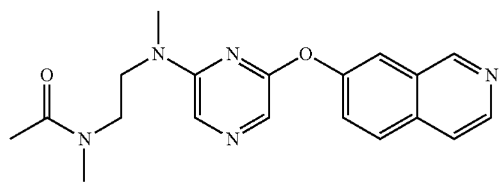 [SMILES: CC(=O)N(C)CCN(C)c1cncc(Oc2ccc3ccncc3c2)n1] | A | 1.43 | N-(2-{[6-(Isoquinolin-7-yloxy)-pyrazin-2-yl]-methyl-amino}-ethyl)-N-methyl-acetamide | 1H NMR (400 MHz, DMSO-d6) ppm = 9.29 (s, 1H), 8.50 (d, J = 5.7, 1H), 8.04 (s, 1H), 7.94-7.84 (m, 3H), 7.68 (s, 1H), 7.68-7.62 (m, 1H), 3.48-3.37 (m, 2H), 3.30-3.16 (m, 2H), 2.94 (s, 3H), 2.57 (s, 3H), 1.81 (s, 3H). |
| 113 | 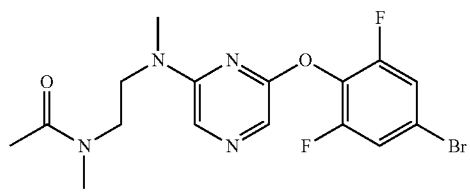 [SMILES: CC(=O)N(C)CCN(C)c1cncc(Oc2c(F)cc(Br)cc2F)n1] | A | 2.26 | N-(2-{[6-(4-Bromo-2,6-difluoro-phenoxy)-pyrazin-2-yl]-methyl-amino}-ethyl)-N-methyl-acetamide | 1H NMR (400 MHz, DMSO-d6) ppm = 7.88 (d, J = 4.8, 1H), 7.79 (d, J = 9.1, 1H), 7.56-7.49 (m, 2H), 3.41 (dt, J = 12.5, 6.5, 2H), 3.26 (dt, J = 16.3, 6.5, 2H), 2.92 (s, 3H), 2.72 (s, 3H), 1.84 (s, 3H). |
| 114 | 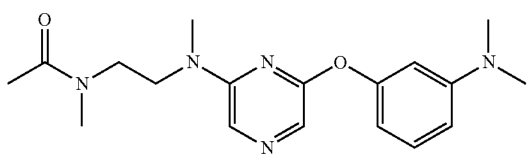 | C | 1.94 | N-(2-{[6-(3-Dimethyl-amino-phenoxy)-pyrazin-2-yl]-methyl-amino}-ethyl)-N-methyl-acetamide | 1H NMR (400 MHz, DMSO-d6) ppm = 7.74 (s, 1H), 7.43 (s, 1H), 7.15 (t, J = 8.1, 1H), 6.52 (dd, J = 8.3, 2.1, 1H), 6.43 (t, J = 2.2, 1H), 6.35 (dd, J = 8.0, 1.8, 1H), 3.52-3.36 (m, 2H), 3.36-3.27 (m, 2H), 2.93 (s, 3H), 2.86 (s, 6H), 2.71 (s, 3H), 1.82 (s, 3H). |
| 115 | 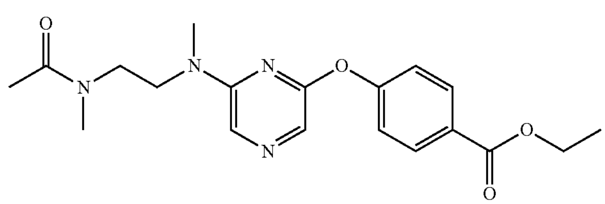 [SMILES: CCOC(=O)c1ccc(Oc2cncc(N(C)CCN(C)C(C)=O)n2)cc1] | B | 2.19 | 4-(6-{[2-(Acetyl-methyl-amino)-ethyl]-methyl-amino}-pyrazin-2-yloxy)-benzoic acid ethyl ester | 1H NMR (400 MHz, DMSO-d6) ppm = 8.00 (d, J = 8.7, 2H), 7.88 (s, 1H), 7.62 (s, 1H), 7.29 (d, J = 8.8, 2H), 4.32 (q, J = 7.1, 2H), 3.54-3.39 (m, 2H), 3.35-3.28 (m, 2H), 2.95 (d, J = 3.4, 3H), 2.73 (s, 3H), 1.84 (s, 3H), 1.33 (t, J = 7.1, 3H). |
| 116 | 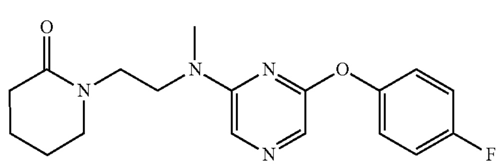 [SMILES: CN(CCN1CCCCC1=O)c1cncc(Oc2ccc(F)cc2)n1] | A | 2.12 | 1-(2-{[6-(4-Fluoro-phenoxy)-pyrazin-2-yl]-methyl-amino}-ethyl)-piperidin-2-one | 1H NMR (400 MHz, DMSO-d6) ppm = 7.78 (s, 1H), 7.55 (s, 1H), 7.30-7.17 (m, 4H), 3.45 (t, J = 6.5, 2H), 3.34-3.30 (m, 3H), 3.03-2.89 (m, 5H), 2.12-1.98 (m, 2H), 1.64-1.48 (m, 4H). |

TABLE 1-continued

| No | Chemical Structure | IC$_{50}$ | HPLC/MS Rt [Min] | Chemical Name | NMR data |
|---|---|---|---|---|---|
| 117 | 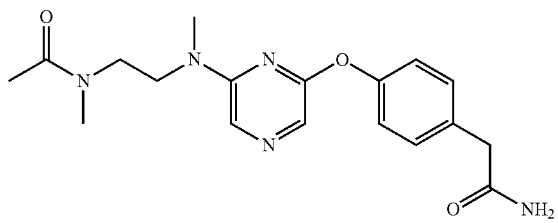 [SMILES: CC(=O)N(C)CCN(C)c1cncc(Oc2ccc(CC(N)=O)cc2)n1] | B | 1.50 | 2-[4-(6-{[2-(Acetyl-methyl-amino)-ethyl]-methyl-amino}-pyrazin-2-yloxy)-phenyl]-acetamide | |
| 118 | 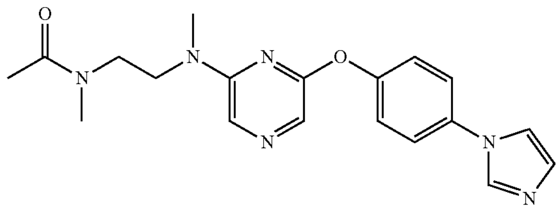 [SMILES: CC(=O)N(C)CCN(C)c1cncc(Oc2ccc(-n3ccnc3)cc2)n1] | A | 1.29 | N-(2-[6-(4-Imidazol-1-yl-phenoxy)-pyrazin-2-yl]-methyl-amino}-ethyl)-N-methyl-acetamide | |
| 119 | 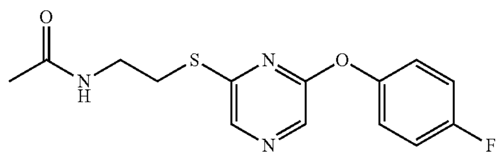 [SMILES: CC(=O)NCCSc1cncc(Oc2ccc(F)cc2)n1] | C | 1.88 | N-{2-[6-(4-Fluoro-phenoxy)-pyrazin-2-ylsulfanyl]-ethyl}-acetamide | 1H NMR (400 MHz, DMSO-d6) ppm = 8.33 (s, 1H), 8.17 (s, 1H), 7.93 (t, J = 5.1, 1H), 7.32-7.25 (m, 4H), 3.11 (dd, J = 6.3, 2H), 2.96 (t, J = 6.5, 2H), 1.78 (s, 3H). |
| 120 | 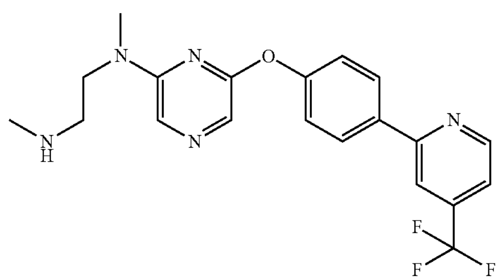 [SMILES: CNCCN(C)c1cncc(Oc2ccc(-c3cc(C(F)(F)F)ccn3)cc2)n1] | C | 1.71 | N,N'-Dimethyl-N-{6-[4-(4-trifluoro-methyl-pyridin-2-yl)-phenoxy]-pyrazin-2-yl}-ethane-1,2-diamine | 1H NMR (400 MHz, DMSO-d6) ppm = 8.93 (d, J = 5.1, 1H), 8.30 (s, 1H), 8.26 (d, J = 8.8, 2H), 7.86 (s, 1H), 7.71 (d, J = 5.0, 1H), 7.58 (s, 1H), 7.31 (d, J = 8.8, 2H), 3.42 (t, J = 6.6, 2H), 2.97 (s, 3H), 2.57 (t, J = 6.5, 2H), 2.16 (s, 3H). |
| 121 | 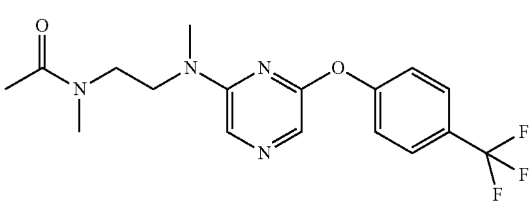 [SMILES: CC(=O)N(C)CCN(C)c1cncc(Oc2ccc(C(F)(F)F)cc2)n1] | B | 2.21 | N-Methyl-N-(2-{methyl-[6-(4-trifluoro-methyl-phenoxy)-pyrazin-2-yl]-amino}-ethyl)-acetamide | 1H NMR (400 MHz, DMSO-d6) ppm = 7.90 (s, 1H), 7.78 (d, J = 8.8, 2H), 7.65 (s, 1H), 7.40 (d, J = 8.6, 2H), 3.44 (dt, J = 9.0, 6.6, 2H), 3.27 (dt, 2H), 2.95 (s, 3H), 2.53 (s, 3H), 1.84 (s, 3H). |
| 122 | 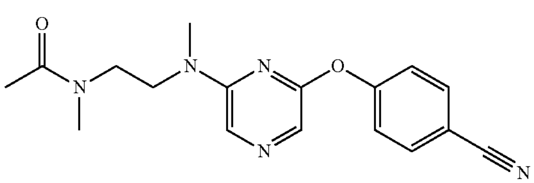 [SMILES: CC(=O)N(C)CCN(C)c1cncc(Oc2ccc(C#N)cc2)n1] | A | 1.86 | N-(2-{[6-(4-Cyano-phenoxy)-pyrazin-2-yl]-methyl-amino}-ethyl)-N-methyl-acetamide | 1H NMR (400 MHz, DMSO-d6) ppm = 7.99-7.84 (m, 3H), 7.64 (s, 1H), 7.34 (d, J = 8.8, 2H), 3.53-3.39 (m, 2H), 3.36-3.24 (m, 2H), 2.95 (s, 3H), 2.75 (s, 3H), 1.85 (s, 3H). |

TABLE 1-continued

| No | Chemical Structure | IC$_{50}$ | HPLC/MS Rt [Min] | Chemical Name | NMR data |
|---|---|---|---|---|---|
| 123 | 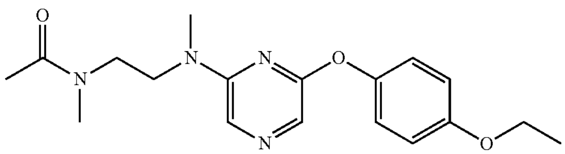 [SMILES: CCOc1ccc(Oc2cncc(N(C)CCN(C)C(C)=O)n2)cc1] | A | 2.04 | N-(2-{[6-(4-Ethoxy-phenoxy)-pyrazin-2-yl]-methyl-amino}-ethyl)-N-methyl-acetamide | 1H NMR (400 MHz, DMSO-d6) ppm = 7.75 (s, 1H), 7.47 (s, 1H), 7.09 (d, J = 9.0, 2H), 6.94 (d, J = 9.0, 2H), 4.01 (q, J = 6.9, 2H), 3.54-3.38 (m, 2H), 3.32-3.21 (m, 2H), 2.93 (s, 3H), 2.72 (s, 3H), 1.85 (s, 3H), 1.33 (t, J = 6.9, 3H). |
| 124 | 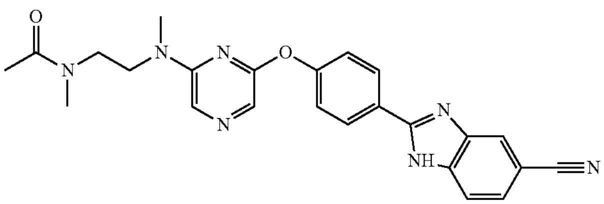 [SMILES: CC(=O)N(C)CCN(C)c1cncc(Oc2ccc(-c3nc4cc(C#N)ccc4[nH]3)cc2)n1] | B | 1.84 | N-[2-({6-[4-(5-Cyano-1H-benzo-imidazo-2-yl)-phenoxy]-pyrazin-2-yl}-methyl-amino)-ethyl]-N-methyl-acetamide | 1H NMR (500 MHz, DMSO-d6) ppm = 13.42 (s, 1H), 8.26 (d, J = 8.7, 2H), 8.19 (s, 1H), 7.88 (d, J = 5.1, 1H), 7.85-7.54 (m, 3H), 7.36 (d, J = 8.7, 2H), 3.53-3.40 (m, 2H), 3.38-3.24 (m, 2H), 2.96 (s, 3H), 2.56 (s, 3H), 1.83 (s, 3H). |
| 125 | 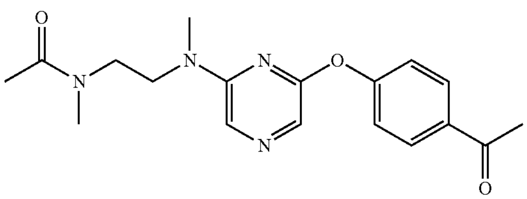 [SMILES: CC(=O)c1ccc(Oc2cncc(N(C)CCN(C)C(C)=O)n2)cc1] | B | 1.81 | N-(2-{[6-(4-Acetyl-phenoxy)-pyrazin-2-yl]-methyl-amino}-ethyl)-N-methyl-acetamide | 1H NMR (400 MHz, DMSO-d6) ppm = 8.01 (d, J = 8.6, 2H), 7.88 (s, 1H), 7.63 (s, 1H), 7.29 (d, J = 8.7, 2H), 3.46 (dt, J = 9.8, 6.5, 2H), 3.33 (dt, 2H), 2.95 (s, 3H), 2.57 (s, 3H), 2.57 (s, 3H), 1.85 (s, 3H). |
| 126 | 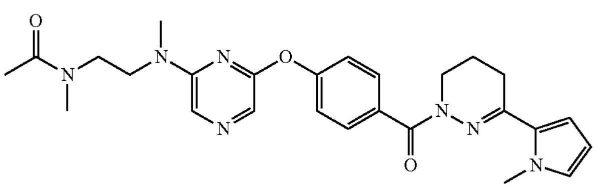 [SMILES: CC(=O)N(C)CCN(C)c1cncc(Oc2ccc(C(=O)N3CCCC(c4cccn4C)=N3)cc2)n1] | C | 2.17 | N-Methyl-N-{2-[methyl-(6-{4-[3-(1-methyl-1H-pyrrol-2-yl)-5,6-dihydro-4H-pyridazine-1-carbonyl]-phenoxy}-pyrazin-2-yl)-amino]-ethyl} acetamide | 1H NMR (500 MHz, DMSO-d6) ppm = 7.86 (s, 1H), 7.63 (s, 1H), 7.57 (d, J = 8.6, 2H), 7.21 (d, J = 8.6, 2H), 6.74 (dd, J = 2.1, 1H), 6.50 (dd, J = 3.9, 1.8, 1H), 5.98 (dd, J = 3.9, 2.6, 1H), 3.87-3.80 (m, 2H), 3.49 (dt, J = 18.0, 6.5, 2H), 3.39-3.25 (m, 2H), 3.23 (s, 3H), 2.96 (s, 3H), 2.63 (s, 3H), 2.66-2.65 (m, 2H), 2.08-1.91 (m, 2H), 1.84 (s, 3H). |
| 127 | 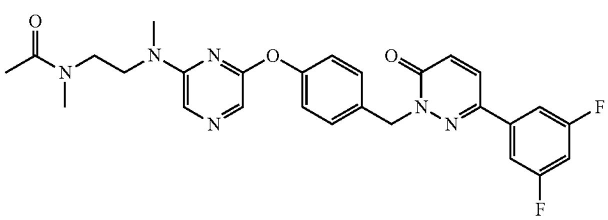 [SMILES: CC(=O)N(C)CCN(C)c1cncc(Oc2ccc(Cn3nc(-c4cc(F)cc(F)c4)ccc3=O)cc2)n1] | C | 2.27 | N-{2-[(6-{4-[3-(3,5-Difluoro-phenyl)-6-oxo-6H-pyridazin-1-ylmethyl]-phenoxy}-pyrazin-2-yl)-methyl-amino]-ethyl}-N-methyl-acetamide | 1H NMR (500 MHz, DMSO-d6) ppm = 8.15 (d, J = 9.7, 1H), 7.78 (s, 1H), 7.69-7.61 (m, 2H), 7.54 (s, 1H), 7.48-7.41 (m, 2H), 7.39-7.29 (m, 1H), 7.20-7.06 (m, 3H), 5.34 (s, 2H), 3.44-3.32 (m, 2H), 3.23 (t, J = 6.5, 2H), 2.92 (s, 3H), 2.45 (s, 3H), 1.77 (s, 3H). |

TABLE 1-continued

| No | Chemical Structure | IC$_{50}$ | HPLC/MS Rt [Min] | Chemical Name | NMR data |
|---|---|---|---|---|---|
| 128 | 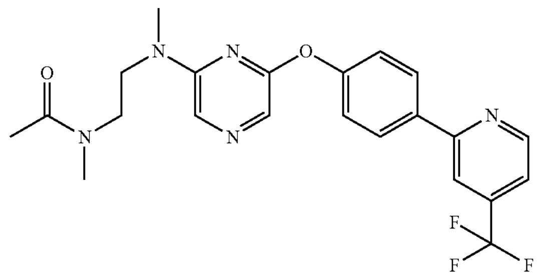 [SMILES: CC(=O)N(C)CCN(C)c1cncc(Oc2ccc(-c3cc(C(F)(F)F)ccn3)cc2)n1] | C | 2.35 | N-Methyl-N-[2-(methyl-{6-[4-(4-trifluoro-methyl-pyridin-2-yl)-phenoxy]-pyrazin-2-yl}-amino)-ethyl]-acetamide | 1H NMR (400 MHz, DMSO-d6) ppm = 8.94 (d, J = 5.0, 1H), 8.31 (s, 1H), 8.26 (d, J = 8.8, 2H), 7.87 (s, 1H), 7.72 (d, J = 5.0, 1H), 7.62 (s, 1H), 7.30 (d, J = 8.8, 2H), 3.53-3.39 (m, 2H), 3.33-3.19 (m, 2H), 2.96 (s, 3H), 2.55 (s, 3H), 1.82 (s, 3H). |
| 129 | 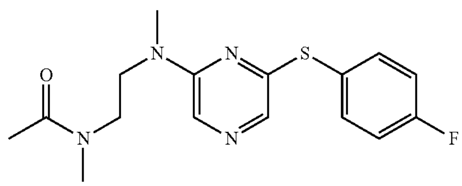 [SMILES: CC(=O)N(C)CCN(C)c1cncc(Sc2ccc(F)cc2)n1] | B | 2.14 | N-(2-{[6-(4-Fluoro-phenyl-sulfanyl)-pyrazin-2-yl]-methyl-amino}-ethyl)-N-methyl-acetamide | 1H NMR (400 MHz, DMSO-d6) ppm = 7.83 (s, 1H), 7.68-7.58 (m, 2H), 7.45 (s, 1H), 7.37-7.25 (m, 2H), 3.58-3.45 (m, 2H), 3.33-3.26 (m, 2H), 2.93 (s, 3H), 2.83 (s, 3H), 1.85 (s, 3H). |
| 130 | 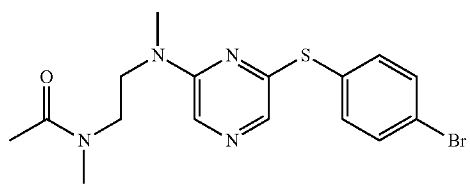 [SMILES: CC(=O)N(C)CCN(C)c1cncc(Sc2ccc(Br)cc2)n1] | C | 2.35 | N-(2-{[6-(4-Bromo-phenyl-sulfanyl)-pyrazin-2-yl]-methyl-amino}-ethyl)-N-methyl-acetamide | 1H NMR (400 MHz, DMSO-d6) ppm = 7.87 (s, 1H), 7.68-7.61 (m, 2H), 7.54 (s, 1H), 7.53-7.46 (m, 2H), 3.57-3.48 (m, 2H), 3.32-3.24 (m, 2H), 2.94 (s, 3H), 2.82 (s, 3H), 1.86 (s, 3H). |
| 131 | 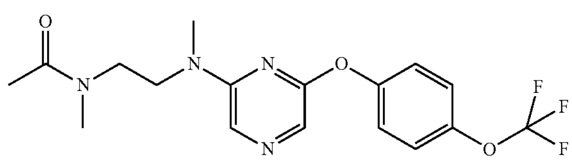 [SMILES: CC(=O)N(C)CCN(C)c1cncc(Oc2ccc(OC(F)(F)F)cc2)n1] | A | 2.25 | N-Methyl-N-(2-{methyl-[6-(4-trifluoro-methoxy)-pyrazin-2-yl]-amino}-ethyl)-acetamide | 1H NMR (500 MHz, DMSO-d6) ppm = 7.84 (s, 1H), 7.60 (s, 1H), 7.41 (d, J = 8.6, 2H), 7.32 (d, J = 9.1, 2H), 3.50-3.36 (m, 2H), 3.29-3.22 (m, 2H), 2.94 (s, 3H), 2.70 (s, 3H), 1.84 (s, 3H). |
| 132 | 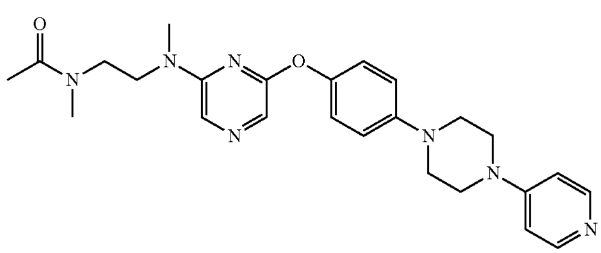 [SMILES: CC(=O)N(C)CCN(C)c1cncc(Oc2ccc(N3CCN(c4ccncc4)CC3)cc2)n1] | A | 1.20 | N-Methyl-N-[2-(methyl-{6-[4-(4-pyridin-4-yl-piperazin-1-yl)-phenoxy]-pyrazin-2-yl}-amino)-ethyl]-acetamide | 1H NMR (400 MHz, DMSO-d6) ppm = 8.24 (d, J = 7.0, 2H), 7.76 (s, 1H), 7.46 (s, 1H), 7.21-6.94 (m, 6H), 3.84-3.65 (m, 4H), 3.51-3.23 (m, 8H), 2.94 (s, 3H), 2.58 (s, 3H), 1.84 (s, 3H). |
| 133 | 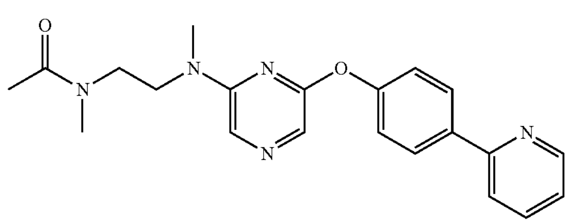 [SMILES: CC(=O)N(C)CCN(C)c1cncc(Oc2ccc(-c3ccccn3)cc2)n1] | A | 1.71 | N-Methyl-N-(2-{methyl-[6-(4-pyridin-2-yl-phenoxy)-pyrazin-2-yl]-amino}-ethyl)-acetamide | 1H NMR (400 MHz, DMSO-d6) ppm = 8.66 (ddd, J = 4.8, 1.8, 0.9, 1H), 8.14 (d, J = 8.7, 2H), 7.96 (d, J = 8.0, 1H), 7.92-7.86 (m, 1H), 7.85 (s, 1H), 7.60 (s, 1H), 7.36 (d, J = 5.0, 1H), 7.29 (d, J = 5.0, 1H), 3.52-3.39 (m, 2H), 3.34-3.24 (m, 2H), 2.96 (s, 3H), 2.54 (s, 3H), 1.82 (s, 3H). |

TABLE 1-continued

| No | Chemical Structure | IC$_{50}$ | HPLC/MS Rt [Min] | Chemical Name | NMR data |
|---|---|---|---|---|---|
| 134 | 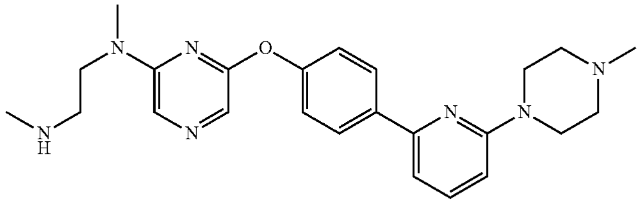 | C | 1.29 | N,N'-Dimethyl-N-(6-{4-[6-(4-methyl-piperazin-1-yl)-pyridin-2-yl]-phenoxy}-pyrazin-2-yl)-ethane-1,2-diamine | 1H NMR (400 MHz, DMSO-d6) ppm = 8.08 (d, J = 8.7, 2H), 7.83 (s, 1H), 7.61 (t, J = 7.9, 1H), 7.53 (s, 1H), 7.28-7.19 (m, 3H), 6.79 (d, J = 8.5, 1H), 3.61-3.54 (m, 4H), 3.41 (t, J = 6.6, 2H), 2.96 (s, 3H), 2.55 (t, J = 6.6, 2H), 2.47-2.39 (m, 4H), 2.23 (s, 3H), 2.17 (s, 3H). |
| 135 | 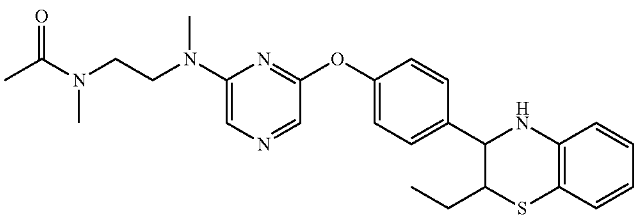 [SMILES: CCC1Sc2ccccc2NC1c1ccc(Oc2cncc(N(C)CCN(C)C(C)=O)n2)cc1] | C | 2.54 | N-[2-({6-[4-(2-Ethyl-3,4-dihydro-2H-benzo[1,4]thiazin-3-yl)-phenoxy]-pyrazin-2-yl}-methyl-amino)-ethyl]-N-methyl-acetamide | 1H NMR (400 MHz, DMSO-d6) ppm = 7.79 (s, 1H), 7.51 (s, 1H), 7.36 (d, J = 8.3, 2H), 7.15 (d, J = 8.6, 2H), 6.93 (d, J = 7.8, 1H), 6.90-6.82 (m, 1H), 6.72-6.64 (m, 1H), 6.56-6.46 (m, 2H), 4.88 (t, J = 2.9, 1H), 3.57-3.39 (m, 2H), 3.30-3.23 (m, 2H), 3.22-3.12 (m, 1H), 2.93 (s, 3H), 2.74 (s, 3H), 1.85 (s, 3H), 1.61-1.42 (m, 1H), 1.15-0.82 (m, 4H). |
| 136 | 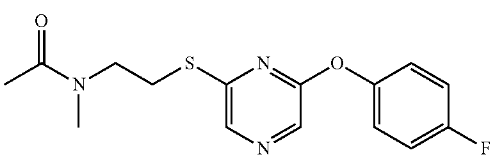 [SMILES: CC(=O)N(C)CCSc1cncc(Oc2ccc(F)cc2)n1] | A | 2.01 | N-{2-[6-(4-Fluoro-phenoxy)-pyrazin-2-ylsulfanyl]-ethyl}-N-methyl-acetamide | 1H NMR (500 MHz, DMSO-d6) ppm = 8.33 (s, 1H), 8.19 (s, 1H), 7.36-7.21 (m, 4H), 3.31-3.24 (m, 2H), 3.13-2.96 (m, 2H), 2.75 (s, 3H), 1.93 (s, 3H). |
| 137 | 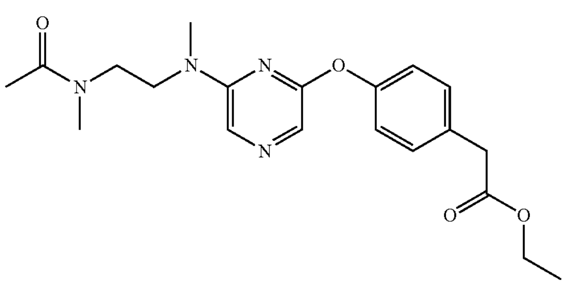 [SMILES: CCOC(=O)Cc1ccc(Oc2cncc(N(C)CCN(C)C(C)=O)n2)cc1] | A | 2.03 | [4-(6-{[2-(Acetyl-methyl-amino)-ethyl]-methyl-amino}-pyrazin-2-yloxy)-phenyl]-acetic acid ethyl ester | 1H NMR (500 MHz, DMSO-d6) ppm = 7.79 (s, 1H), 7.53 (s, 1H), 7.30 (d, J = 8.4, 2H), 7.12 (d, J = 8.5, 2H), 4.09 (q, J = 7.1, 2H), 3.66 (s, 2H), 3.51-3.38 (m, 2H), 3.29-3.22 (m, 2H), 2.94 (s, 3H), 2.68 (s, 3H), 1.84 (s, 3H), 1.19 (t, J = 7.1, 3H). |
| 138 | 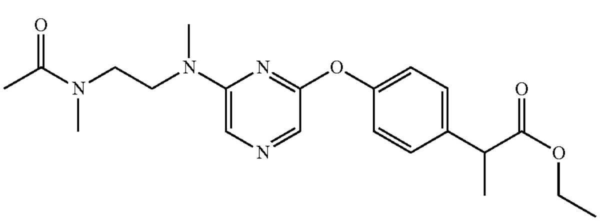 [SMILES: CCOC(=O)C(C)c1ccc(Oc2cncc(N(C)CCN(C)C(C)=O)n2)cc1] | B | 2.14 | 2-[4-(6-{[2-(Acetyl-methyl-amino)-ethyl]-methyl-amino}-pyrazin-2-yloxy)-phenyl]-propionic acid ethyl ester | 1H NMR (500 MHz, DMSO-d6) ppm = 7.81 (s, 1H), 7.53 (s, 1H), 7.31 (d, J = 7.5, 2H), 7.14 (d, J = 8.6, 2H), 4.07 (q, J = 7.2, 2H), 3.79 (q, J = 7.1, 1H), 3.43 (dt, J = 13.3, 6.5, 2H), 3.26 (dt, J = 30.6, 6.3, 2H), 2.97 (d, J = 32.7, 3H), 2.53 (s, 3H), 1.84 (s, 3H), 1.39 (d, J = 7.2, 3H), 1.13 (t, J = 7.1, 3H). |

| No | Chemical Structure | IC$_{50}$ | HPLC/MS Rt [Min] | Chemical Name | NMR data |
|---|---|---|---|---|---|
| 139 | 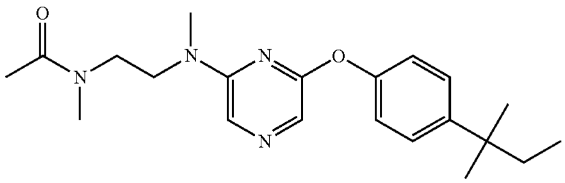 [SMILES: CCC(C)(C)c1ccc(Oc2cncc(N(C)CCN(C)C(C)=O)n2)cc1] | B | 2.58 | N-[2-({6-[4-(1,1-Dimethyl-propyl)-phenoxy]-pyrazin-2-yl}-methyl-amino)-ethyl]-N-methyl-acetamide | 1H NMR (500 MHz, DMSO-d6) ppm = 7.77 (s, 1H), 7.50 (s, 1H), 7.35 (d, J = 8.6, 2H), 7.09 (d, J = 8.7, 2H), 3.48-3.37 (m, 2H), 3.30-3.21 (m, 2H), 2.94 (s, 3H), 2.69 (s, 3H), 1.83 (s, 3H), 1.61 (q, J = 7.4, 2H), 1.25 (s, 6H), 0.63 (t, J = 7.4, 3H). |
| 140 | 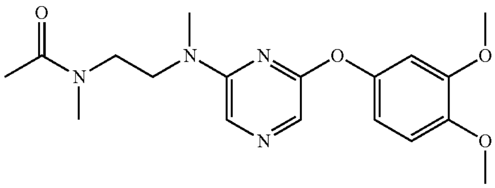 [SMILES: COc1ccc(Oc2cncc(N(C)CCN(C)C(C)=O)n2)cc1OC] | C | 1.78 | N-(2-{[6-(3,4-Dimethoxy-phenoxy)-pyrazin-2-yl]-methyl-amino}-ethyl)-N-methyl-acetamide | 1H NMR (500 MHz, DMSO-d6) ppm = 7.77 (s, 1H), 7.47 (s, 1H), 6.95 (d, J = 8.7, 1H), 6.81 (d, J = 2.7, 1H), 6.66 (dd, J = 8.7, 2.7, 1H), 3.75 (s, 3H), 3.73 (s, 3H), 3.53-3.38 (m, 2H), 3.29-3.25 (m, 2H), 2.95 (s, 3H), 2.73 (s, 3H), 1.85 (s, 3H). |
| 141 | 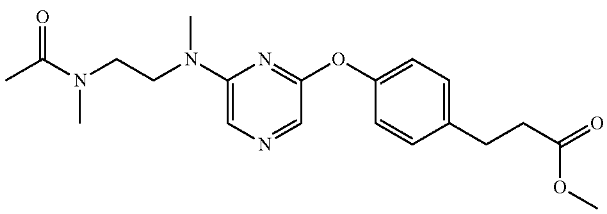 [SMILES: COC(=O)CCc1ccc(Oc2cncc(N(C)CCN(C)C(C)=O)n2)cc1] | C | 2.00 | 3-[4-(6-{[2-(Acetyl-methyl-amino)-ethyl]-methyl-amino}-pyrazin-2-yloxy)-phenyl]-propionic acid methyl ester | 1H NMR (500 MHz, DMSO-d6) ppm = 7.77 (s, 1H), 7.50 (s, 1H), 7.25 (d, J = 8.4, 2H), 7.08 (d, J = 8.5, 2H), 3.58 (s, 3H), 3.49-3.37 (m, 2H), 3.28-3.21 (m, 2H), 2.94 (s, 3H), 2.86 (t, J = 7.5, 2H), 2.69 (s, 3H), 2.63 (t, J = 7.6, 2H), 1.84 (s, 3H). |
| 142 | 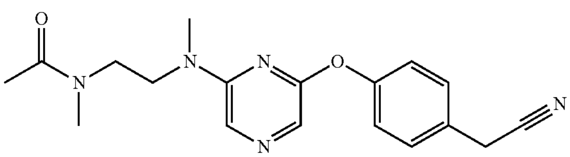 [SMILES: CC(=O)N(C)CCN(C)c1cncc(Oc2ccc(CC#N)cc2)n1] | A | 1.86 | N-(2-{[6-(4-Cyano-methyl-phenoxy)-pyrazin-2-yl]-methyl-amino}-ethyl)-N-methyl-acetamide | 1H NMR (400 MHz, DMSO-d6) ppm = 7.81 (s, 1H), 7.56 (s, 1H), 7.39 (d, J = 8.5, 2H), 7.21 (d, J = 8.6, 2H), 4.04 (s, 2H), 3.54-3.35 (m, 2H), 2.94 (s, 3H), 2.68 (s, 3H), 1.85 (s, 3H). |
| 143 | 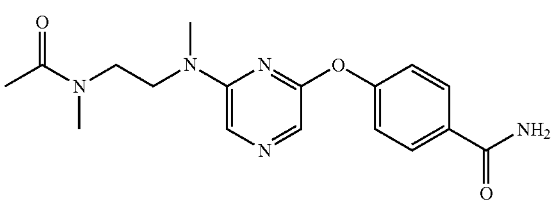 [SMILES: CC(=O)N(C)CCN(C)c1cncc(Oc2ccc(C(N)=O)cc2)n1] | B | 1.50 | 4-(6-{[2-(Acetyl-methyl-amino)-ethyl]-methyl-amino}-pyrazin-2-yloxy)-benzamide | 1H NMR (400 MHz, DMSO-d6) ppm = 8.00-7.88 (m, 3H), 7.85 (s, 1H), 7.59 (s, 1H), 7.32 (s, 1H), 7.22 (d, J = 8.7, 2H), 3.51-3.37 (m, 2H), 3.30-3.19 (m, 2H), 2.95 (s, 3H), 2.70 (s, 3H), 1.84 (s, 3H). |
| 144 | 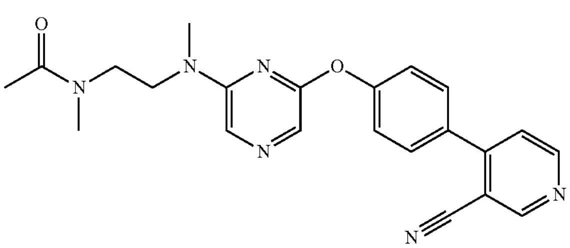 [SMILES: CC(=O)N(C)CCN(C)c1cncc(Oc2ccc(-c3ccncc3C#N)cc2)n1] | A | 1.91 | N-[2-({6-[4-(3-Cyano-pyridin-4-yl)-phenoxy]-pyrazin-2-yl}-methyl-amino)-ethyl]-N-methyl-acetamide | 1H NMR (500 MHz, DMSO-d6) ppm = 9.10 (s, 1H), 8.89 (d, J = 5.2, 1H), 7.88 (s, 1H), 7.76 (d, J = 8.6, 2H), 7.74 (d, J = 5.5, 1H), 7.64 (s, 1H), 7.41 (d, J = 8.6, 2H), 3.54-3.41 (m, 2H), 3.36-3.31 (m, 2H), 2.96 (s, 3H), 2.71 (s, 3H), 1.83 (s, 3H). |

TABLE 1-continued

| No | Chemical Structure | IC$_{50}$ | HPLC/MS Rt [Min] | Chemical Name | NMR data |
|---|---|---|---|---|---|
| 145 | 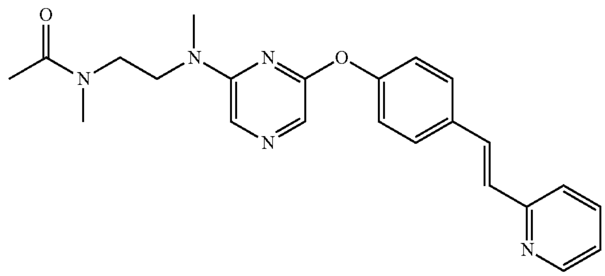 [SMILES: CC(=O)N(C)CCN(C)c1cncc(Oc2ccc(/C=C/c3ccccn3)cc2)n1] | A | 1.65 | N-Methyl-N-[2-(methyl-{6-[4-((E)-2-pyridin-2-yl-vinyl)-phenoxy]-pyrazin-2-yl}-amino)-ethyl]-acetamide | 1H NMR (400 MHz, DMSO-d6) ppm = 8.61-8.53 (m, 1H), 7.87-7.75 (m, 2H), 7.75-7.49 (m, 5H), 7.32-7.14 (m, 4H), 3.53-3.39 (m, 2H), 3.30-3.21 (m, 2H), 2.95 (s, 3H), 2.56 (s, 3H), 1.84 (s, 3H). |
| 146 | 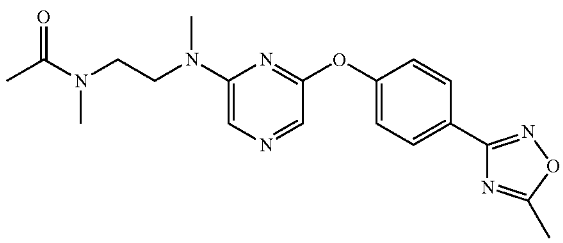 [SMILES: CC(=O)N(C)CCN(C)c1cncc(Oc2ccc(-c3noc(C)n3)cc2)n1] | B | 1.97 | N-Methyl-N-[2-(methyl-{6-[4-(5-methyl-[1,2,4]oxadiazol-3-yl)-phenoxy]-pyrazin-2-yl}-amino)-ethyl]-acetamide | 1H NMR (400 MHz, DMSO-d6) ppm = 8.03 (d, J = 8.8, 2H), 7.88 (s, 1H), 7.63 (s, 1H), 7.35 (d, J = 8.8, 2H), 3.45 (dd, J = 6.6, 3H), 3.26 (dd, J = 7.6, 6.0, 1H), 2.95 (s, 3H), 2.67 (s, 3H), 2.55 (s, 3H), 1.83 (s, 3H). |
| 147 | 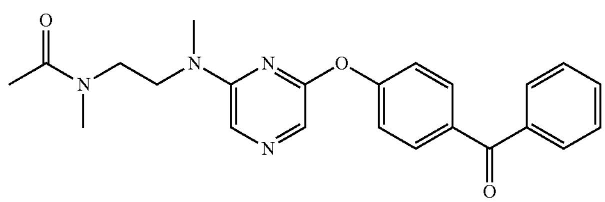 [SMILES: CC(=O)N(C)CCN(C)c1cncc(Oc2ccc(C(=O)c3ccccc3)cc2)n1] | B | 2.16 | N-(2-{6-(4-Benzoyl-phenoxy)-pyrazin-2-yl]-methyl-amino}-ethyl)-N-methyl-acetamide | 1H NMR (400 MHz, DMSO-d6) ppm = 7.91 (s, 1H), 7.81 (d, J = 8.6, 2H), 7.76-7.61 (m, 4H), 7.58 (t, J = 7.6, 2H), 7.35 (d, J = 8.6, 2H), 3.55-3.44 (m, 2H), 3.43-3.33 (m, 2H), 2.97 (s, 3H), 2.75 (s, 3H), 1.84 (s, 3H). |
| 148 | 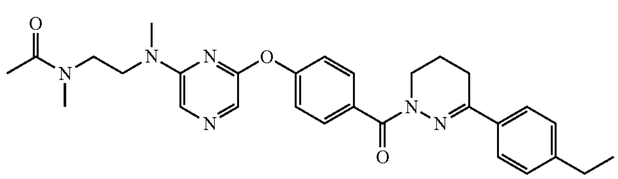 [SMILES: CCc1ccc(C2=NN(C(=O)c3ccc(Oc4cncc(N(C)CCN(C)C(C)=O)n4)cc3)CCC2)cc1] | C | 2.41 | N-{2-[(6-{4-[3-(4-Ethyl-phenyl)-5,6-dihydro-4H-pyridazine-1-carbonyl]-phenoxy}-pyrazin-2-yl)-methyl-amino]-ethyl}-N-methyl-acetamide | 1H NMR (400 MHz, DMSO-d6) ppm = 7.86 (s, 1H), 7.74 (d, J = 8.8, 2H), 7.63 (s, 1H), 7.52 (d, J = 8.1, 2H), 7.25 (d, J = 8.7, 2H), 7.17 (d, J = 8.2, 2H), 3.92-3.83 (m, 2H), 3.53-3.34 (m, 2H), 3.29-3.20 (m, 2H), 2.97 (s, 3H), 2.69 (t, J = 6.4, 2H), 2.67-2.54 (m, 5H), 2.09-1.97 (m, 2H), 1.74 (s, 3H), 1.15 (t, J = 7.6, 3H). |
| 149 | 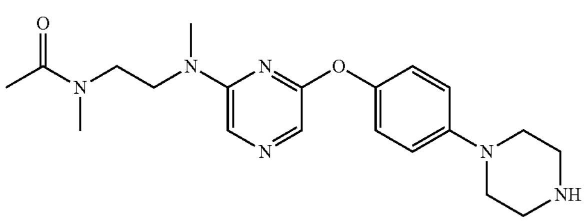 [SMILES: CC(=O)N(C)CCN(C)c1cncc(Oc2ccc(N3CCNCC3)cc2)n1] | C | 1.32 | N-Methyl-N-(2-{methyl-[6-(4-piperazin-1-yl-phenoxy)-pyrazin-2-yl]-amino}-ethyl)-acetamide | 1H NMR (400 MHz, DMSO-d6) ppm = 7.75 (s, 1H), 7.45 (s, 1H), 7.03 (d, J = 9.1, 2H), 6.94 (d, J = 9.2, 2H), 3.45 (dt, J = 12.6, 6.4, 2H), 3.30-3.20 (m, 2H), 3.06-3.00 (m, 4H), 2.94 (s, 3H), 2.90-2.81 (m, 4H), 2.71 (s, 3H), 1.85 (s, 3H). |

| No | Chemical Structure | IC$_{50}$ | HPLC/MS Rt [Min] | Chemical Name | NMR data |
|---|---|---|---|---|---|
| 150 | 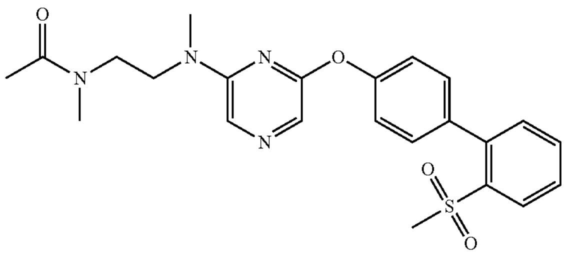 [SMILES: CC(=O)N(C)CCN(C)c1cncc(Oc2ccc(-c3ccccc3S(C)(=O)=O)cc2)n1] | A | 2.01 | N-(2-{[6-(2'-Methane-sulfonyl-biphenyl-4-yloxy)-pyrazin-2-yl]-methyl-amino}-ethyl)-N-methyl-acetamide | 1H NMR (400 MHz, DMSO-d6) ppm = 8.11 (dd, J = 7.9, 1.4, 1H), 7.83 (s, 1H), 7.81-7.76 (m, 1H), 7.68 (td, J = 7.7, 1.4, 1H), 7.59 (s, 1H), 7.45 (d, J = 8.6, 2H), 7.43-7.38 (m, 1H), 7.25 (d, J = 8.5, 2H), 3.54-3.47 (m, 2H), 3.39-3.32 (m, 2H), 2.95 (s, 3H), 2.84 (s, 3H), 2.80 (s, 3H), 1.85 (s, 3H). |
| 151 | 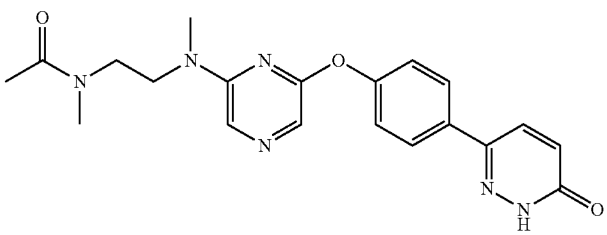 [SMILES: CC(=O)N(C)CCN(C)c1cncc(Oc2ccc(-c3ccc(=O)[nH]n3)cc2)n1] | B | 1.67 | N-Methyl-N-[2-(methyl-{6-[4-(6-oxo-1,6-dihydro-pyridazin-3-yl)-phenoxy]-pyrazin-2-yl}-amino)-ethyl]-acetamide | |
| 152 | 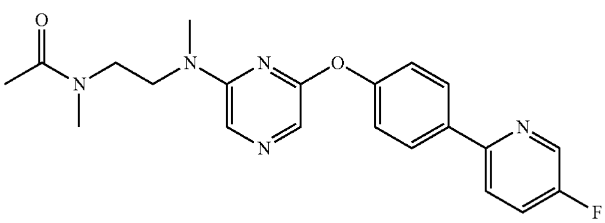 [SMILES: CC(=O)N(C)CCN(C)c1cncc(Oc2ccc(-c3ccc(F)cn3)cc2)n1] | A | 2.10 | N-[2-({6-[4-(5-Fluoro-pyridin-2-yl)-phenoxy]-pyrazin-2-yl}-methyl-amino)-ethyl]-N-methyl-acetamide | 1H NMR (400 MHz, DMSO-d6) ppm = 8.64 (d, J = 2.9, 1H), 8.09 (d, J = 8.7, 2H), 8.07-8.01 (m, 1H), 7.89-7.76 (m, 2H), 7.60 (s, 1H), 7.28 (d, J = 8.8, 2H), 3.49-3.43 (m, 2H), 3.37-3.21 (m, 2H), 2.95 (s, 3H), 2.54 (s, 3H), 1.83 (s, 3H). |
| 153 | 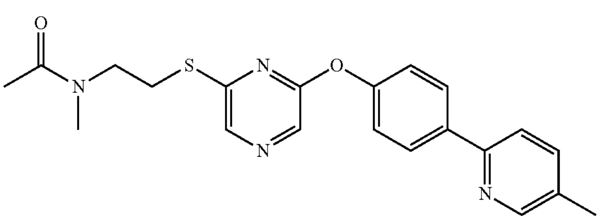 [SMILES: CC(=O)N(C)CCSc1cncc(Oc2ccc(-c3ccc(C)cn3)cc2)n1] | A | 1.81 | N-Methyl-N-(2-{6-[4-(5-methyl-pyridin-2-yl)-phenoxy]-pyrazin-2-ylsulfanyl}-ethyl)-acetamide | 1H NMR (400 MHz, DMSO-d6) ppm = 8.53-8.48 (m, 1H), 8.38 (s, 1H), 8.24 (s, 1H), 8.13 (d, J = 8.7, 2H), 7.87 (d, J = 8.1, 1H), 7.71 (dd, J = 8.1, 1.7, 1H), 7.33 (d, J = 8.7, 2H), 3.28-3.23 (m, 2H), 3.14-3.05 (m, 1H), 3.05-2.96 (m, 1H), 2.67 (s, 3H), 2.34 (s, 3H), 1.86 (s, 3H). |
| 154 | 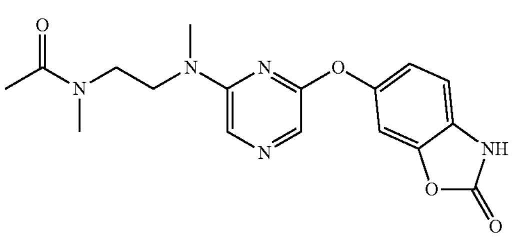 [SMILES: CC(=O)N(C)CCN(C)c1cncc(Oc2ccc3[nH]c(=O)oc3c2)n1] | C | 1.64 | N-Methyl-N-(2-{methyl-[6-(2-oxo-2,3-dihydro-benzooxazol-6-yloxy)-pyrazin-2-yl]-amino}-ethyl)-acetamide | 1H NMR (400 MHz, DMSO-d6) ppm = 11.59 (s, 1H), 7.78 (s, 1H), 7.52 (s, 1H), 7.25 (d, J = 2.2, 1H), 7.09 (d, J = 8.4, 1H), 6.96 (dd, J = 8.6, 2.3, 1H), 3.42 (t, J = 6.4, 2H), 3.37-3.21 (m, 2H), 2.93 (s, 3H), 2.71 (s, 3H), 1.84 (s, 3H). |

TABLE 1-continued

| No | Chemical Structure | IC$_{50}$ | HPLC/MS Rt [Min] | Chemical Name | NMR data |
|---|---|---|---|---|---|
| 155 | 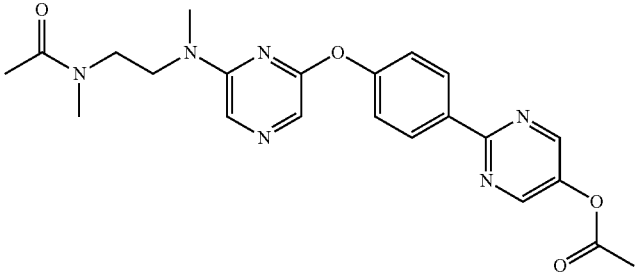 [SMILES: CC(=O)Oc1cnc(-c2ccc(Oc3cncc(N(C)CCN(C)C(C)=O)n3)cc2)nc1] | C | 2.06 | Acetic acid 2-[4-(6-{[2-(acetyl-methyl-amino)-ethyl]-methyl-amino}-pyrazin-2-yloxy)-phenyl]-pyrimidin-5-yl ester | |
| 156 | 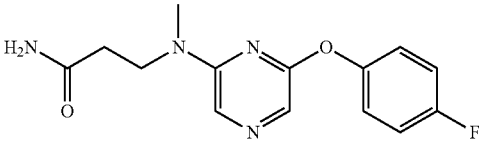 [SMILES: CN(CCC(N)=O)c1cncc(Oc2ccc(F)cc2)n1] | C | 1.79 | 3-{[6-(4-Fluoro-phenoxy)-pyrazin-2-yl]-methyl-amino}-propion-amide | 1H NMR (400 MHz, DMSO-d6) ppm = 7.81 (s, 1H), 7.51 (s, 1H), 7.26 (s, 1H), 7.23 (d, J = 6.5, 4H), 6.79 (s, 1H), 3.55 (t, J = 7.0, 2H), 2.92 (s, 3H), 2.24 (t, J = 6.9, 2H). |
| 157 | 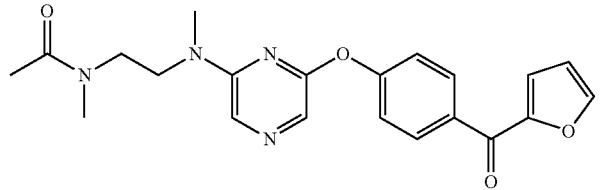 [SMILES: CC(=O)N(C)CCN(C)c1cncc(Oc2ccc(C(=O)c3ccco3)cc2)n1] | A | 2.01 | N-[2-({6-[4-(Furan-2-carbonyl)-phenoxy]-pyrazin-2-yl}-methyl-amino)-ethyl]-N-methyl-acetamide | 1H NMR (500 MHz, DMSO-d6) ppm = 11.06 (s, 1H), 7.76 (s, 1H), 7.57-7.44 (m, 2H), 7.33 (s, 1H), 7.18 (d, J = 1.7, 1H), 6.81 (dd, J = 8.5, 2.1, 1H), 6.43 (s, 1H), 3.45-3.38 (m, 2H), 3.29-3.19 (m, 2H), 2.94 (s, 3H), 2.58 (s, 3H), 1.82 (s, 3H). |
| 158 | 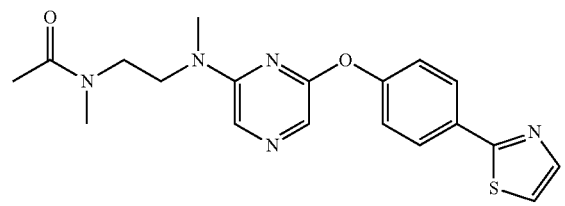 [SMILES: CC(=O)N(C)CCN(C)c1cncc(Oc2ccc(-c3nccs3)cc2)n1] | A | 2.02 | N-Methyl-N-(2-{methyl-[6-(4-thiazol-2-yl-phenoxy)-pyrazin-2-yl]-amino}-ethyl)-acetamide | 1H NMR (400 MHz, DMSO-d6) ppm = 7.99 (d, J = 8.7, 2H), 7.92 (d, J = 3.2, 1H), 7.86 (s, 1H), 7.77 (d, J = 3.2, 1H), 7.62 (s, 1H), 7.31 (d, J = 8.8, 2H), 3.50-3.44 (m, 2H), 3.31-3.20 (m, 2H), 2.96 (s, 3H), 2.72 (s, 3H), 1.83 (s, 3H). |
| 159 | 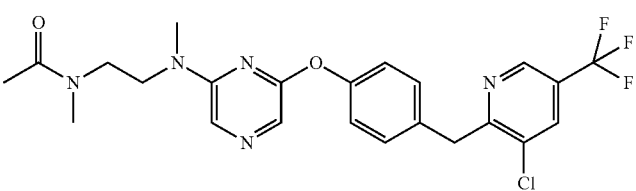 [SMILES: CC(=O)N(C)CCN(C)c1cncc(Oc2ccc(Cc3ncc(C(F)(F)F)cc3Cl)cc2)n1] | B | 2.39 | N-[2-({6-[4-(3-Chloro-5-trifluoro-methyl-pyridin-2-ylmethyl)-phenoxy]-pyrazin-2-yl}-methyl-amino)-ethyl]-N-methyl-acetamide | 1H NMR (400 MHz, DMSO-d6) ppm = 8.91 (s, 1H), 8.44 (s, 1H), 7.79 (s, 1H), 7.51 (s, 1H), 7.28 (d, J = 8.7, 2H), 7.11 (d, J = 8.6, 2H), 4.35 (s, 2H), 3.49-3.42 (m, 2H), 3.25-3.18 (m, 2H), 2.93 (s, 3H), 2.60 (s, 3H), 1.81 (s, 3H). |

TABLE 1-continued

| No | Chemical Structure | IC$_{50}$ | HPLC/MS Rt [Min] | Chemical Name | NMR data |
|---|---|---|---|---|---|
| 160 | 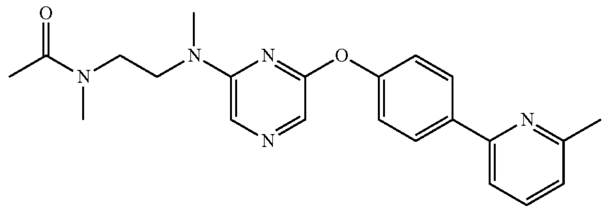 [SMILES: CC(=O)N(C)CCN(C)c1cncc(Oc2ccc(-c3cccc(C)n3)cc2)n1] | A | 1.64 | N-Methyl-N-[2-(methyl-{6-[4-(6-methyl-pyridin-2-yl)-phenoxy]-pyrazin-2-yl}-amino)-ethyl]-acetamide | 1H NMR (500 MHz, DMSO-d6) ppm = 8.11 (d, J = 8.7, 2H), 7.84 (d, J = 6.8, 1H), 7.80-7.71 (m, 1H), 7.75 (s, 1H), 7.59 (s, 1H), 7.27 (d, J = 8.7, 2H), 7.20 (d, J = 7.2, 1H), 3.50-3.40 (m, 2H), 3.35-3.23 (m, 2H), 2.96 (s, 3H), 2.54 (s, 6H), 1.83 (s, 3H). |
| 161 | 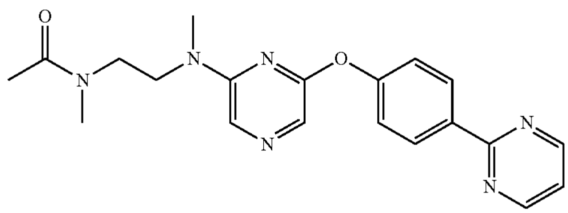 [SMILES: CC(=O)N(C)CCN(C)c1cncc(Oc2ccc(-c3ncccn3)cc2)n1] | B | 1.93 | N-Methyl-N-(2-{methyl-[6-(4-pyrimidin-2-yl-phenoxy)-pyrazin-2-yl]-amino}-ethyl)-acetamide | 1H NMR (500 MHz, DMSO-d6) ppm = 8.91 (d, J = 4.8, 2H), 8.44 (d, J = 8.7, 2H), 7.88 (s, 1H), 7.63 (s, 1H), 7.44 (t, J = 4.8, 1H), 7.32 (d, J = 8.8, 2H), 3.53-3.43 (m, 2H), 3.30-3.25 (m, 2H), 2.97 (s, 3H), 2.72 (s, 3H), 1.83 (s, 3H). |
| 162 | 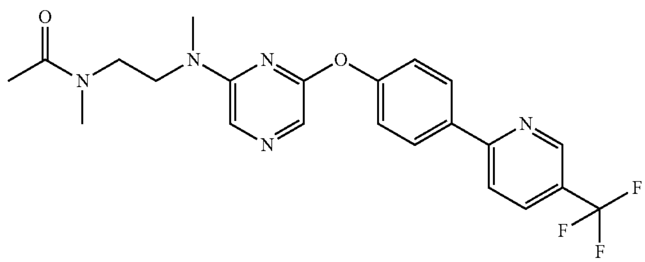 [SMILES: CC(=O)N(C)CCN(C)c1cncc(Oc2ccc(-c3ccc(C(F)(F)F)cn3)cc2)n1] | B | 2.31 | N-Methyl-N-[2-(methyl-{6-[4-(5-trifluoro-methyl-pyridin-2-yl)-phenoxy]-pyrazin-2-yl}-amino)-ethyl]-acetamide | 1H NMR (500 MHz, DMSO-d6) ppm = 9.03 (s, 1H), 8.28 (d, J = 8.4, 1H), 8.26-8.18 (m, 3H), 7.87 (s, 1H), 7.62 (s, 1H), 7.34 (d, J = 8.8, 2H), 3.52-3.42 (m, 2H), 3.31-3.24 (m, 2H), 2.96 (s, 3H), 2.71 (s, 3H), 1.83 (s, 3H). |
| 163 | 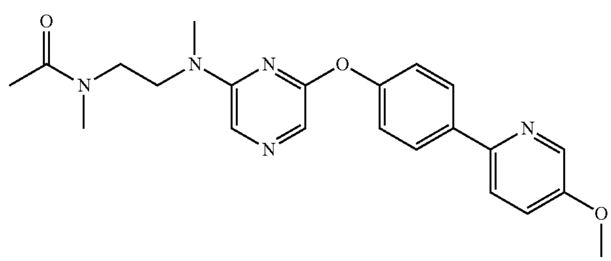 [SMILES: COc1ccc(-c2ccc(Oc3cncc(N(C)CCN(C)C(C)=O)n3)cc2)nc1] | A | 1.95 | N-[2-({6-[4-(5-Methoxy-pyridin-2-yl)-phenoxy]-pyrazin-2-yl}-methyl-amino)-ethyl]-N-methyl-acetamide | 1H NMR (500 MHz, DMSO-d6) ppm = 8.37 (d, J = 2.9, 1H), 8.05 (d, J = 8.6, 2H), 7.91 (d, J = 8.8, 1H), 7.84 (s, 1H), 7.58 (s, 1H), 7.47 (dd, J = 8.7, 2.8, 1H), 7.25 (d, J = 8.7, 2H), 3.88 (s, 3H), 3.54-3.38 (m, 2H), 3.38-3.17 (m, 2H), 2.95 (s, 3H), 2.70 (s, 3H), 1.82 (s, 3H). |
| 164 | 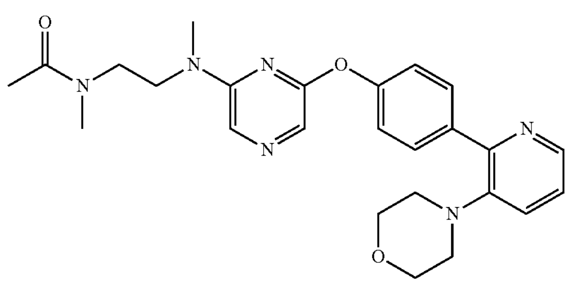 [SMILES: CC(=O)N(C)CCN(C)c1cncc(Oc2ccc(-c3ncccc3N3CCOCC3)cc2)n1] | C | 1.60 | N-Methyl-N-[2-(methyl-{6-[4-(3-morpholin-4-yl-pyridin-2-yl)-phenoxy]-pyrazin-2-yl}-amino)-ethyl]-acetamide | 1H NMR (500 MHz, DMSO-d6) ppm = 8.32 (ddd, J = 4.6, 1.5, 1H), 8.04 (d, J = 8.7, 2H), 7.84 (s, 1H), 7.60 (s, 1H), 7.51 (ddd, J = 8.2, 2.5, 1.5, 1H), 7.31 (dd, J = 8.1, 4.6, 1H), 7.25 (d, J = 8.7, 2H), 3.66-3.57 (m, 4H), 3.54-3.44 (m, 4H), 3.35 (t, J = 6.4, 2H), 2.96 (s, 3H), 2.88-2.78 (m, 4H), 2.76 (s, 3H), 1.85 (s, 3H). |

TABLE 1-continued

| No | Chemical Structure | IC$_{50}$ | HPLC/MS Rt [Min] | Chemical Name | NMR data |
|---|---|---|---|---|---|
| 165 | 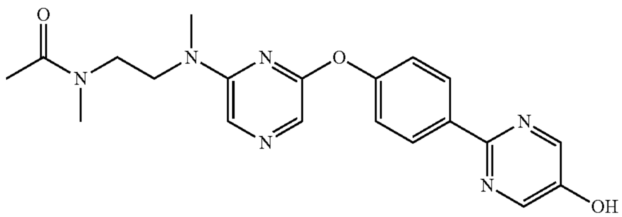 [SMILES: CC(=O)N(C)CCN(C)c1cncc(Oc2ccc(-c3ncc(O)cn3)cc2)n1] | C | 1.81 | N-[2-({6-[4-(5-Hydroxy-pyrimidin-2-yl)-phenoxy]-pyrazin-2-yl}-methyl-amino)-ethyl]-N-methyl-acetamide | 1H NMR (500 MHz, DMSO-d6) ppm = 8.84 (s, 1H), 8.21-8.12 (m, 2H), 7.95 (s, 1H), 7.84 (d, J = 3.5, 1H), 7.76 (t, J = 7.9, 1H), 7.72-7.62 (m, 2H), 3.64-3.52 (m, 2H), 3.33-3.26 (m, 2H), 3.01 (s, 3H), 2.77 (s, 3H), 1.82 (s, 3H). |
| 166 | 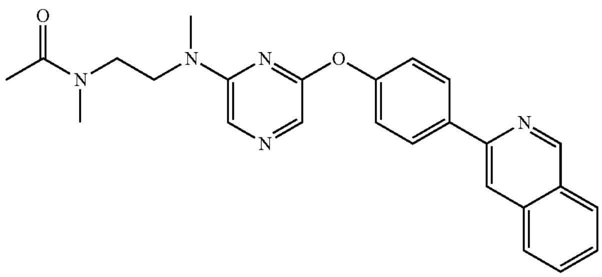 [SMILES: CC(=O)N(C)CCN(C)c1cncc(Oc2ccc(-c3cc4ccccc4cn3)cc2)n1] | B | 2.14 | N-(2-{[6-(4-Isoquinolin-3-yl-phenoxy)-pyrazin-2-yl]-methyl-amino}-ethyl)-N-methyl-acetamide | 1H NMR (400 MHz, DMSO-d6) ppm = 9.41 (s, 1H), 8.42 (s, 1H), 8.27 (d, J = 8.8, 2H), 8.14 (d, J = 8.2, 1H), 8.03 (d, J = 8.2, 1H), 7.86 (s, 1H), 7.80 (ddd, J = 8.2, 6.8, 1.2, 1H), 7.67 (dd, 1H), 7.62 (s, 1H), 7.33 (d, J = 8.7, 2H), 3.51-3.43 (m, 2H), 3.38-3.23 (m, 2H), 2.97 (s, 3H), 2.71 (s, 3H), 1.82 (s, 3H). |
| 167 | 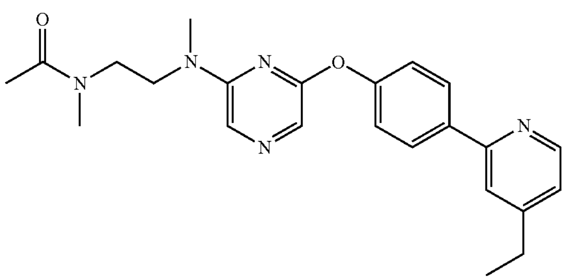 [SMILES: CCc1ccnc(-c2ccc(Oc3cncc(N(C)CCN(C)C(C)=O)n3)cc2)c1] | B | 1.74 | N-[2-({6-[4-(4-Ethyl-pyridin-2-yl)-phenoxy]-pyrazin-2-yl}-methyl-amino)-ethyl]-N-methyl-acetamide | 1H NMR (400 MHz, DMSO-d6) ppm = 8.53 (d, J = 5.0, 1H), 8.14 (d, J = 8.8, 2H), 7.85 (s, 1H), 7.81 (s, 1H), 7.60 (s, 1H), 7.24 (d, J = 8.7, 2H), 7.20 (d, J = 4.8, 1H), 3.53-3.41 (m, 2H), 3.39-3.23 (m, 2H), 2.95 (s, 3H), 2.74-2.53 (m, 5H), 1.82 (s, 3H), 1.25 (t, J = 7.6, 3H). |
| 168 | 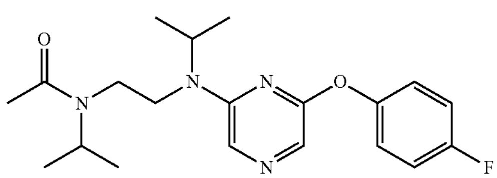 [SMILES: CC(=O)N(CCN(c1cncc(Oc2ccc(F)cc2)n1)C(C)C)C(C)C] | B | 2.35 | N-(2-{[6-(4-Fluoro-phenoxy)-pyrazin-2-yl]-isopropyl-amino}-ethyl)-N-isopropyl-acetamide | 1H NMR (500 MHz, DMSO-d6) ppm = 8.13 (s, 1H), 7.54 (s, 1H), 7.28-7.19 (m, 2H), 7.21-7.12 (m, 2H), 4.29 (p, J = 6.6, 1H), 3.94 (p, J = 6.8, 1H), 3.27-3.03 (m, 4H), 2.03 (s, 3H), 1.11 (d, J = 6.7, 6H), 0.98 (d, J = 6.6, 6H). |
| 169 | 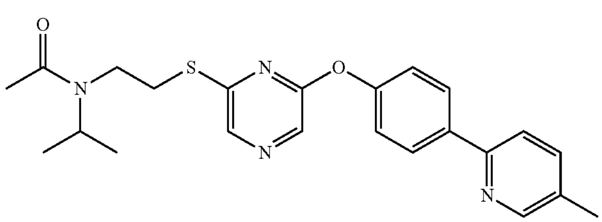 [SMILES: CC(=O)N(CCSc1cncc(Oc2ccc(-c3ccc(C)cn3)cc2)n1)C(C)C] | A | 2.02 | N-Isopropyl-N-(2-{6-[4-(5-methyl-pyridin-2-yl)-phenoxy]-pyrazin-2-ylsulfanyl}-ethyl)-acetamide | 1H NMR (400 MHz, DMSO-d6) ppm = 8.53-8.47 (m, 1H), 8.44 (s, 1H), 8.21 (s, 1H), 8.13 (d, J = 8.8, 2H), 7.86 (d, J = 8.1, 1H), 7.70 (dd, J = 8.1, 1.8, 1H), 7.30 (d, J = 8.7, 2H), 3.84 (h, J = 6.7, 1H), 3.24-3.14 (m, 2H), 3.11-2.96 (m, 2H), 2.34 (s, 3H), 1.95 (s, 3H), 0.88 (d, J = 6.7, 5H). |

TABLE 1-continued

| No | Chemical Structure | IC$_{50}$ | HPLC/MS Rt [Min] | Chemical Name | NMR data |
|---|---|---|---|---|---|
| 170 | 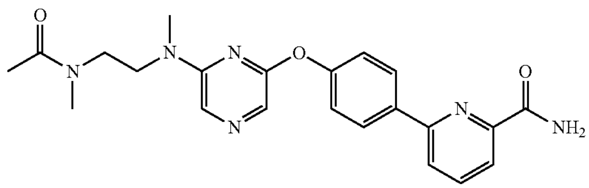 [SMILES: CC(=O)N(C)CCN(C)c1cncc(Oc2ccc(-c3cccc(C(N)=O)n3)cc2)n1] | A | 1.86 | 6-[4-(6-{[2-(Acetyl-methyl-amino)-ethyl]-methyl-amino}-pyrazin-2-yloxy)-phenyl]-pyridine-2-carboxylic acid amide | 1H NMR (400 MHz, DMSO-d6) ppm = 8.36 (d, J = 8.8, 2H), 8.31 (s, 1H), 8.17 (d, J = 7.9, 1H), 8.05 (t, J = 7.8, 1H), 7.97 (d, J = 7.5, 1H), 7.86 (s, 1H), 7.72-7.53 (m, 2H), 7.30 (d, J = 8.8, 2H), 3.54-3.42 (m, 2H), 3.40-3.30 (m, 2H), 2.96 (s, 3H), 2.63 (s, 3H), 1.82 (s, 3H). |
| 171 | 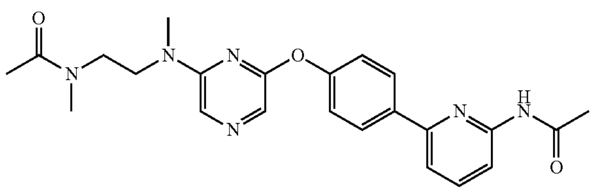 [SMILES: CC(=O)Nc1cccc(-c2ccc(Oc3cncc(N(C)CCN(C)C(C)=O)n3)cc2)n1] | A | 1.94 | N-[2-({6-[4-(6-Acetylamino-pyridin-2-yl)-phenoxy]-pyrazin-2-yl}-methyl-amino)-ethyl]-N-methyl-acetamide | 1H NMR (400 MHz, DMSO-d6) ppm = 10.45 (s, 1H), 8.11 (d, J = 8.8, 2H), 8.01 (d, J = 7.9, 1H), 7.89-7.79 (m, 2H), 7.66 (s, 1H), 7.60 (s, 1H), 7.29 (d, J = 8.8, 2H), 3.57-3.40 (m, 2H), 3.37-3.22 (m, 2H), 2.95 (s, 3H), 2.70 (s, 3H), 2.13 (s, 3H), 1.82 (s, 3H). |
| 172 | 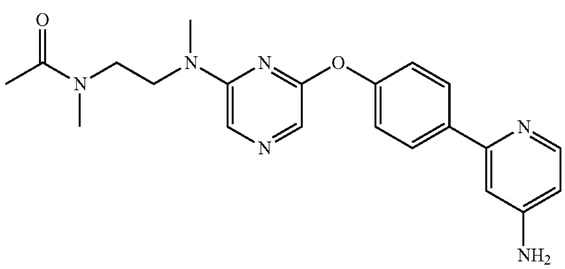 [SMILES: CC(=O)N(C)CCN(C)c1cncc(Oc2ccc(-c3cc(N)ccn3)cc2)n1] | B | 1.70 | N-[2-({6-[4-(4-Amino-pyridin-2-yl)-phenoxy]-pyrazin-2-yl}-methyl-amino)-ethyl]-N-methyl-acetamide | 1H NMR (400 MHz, DMSO-d6) ppm = 8.07 (d, J = 5.6, 1H), 7.94 (d, J = 8.7, 2H), 7.84 (s, 1H), 7.58 (s, 1H), 7.23 (d, J = 8.7, 2H), 6.99 (d, J = 1.9, 1H), 6.45 (dd, J = 5.5, 2.0, 1H), 6.05 (s, 2H), 3.51-3.39 (m, 2H), 3.28-3.23 (m, 2H), 2.95 (s, 3H), 2.70 (s, 3H), 1.83 (s, 3H). |
| 173 | 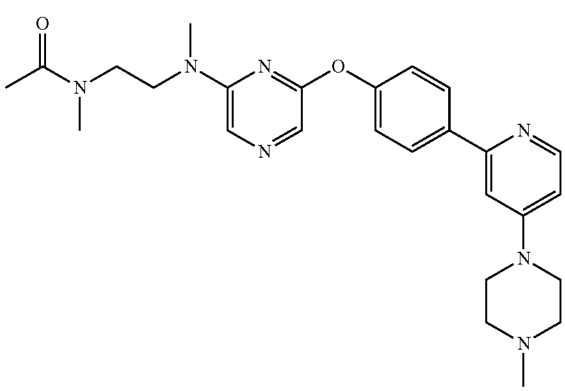 [SMILES: CC(=O)N(C)CCN(C)c1cncc(Oc2ccc(-c3cc(N4CCN(C)CC4)ccn3)cc2)n1] | C | 1.56 | N-Methyl-N-{2-[methyl-(6-{4-[4-(4-methyl-piperazin-1-yl)-pyridin-2-yl]-phenoxy}-pyrazin-2-yl)-amino]-ethyl}-acetamide | 1H NMR (400 MHz, DMSO-d6) ppm = 8.24 (d, J = 5.9, 1H), 8.17-8.05 (m, 2H), 7.84 (s, 1H), 7.58 (s, 1H), 7.35-7.29 (m, 1H), 7.26-7.16 (m, 2H), 6.79 (dd, J = 6.0, 2.4, 1H), 3.55-3.37 (m, 6H), 3.26 (t, J = 6.8, 2H), 2.95 (s, 3H), 2.70 (s, 3H), 2.44 (t, J = 5.1, 4H), 2.23 (s, 3H), 1.83 (s, 3H). |
| 174 | 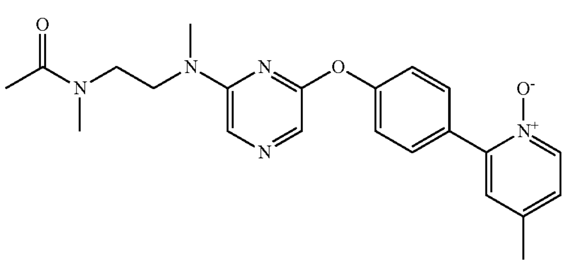 [SMILES: CC(=O)N(C)CCN(C)c1cncc(Oc2ccc(-c3cc(C)cc[n+]3[O-])cc2)n1] | B | 1.90 | N-Methyl-N-[2-(methyl-{6-[4-(4-methyl-1-oxy-pyridin-2-yl)-phenoxy]-pyrazin-2-yl}-amino)-ethyl]-acetamide | 1H NMR (400 MHz, DMSO-d6) ppm = 8.22 (d, J = 6.6, 1H), 8.00-7.89 (m, 2H), 7.85 (s, 1H), 7.60 (s, 1H), 7.50 (dd, J = 6.4, 2.5, 1H), 7.34-7.15 (m, 3H), 3.46 (t, 2H), 3.39-3.22 (m, 2H), 2.97 (s, 3H), 2.73 (s, 3H), 2.34 (s, 3H), 1.84 (s, 3H). |

TABLE 1-continued

| No | Chemical Structure | IC$_{50}$ | HPLC/MS Rt [Min] | Chemical Name | NMR data |
|---|---|---|---|---|---|
| 175 | 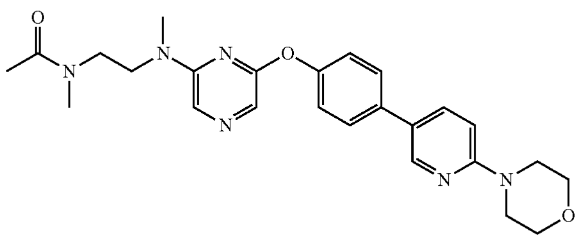 [SMILES: CC(=O)N(C)CCN(C)c1cncc(Oc2ccc(-c3ccc(N4CCOCC4)nc3)cc2)n1] | A | 1.86 | N-Methyl-N-[2-(methyl-{6-[4-(6-morpholin-4-yl-pyridin-3-yl)-phenoxy]-pyrazin-2-yl}-amino)-ethyl]-acetamide | 1H NMR (400 MHz, DMSO-d6) ppm = 8.47 (d, J = 2.7, 1H), 7.88 (dd, J = 8.8, 3.0, 1H), 7.82 (s, 1H), 7.66 (d, J = 8.6, 2H), 7.56 (s, 1H), 7.23 (d, J = 8.7, 2H), 6.92 (d, J = 8.8, 1H), 3.75-3.69 (m, 4H), 3.53-3.47 (m, 4H), 3.47-3.41 (m, 2H), 3.27-3.22 (m, 2H), 2.96 (s, 3H), 2.70 (s, 3H), 1.83 (s, 3H). |
| 176 | 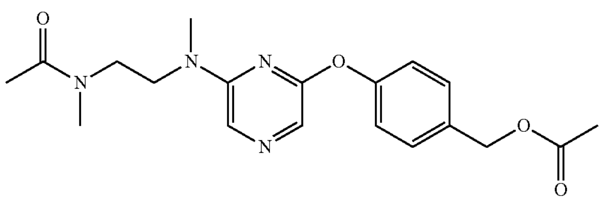 [SMILES: CC(=O)OCc1ccc(Oc2cncc(N(C)CCN(C)C(C)=O)n2)cc1] | A | 1.92 | Acetic acid 4-(6-{[2-(acetyl-methyl-amino)-ethyl]-methyl-amino}-pyrazin-2-yloxy)-benzyl ester | |
| 177 | 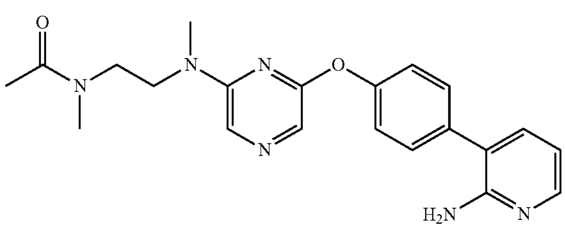 [SMILES: CC(=O)N(C)CCN(C)c1cncc(Oc2ccc(-c3cccnc3N)cc2)n1] | A | 1.69 | N-[2-({6-[4-(2-Amino-pyridin-3-yl)-phenoxy]-pyrazin-2-yl}-methyl-amino)-ethyl]-N-methyl-acetamide | 1H NMR (500 MHz, DMSO-d6) ppm = 8.00-7.93 (m, 1H), 7.83 (s, 1H), 7.58 (s, 1H), 7.48 (d, 2H), 7.34 (t, J = 7.1, 1H), 7.27 (d, 2H), 6.73-6.63 (m, 1H), 5.60 (s, 2H), 3.58-3.44 (m, 2H), 3.40-3.32 (m, 2H), 2.99 (s, 3H), 2.76 (s, 3H), 1.84 (s, 3H). |
| 178 | 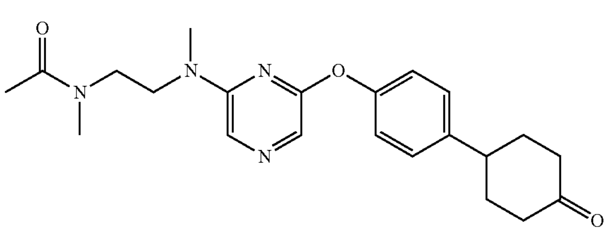 [SMILES: CC(=O)N(C)CCN(C)c1cncc(Oc2ccc(C3CCC(=O)CC3)cc2)n1] | A | 1.97 | N-Methyl-N-[2-(methyl-{6-[4-(4-oxo-cyclohexyl)-phenoxy]-pyrazin-2-yl}-amino)-ethyl]-acetamide | 1H NMR (500 MHz, DMSO-d6) ppm = 7.79 (s, 1H), 7.51 (s, 1H), 7.33 (d, J = 8.3, 2H), 7.11 (d, J = 8.5, 2H), 3.49-3.38 (m, 2H), 3.34-3.21 (m, 2H), 3.13-3.04 (m, 1H), 2.95 (s, 3H), 2.72-2.52 (m, 5H), 2.33-2.23 (m, 2H), 2.14-2.01 (m, 2H), 1.95-1.84 (m, 2H), 1.84 (s, 3H). |

TABLE 1-continued

| No | Chemical Structure | IC$_{50}$ | HPLC/MS Rt [Min] | Chemical Name | NMR data |
|---|---|---|---|---|---|
| 179 | 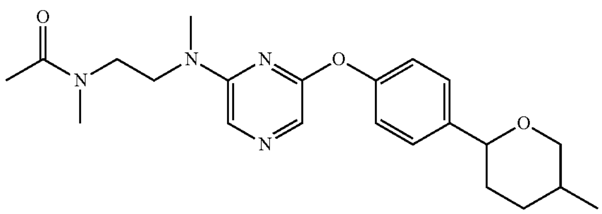 [SMILES: CC(=O)N(C)CCN(C)c1cncc(Oc2ccc(C3CCC(C)CO3)cc2)n1] | A | 2.33 | N-Methyl-N-[2-(methyl-{6-[4-(5-methyl-tetrahydro-pyran-2-yl)-phenoxy]-pyrazin-2-yl}-amino)-ethyl]-acetamide | 1H NMR (500 MHz, DMSO-d6) ppm = 7.81 (s, 1H), 7.53 (s, 1H), 7.36 (d, J = 8.5, 2H), 7.12 (d, J = 8.5, 2H), 4.27 (dt, J = 11.2, 1.9, 1H), 3.94 (ddd, J = 11.1, 4.4, 2.0, 1H), 3.49-3.40 (m, 2H), 3.34-3.31 (m, 1H), 3.29-3.22 (m, 1H), 3.17-3.02 (m, 1H), 2.95 (s, 3H), 2.56 (s, 3H), 1.94-1.72 (m, 5H), 1.72-1.63 (m, 1H), 1.48 (dddt, J = 21.5, 13.0, 6.5, 3.6, 1H), 1.30 (qd, J = 12.6, 3.6, 1H), 0.82 (d, J = 6.6, 3H). |
| 180 | 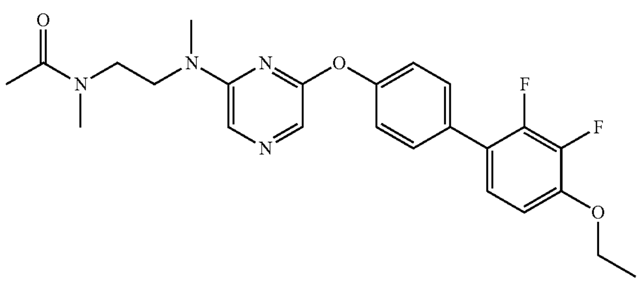 [SMILES: CCOc1ccc(-c2ccc(Oc3cncc(N(C)CCN(C)C(C)=O)n3)cc2)c(F)c1F] | B | 2.43 | N-(2-{[6-(4'-Ethoxy-2',3'-difluoro-biphenyl-4-yloxy)-pyrazin-2-yl]-methyl-amino}-ethyl)-N-methyl-acetamide | 1H NMR (500 MHz, DMSO-d6) ppm = 7.85 (s, 1H), 7.61 (s, 1H), 7.58 (d, J = 7.7, 2H), 7.34-7.23 (m, 3H), 7.16-7.08 (m, 1H), 4.21 (q, J = 7.0, 2H), 3.55-3.41 (m, 2H), 3.30-3.24 (m, 2H), 2.97 (s, 3H), 2.71 (s, 3H), 1.85 (s, 3H), 1.39 (t, J = 7.0, 3H). |
| 181 | 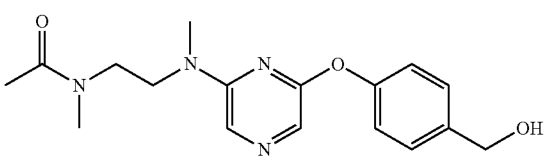 [SMILES: CC(=O)N(C)CCN(C)c1cncc(Oc2ccc(CO)cc2)n1] | A | 1.57 | N-(2-{[6-(4-Hydroxymethyl-phenoxy)-pyrazin-2-yl]-methyl-amino}-ethyl)-N-methyl-acetamide | 1H NMR (400 MHz, DMSO-d6) ppm = 7.79 (s, 1H), 7.52 (s, 1H), 7.35 (d, J = 8.2, 2H), 7.13 (d, J = 8.6, 2H), 5.19 (td, J = 5.7, 3.5, 1H), 4.54-4.45 (m, 2H), 3.51-3.39 (m, 2H), 3.32-3.22 (m, 2H), 2.95 (s, 3H), 2.71 (s, 3H), 1.86 (s, 3H). |
| 182 | 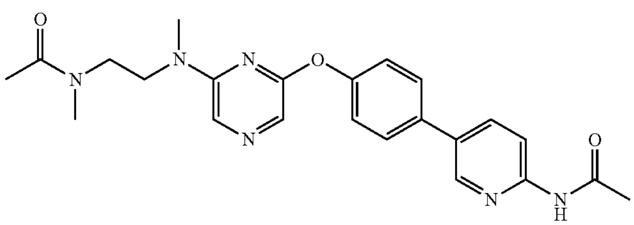 [SMILES: CC(=O)Nc1ccc(-c2ccc(Oc3cncc(N(C)CCN(C)C(C)=O)n3)cc2)cn1] | A | 1.82 | N-{5-[4-(6-{[2-(Acetyl-methyl-amino)-ethyl]-methyl-amino}-pyrazin-2-yloxy)-phenyl]-pyridin-2-yl}-acetamide | 1H NMR (500 MHz, DMSO-d6) ppm = 10.56 (s, 1H), 8.64 (d, J = 2.9, 1H), 8.15 (d, J = 8.6, 1H), 8.08 (dd, J = 8.7, 2.6, 1H), 7.84 (s, 1H), 7.75 (d, J = 8.6, 2H), 7.59 (s, 1H), 7.28 (d, J = 8.6, 2H), 3.53-3.40 (m, 2H), 3.37-3.21 (m, 2H), 2.96 (s, 3H), 2.55 (s, 3H), 2.12 (s, 3H), 1.83 (s, 3H). |

TABLE 1-continued

| No | Chemical Structure | IC$_{50}$ | HPLC/MS Rt [Min] | Chemical Name | NMR data |
|---|---|---|---|---|---|
| 183 | 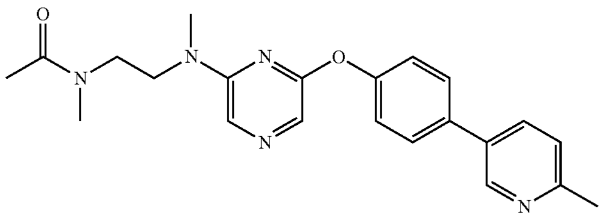 [SMILES: CC(=O)N(C)CCN(C)c1cncc(Oc2ccc(-c3ccc(C)nc3)cc2)n1] | A | 1.48 | N-Methyl-N-[2-(methyl-{6-[4-(6-methyl-pyridin-3-yl)-phenoxy]-pyrazin-2-yl}-amino)-ethyl]-acetamide | 1H NMR (400 MHz, DMSO-d6) ppm = 8.76 (d, J = 2.3, 1H), 7.96 (dd, J =8.0, 2.6, 1H), 7.84 (s, 1H), 7.74 (d, J = 8.6, 2H), 7.59 (s, 1H), 7.34 (d, J = 8.1, 1H), 7.29 (d, J = 8.7, 2H), 3.56-3.40 (m, 2H), 3.40-3.20 (m, 2H), 2.96 (s, 3H), 2.70 (s, 3H), 2.51 (s, 3H), 1.83 (s, 3H). |
| 184 | 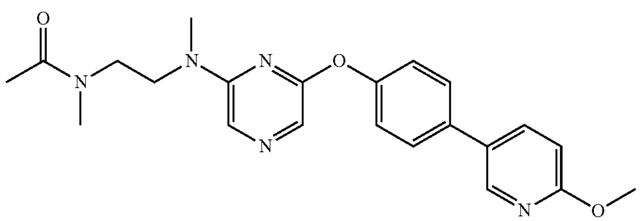 [SMILES: COc1ccc(-c2ccc(Oc3cncc(N(C)CCN(C)C(C)=O)n3)cc2)cn1] | A | 2.21 | N-[2-({6-[4-(6-Methoxy-pyridin-3-yl)-phenoxy]-pyrazin-2-yl}-methyl-amino)-ethyl]-N-methyl-acetamide | 1H NMR (400 MHz, DMSO-d6) ppm = 8.48 (d, J = 2.8, 1H), 8.01 (dd, J = 8.6, 2.8, 1H), 7.83 (s, 1H), 7.70 (d, J = 8.4, 2H), 7.58 (s, 1H), 7.24 (d, J = 8.7, 2H), 6.91 (d, J = 8.6, 1H), 3.90 (s, 3H), 3.49-3.40 (m, 2H), 3.37-3.18 (m, 2H), 2.96 (s, 3H), 2.70 (s, 3H), 1.83 (s, 3H). |
| 185 | 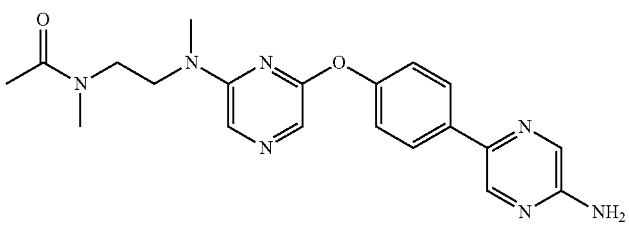 [SMILES: CC(=O)N(C)CCN(C)c1cncc(Oc2ccc(-c3cnc(N)cn3)cc2)n1] | A | 1.71 | N-[2-({6-[4-(5-Amino-pyrazin-2-yl)-phenoxy]-pyrazin-2-yl}-methyl-amino)-ethyl]-N-methyl-acetamide | 1H NMR (400 MHz, DMSO-d6) ppm = 8.49 (s, 1H), 8.00-7.91 (m, 3H), 7.81 (s, 1H), 7.57 (s, 1H), 7.21 (d, J = 8.8, 2H), 6.50 (s, 2H), 3.52-3.37 (m, 2H), 3.35-3.31 (m, 2H), 2.95 (s, 3H), 2.70 (s, 3H), 1.83 (s, 3H). |
| 186 | 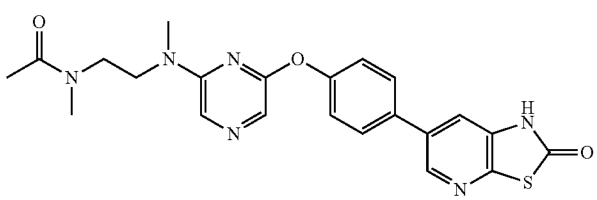 [SMILES: CC(=O)N(C)CCN(C)c1cncc(Oc2ccc(-c3cnc4sc(=O)[nH]c4c3)cc2)n1] | A | 2.14 | N-Methyl-N-[2-(methyl-{6-[4-(2-oxo-1,2-dihydro-thiazolo[5,4-b]pyridin-6-yl)-phenoxy]-pyrazin-2-yl}-amino)-ethyl]-acetamide | 1H NMR (400 MHz, DMSO-d6) ppm = 11.96 (s, 1H), 7.84 (s, 1H), 7.73-7.57 (m, 4H), 7.44-7.39 (m, 1H), 7.33-7.20 (m, 3H), 3.49-3.42 (m, 2H), 3.36-3.32 (m, 2H), 2.96 (s, 3H), 2.70 (s, 3H), 1.84 (s, 3H). |
| 187 | 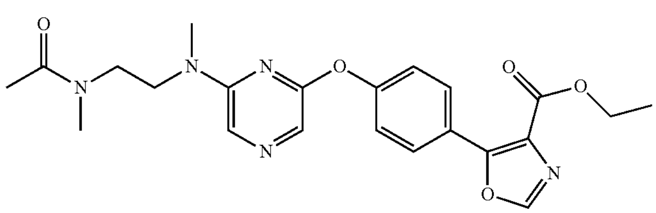 [SMILES: CCOC(=O)c1ncoc1-c1ccc(Oc2cncc(N(C)CCN(C)C(C)=O)n2)cc1] | B | 2.04 | 5-[4-(6-{[2-(Acetyl-methyl-amino)-ethyl]-methyl-amino}-pyrazin-2-yloxy)-phenyl]-oxazole-4-carboxylic acid ethyl ester | 1H NMR (500 MHz, DMSO-d6) ppm = 8.55 (s, 1H), 8.02 (d, J = 8.8, 2H), 7.88 (s, 1H), 7.63 (s, 1H), 7.34 (d, J = 8.8, 2H), 4.30 (q, J = 7.1, 2H), 3.57-3.37 (m, 2H), 3.37-3.19 (m, 2H), 2.96 (s, 3H), 2.56 (s, 3H), 1.83 (s, 3H), 1.27 (t, J = 7.1, 3H). |

TABLE 1-continued

| No | Chemical Structure | IC$_{50}$ | HPLC/MS Rt [Min] | Chemical Name | NMR data |
|---|---|---|---|---|---|
| 188 | 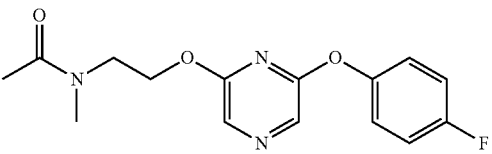 | C | 1.99 | N-{2-[6-(4-Fluoro-phenoxy)-pyrazin-2-yloxy]-ethyl}-N-methyl-acetamide | 1H NMR (500 MHz, DMSO-d6) ppm = 8.02 (s, 1H), 8.01 (s, 1H), 7.34-7.22 (m, 4H), 4.17 (t, J = 5.8, 2H), 3.52 (t, J = 5.7, 2H), 2.90 (s, 3H), 1.94 (s, 3H). |
| 189 | 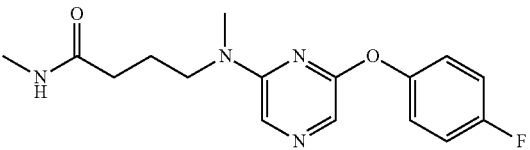 [SMILES: CNC(=O)CCCN(C)c1cncc(Oc2ccc(F)cc2)n1] | C | 1.96 | 4-{[6-(4-Fluoro-phenoxy)-pyrazin-2-yl]-methyl-amino}-N-methyl-butyramide | 1H NMR (400 MHz, DMSO-d6) ppm = 7.80 (s, 1H), 7.64 (s, 1H), 7.49 (s, 1H), 7.27-7.15 (m, 4H), 3.34-3.29 (m, 2H), 2.90 (s, 3H), 2.55 (s, 3H), 1.96 (t, J = 7.4, 2H), 1.65 (p, J = 7.5, 2H). |
| 190 | 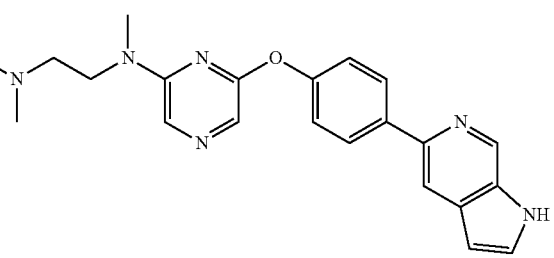 | A | 1.48 | N-Methyl-N-[2-(methyl-{6-[4-(1H-pyrrolo[2,3-c]pyridin-5-yl)-phenoxy]-pyrazin-2-yl}-amino)-ethyl]-acetamide | 1H NMR (500 MHz, DMSO-d6) ppm = 11.60 (s, 1H), 8.82 (s, 1H), 8.12 (d, J = 8.2, 2H), 8.09 (s, 1H), 7.83 (s, 1H), 7.64 (d, J = 14.7, 1H), 7.58 (d, 1H), 7.23 (d, J = 8.4, 2H), 6.55 (s, 1H), 3.52-3.41 (m, 2H), 3.31-3.22 (m, 2H), 2.96 (s, 3H), 2.55 (s, 3H), 1.82 (s, 3H). |
| 191 | 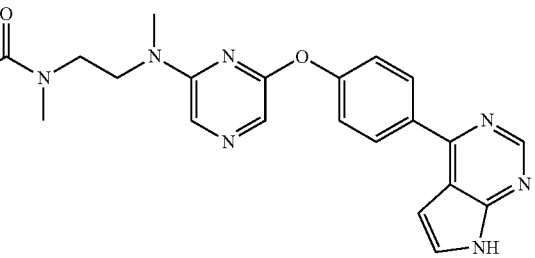 | A | 1.65 | N-Methyl-N-[2-(methyl-{6-[4-(7H-pyrrolo[2,3-d]pyrimidin-4-yl)-phenoxy]-pyrazin-2-yl}-amino)-ethyl]-acetamide | 1H NMR (500 MHz, DMSO-d6) ppm = 12.24 (s, 1H), 8.82 (s, 1H), 8.26 (d, J = 8.8, 2H), 7.88 (s, 1H), 7.75-7.60 (m, 2H), 7.38 (d, J = 8.7, 2H), 6.95-6.87 (m, 1H), 3.55-3.40 (m, 2H), 3.37-3.31 (m, 2H), 2.97 (s, 3H), 2.70 (s, 3H), 1.82 (s, 3H). |
| 192 | 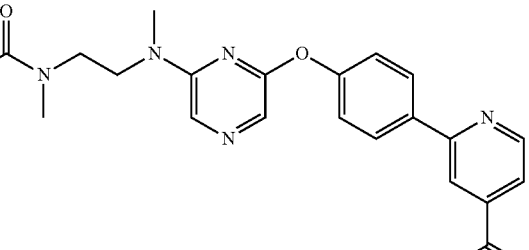 | B | 1.67 | 2-[4-(6-{[2-(Acetyl-methyl-amino)-ethyl]-methyl-amino}-pyrazin-2-yloxy)-phenyl]-isonico-tinamide | 1H NMR (500 MHz, DMSO-d6) ppm = 8.78 (d, J = 5.0, 1H), 8.32 (s, 2H), 8.20 (d, J = 8.8, 2H), 7.86 (s, 1H), 7.75 (s, 1H), 7.71 (d, J = 5.0, 1H), 7.61 (s, 1H), 7.32 (d, J = 8.7, 2H), 3.52-3.40 (m, 2H), 3.36-3.31 (m, 2H), 2.96 (s, 3H), 2.71 (s, 3H), 1.82 (s, 3H). |

| No | Chemical Structure | IC$_{50}$ | HPLC/MS Rt [Min] | Chemical Name | NMR data |
|---|---|---|---|---|---|
| 193 | 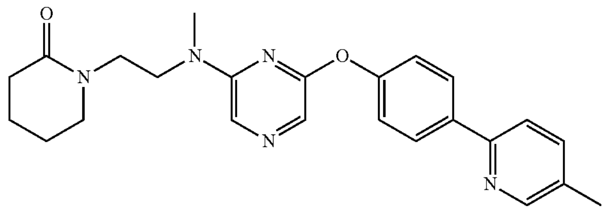 [SMILES: Cc1ccc(-c2ccc(Oc3cncc(N(C)CCN4CCCCC4=O)n3)cc2)nc1] | A | 1.96 | 1-[2-(Methyl-{6-[4-(5-methyl-pyridin-2-yl)-phenoxy]-pyrazin-2-yl}-amino)-ethyl]-piperidin-2-one | 1H NMR (500 MHz, DMSO-d6) ppm = 8.51-8.47 (m, 1H), 8.12 (d, J = 8.7, 2H), 7.87 (d, J = 8.1, 1H), 7.81 (s, 1H), 7.69 (dd, J = 8.1, 1.6, 1H), 7.60 (s, 1H), 7.26 (d, J = 8.7, 2H), 3.46 (t, J = 6.5, 2H), 3.30-3.26 (m, 2H), 2.97 (s, 3H), 2.92 (t, J = 5.4, 2H), 2.34 (s, 3H), 2.03 (t, J = 6.5, 2H), 1.57-1.37 (m, 4H). |
| 194 | 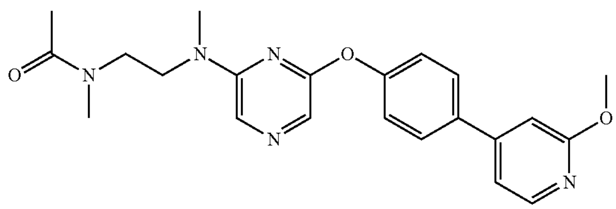 [SMILES: COc1cc(-c2ccc(Oc3cncc(N(C)CCN(C)C(C)=O)n3)cc2)ccn1] | B | 2.17 | N-[2-({6-[4-(2-Methoxy-pyridin-4-yl)-phenoxy]-pyrazin-2-yl}-methyl-amino)-ethyl]-N-methyl-acetamide | 1H NMR (500 MHz, DMSO-d6) ppm = 8.22 (d, J = 5.3, 1H), 7.91-7.80 (m, 3H), 7.60 (s, 1H), 7.38-7.20 (m, 3H), 7.17-7.05 (m, 1H), 3.90 (s, 3H), 3.52-3.40 (m, 2H), 3.30 (s, 2H), 2.96 (s, 3H), 2.54 (s, 3H), 1.83 (s, 3H). |
| 195 | 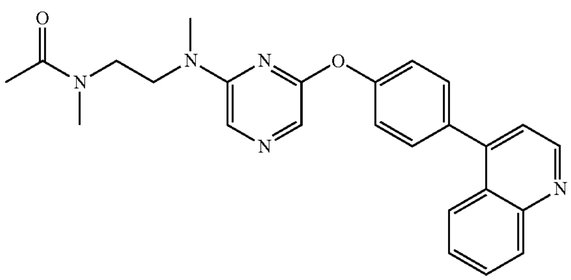 [SMILES: CC(=O)N(C)CCN(C)c1cncc(Oc2ccc(-c3ccnc4ccccc34)cc2)n1] | A | 1.83 | N-Methyl-N-(2-{methyl-[6-(4-quinolin-4-yl-phenoxy)-pyrazin-2-yl]-amino}-ethyl)-acetamide | 1H NMR (500 MHz, DMSO-d6) ppm = 8.96 (d, J = 4.4, 1H), 8.12 (d, J = 8.3, 1H), 7.91 (t, J = 8.1, 1H), 7.88 (s, 1H), 7.81 (t, J = 7.6, 1H), 7.65 (s, 1H), 7.64-7.59 (m, 3H), 7.49 (d, J = 4.4, 1H), 7.40 (d, J = 8.6, 2H), 3.59-3.46 (m, 2H), 3.42-3.32 (m, 2H), 2.99 (s, 3H), 2.76 (s, 3H), 1.84 (s, 3H). |
| 196 | 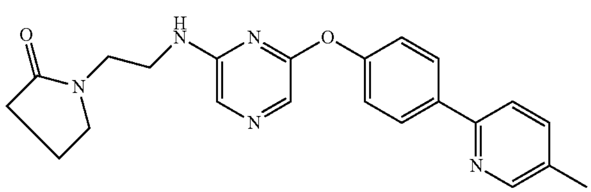 [SMILES: Cc1ccc(-c2ccc(Oc3cncc(NCCN4CCCC4=O)n3)cc2)nc1] | A | 1.69 | 1-(2-{6-[4-(5-Methyl-pyridin-2-yl)-phenoxy]-pyrazin-2-ylamino}-ethyl)-pyrrolidin-2-one | 1H NMR (500 MHz, DMSO-d6) ppm = 8.49 (s, 1H), 8.10 (d, J = 8.3, 2H), 7.85 (d, J = 8.1, 1H), 7.69 (dd, J = 8.0, 2.4, 1H), 7.65 (s, 1H), 7.47 (s, 1H), 7.25 (d, J = 8.5, 2H), 3.27-3.13 (m, 5H), 3.09 (t, J = 7.0, 2H), 2.33 (s, 3H), 2.09 (t, J = 8.1, 2H), 1.72 (p, J = 7.5, 2H). |
| 197 | 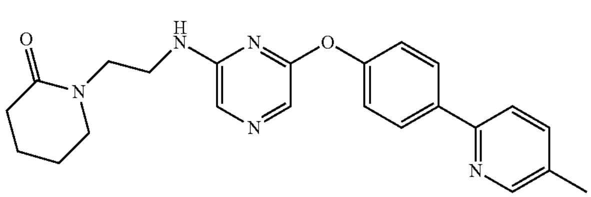 [SMILES: Cc1ccc(-c2ccc(Oc3cncc(NCCN4CCCCC4=O)n3)cc2)nc1] | A | 1.84 | 1-(2-{6-[4-(5-Methyl-pyridin-2-yl)-phenoxy]-pyrazin-2-ylamino}-ethyl)-piperidin-2-one | 1H NMR (400 MHz, DMSO-d6) ppm = 8.49 (s, 1H), 8.10 (d, J = 8.5, 2H), 7.86 (d, J = 8.1, 1H), 7.69 (d, J = 8.2, 1H), 7.64 (s, 1H), 7.49 (s, 1H), 7.30 (t, J = 5.3, 1H), 7.24 (d, J = 8.3, 2H), 3.27-3.15 (m, 4H), 2.91 (t, J = 6.0, 2H), 2.34 (s, 3H), 2.09 (t, J = 6.4, 2H), 1.59-1.47 (m, 2H), 1.47-1.36 (m, 2H). |

TABLE 1-continued

| No | Chemical Structure | IC$_{50}$ | HPLC/MS Rt [Min] | Chemical Name | NMR data |
|---|---|---|---|---|---|
| 198 | 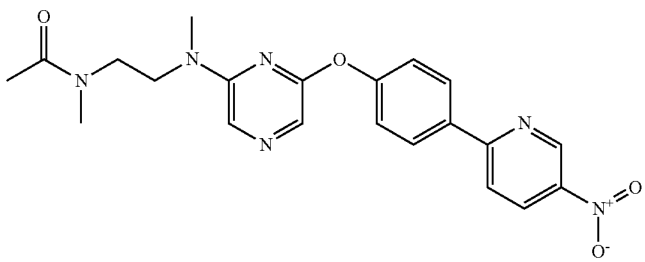 [SMILES: CC(=O)N(C)CCN(C)c1cncc(Oc2ccc(-c3ccc([N+](=O)[O-])cn3)cc2)n1] | A | 2.24 | N-Methyl-N-[2-(methyl-{6-[4-(5-nitro-pyridin-2-yl)-phenoxy]-pyrazin-2-yl}-amino)-ethyl]-acetamide | 1H NMR (400 MHz, DMSO-d6) ppm = 9.44 (d, J = 2.6, 1H), 8.72-8.57 (m, 1H), 8.34-8.24 (m, 3H), 7.88 (s, 1H), 7.64 (s, 1H), 7.36 (d, J = 8.8, 2H), 3.51-3.42 (m, 2H), 3.29-3.23 (m, 2H), 2.96 (s, 3H), 2.71 (s, 3H), 1.83 (s, 3H). |
| 199 | 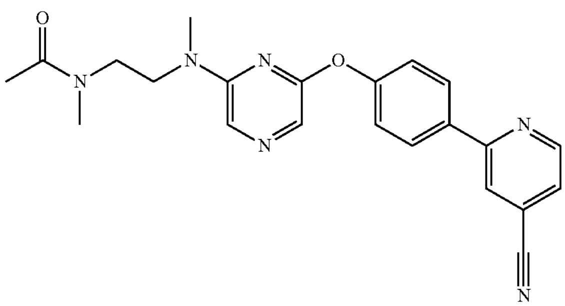 [SMILES: CC(=O)N(C)CCN(C)c1cncc(Oc2ccc(-c3cc(C#N)ccn3)cc2)n1] | A | 2.12 | N-[2-({6-[4-(4-Cyano-pyridin-2-yl)-phenoxy]-pyrazin-2-yl}-methyl-amino)-ethyl]-N-methyl-acetamide | 1H NMR (400 MHz, DMSO-d6) ppm = 8.89 (d, J = 5.0, 1H), 8.49 (s, 1H), 8.22 (d, J = 8.8, 2H), 7.87 (s, 1H), 7.79 (d, J = 5.0, 1H), 7.62 (s, 1H), 7.32 (d, J = 8.8, 2H), 3.45 (t, J = 6.8, 2H), 3.33 (t, J = 6.5, 2H), 2.96 (s, 3H), 2.71 (s, 3H), 1.83 (s, 3H). |
| 200 | 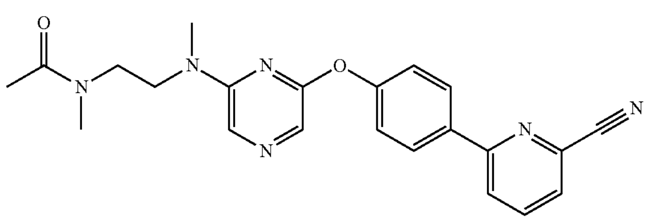 [SMILES: CC(=O)N(C)CCN(C)c1cncc(Oc2ccc(-c3cccc(C#N)n3)cc2)n1] | A | 2.16 | N-[2-({6-[4-(6-Cyano-pyridin-2-yl)-phenoxy]-pyrazin-2-yl}-methyl-amino)-ethyl]-N-methyl-acetamide | 1H NMR (400 MHz, DMSO-d6) ppm = 8.32 (d, J = 8.1, 1H), 8.21-8.11 (m, 3H), 7.98 (d, J = 7.6, 1H), 7.87 (s, 1H), 7.62 (s, 1H), 7.34 (d, J = 8.7, 2H), 3.52-3.43 (m, 2H), 3.31-3.25 (m, 2H), 2.96 (s, 3H), 2.71 (s, 3H), 1.83 (s, 3H). |
| 201 | 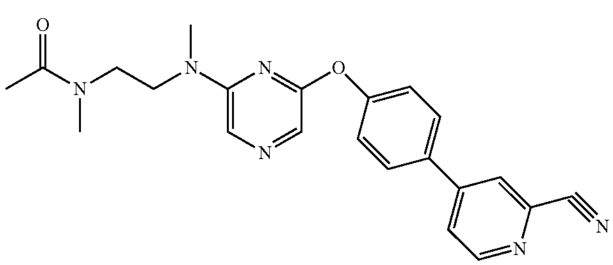 [SMILES: CC(=O)N(C)CCN(C)c1cncc(Oc2ccc(-c3ccnc(C#N)c3)cc2)n1] | A | 2.07 | N-[2-({6-[4-(2-Cyano-pyridin-4-yl)-phenoxy]-pyrazin-2-yl}-methyl-amino)-ethyl]-N-methyl-acetamide | 1H NMR (400 MHz, DMSO-d6) ppm = 9.12 (d, J = 1.6, 1H), 8.36 (d, J = 8.2, 1H), 8.12 (dd, J = 8.2, 1.3, 1H), 7.91 (d, J = 8.8, 2H), 7.86 (s, 1H), 7.61 (s, 1H), 7.33 (d, J = 8.7, 2H), 3.57-3.41 (m, 2H), 3.41-3.17 (m, 2H), 2.96 (s, 3H), 2.71 (s, 3H), 1.83 (s, 3H). |
| 202 | 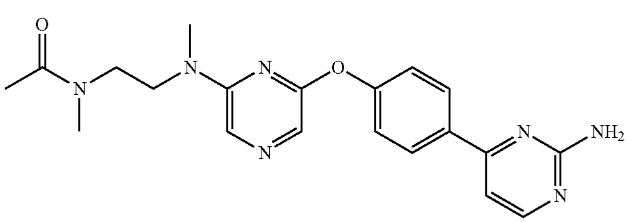 [SMILES: CC(=O)N(C)CCN(C)c1cncc(Oc2ccc(-c3ccnc(N)n3)cc2)n1] | A | 1.57 | N-[2-({6-[4-(2-Amino-pyrimidin-4-yl)-phenoxy]-pyrazin-2-yl}-methyl-amino)-ethyl]-N-methyl-acetamide | 1H NMR (400 MHz, DMSO-d6) ppm = 8.30 (d, J = 5.2, 1H), 8.12 (d, J = 8.8, 2H), 7.86 (s, 1H), 7.61 (s, 1H), 7.29 (d, J = 8.7, 2H), 7.12 (d, J = 5.2, 1H), 6.62 (s, 2H), 3.61-3.40 (m, 2H), 3.40-3.18 (m, 2H), 2.95 (s, 3H), 2.70 (s, 3H), 1.83 (s, 3H). |

TABLE 1-continued

| No | Chemical Structure | IC$_{50}$ | HPLC/MS Rt [Min] | Chemical Name | NMR data |
|---|---|---|---|---|---|
| 203 | 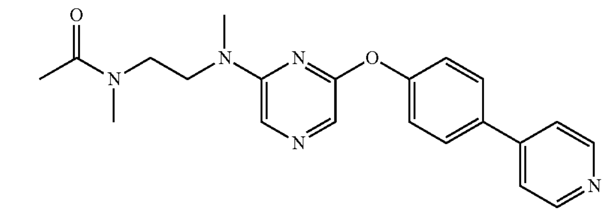 [SMILES: CC(=O)N(C)CCN(C)c1cncc(Oc2ccc(-c3ccncc3)cc2)n1] | A | 1.42 | N-Methyl-N-(2-{methyl-[6-(4-pyridin-4-yl-phenoxy)-pyrazin-2-yl]-amino}-ethyl)-acetamide | 1H NMR (400 MHz, DMSO-d6) ppm = 8.63 (d, J = 4.8, 2H), 7.94-7.79 (m, 3H), 7.71 (d, J = 4.1, 2H), 7.61 (s, 1H), 7.33 (d, J = 8.7, 2H), 3.59-3.40 (m, 2H), 3.39-3.17 (m, 2H), 2.96 (s, 3H), 2.70 (s, 3H), 1.83 (s, 3H). |
| 204 | 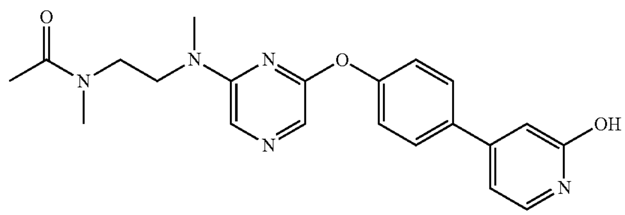 [SMILES: CC(=O)N(C)CCN(C)c1cncc(Oc2ccc(-c3ccnc(O)c3)cc2)n1] | B | 1.65 | N-[2-({6-[4-(2-Hydroxy-pyridin-4-yl)-phenoxy]-pyrazin-2-yl}-methyl-amino)-ethyl]-N-methyl-acetamide | 1H NMR (400 MHz, DMSO-d6) ppm = 11.57 (s, 1H), 7.85 (s, 1H), 7.75 (d, J = 8.6, 2H), 7.60 (s, 1H), 7.44 (d, J = 6.8, 1H), 7.27 (d, J = 8.7, 2H), 6.59-6.56 (m, 1H), 6.55-6.45 (m, 1H), 3.50-3.40 (m, 2H), 3.35-3.22 (m, 2H), 2.96 (s, 3H), 2.54 (s, 3H), 1.84 (s, 3H). |
| 205 | 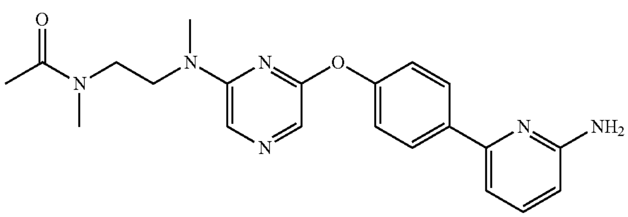 [SMILES: CC(=O)N(C)CCN(C)c1cncc(Oc2ccc(-c3cccc(N)n3)cc2)n1] | A | 1.40 | N-[2-({6-[4-(6-Amino-pyridin-2-yl)-phenoxy]-pyrazin-2-yl}-methyl-amino)-ethyl]-N-methyl-acetamide | 1H NMR (500 MHz, DMSO-d6) ppm = 8.01 (d, J = 8.7, 2H), 7.83 (d, J = 7.6, 1H), 7.58 (s, 1H), 7.45 (t, J = 7.8, 1H), 7.22 (d, J = 8.7, 2H), 7.04 (d, J = 7.4, 1H), 6.42 (s, 1H), 5.95 (s, 2H), 3.54-3.38 (m, 2H), 3.37-3.21 (m, 2H), 2.95 (s, 3H), 2.70 (s, 3H), 1.83 (s, 3H). |
| 206 | 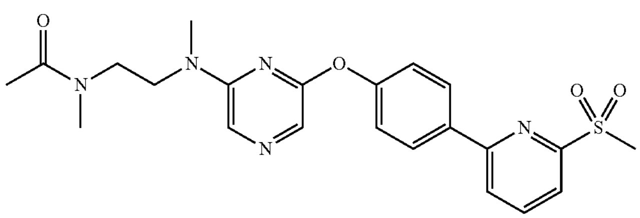 [SMILES: CC(=O)N(C)CCN(C)c1cncc(Oc2ccc(-c3cccc(S(C)(=O)=O)n3)cc2)n1] | A | 1.96 | N-[2-({6-[4-(6-Methane-sulfonyl-pyridin-2-yl)-phenoxy]-pyrazin-2-yl}-methyl-amino)-ethyl]-N-methyl-acetamide | 1H NMR (500 MHz, DMSO-d6) ppm = 8.32 (s, 1H), 8.25 (d, J = 9.0, 2H), 8.24-8.22 (m, 1H), 7.99 (d, J = 7.6, 1H), 7.87 (d, J = 7.3, 1H), 7.63 (s, 1H), 7.37 (d, J = 8.7, 2H), 3.48 (dt, J = 13.7, 6.5, 2H), 3.39 (s, 3H), 3.36-3.26 (m, 2H), 2.97 (s, 3H), 2.73 (s, 3H), 1.84 (s, 3H). |
| 207 | 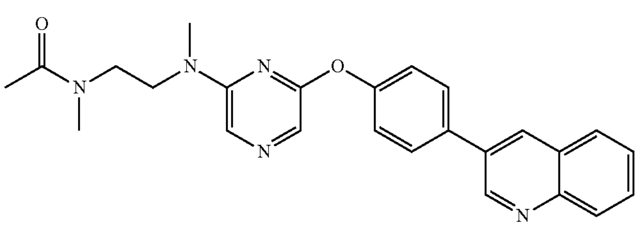 [SMILES: CC(=O)N(C)CCN(C)c1cncc(Oc2ccc(-c3cnc4ccccc4c3)cc2)n1] | B | 2.07 | N-Methyl-N-(2-{methyl-[6-(4-quinolin-3-yl-phenoxy)-pyrazin-2-yl]-amino}-ethyl)-acetamide | 1H NMR (400 MHz, DMSO-d6) ppm = 9.27 (t, J = 2.5, 1H), 8.71-8.62 (m, 1H), 8.07 (d, J = 8.4, 2H), 7.95 (d, J = 8.7, 2H), 7.86 (s, 1H), 7.78 (dd, J = 8.4, 7.1, 1H), 7.66 (dd, J = 8.1, 6.9, 1H), 7.62 (s, 1H), 7.37 (d, J = 8.6, 2H), 3.53-3.41 (m, 2H), 3.33-3.24 (m, 2H), 2.98 (s, 3H), 2.72 (s, 3H), 1.83 (s, 3H). |

TABLE 1-continued

| No | Chemical Structure | IC$_{50}$ | HPLC/MS Rt [Min] | Chemical Name | NMR data |
|---|---|---|---|---|---|
| 208 | 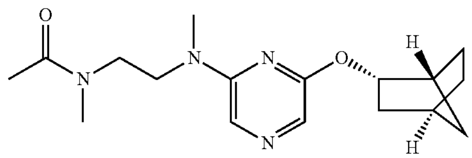 | C | 2.26 | N-(2-{[6-((1R,2S,4S)-Bicyclo[2.2.1]hept-2-yloxy)-pyrazin-2-yl]-methyl-amino}-ethyl)-N-methyl-acetamide | 1H NMR (500 MHz, DMSO-d6) ppm = 7.58 (s, 1H), 7.37 (s, 1H), 5.17-4.95 (m, 1H), 3.72-3.40 (m, 4H), 3.01 (s, 3H), 2.94 (s, 3H), 2.61-2.54 (m, 1H), 2.26-2.18 (m, 1H), 2.15-1.98 (m, 1H), 1.90 (s, 3H), 1.82-1.72 (m, 1H), 1.62-1.48 (m, 1H), 1.48-1.38 (m, 1H), 1.38-1.23 (m, 3H), 1.06-0.95 (m, 1H). |
| 209 | 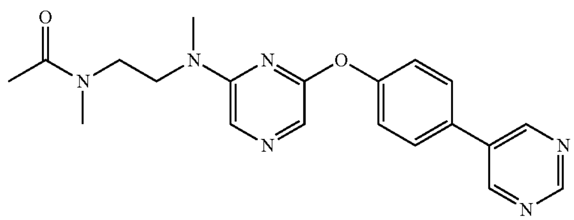 [SMILES: CC(=O)N(C)CCN(C)c1cncc(Oc2ccc(-c3cncnc3)cc2)n1] | A | 1.77 | N-Methyl-N-(2-{methyl-[6-(4-pyrimidin-5-yl-phenoxy)-pyrazin-2-yl]-amino}-ethyl)-acetamide | 1H NMR (400 MHz, DMSO-d6) ppm = 9.18 (s, 1H), 9.16 (s, 2H), 7.95-7.78 (m, 3H), 7.61 (s, 1H), 7.33 (d, J = 11.4, 2H), 3.45 (t, J = 6.5, 2H), 3.39-3.21 (m, 2H), 2.96 (s, 3H), 2.71 (s, 3H), 1.84 (s, 3H). |
| 210 | 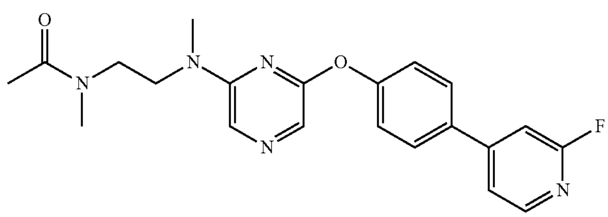 [SMILES: CC(=O)N(C)CCN(C)c1cncc(Oc2ccc(-c3ccnc(F)c3)cc2)n1] | A | 2.11 | N-[2-({6-[4-(2-Fluoro-pyridin-4-yl)-phenoxy]-pyrazin-2-yl}-methyl-amino)-ethyl]-N-methyl-acetamide | 1H NMR (400 MHz, DMSO-d6) ppm = 8.30 (dd, J = 5.3, 1.7, 1H), 7.93 (d, J = 8.8, 2H), 7.86 (d, J = 4.9, 1H), 7.76-7.68 (m, 1H), 7.62 (s, 1H), 7.55 (s, 1H), 7.34 (d, J = 8.8, 2H), 3.52-3.39 (m, 2H), 3.34-3.25 (m, 2H), 2.96 (s, 3H), 2.70 (s, 3H), 1.83 (s, 3H). |
| 211 | 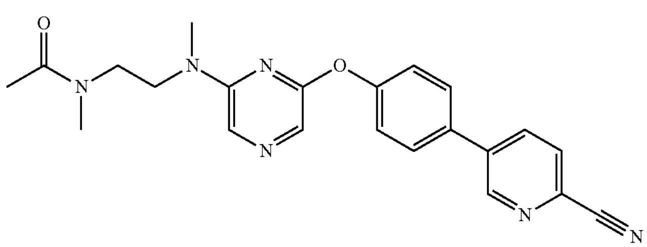 [SMILES: CC(=O)N(C)CCN(C)c1cncc(Oc2ccc(-c3ccc(C#N)nc3)cc2)n1] | A | 2.07 | N-[2-({6-[4-(6-Cyano-pyridin-3-yl)-phenoxy]-pyrazin-2-yl}-methyl-amino)-ethyl]-N-methyl-acetamide | 1H NMR (500 MHz, DMSO-d6) ppm = 9.12 (t, J = 2.2, 1H), 8.36 (dt, J = 8.2, 2.4, 1H), 8.12 (ddd, J = 8.1, 2.6, 0.8, 1H), 7.90 (d, J = 8.8, 2H), 7.86 (s, 1H), 7.61 (s, 1H), 7.35 (d, J = 8.7, 2H), 3.51-3.41 (m, 2H), 3.39-3.21 (m, 2H), 2.96 (s, 3H), 2.56 (s, 3H), 1.83 (s, 3H). |
| 212 | 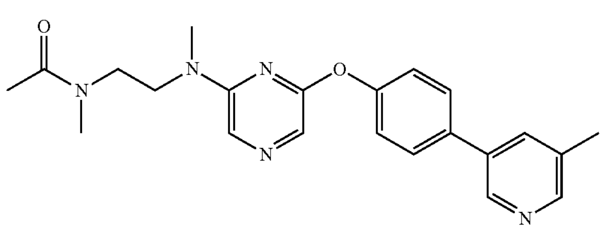 [SMILES: CC(=O)N(C)CCN(C)c1cncc(Oc2ccc(-c3cncc(C)c3)cc2)n1] | B | 1.58 | N-Methyl-N-[2-(methyl-{6-[4-(5-methyl-pyridin-3-yl)-phenoxy]-pyrazin-2-yl}-amino)-ethyl]-acetamide | 1H NMR (500 MHz, DMSO-d6) ppm = 8.70 (t, J = 2.8, 1H), 8.44-8.38 (m, 1H), 7.91 (d, J = 2.5, 1H), 7.85 (s, 1H), 7.77 (d, J = 8.7, 2H), 7.60 (s, 1H), 7.31 (d, J = 8.6, 2H), 3.47 (dt, J = 12.3, 6.6, 2H), 3.29 (dt, 2H), 2.97 (s, 3H), 2.56 (s, 3H), 2.39 (s, 3H), 1.84 (s, 3H). |

TABLE 1-continued

| No | Chemical Structure | IC$_{50}$ | HPLC/MS Rt [Min] | Chemical Name | NMR data |
|---|---|---|---|---|---|
| 213 | 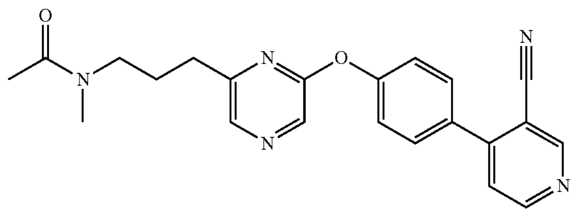 [SMILES: CC(=O)N(C)CCCc1cncc(Oc2ccc(-c3ccncc3C#N)cc2)n1] | B | 1.92 | N-(3-{6-[4-(3-Cyano-pyridin-4-yl)-phenoxy]-pyrazin-2-yl}-propyl)-N-methyl-acetamide | 1H NMR (400 MHz, DMSO-d6) ppm = 9.11 (s, 1H), 8.95-8.84 (m, 1H), 8.47-8.31 (m, 2H), 7.83-7.69 (m, 3H), 7.48-7.39 (m, 2H), 3.24 (t, 2H), 2.85 (s, 3H), 2.63 (t, J = 7.5, 2H), 1.92 (s, 3H), 1.76 (p, J = 7.3, 2H). |
| 214 | 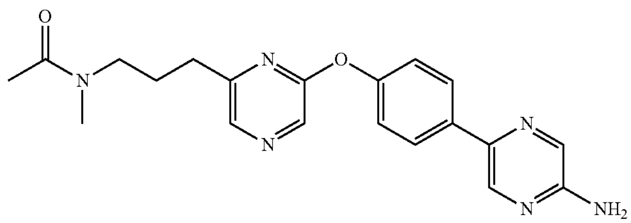 [SMILES: CC(=O)N(C)CCCc1cncc(Oc2ccc(-c3cnc(N)cn3)cc2)n1] | B | 1.70 | N-(3-{6-[4-(5-Amino-pyrazin-2-yl)-phenoxy]-pyrazin-2-yl}-propyl)-N-methyl-acetamide | 1H NMR (400 MHz, DMSO-d6) ppm = 8.51 (d, J = 1.5, 1H), 8.33 (s, 1H), 8.30 (s, 1H), 8.03-7.88 (m, 3H), 7.24 (d, J = 8.8, 2H), 6.52 (s, 2H), 3.29-3.15 (m, 2H), 2.85 (s, 3H), 2.60 (t, J = 7.5, 2H), 2.07 (s, 3H), 1.75 (p, J = 7.5, 2H). |
| 215 | 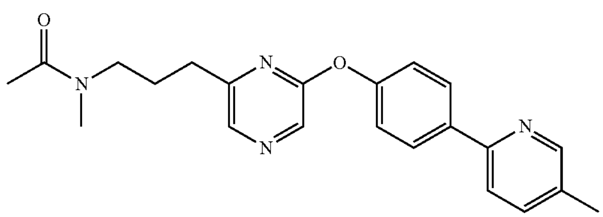 [SMILES: CC(=O)N(C)CCCc1cncc(Oc2ccc(-c3ccc(C)cn3)cc2)n1] | B | 1.71 | N-Methyl-N-(3-{6-[4-(5-methyl-pyridin-2-yl)-phenoxy]-pyrazin-2-yl}-propyl)-acetamide | 1H NMR (400 MHz, DMSO-d6) ppm = 8.50 (d, J = 2.0, 1H), 8.36 (d, J = 8.7, 1H), 8.32 (s, 1H), 8.11 (d, J = 8.8, 2H), 7.86 (s, 1H), 7.70 (dd, J = 8.1, 1.8, 1H), 7.29 (d, J = 8.8, 2H), 3.27-3.17 (m, 2H), 2.85 (s, 3H), 2.61 (t, J = 7.5, 2H), 2.34 (s, 3H), 1.91 (s, 3H), 1.75 (p, J = 7.3, 2H). |
| 216 | 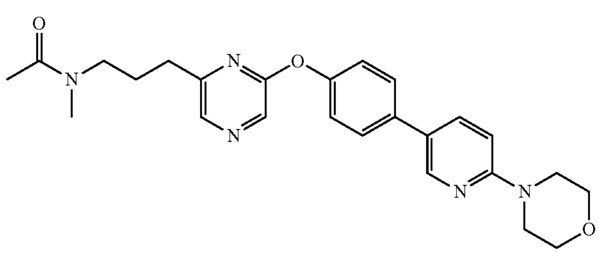 [SMILES: CC(=O)N(C)CCCc1cncc(Oc2ccc(-c3ccc(N4CCOCC4)nc3)cc2)n1] | B | 1.70 | N-Methyl-N-(3-{6-[4-(6-morpholin-4-yl-pyridin-3-yl)-phenoxy]-pyrazin-2-yl}-propyl)-acetamide | 1H NMR (400 MHz, DMSO-d6) ppm = 8.52-8.46 (m, 1H), 8.35 (s, 1H), 8.30 (s, 1H), 7.90 (dt, J = 8.9, 2.4, 1H), 7.68 (d, J = 8.8, 2H), 7.26 (d, J = 8.7, 2H), 6.93 (d, J = 8.9, 1H), 3.78-3.66 (m, 4H), 3.55-3.44 (m, 4H), 3.27-3.18 (m, 2H), 2.85 (s, 3H), 2.67-2.56 (m, 2H), 2.07 (s, 3H), 1.79 (dt, J = 28.9, 7.4, 2H). |
| 217 | 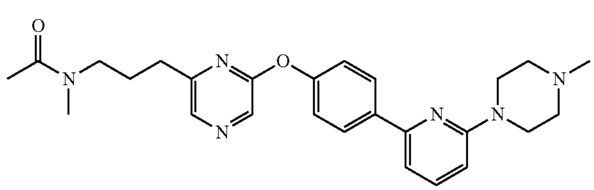 [SMILES: CC(=O)N(C)CCCc1cncc(Oc2ccc(-c3cccc(N4CCN(C)CC4)n3)cc2)n1] | B | 1.54 | N-Methyl-N-[3-(6-{4-[6-(4-methyl-piperazin-1-yl)-pyridin-2-yl]-phenoxy}-pyrazin-2-yl)-propyl]-acetamide | 1H NMR (400 MHz, DMSO-d6) ppm = 8.34 (s, 1H), 8.31 (s, 1H), 8.09 (d, J = 8.7, 2H), 7.62 (dd, J = 8.5, 7.5, 1H), 7.27 (d, J = 8.8, 2H), 7.23 (d, J = 7.4, 1H), 6.80 (d, J = 8.5, 1H), 3.58 (t, J = 5.1, 4H), 3.30-3.19 (m, 4H), 2.85 (s, 3H), 2.43 (t, J = 5.1, 4H), 2.23 (s, 3H), 2.07 (s, 3H), 1.86-1.69 (m, 2H). |

TABLE 1-continued

| No | Chemical Structure | IC$_{50}$ | HPLC/MS Rt [Min] | Chemical Name | NMR data |
|---|---|---|---|---|---|
| 218 | 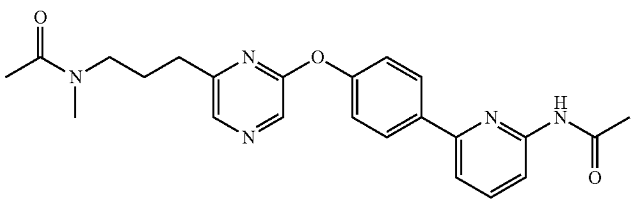 [SMILES: CC(=O)Nc1cccc(-c2ccc(Oc3cncc(CCCN(C)C(C)=O)n3)cc2)n1] | B | 1.94 | N-(3-{6-[4-(6-Acetylamino-pyridin-2-yl)-phenoxy]-pyrazin-2-yl}-propyl)-N-methyl-acetamide | 1H NMR (400 MHz, DMSO-d6) ppm = 10.46 (s, 1H), 8.43-8.28 (m, 2H), 8.20-8.08 (m, 2H), 8.02 (d, J = 8.2, 1H), 7.85 (t, J = 7.9, 1H), 7.66 (d, J = 7.6, 1H), 7.40-7.26 (m, 2H), 3.28-3.17 (m, 2H), 2.85 (s, 3H), 2.62 (t, J = 7.5, 2H), 2.07 (s, 3H), 1.92 (s, 3H), 1.75 (p, J = 7.4, 2H). |
| 219 | 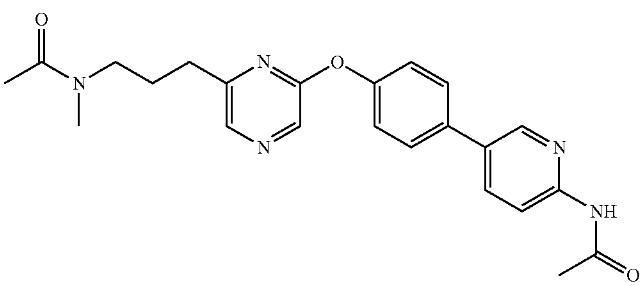 [SMILES: CC(=O)Nc1ccc(-c2ccc(Oc3cncc(CCCN(C)C(C)=O)n3)cc2)cn1] | B | 1.80 | N-(3-{6-[4-(6-Acetylamino-pyridin-3-yl)-phenoxy]-pyrazin-2-yl}-propyl)-N-methyl-acetamide | 1H NMR (500 MHz, DMSO-d6) ppm = 10.56 (s, 1H), 8.65 (s, 1H), 8.35 (s, 1H), 8.31 (s, 1H), 8.16 (d, J = 8.7, 1H), 8.10 (d, J = 8.8, 1H), 7.76 (d, J = 8.6, 2H), 7.31 (d, J = 8.7, 2H), 3.28-3.16 (m, 2H), 2.85 (s, 3H), 2.68-2.58 (m, 2H), 2.12 (s, 3H), 1.92 (s, 3H), 1.79 (dp, J = 37.5, 7.4, 2H). |
| 220 | 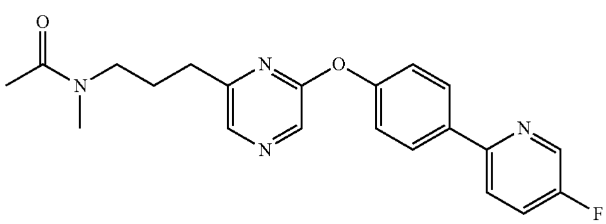 [SMILES: CC(=O)N(C)CCCc1cncc(Oc2ccc(-c3ccc(F)cn3)cc2)n1] | C | 2.13 | N-(3-{6-[4-(5-Fluoro-pyridin-2-yl)-phenoxy]-pyrazin-2-yl}-propyl)-N-methyl-acetamide | 1H NMR (500 MHz, DMSO-d6) ppm = 8.65 (d, J = 3.0, 1H), 8.36 (s, 1H), 8.32 (s, 1H), 8.11 (d, J = 8.6, 2H), 8.06 (dd, J = 8.9, 4.3, 1H), 7.83 (td, J = 8.7, 3.0, 1H), 7.32 (d, J = 8.8, 2H), 3.27-3.18 (m, 2H), 2.85 (s, 3H), 2.73-2.57 (m, 2H), 1.91 (s, 3H), 1.87-1.69 (m, 2H). |
| 221 | 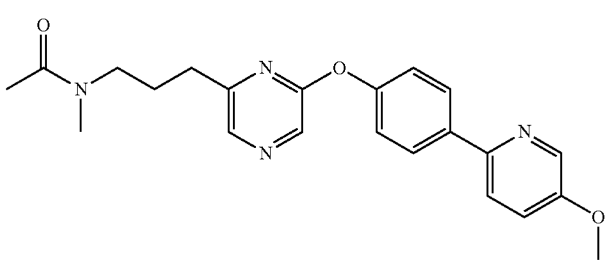 [SMILES: COc1ccc(-c2ccc(Oc3cncc(CCCN(C)C(C)=O)n3)cc2)nc1] | B | 1.97 | N-(3-{6-[4-(5-Methoxy-pyridin-2-yl)-phenoxy]-pyrazin-2-yl}-propyl)-N-methyl-acetamide | 1H NMR (500 MHz, DMSO-d6) ppm = 8.41-8.28 (m, 3H), 8.07 (d, J = 8.7, 2H), 7.92 (s, 1H), 7.48 (dd, J = 8.8, 3.0, 1H), 7.27 (d, J = 8.7, 2H), 3.88 (s, 3H), 3.27-3.13 (m, 2H), 2.91-2.57 (m, 5H), 1.91 (s, 3H), 1.85-1.70 (m, 2H). |
| 222 | 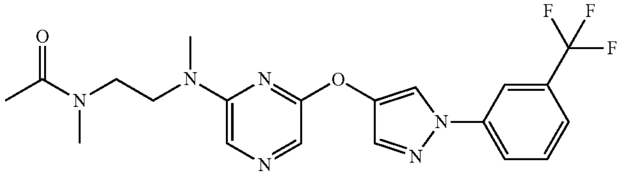 [SMILES: CC(=O)N(C)CCN(C)c1cncc(Oc2cnn(-c3cccc(C(F)(F)F)c3)c2)n1] | C | 2.35 | N-Methyl-N-[2-(methyl-{6-[1-(3-trifluoromethyl-phenyl)-1H-pyrazol-4-yloxy]-pyrazin-2-yl}-amino)-ethyl]-acetamide | 1H NMR (500 MHz, DMSO-d6) ppm = 8.84 (s, 1H), 8.21-8.12 (m, 2H), 7.95 (s, 1H), 7.84 (d, J = 3.5, 1H), 7.76 (t, J = 7.9, 1H), 7.72-7.62 (m, 2H), 3.64-3.52 (m, 2H), 3.33-3.26 (m, 2H), 3.01 (s, 3H), 2.77 (s, 3H), 1.82 (s, 3H). |

TABLE 1-continued

| No | Chemical Structure | IC$_{50}$ | HPLC/MS Rt [Min] | Chemical Name | NMR data |
|---|---|---|---|---|---|
| 223 | 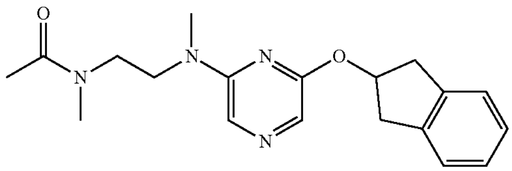 [SMILES: CC(=O)N(C)CCN(C)c1cncc(OC2Cc3ccccc3C2)n1] | B | 2.18 | N-(2-{[6-(Indan-2-yloxy)-pyrazin-2-yl]-methyl-amino}-ethyl)-N-methyl-acetamide | 1H NMR (400 MHz, DMSO-d6) ppm = 7.63 (s, 1H), 7.33 (s, 1H), 7.30-7.22 (m, 2H), 7.22-7.13 (m, 2H), 5.74-5.64 (m, 1H), 3.65 (t, J = 6.5, 2H), 3.49 (t, J = 6.6, 2H), 3.45-3.33 (m, 2H), 3.09-2.99 (m, 5H), 2.97 (s, 3H), 1.92 (s, 3H). |
| 224 | 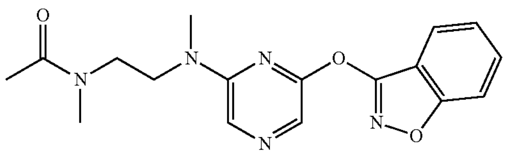 [SMILES: CC(=O)N(C)CCN(C)c1cncc(Oc2noc3ccccc23)n1] | A | 2.03 | N-(2-{[6-(Benzo[d]isoxazol-3-yloxy)-pyrazin-2-yl]-methyl-amino}-ethyl)-N-methyl-acetamide | 1H NMR (500 MHz, DMSO-d6) ppm = 8.01 (s, 1H), 7.88 (s, 1H), 7.78 (d, J = 8.4, 1H), 7.75-7.65 (m, 1H), 7.57-7.48 (m, 1H), 7.48-7.25 (m, 1H), 3.48-3.06 (m, 4H), 2.88 (s, 3H), 2.48 (s, 3H), 1.81 (s, 3H). |
| 225 | 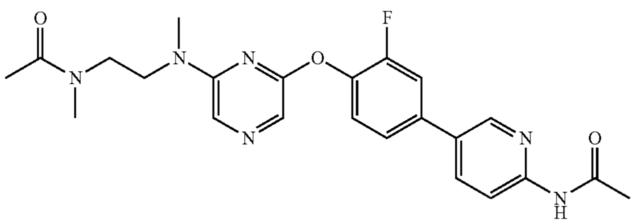 [SMILES: CC(=O)Nc1ccc(-c2ccc(Oc3cncc(N(C)CCN(C)C(C)=O)n3)c(F)c2)cn1] | A | 1.91 | N-[2-({6-[4-(6-Acetylamino-pyridin-3-yl)-2-fluoro-phenoxy]-pyrazin-2-yl}-methyl-amino)-ethyl]-N-methyl-acetamide | 1H NMR (500 MHz, DMSO-d6) ppm = 10.60 (s, 1H), 8.69 (s, 1H), 8.27-8.03 (m, 2H), 7.83 (d, J = 11.6, 1H), 7.82-7.76 (m, 1H), 7.67 (s, 1H), 7.65-7.54 (m, 1H), 7.54-7.29 (m, 1H), 3.47-3.34 (m, 2H), 3.26-3.18 (m, 2H), 2.93 (s, 3H), 2.64 (s, 3H), 2.12 (s, 3H), 1.82 (s, 3H). |
| 226 | 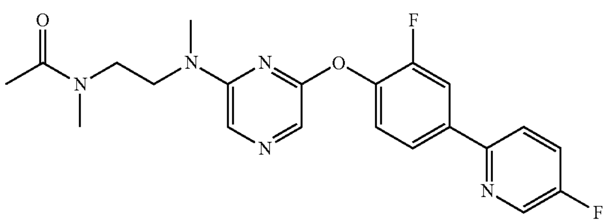 [SMILES: CC(=O)N(C)CCN(C)c1cncc(Oc2ccc(-c3ccc(F)cn3)cc2F)n1] | A | 2.24 | N-[2-({6-[2-Fluoro-4-(5-fluoro-pyridin-2-yl)-phenoxy]-pyrazin-2-yl}-methyl-amino)-ethyl]-N-methyl-acetamide | 1H NMR (500 MHz, DMSO-d6) ppm = 8.67 (s, 1H), 8.12 (d, J = 8.8, 1H), 8.09-8.02 (m, 1H), 8.01-7.91 (m, 1H), 7.91-7.79 (m, 2H), 7.68 (s, 1H), 7.52-7.40 (m, 1H), 3.48-3.35 (m, 2H), 3.25-3.17 (m, 2H), 2.92 (s, 3H), 2.65 (s, 3H), 1.81 (s, 3H). |
| 227 | 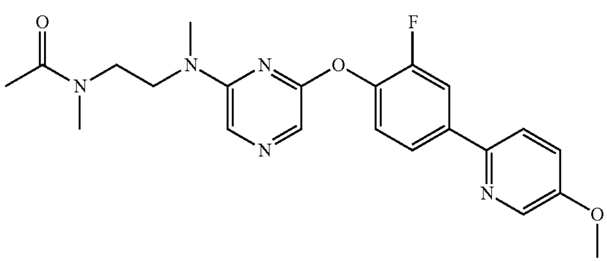 [SMILES: COc1ccc(-c2ccc(Oc3cncc(N(C)CCN(C)C(C)=O)n3)c(F)c2)nc1] | A | 2.16 | N-[2-({6-[2-Fluoro-4-(5-methoxy-pyridin-2-yl)-phenoxy]-pyrazin-2-yl}-methyl-amino)-ethyl]-N-methyl-acetamide | 1H NMR (500 MHz, DMSO-d6) ppm = 8.39 (d, J = 2.9, 1H), 8.03-7.95 (m, 2H), 7.91 (d, J = 8.5, 1H), 7.84 (s, 1H), 7.67 (s, 1H), 7.50 (dd, J = 8.7, 2.8, 1H), 7.40 (t, J = 8.4, 1H), 3.89 (s, 3H), 3.45-3.35 (m, 2H), 3.26-3.18 (m, 2H), 2.92 (s, 3H), 2.64 (s, 3H), 1.80 (s, 3H). |

TABLE 1-continued

| No | Chemical Structure | IC$_{50}$ | HPLC/MS Rt [Min] | Chemical Name | NMR data |
|---|---|---|---|---|---|
| 228 | 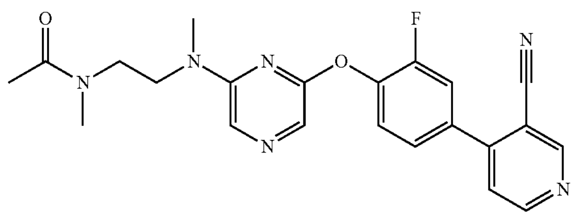 [SMILES: CC(=O)N(C)CCN(C)c1cncc(Oc2ccc(-c3ccncc3C#N)cc2F)n1] | A | 2.05 | N-[2-({6-[4-(3-Cyano-pyridin-4-yl)-2-fluoro-phenoxy]-pyrazin-2-yl}-methyl-amino)-ethyl]-N-methyl-acetamide | 1H NMR (500 MHz, DMSO-d6) ppm = 9.13 (s, 1H), 8.92 (d, J = 5.2, 1H), 7.87 (s, 1H), 7.84-7.71 (m, 3H), 7.65-7.50 (m, 2H), 3.49-3.35 (m, 2H), 3.35-3.17 (m, 2H), 2.93 (s, 3H), 2.67 (s, 3H), 1.82 (s, 3H). |
| 229 | 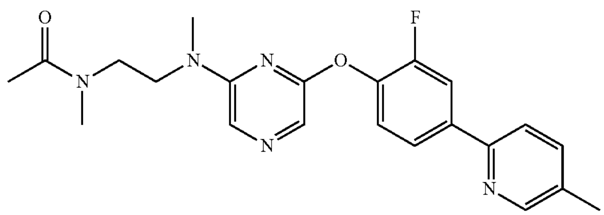 [SMILES: CC(=O)N(C)CCN(C)c1cncc(Oc2ccc(-c3ccc(C)cn3)cc2F)n1] | A | 2.07 | N-[2-({6-[2-Fluoro-4-(5-methyl-pyridin-2-yl)-phenoxy]-pyrazin-2-yl}-methyl-amino)-ethyl]-N-methyl-acetamide | 1H NMR (500 MHz, DMSO-d6) ppm = 8.52 (s, 1H), 8.09-8.00 (m, 1H), 7.99-7.94 (m, 1H), 7.93 (d, J = 8.1, 1H), 7.84 (s, 1H), 7.76-7.66 (m, 2H), 7.42 (d, J = 8.4, 1H), 3.29-3.24 (m, 2H), 3.24-3.18 (m, 2H), 2.92 (s, 3H), 2.64 (s, 3H), 2.35 (s, 3H), 1.80 (s, 3H). |
| 230 | 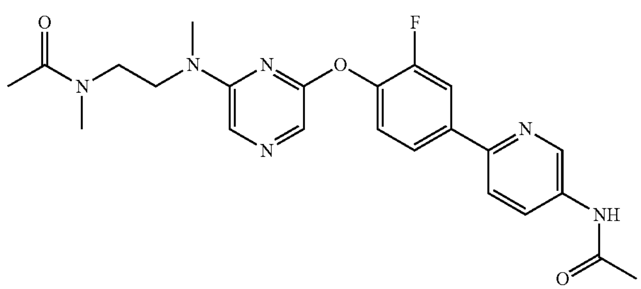 [SMILES: CC(=O)Nc1ccc(-c2ccc(Oc3cncc(N(C)CCN(C)C(C)=O)n3)c(F)c2)nc1] | A | 2.05 | N-{6-[4-(6-{[2-(Acetyl-methyl-amino)-ethyl]-methyl-amino}-pyrazin-2-yloxy)-3-fluoro-phenyl]-pyridin-3-yl}-acetamide | 1H NMR (500 MHz, DMSO-d6) ppm = 10.48 (s, 1H), 8.08 (dd, J = 12.3, 5.4, 1H), 8.04 (s, 1H), 7.98 (ddd, J = 8.2, 5.7, 2.0, 1H), 7.91-7.79 (m, 2H), 7.78-7.66 (m, 2H), 7.48 (t, J = 8.3, 1H), 3.46-3.36 (m, 2H) 3.27 (t, J = 6.4, 1H), 3.22 (t, J = 6.7, 1H), 2.92 (s, 3H), 2.50 (s, 3H), 2.14 (s, 3H), 1.81 (s, 3H). |
| 231 | 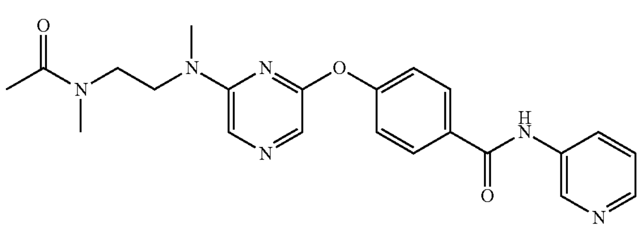 [SMILES: CC(=O)N(C)CCN(C)c1cncc(Oc2ccc(C(=O)Nc3cccnc3)cc2)n1] | A | 1.50 | 4-(6-{[2-(Acetyl-methyl-amino)-ethyl]-methyl-amino}-pyrazin-2-yloxy)-N-pyridin-3-yl-benzamide | 1H NMR (500 MHz, DMSO-d6) ppm = 16.00 (s, 1H), 8.24 (s, 1H), 8.09 (d, J = 8.7, 1H), 7.79 (t, J = 7.8, 1H), 7.73 (d, J = 8.7, 1H), 7.47 (d, J = 11.7, 1H), 7.38 (d, J = 8.1, 1H), 5.16 (s, 2H), 3.38 (s, 1H), 3.22 (dt, J = 13.8, 7.1, 1H), 3.01 (dt, J = 13.0, 6.1, 1H), 2.77 (dt, J = 13.8, 7.1, 1H), 2.50 (p, J = 1.7, 4H), 2.38 (ddt, J = 21.0, 11.4, 5.4, 4H). |

| No | Chemical Structure | IC$_{50}$ | HPLC/MS Rt [Min] | Chemical Name | NMR data |
|---|---|---|---|---|---|
| 232 | 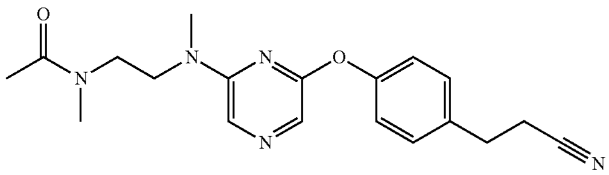 [SMILES: CC(=O)N(C)CCN(C)c1cncc(Oc2ccc(CCC#N)cc2)n1] | A | 1.90 | N-[2-({6-[4-(2-Cyano-ethyl)-phenoxy]-pyrazin-2-yl}-methyl-amino)-ethyl]-N-methyl-acetamide | 1H NMR (500 MHz, DMSO-d6) ppm = 16.02 (s, 1H), 8.25 (s, 1H), 8.09 (s, 1H), 7.80 (t, J = 7.8, 1H), 7.74 (d, J = 8.7, 1H), 7.49 (d, J = 11.7, 1H), 7.40 (s, 1H), 5.17 (s, 2H), 3.39 (s, 1H), 3.25 (d, J = 7.2, 1H), 3.03 (d, J = 6.7, 1H), 2.84-2.70 (m, 1H), 2.51 (p, J = 1.7, 4H), 2.39 (dt, J = 15.2, 5.4, 4H). |
| 233 | 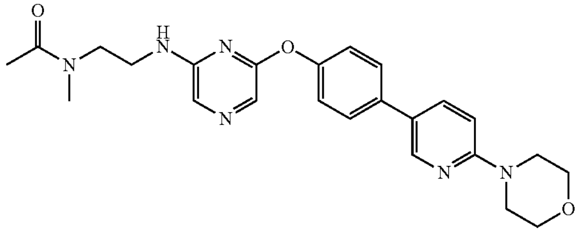 [SMILES: CC(=O)N(C)CCNc1cncc(Oc2ccc(-c3ccc(N4CCOCC4)nc3)cc2)n1] | C | 1.49 | N-Methyl-N-(2-{6-[4-(6-morpholin-4-yl-pyridin-3-yl)-phenoxy]-pyrazin-2-ylamino}-ethyl)-acetamide | 1H NMR (500 MHz, DMSO-d6) ppm = 8.34-8.28 (m, 1H), 8.02 (d, J = 8.7, 2H), 7.86 (s, 1H), 7.55 (s, 1H), 7.53-7.45 (m, 1H), 7.33-7.27 (m, 1H), 7.23 (d, J = 8.7, 2H), 3.67-3.57 (m, 4H), 3.44 (t, J = 6.3, 2H), 3.19-3.12 (m, 2H), 2.95 (s, 3H), 2.85-2.79 (m, 4H), 2.07 (s, 3H). |
| 234 | 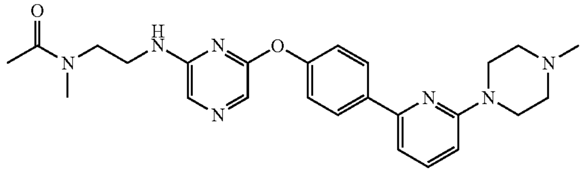 [SMILES: CC(=O)N(C)CCNc1cncc(Oc2ccc(-c3cccc(N4CCN(C)CC4)n3)cc2)n1] | A | 1.53 | N-Methyl-N-[2-(6-{4-[6-(4-methyl-piperazin-1-yl)-pyridin-2-yl]-phenoxy}-pyrazin-2-ylamino)-ethyl]-acetamide | 1H NMR (500 MHz, DMSO-d6) ppm = 8.08 (d, J = 8.8, 2H), 7.89-7.81 (m, 2H), 7.62 (dd, J = 8.4, 7.5, 1H), 7.53 (s, 1H), 7.28-7.16 (m, 3H), 6.79 (d, J = 8.5, 1H), 3.58 (t, J = 5.1, 4H), 3.44 (t, J = 6.3, 2H), 3.16 (t, J = 6.3, 2H), 2.95 (s, 3H), 2.47 (t, J = 5.0, 4H), 2.26 (s, 3H), 1.74 (s, 3H). |
| 235 | 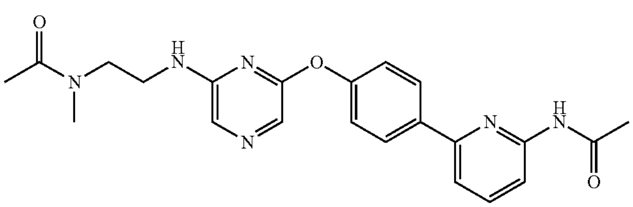 [SMILES: CC(=O)Nc1cccc(-c2ccc(Oc3cncc(NCCN(C)C(C)=O)n3)cc2)n1] | B | 1.73 | N-(2-{6-[4-(6-Acetylamino-pyridin-2-yl)-phenoxy]-pyrazin-2-ylamino}-ethyl)-N-methyl-acetamide | 1H NMR (500 MHz, DMSO-d6) ppm = 10.55 (s, 1H), 8.68-8.60 (m, 1H), 8.21-8.12 (m, 1H), 8.12-8.04 (m, 1H), 7.87 (s, 1H), 7.84 (t, J = 5.6, 1H), 7.74 (d, J = 8.7, 2H), 7.53 (s, 1H), 7.27 (d, J = 8.7, 2H), 3.44 (t, J = 6.4, 2H), 3.21-3.11 (m, 2H), 2.96 (s, 3H), 2.12 (s, 3H), 1.73 (s, 3H). |
| 236 | 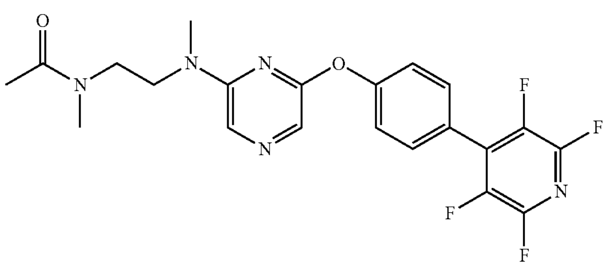 [SMILES: CC(=O)N(C)CCN(C)c1cncc(Oc2ccc(-c3c(F)c(F)nc(F)c3F)cc2)n1] | A | 2.43 | N-Methyl-N-[2-(methyl-{6-[4-(2,3,5,6-tetrafluoro-pyridin-4-yl)-phenoxy]-pyrazin-2-yl}-amino)-ethyl]-acetamide | 1H NMR (500 MHz, DMSO-d6) ppm = 7.89 (s, 1H), 7.74-7.62 (m, 3H), 7.42 (d, J =8.7, 2H), 3.56-3.42 (m, 2H), 3.34-3.20 (m, 2H), 2.97 (s, 3H), 2.57 (s, 3H), 1.84 (s, 3H). |

| No | Chemical Structure | IC$_{50}$ | HPLC/MS Rt [Min] | Chemical Name | NMR data |
|---|---|---|---|---|---|
| 237 | 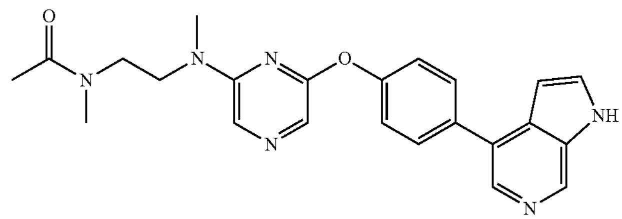 [SMILES: CC(=O)N(C)CCN(C)c1cncc(Oc2ccc(-c3cncc4[nH]ccc34)cc2)n1] | B | 1.49 | N-Methyl-N-[2-(methyl-{6-[4-(1H-pyrrolo[2,3-c]pyridin-4-yl)-phenoxy]-pyrazin-2-yl}-amino)-ethyl]-acetamide | 1H NMR (500 MHz, DMSO-d6) ppm = 11.78 (s, 1H), 8.75 (s, 1H), 8.21 (s, 1H), 7.85 (s, 1H), 7.76 (d, J = 8.4, 2H), 7.72-7.54 (m, 2H), 7.34 (d, J = 8.6, 2H), 6.65 (d, J = 6.5, 1H), 3.59-3.43 (m, 2H), 3.32-3.19 (m, 2H), 2.98 (s, 3H), 2.55 (s, 3H), 1.82 (s, 3H). |
| 238 | 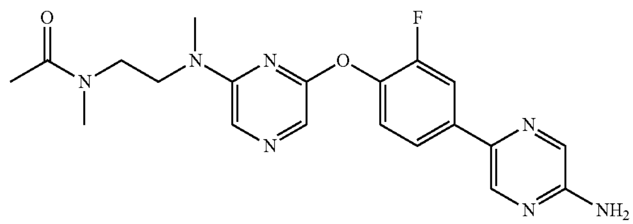 [SMILES: CC(=O)N(C)CCN(C)c1cncc(Oc2ccc(-c3cnc(N)cn3)cc2F)n1] | A | 1.82 | N-[2-({6-[4-(5-Amino-pyrazin-2-yl)-2-fluoro-phenoxy]-pyrazin-2-yl}-methyl-amino)-ethyl]-N-methyl-acetamide | 1H NMR (500 MHz, DMSO-d6) ppm = 8.56 (s, 1H), 7.97 (s, 1H), 7.88 (d, J = 12.4, 1H), 7.84-7.78 (m, 2H), 7.66 (s, 1H), 7.36 (t, J = 8.4, 1H), 6.64 (s, 2H), 3.46-3.39 (m, 2H), 3.29-3.20 (m, 2H), 2.92 (s, 3H), 2.64 (s, 3H), 1.81 (s, 3H). |
| 239 | 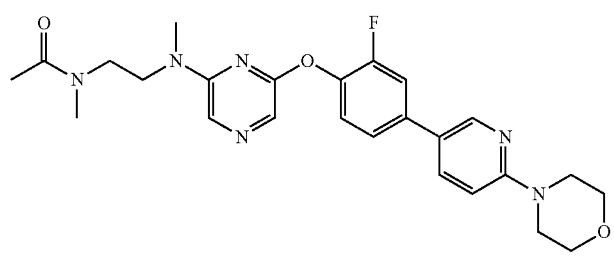 [SMILES: CC(=O)N(C)CCN(C)c1cncc(Oc2ccc(-c3ccc(N4CCOCC4)nc3)cc2F)n1] | A | 1.88 | N-[2-({6-[2-Fluoro-4-(6-morpholin-4-yl-pyridin-3-yl)-phenoxy]-pyrazin-2-yl}-methyl-amino)-ethyl]-N-methyl-acetamide | 1H NMR (500 MHz, DMSO-d6) ppm = 8.52 (d, J = 3.0, 1H), 7.97-7.88 (m, 1H), 7.82 (s, 1H), 7.75-7.64 (m, 2H), 7.52 (d, J = 8.4, 1H), 7.37 (t, J = 8.5, 1H), 6.93 (d, J = 8.9, 1H), 3.81-3.66 (m, 4H), 3.58-3.47 (m, 4H), 3.44-3.36 (m, 2H), 3.28-3.18 (m, 2H), 2.93 (s, 3H), 2.64 (s, 3H), 1.82 (s, 3H). |
| 240 | 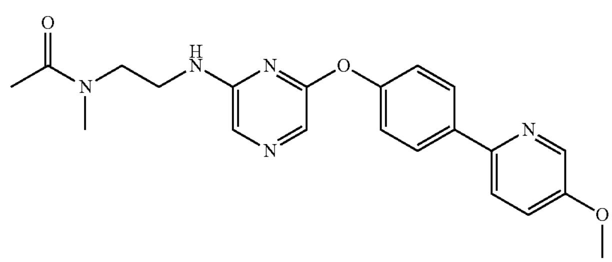 [SMILES: COc1ccc(-c2ccc(Oc3cncc(NCCN(C)C(C)=O)n3)cc2)nc1] | B | 1.89 | N-(2-{6-[4-(5-Methoxy-pyridin-2-yl)-phenoxy]-pyrazin-2-ylamino}-ethyl)-N-methyl-acetamide | 1H NMR (400 MHz, DMSO-d6) ppm = 8.37 (d, J = 2.9, 1H), 8.05 (d, J = 8.7, 2H), 7.96-7.81 (m, 2H), 7.57-7.44 (m, 2H), 7.24 (d, J = 8.8, 2H), 3.88 (s, 3H), 3.52-3.38 (m, 2H), 3.28-3.11 (m, 2H), 2.95 (s, 3H), 1.74 (s, 3H). |
| 241 | 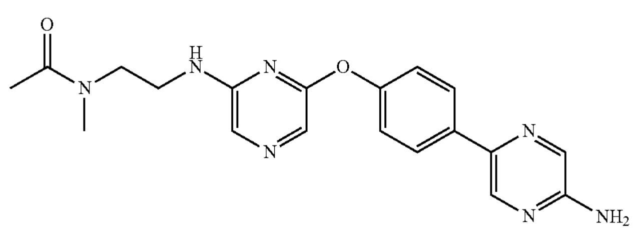 [SMILES: CC(=O)N(C)CCNc1cncc(Oc2ccc(-c3cnc(N)cn3)cc2)n1] | C | 1.99 | N-(2-{6-[4-(5-Amino-pyrazin-2-yl)-phenoxy]-pyrazin-2-ylamino}-ethyl)-N-methyl-acetamide | 1H NMR (400 MHz, DMSO-d6) ppm = 8.49 (d, J = 1.5, 1H), 7.95 (d, J = 1.4, 2H), 7.93-7.92 (m, 1H), 7.67 (s, 1H), 7.48 (s, 1H), 7.35 (s, 1H), 7.17 (d, J = 8.7, 2H), 6.50 (s, 1H), 6.50 (s, 1H), 3.28-3.08 (m, 4H), 2.60 (s, 3H), 1.75 (s, 3H). |

TABLE 1-continued

| No | Chemical Structure | IC$_{50}$ | HPLC/MS Rt [Min] | Chemical Name | NMR data |
|---|---|---|---|---|---|
| 242 | 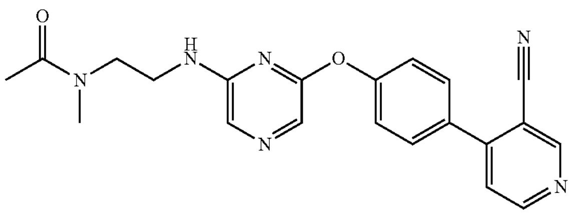 [SMILES: CC(=O)N(C)CCNc1cncc(Oc2ccc(-c3ccncc3C#N)cc2)n1] | C | 1.86 | N-(2-{6-[4-(3-Cyano-pyridin-4-yl)-phenoxy]-pyrazin-2-ylamino}-ethyl)-N-methyl-acetamide | 1H NMR (400 MHz, DMSO-d6) ppm = 9.10 (s, 1H), 8.89 (d, J = 5.3, 1H), 7.80-7.66 (m, 4H), 7.55 (s, 1H), 7.46-7.28 (m, 3H), 3.28-3.14 (m, 4H), 2.62 (s, 3H), 1.89 (s, 3H). |
| 243 | 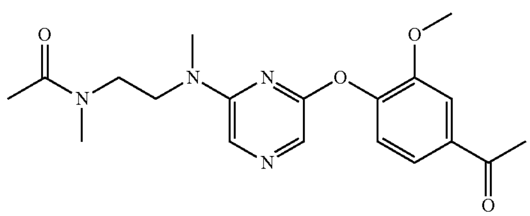 [SMILES: COc1cc(C(C)=O)ccc1Oc1cncc(N(C)CCN(C)C(C)=O)n1] | C | 1.99 | N-(2-{[6-(4-Acetyl-2-methoxy-phenoxy)-pyrazin-2-yl]-methyl-amino}-ethyl)-N-methyl-acetamide | 1H NMR (400 MHz, DMSO-d6) ppm = 7.88 (s, 1H), 7.66 (s, 1H), 7.60 (s, 1H), 7.03-6.95 (m, 1H), 6.83-6.72 (m, 1H), 3.88 (s, 3H), 3.47 (t, J = 6.5, 2H), 3.34 (t, J = 6.5, 2H), 2.97 (s, 3H), 2.75 (s, 3H), 2.52 (s, 3H), 1.85 (s, 3H). |
| 244 | 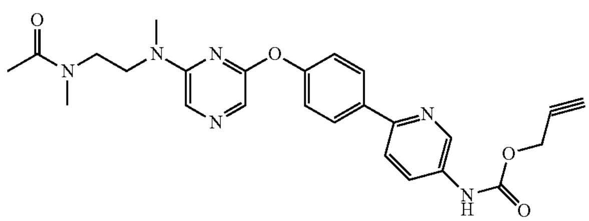 [SMILES: C#CCOC(=O)Nc1ccc(-c2ccc(Oc3cncc(N(C)CCN(C)C(C)=O)n3)cc2)nc1] | A | 2.01 | {6-[4-(6-{[2-(Acetyl-methyl-amino)-ethyl]-methyl-amino}-pyrazin-2-yloxy)-phenyl]-pyridin-3-yl}-carbamic acid prop-2-ynyl ester | 1H NMR (500 MHz, DMSO-d6) ppm = 10.15 (s, 1H), 8.71 (d, J = 2.4, 1H), 8.07 (d, J = 8.7, 2H), 7.97 (dd, J = 8.8, 2.6, 1H), 7.93 (d, J = 8.6, 1H), 7.84 (s, 1H), 7.62 (s, 1H), 7.26 (d, J = 8.7, 2H), 4.81 (d, J = 2.4, 2H), 3.58 (t, J = 2.4, 1H), 3.44 (t, J = 6.6, 2H), 3.26 (t, J = 6.7, 2H), 2.95 (s, 3H), 2.70 (s, 3H), 1.82 (s, 3H). |
| 245 | 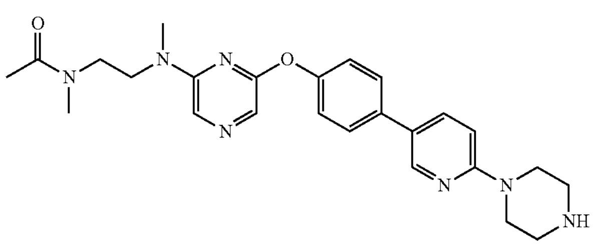 [SMILES: CC(=O)N(C)CCN(C)c1cncc(Oc2ccc(-c3ccc(N4CCNCC4)nc3)cc2)n1] | A | 1.50 | N-Methyl-N-[2-(methyl-{6-[4-(6-piperazin-1-yl-pyridin-3-yl)-phenoxy]-pyrazin-2-yl}-amino)-ethyl]-acetamide | 1H NMR (400 MHz, DMSO-d6) ppm = 8.46 (d, J = 2.5, 1H), 7.83 (s, 1H), 7.77 (d, J = 8.7, 1H), 7.70 (d, J = 8.3, 2H), 7.57 (s, 1H), 7.36 (d, J = 8.7, 1H), 7.26 (d, J = 8.7, 2H), 4.26 (s, 2H), 3.89-3.83 (m, 4H), 3.47-3.32 (m, 4H), 3.23-3.19 (m, 4H), 2.96 (s, 3H), 2.71 (s, 3H), 1.84 (s, 4H). |
| 246 | 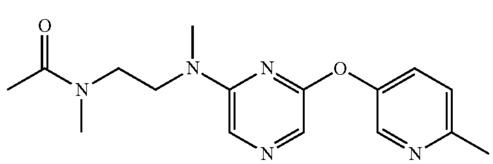 [SMILES: CC(=O)N(C)CCN(C)c1cncc(Oc2ccc(C)nc2)n1] | C | 1.38 | N-Methyl-N-(2-{methyl-[6-(6-methyl-pyridin-3-yloxy)-pyrazin-2-yl]-amino}-ethyl)-acetamide | 1H NMR (400 MHz, DMSO-d6) ppm = 8.34 (d, J = 2.8, 1H), 7.81 (s, 1H), 7.61 (s, 1H), 7.56 (dd, J = 8.4, 2.9, 1H), 7.31 (d, J = 8.4, 1H), 3.39 (t, J = 6.5, 2H), 3.36-3.17 (m, 2H), 2.93 (s, 3H), 2.69 (s, 3H), 2.47 (s, 3H), 1.85 (s, 3H). |

TABLE 1-continued

| No | Chemical Structure | IC$_{50}$ | HPLC/MS Rt [Min] | Chemical Name | NMR data |
|---|---|---|---|---|---|
| 247 | 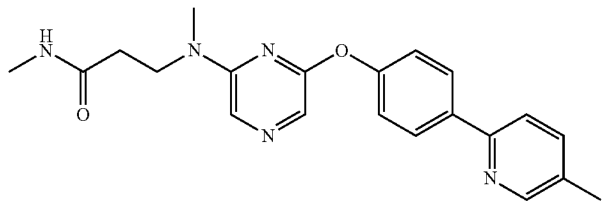 | A | 1.62 | N-Methyl-3-(methyl-{6-[4-(5-methyl-pyridin-2-yl)-phenoxy]-pyrazin-2-yl}-amino)-propionamide | 1H NMR (400 MHz, DMSO-d6) ppm = 8.49 (d, J = 2.0, 1H), 8.09 (d, J = 8.8, 2H), 7.90-7.81 (m, 2H), 7.77-7.65 (m, 2H), 7.55 (s, 1H), 7.26 (d, J = 8.8, 2H), 3.59 (t, J = 6.9, 2H), 2.92 (s, 3H), 2.51 (d, J = 4.6, 3H), 2.33 (s, 3H), 2.26 (t, J = 6.9, 2H). |
| 248 | 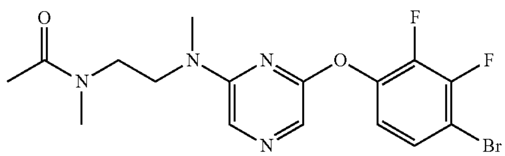 [SMILES: CC(=O)N(C)CCN(C)c1cncc(Oc2ccc(Br)c(F)c2F)n1] | B | 2.37 | N-(2-{[6-(4-Bromo-2,3-difluoro-phenoxy)-pyrazin-2-yl]-methyl-amino}-ethyl)-N-methyl-acetamide | 1H NMR (400 MHz, DMSO-d6) ppm = 7.86 (s, 1H), 7.70 (s, 1H), 7.68-7.55 (m, 1H), 7.31-7.16 (m, 1H), 3.48-3.33 (m, 2H), 3.28-3.18 (m, 2H), 2.92 (s, 3H), 2.72 (s, 3H), 1.85 (s, 3H). |
| 249 | 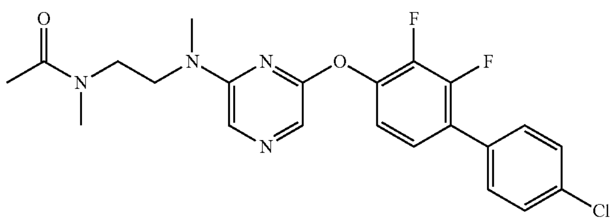 [SMILES: CC(=O)N(C)CCN(C)c1cncc(Oc2ccc(-c3ccc(Cl)cc3)c(F)c2F)n1] | B | 2.67 | N-(2-{[6-(4'-Chloro-2,3-difluoro-biphenyl-4-yloxy)-pyrazin-2-yl]-methyl-amino}-ethyl)-N-methyl-acetamide | 1H NMR (400 MHz, DMSO-d6) ppm = 7.86 (s, 1H), 7.72 (s, 1H), 7.68-7.54 (m, 4H), 7.47-7.36 (m, 1H), 7.36-7.25 (m, 1H), 3.41 (t, J = 6.5, 2H), 3.34-3.21 (m, 2H), 2.95 (s, 3H), 2.70 (s, 3H), 1.83 (s, 3H). |
| 250 | 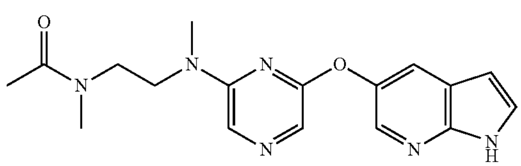 [SMILES: CC(=O)N(C)CCN(C)c1cncc(Oc2cnc3[nH]ccc3c2)n1] | C | 1.69 | N-Methyl-N-(2-{methyl-[6-(1H-pyrrolo[2,3-b]pyridin-5-yloxy)-pyrazin-2-yl]-amino}-ethyl)-acetamide | 1H NMR (400 MHz, DMSO-d6) ppm = 11.67 (s, 1H), 8.09 (d, J = 2.6, 1H), 7.85-7.73 (m, 2H), 7.57 (s, 1H), 7.54-7.46 (m, 1H), 6.48-6.40 (m, 1H), 3.36 (t, 2H), 3.24 (t, J = 6.5, 2H), 2.91 (s, 3H), 2.37 (s, 3H), 1.81 (s, 3H). |
| 251 | 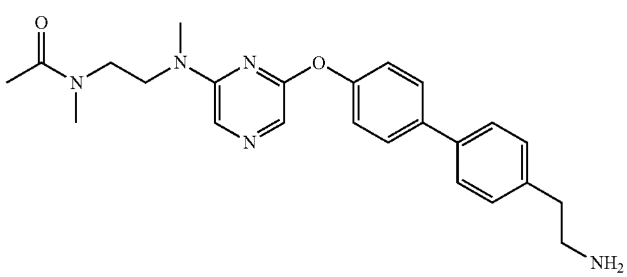 [SMILES: CC(=O)N(C)CCN(C)c1cncc(Oc2ccc(-c3ccc(CCN)cc3)cc2)n1] | A | 1.77 | N-[2-({6-[4'-(2-Amino-ethyl)-biphenyl-4-yloxy]-pyrazin-2-yl}-methyl-amino)-ethyl]-N-methyl-acetamide | 1H NMR (400 MHz, DMSO-d6) ppm = 7.83 (s, 1H), 7.68 (d, J = 8.6, 2H), 7.65 (s, 1H), 7.58 (d, J = 7.6, 2H), 7.33 (d, J = 8.1, 2H), 7.25 (d, J = 12.1, 2H), 3.51-3.40 (m, 2H), 3.30 (dd, J = 27.0, 6.7, 2H), 3.02 (s, 3H), 3.00-2.92 (m, 2H), 2.87-2.77 (m, 2H), 2.70 (s, 3H), 1.83 (s, 3H). |
| 252 | 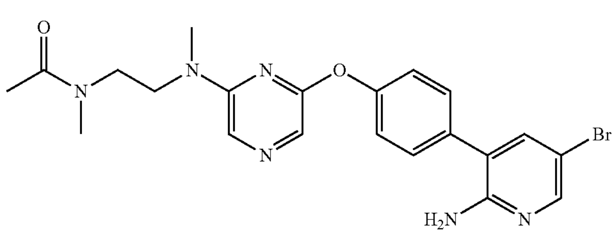 [SMILES: CC(=O)N(C)CCN(C)c1cncc(Oc2ccc(-c3cc(Br)cnc3N)cc2)n1] | B | 1.97 | N-[2-({6-[4-(2-Amino-5-bromo-pyridin-3-yl)-phenoxy]-pyrazin-2-yl}-methyl-amino)-ethyl]-N-methyl-acetamide | 1H NMR (400 MHz, DMSO-d6) ppm = 8.02 (d, J = 2.1, 1H), 7.82 (s, 1H), 7.57 (s, 1H), 7.53-7.44 (m, 3H), 7.30-7.17 (m, 2H), 5.89 (s, 2H), 3.63-3.40 (m, 2H), 3.40-3.20 (m, 2H), 2.98 (s, 3H), 2.76 (s, 3H), 1.83 (s, 3H). |

TABLE 1-continued

| No | Chemical Structure | IC$_{50}$ | HPLC/MS Rt [Min] | Chemical Name | NMR data |
|---|---|---|---|---|---|
| 253 | 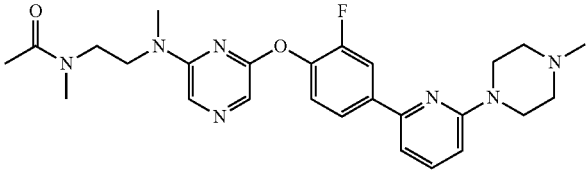 [SMILES: CC(=O)N(C)CCN(C)c1cncc(Oc2ccc(-c3cccc(N4CCN(C)CC4)n3)cc2F)n1] | A | 1.62 | N-{2-[(6-{2-Fluoro-4-[6-(4-methyl-piperazin-1-yl)-pyridin-2-yl]-phenoxy}-pyrazin-2-yl)-methyl-amino]-ethyl}-N-methyl-acetamide | 1H NMR (500 MHz, DMSO-d6) ppm = 8.00 (dd, J = 12.3, 2.1, 1H), 7.93 (dd, J = 8.5, 2.0, 1H), 7.81 (s, 1H), 7.67 (s, 1H), 7.63 (t, J = 7.9, 1H), 7.46-7.36 (m, 1H), 7.28 (dd, J = 7.4, 1.9, 1H), 6.83 (d, J = 8.5, 1H), 3.58 (t, J = 5.0, 4H), 3.39 (dq, J = 16.9, 10.4, 8.5, 2H), 3.24 (dt, J = 26.0, 6.6, 2H), 2.92 (s, 3H), 2.50 (s, 3H), 2.45 (t, J = 5.0, 4H), 2.24 (s, 3H), 1.81 (s, 3H). |
| 254 | 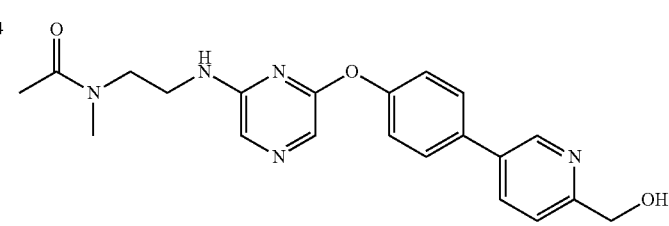 | B | 1.46 | N-(2-{6-[4-(6-Hydroxy-methyl-pyridin-3-yl)-phenoxy]-pyrazin-2-ylamino}-ethyl)-N-methyl-acetamide | 1H NMR (400 MHz, DMSO-d6) ppm = 8.78 (d, J = 2.0, 1H), 8.07 (dd, J = 8.1, 2.4, 1H), 7.76 (d, J = 8.7, 2H), 7.68 (s, 1H), 7.55 (d, J = 8.2, 1H), 7.50 (s, 1H), 7.44-7.19 (m, 3H), 5.41 (t, J = 5.8, 1H), 4.61 (d, J = 5.7, 2H), 3.27-3.11 (m, 4H), 2.59 (s, 3H), 1.75 (s, 3H). |
| 255 | 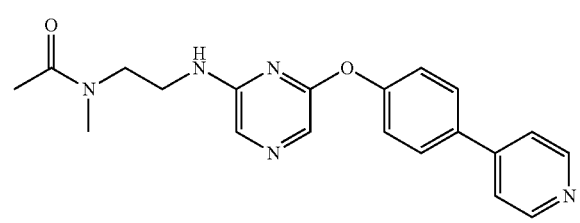 [SMILES: CC(=O)N(C)CCNc1cncc(Oc2ccc(-c3ccncc3)cc2)n1] | C | 1.40 | N-Methyl-N-{2-[6-(4-pyridin-4-yl-phenoxy)-pyrazin-2-ylamino]-ethyl}-acetamide | |
| 256 | 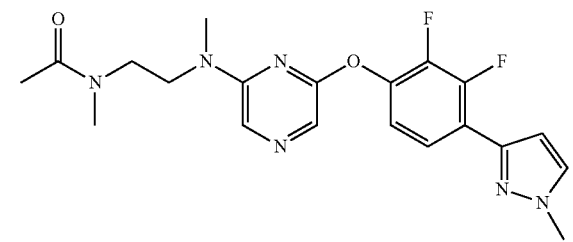 [SMILES: CC(=O)N(C)CCN(C)c1cncc(Oc2ccc(-c3ccn(C)n3)c(F)c2F)n1] | B | 2.01 | N-[2-({6-[2,3-Difluoro-4-(1-methyl-1H-pyrazol-3-yl)-phenoxy]-pyrazin-2-yl}-methyl-amino)-ethyl]-N-methyl-acetamide | 1H NMR (400 MHz, DMSO-d6) ppm = 8.19 (s, 1H), 7.92 (s, 1H), 7.85 (d, J = 9.0, 1H), 7.68 (s, 1H), 7.60-7.48 (m, 1H), 7.25-7.15 (m, 1H), 3.91 (s, 3H), 3.48-3.34 (m, 2H), 3.28-3.20 (m, 2H), 2.92 (s, 3H), 2.53 (s, 3H), 1.82 (s, 3H). |
| 257 | 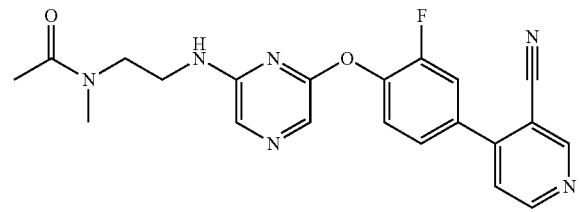 [SMILES: CC(=O)N(C)CCNc1cncc(Oc2ccc(-c3ccncc3C#N)cc2F)n1] | B | 1.90 | N-(2-{6-[4-(3-Cyano-pyridin-4-yl)-2-fluoro-phenoxy]-pyrazin-2-ylamino}-ethyl)-N-methyl-acetamide | |

… 115 …

TABLE 1-continued

| No | Chemical Structure | IC$_{50}$ | HPLC/ MS Rt [Min] | Chemical Name | NMR data |
|---|---|---|---|---|---|
| 258 | 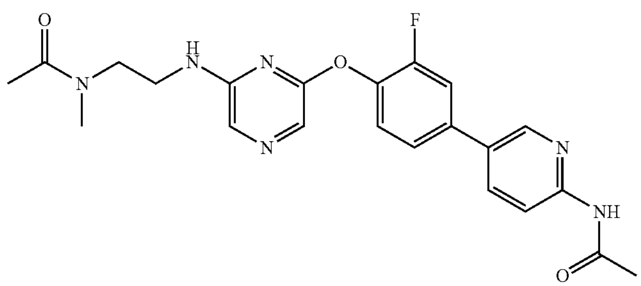 [SMILES: CC(=O)Nc1ccc(-c2ccc(Oc3cncc(NCCN(C)C(C)=O)n3)c(F)c2)cn1] | B | 1.83 | N-[5-(4-{6-[2-(Acetyl-methyl-amino)-ethylamino]-pyrazin-2-yloxy}-3-fluoro-phenyl)-pyridin-2-yl]-acetamide | |
| 259 | 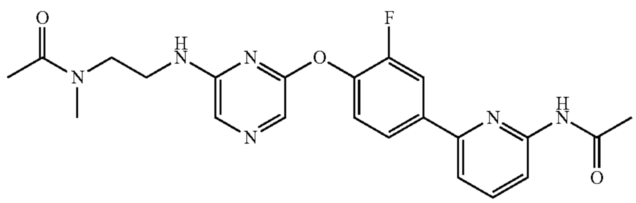 [SMILES: CC(=O)Nc1cccc(-c2ccc(Oc3cncc(NCCN(C)C(C)=O)n3)c(F)c2)n1] | C | 1.97 | N-(2-{6-[4-(6-Acetylamino-pyridin-2-yl)-2-fluoro-phenoxy]-pyrazin-2-ylamino}-ethyl)-N-methyl-acetamide | |
| 260 | 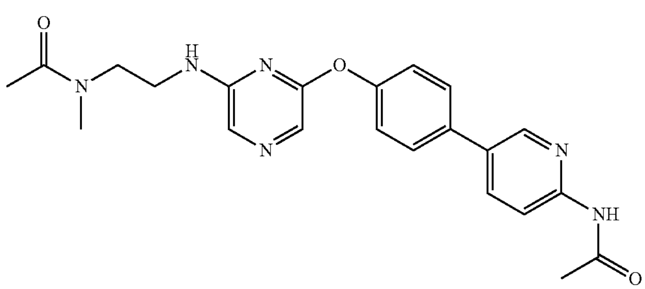 [SMILES: CC(=O)Nc1ccc(-c2ccc(Oc3cncc(NCCN(C)C(C)=O)n3)cc2)cn1] | B | 1.75 | N-(2-{6-[4-(6-Acetylamino-pyridin-3-yl)-phenoxy]-pyrazin-2-ylamino}-ethyl)-N-methyl-acetamide | 1H NMR (400 MHz, DMSO-d6) ppm = 10.54 (s, 1H), 8.62 (d, J = 2.3, 1H), 8.15 (d, J = 8.7, 1H), 8.07 (dd, J = 8.7, 2.5, 1H), 7.74 (d, J = 8.7, 2H), 7.68 (s, 1H), 7.49 (s, 1H), 7.41-7.17 (m, 3H), 3.27-3.10 (m, 4H), 2.60 (s, 3H), 2.12 (s, 3H), 1.75 (s, 3H). |
| 261 | 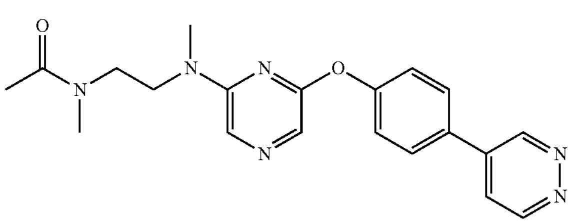 [SMILES: CC(=O)N(C)CCN(C)c1cncc(Oc2ccc(-c3ccnnc3)cc2)n1] | A | 1.70 | N-Methyl-N-(2-{methyl-[6-(4-pyridazin-4-yl-phenoxy)-pyrazin-2-yl]-amino}-ethyl)-acetamide | 1H NMR (500 MHz, DMSO-d6) ppm = 9.68-9.63 (m, 1H), 9.29-9.24 (m, 1H), 8.05-7.97 (m, 3H), 7.87 (s, 1H), 7.62 (s, 1H), 7.38 (d, J = 8.7, 2H), 3.51-3.40 (m, 2H), 3.36-3.24 (m, 2H), 2.96 (s, 3H), 2.55 (s, 3H), 1.83 (s, 3H). |
| 262 | 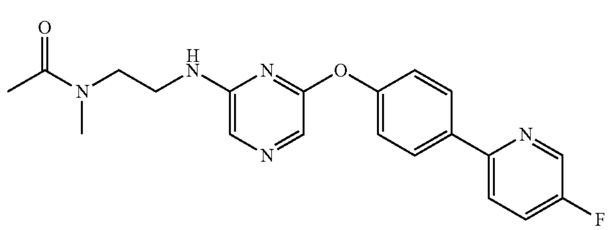 [SMILES: CC(=O)N(C)CCNc1cncc(Oc2ccc(-c3ccc(F)cn3)cc2)n1] | C | 2.06 | N-(2-{6-[4-(5-Fluoro-pyridin-2-yl)-phenoxy]-pyrazin-2-ylamino}-ethyl)-N-methyl-acetamide | 1H NMR (400 MHz, DMSO-d6) ppm = 8.64 (d, J = 3.0, 1H), 8.09 (d, J = 8.8, 2H), 8.03 (dd, J = 8.8, 4.3, 1H), 7.81 (tdd, J = 8.4, 2.8, 0.9, 1H), 7.69 (s, 1H), 7.51 (s, 1H), 7.43-7.33 (m, 1H), 7.23 (d, J = 8.8, 2H), 3.28-3.11 (m, 4H), 2.59 (s, 3H), 1.74 (s, 3H). |

TABLE 1-continued

| No | Chemical Structure | IC$_{50}$ | HPLC/MS Rt [Min] | Chemical Name | NMR data |
|---|---|---|---|---|---|
| 263 | 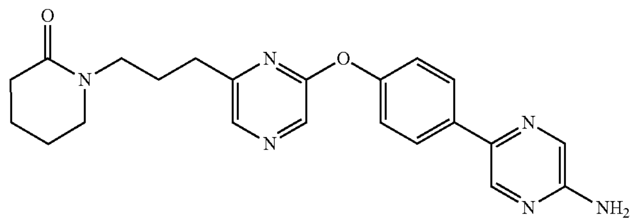 [SMILES: Nc1cnc(-c2ccc(Oc3cncc(CCCN4CCCCC4=O)n3)cc2)cn1] | A | 1.80 | 1-(3-{6-[4-(5-Amino-pyrazin-2-yl)-phenoxy]-pyrazin-2-yl}-propyl)-piperidin-2-one | 1H NMR (400 MHz, DMSO-d6) ppm = 8.59 (s, 1H), 8.18 (s, 1H), 8.13 (s, 2H), 7.86 (d, J = 8.7, 2H), 7.19 (d, J = 8.7, 2H), 3.26 (d, J = 14.6, 2H), 1.82-1.79 (m, 1H), 3.11 (t, J = 4.9, 2H), 2.59 (t, J = 7.2, 2H), 2.55-2.52 (m, 1H), 2.27 (p, J = 3.3, 2H), 1.82 (s, 1H), 1.79 (d, J = 7.3, 1H), 1.57 (p, J = 3.0, 4H). |
| 264 | 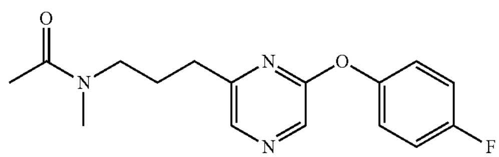 [SMILES: CC(=O)N(C)CCCc1cncc(Oc2ccc(F)cc2)n1] | C | 1.98 | N-{3-[6-(4-Fluoro-phenoxy)-pyrazin-2-yl]-propyl}-N-methyl-acetamide | 1H NMR (400 MHz, DMSO-d6) ppm = 8.31 (s, 1H), 8.28 (s, 1H), 7.32-7.17 (m, 4H), 3.22 (t, J = 7.2, 2H), 2.85 (s, 3H), 2.58 (t, J = 7.5, 2H), 1.92 (s, 3H), 1.73 (p, J = 7.5, 2H). |
| 265 | 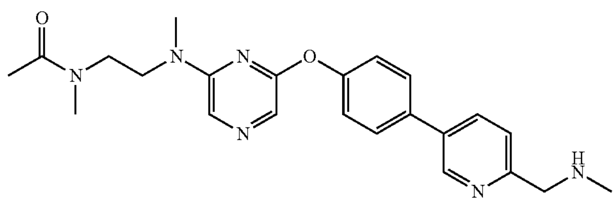 [SMILES: CNCc1ccc(-c2ccc(Oc3cncc(N(C)CCN(C)C(C)=O)n3)cc2)cn1] | A | 1.45 | N-Methyl-N-[2-(methyl-{6-[4-(6-methylamino methyl-pyridin-3-yl)-phenoxy]-pyrazin-2-yl}-amino)-ethyl]-acetamide | 1H NMR (400 MHz, DMSO-d6) ppm = 8.87 (s, 1H), 8.11 (d, J = 8.1, 1H), 7.89-7.72 (m, 3H), 7.59 (s, 1H), 7.53 (d, J = 8.1, 1H), 7.28 (d, J = 8.7, 2H), 4.01 (s, 2H), 3.48-3.42 (m, 2H), 3.37-3.30 (m, 2H), 2.96 (s, 3H), 2.71 (s, 3H), 2.47 (s, 3H), 1.83 (s, 3H). |
| 266 | 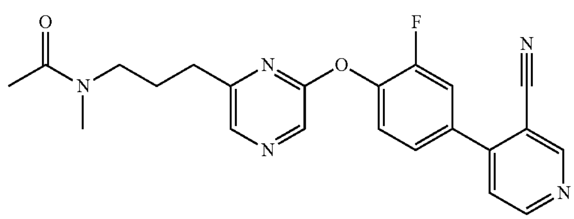 [SMILES: CC(=O)N(C)CCCc1cncc(Oc2ccc(-c3ccncc3C#N)cc2F)n1] | A | 1.96 | N-(3-{6-[4-(3-Cyano-pyridin-4-yl)-2-fluoro-phenoxy]-pyrazin-2-yl}-propyl)-N-methyl-acetamide | 1H NMR (400 MHz, DMSO-d6) ppm = 9.14 (s, 1H), 8.93 (d, J = 5.2, 1H), 8.51 (s, 1H), 8.36 (s, 1H), 7.87-7.75 (m, 2H), 7.69-7.59 (m, 2H), 3.25-3.16 (m, 2H), 2.82 (s, 3H), 2.60 (t, J = 7.4, 2H), 1.90 (s, 3H), 1.72 (p, J = 7.5, 2H). |
| 267 | 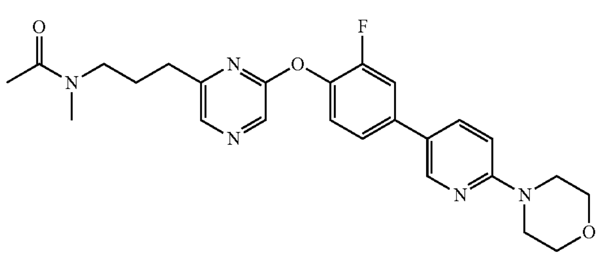 [SMILES: CC(=O)N(C)CCCc1cncc(Oc2ccc(-c3ccc(N4CCOCC4)nc3)cc2F)n1] | B | 1.86 | N-(3-{6-[2-Fluoro-4-(6-morpholin-4-yl-pyridin-3-yl)-phenoxy]-pyrazin-2-yl}-propyl)-N-methyl-acetamide | 1H NMR (400 MHz, DMSO-d6) ppm = 8.54 (d, J = 2.5, 1H), 8.44 (s, 1H), 8.32 (s, 1H), 7.95 (dt, J = 8.9, 2.9, 1H), 7.69 (dd, J = 3.2, 2.2, 1H), 7.54 (dt, J = 8.4, 2.5, 1H), 7.43 (td, J = 8.4, 2.3, 1H), 6.94 (s, 1H), 3.72 (dd, J = 5.8, 3.9, 4H), 3.56-3.43 (m, 4H), 3.20 (q, J = 7.7, 2H), 2.81 (s, 3H), 2.69-2.48 (m, 2H), 2.07 (s, 3H), 1.75 (dp, J = 29.6, 7.3, 2H). |

TABLE 1-continued

| No | Chemical Structure | IC$_{50}$ | HPLC/MS Rt [Min] | Chemical Name | NMR data |
|---|---|---|---|---|---|
| 268 | 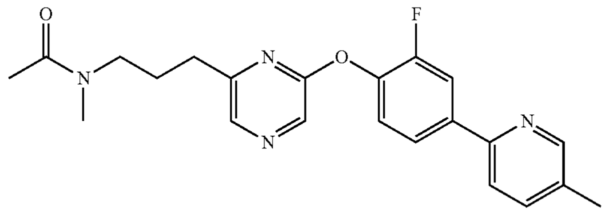 [SMILES: CC(=O)N(C)CCCc1cncc(Oc2ccc(-c3ccc(C)cn3)cc2F)n1] | A | 2.06 | N-(3-{6-[2-Fluoro-4-(5-methyl-pyridin-2-yl)-phenoxy]-pyrazin-2-yl}-propyl)-N-methyl-acetamide | 1H NMR (400 MHz, DMSO-d6) ppm = 8.52 (d, J = 2.4, 1H), 8.46 (s, 1H), 8.33 (s, 1H), 8.05 (dd, J = 12.3, 2.1, 1H), 8.01-7.96 (m, 1H), 7.94 (d, J = 8.1, 1H), 7.73 (dd, J = 8.2, 1.8, 1H), 7.48 (t, J = 8.3, 1H), 3.19 (q, J = 7.9, 2H), 2.80 (s, 3H), 2.58 (t, J = 7.4, 2H), 2.35 (s, 3H), 1.89 (s, 3H), 1.70 (p, J = 7.5, 2H). |
| 269 | 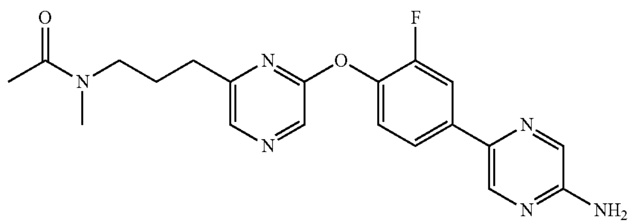 [SMILES: CC(=O)N(C)CCCc1cncc(Oc2ccc(-c3cnc(N)cn3)cc2F)n1] | B | 1.81 | N-(3-{6-[4-(5-Amino-pyrazin-2-yl)-2-fluoro-phenoxy]-pyrazin-2-yl}-propyl)-N-methyl-acetamide | 1H NMR (400 MHz, DMSO-d6) ppm = 8.58 (s, 1H), 8.44 (s, 1H), 8.31 (s, 1H), 7.97 (s, 1H), 7.94-7.86 (m, 1H), 7.86-7.78 (m, 1H), 7.42 (t, J = 8.4, 1H), 6.65 (s, 2H), 3.20 (t, J = 7.2, 2H), 2.81 (s, 3H), 2.58 (t, J = 7.4, 2H), 1.90 (s, 3H), 1.70 (p, J = 7.3, 2H). |
| 270 | 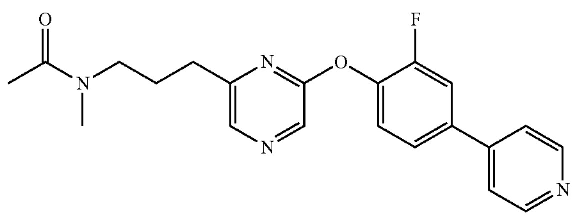 [SMILES: CC(=O)N(C)CCCc1cncc(Oc2ccc(-c3ccncc3)cc2F)n1] | B | 1.53 | N-{3-[6-(2-Fluoro-4-pyridin-4-yl-phenoxy)-pyrazin-2-yl]-propyl}-N-methyl-acetamide | 1H NMR (400 MHz, DMSO-d6) ppm = 8.67 (d, J = 6.0, 2H), 8.48 (s, 1H), 8.34 (s, 1H), 7.97-7.90 (m, 1H), 7.81-7.71 (m, 3H), 7.60-7.52 (m, 1H), 3.25-3.14 (m, 2H), 2.81 (s, 3H), 2.59 (t, J = 7.4, 2H), 1.90 (s, 3H), 1.71 (p, J = 7.6, 2H). |
| 271 | 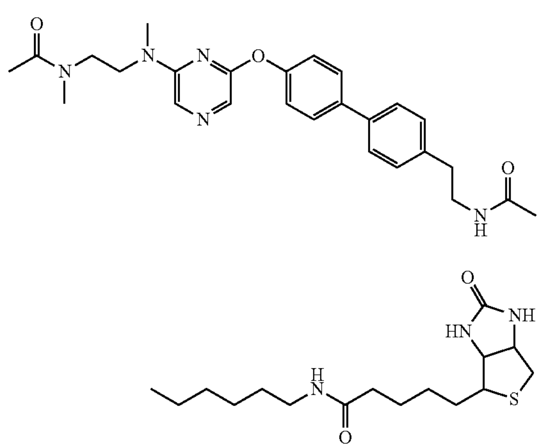 | A | 2.06 | 6-[5-(2-Oxo-hexahydro-thieno[3,4-d]imidazol-6-yl)-pentanoyl-amino]-hexanoic acid {2-[4'-(6-{[2-(acetyl-methyl-amino)-ethyl]-methyl-amino}-pyrazin-2-yloxy)-biphenyl-4-yl]-ethyl}-amide | 1H NMR (400 MHz, DMSO-d6) ppm = 7.87-7.84 (m, 1H), 7.83 (s, 1H), 7.72-7.66 (m, 3H), 7.59 (d, J = 8.1, 2H), 7.58 (s, 1H), 7.29 (d, J = 8.0, 2H), 7.25 (d, J = 8.6, 2H), 6.38 (s, 1H), 6.32 (s, 1H), 4.35-4.23 (m, 1H), 4.12 (ddd, J = 7.7, 4.5, 1.9, 1H), 3.45 (dt, J = 10.3, 6.5, 2H), 3.35-3.20 (m, 4H), 3.08 (ddd, J = 8.6, 6.1, 4.6, 1H), 3.05-2.91 (m, 5H), 2.80 (d, J = 5.1, 1H), 2.74 (t, J = 7.3, 2H), 2.57 (d, J = 12.4, 1H), 2.54 (s, 3H), 2.04 (t, J = 7.0, 4H), 1.83 (s, 3H), 1.61 (ddt, J = 12.4, 9.6, 6.1, 1H), 1.56-1.41 (m, 5H), 1.40-1.11 (m, 6H). |

TABLE 1-continued

| No | Chemical Structure | IC$_{50}$ | HPLC/MS Rt [Min] | Chemical Name | NMR data |
|---|---|---|---|---|---|
| 272 | 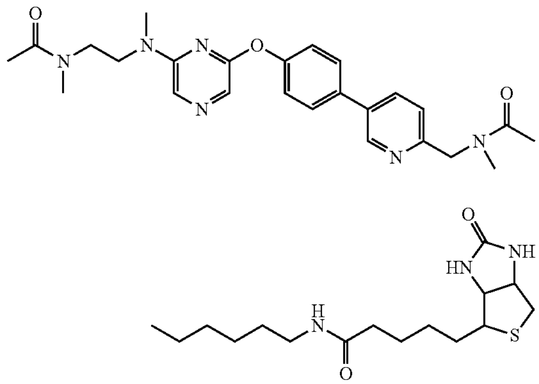 | A | 1.80 | 6-[5-(2-Oxo-hexahydro-thieno[3,4-d]imidazol-6-yl)-pentanoyl-amino]-hexanoic acid {5-[4-(6-{[2-(acetyl-methyl-amino)-ethyl]-methyl-amino}-pyrazin-2-yloxy)-phenyl]-pyridin-2-ylmethyl}-methyl-amide | 1H NMR (500 MHz, DMSO-d6) ppm = 8.82 (d, J = 2.8, 1H), 8.10 (dd, J = 8.1, 2.5, 1H), 7.84 (s, 1H), 7.76 (d, J = 8.9, 2H), 7.72 (t, J = 5.4, 1H), 7.59 (s, 1H), 7.39-7.22 (m, 3H), 6.32 (s, 2H), 4.63 (s, 2H), 4.33-4.26 (m, 1H), 4.15-4.09 (m, 1H), 3.53-3.41 (m, 2H), 3.14-2.78 (m, 10H), 2.71-2.63 (m, 2H), 2.54 (s, 3H), 2.44-2.37 (m, 2H), 2.14-1.93 (m, 2H), 1.83 (s, 3H), 1.68-1.14 (m, 13H). |
| 273 | 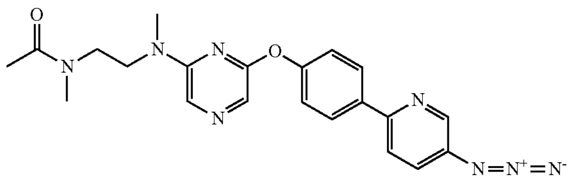 [SMILES: CC(=O)N(C)CCN(C)c1cncc(Oc2ccc(-c3ccc(N=[N+]=[N-])cn3)cc2)n1] | A | 2.29 | N-[2-({6-[4-(5-Azido-pyridin-2-yl)-phenoxy]-pyrazin-2-yl}-methyl-amino)-ethyl]-N-methyl-acetamide | 1H NMR (500 MHz, DMSO-d6) ppm = 8.46 (d, J = 2.7, 1H), 8.12 (d, J = 8.8, 2H), 8.02 (d, J = 8.6, 1H), 7.86 (s, 1H), 7.70 (dd, J = 8.6, 2.8, 1H), 7.61 (s, 1H), 7.29 (d, J = 8.7, 2H), 3.52-3.39 (m, 2H), 3.31-3.22 (m, 2H), 2.96 (s, 3H), 2.71 (s, 3H), 1.84 (s, 3H). |
| 274 | 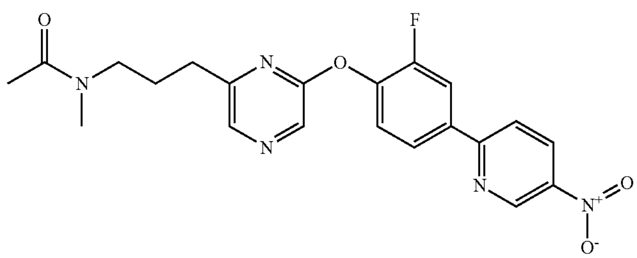 [SMILES: CC(=O)N(C)CCCc1cncc(Oc2ccc(-c3ccc([N+](=O)[O-])cn3)cc2F)n1] | C | 2.27 | N-(3-{6-[2-Fluoro-4-(5-nitro-pyridin-2-yl)-phenoxy]-pyrazin-2-yl}-propyl)-N-methyl-acetamide | 1H NMR (500 MHz, DMSO-d6) ppm = 9.46 (d, J = 2.7, 0.7, 1H), 8.69 (dd, J = 8.8, 2.0, 1H), 8.50 (s, 1H), 8.43-8.32 (m, 2H), 8.29-8.20 (m, 1H), 8.20-8.08 (m, 1H), 7.60 (t, J = 8.3, 1H), 3.24-3.10 (m, 2H), 2.81 (s, 3H), 2.59 (t, J = 7.4, 2H), 1.90 (s, 3H), 1.71 (p, J = 7.4, 2H). |
| 275 | 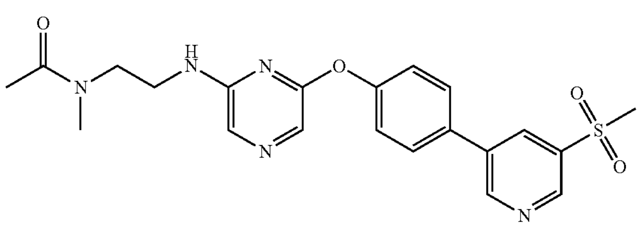 [SMILES: CC(=O)N(C)CCNc1cncc(Oc2ccc(-c3cncc(S(C)(=O)=O)c3)cc2)n1] | C | 1.78 | N-(2-{6-[4-(5-Methane-sulfonyl-pyridin-3-yl)-phenoxy]-pyrazin-2-ylamino}-ethyl)-N-methyl-acetamide | 1H NMR (400 MHz, DMSO-d6) ppm = 9.24 (d, J = 2.2, 1H), 9.04 (dd, J = 2.1, 1.0, 1H), 8.53 (t, J = 2.2, 1H), 7.92 (d, J = 8.6, 2H), 7.71 (s, 1H), 7.53 (s, 1H), 7.42-7.38 (m, 1H), 7.32 (d, J = 8.7, 2H), 3.41 (s, 3H), 3.29-3.13 (m, 4H), 2.61 (s, 3H), 1.76 (s, 3H). |
| 276 | 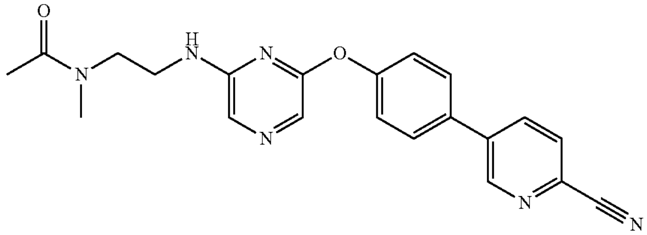 [SMILES: CC(=O)N(C)CCNc1cncc(Oc2ccc(-c3ccc(C#N)nc3)cc2)n1] | B | 1.99 | N-(2-{6-[4-(6-Cyano-pyridin-3-yl)-phenoxy]-pyrazin-2-ylamino}-ethyl)-N-methyl-acetamide | 1H NMR (500 MHz, DMSO-d6) ppm = 9.11 (d, J = 1.8, 1H), 8.35 (d, J = 8.2, 1H), 8.12 (dd, J = 8.2, 1.7, 1H), 7.90 (d, J = 8.7, 2H), 7.71 (s, 1H), 7.53 (s, 1H), 7.45-7.24 (m, 3H), 3.29-3.12 (m, 4H), 2.60 (s, 3H), 1.89 (s, 3H). |

TABLE 1-continued

| No | Chemical Structure | IC$_{50}$ | HPLC/MS Rt [Min] | Chemical Name | NMR data |
|---|---|---|---|---|---|
| 277 | 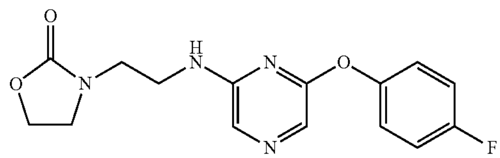 [SMILES: O=C1OCCN1CCNc1cncc(Oc2ccc(F)cc2)n1] | C | 1.92 | 3-{2-[6-(4-Fluoro-phenoxy)-pyrazin-2-ylamino]-ethyl}-oxazolidin-2-one | 1H NMR (400 MHz, DMSO-d6) ppm = 7.64 (s, 1H), 7.41 (s, 1H), 7.33-7.25 (m, 1H), 7.25-7.16 (m, 4H), 4.17 (t, J = 7.9, 2H), 3.43-3.38 (m, 2H), 3.26-3.15 (m, 4H). |
| 278 | 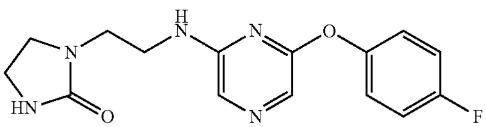 [SMILES: O=C1NCCN1CCNc1cncc(Oc2ccc(F)cc2)n1] | B | 1.87 | 1-{2-[6-(4-Fluoro-phenoxy)-pyrazin-2-ylamino]-ethyl}-imidazolidin-2-one | 1H NMR (400 MHz, DMSO-d6) ppm = 7.63 (s, 1H), 7.40 (s, 1H), 7.30-7.13 (m, 5H), 6.22 (s, 1H), 3.20-3.12 (m, 6H), 3.06 (t, J = 6.3, 2H). |
| 279 | 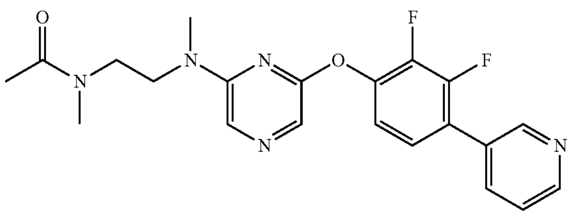 [SMILES: CC(=O)N(C)CCN(C)c1cncc(Oc2ccc(-c3cccnc3)c(F)c2F)n1] | A | 1.88 | N-(2-{[6-(2,3-Difluoro-4-pyridin-3-yl-phenoxy)-pyrazin-2-yl]-methyl-amino}-ethyl)-N-methyl-acetamide | 1H NMR (400 MHz, DMSO-d6) ppm = 8.86-8.74 (m, 1H), 8.69-8.61 (m, 1H), 8.08-7.97 (m, 1H), 7.86 (s, 1H), 7.72 (s, 1H), 7.61-7.53 (m, 1H), 7.53-7.42 (m, 1H), 7.40-7.29 (m, 1H), 3.42 (t, J = 6.5, 2H), 3.31 (t, J = 6.4, 2H), 2.95 (s, 3H), 2.71 (s, 3H), 1.83 (s, 3H). |
| 280 | 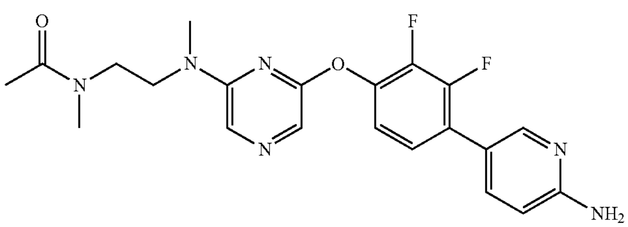 [SMILES: CC(=O)N(C)CCN(C)c1cncc(Oc2ccc(-c3ccc(N)nc3)c(F)c2F)n1] | A | 1.49 | N-[2-({6-[4-(6-Amino-pyridin-3-yl)-2,3-difluoro-phenoxy]-pyrazin-2-yl}-methyl-amino)-ethyl]-N-methyl-acetamide | 1H NMR (400 MHz, DMSO-d6) ppm = 8.17-8.09 (m, 1H), 7.84 (s, 1H), 7.69 (s, 1H), 7.64-7.55 (m, 1H), 7.40-7.29 (m, 1H), 7.29-7.13 (m, 1H), 6.61-6.48 (m, 1H), 6.20 (s, 2H), 3.51-3.36 (m, 2H), 3.26-3.19 (m, 1H), 2.94 (s, 3H), 2.55 (s, 3H), 1.83 (s, 3H). |
| 281 | 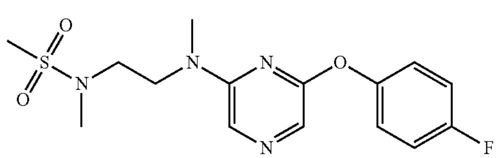 [SMILES: CN(CCN(C)S(C)(=O)=O)c1cncc(Oc2ccc(F)cc2)n1] | C | 2.15 | N-(2-{[6-(4-Fluoro-phenoxy)-pyrazin-2-yl]-methyl-amino}-ethyl)-N-methyl-methane-sulfonamide | 1H NMR (400 MHz, DMSO-d6) ppm = 7.80 (s, 1H), 7.58 (s, 1H), 7.28-7.17 (m, 4H), 3.49 (t, J = 6.5, 2H), 3.08 (t, J = 6.5, 2H), 2.98 (s, 3H), 2.79 (s, 3H), 2.56 (s, 3H). |

TABLE 1-continued

| No | Chemical Structure | IC$_{50}$ | HPLC/MS Rt [Min] | Chemical Name | NMR data |
|---|---|---|---|---|---|
| 282 | 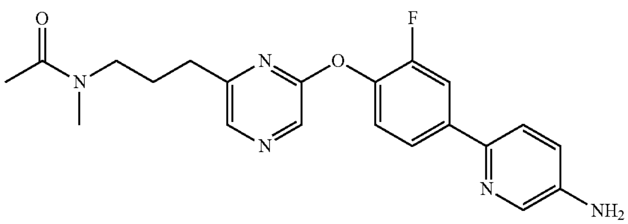 [SMILES: CC(=O)N(C)CCCc1cncc(Oc2ccc(-c3ccc(N)cn3)cc2F)n1] | A | 1.54 | N-(3-{6-[4-(5-Amino-pyridin-2-yl)-2-fluoro-phenoxy]-pyrazin-2-yl}-propyl)-N-methyl-acetamide | 1H NMR (500 MHz, DMSO-d6) ppm = 8.45 (d, J = 13.5, 1H), 8.33 (d, J = 16.3, 1H), 8.04 (d, J = 2.8, 1H), 2.84-2.63 (m, 3H), 7.89 (dt, J = 12.7, 1.7, 1H), 7.81 (dt, J = 8.5, 2.5, 1H), 7.70 (d, J = 8.5, 1H), 7.39 (td, J = 8.4, 3.0, 1H), 7.02 (dd, J = 8.5, 2.8, 1H), 5.56 (s, 2H), 3.20 (dt, J = 10.2, 7.3, 2H), 2.61 (dt, 2H), 1.90 (s, 3H), 1.75 (dp, J = 38.2, 7.4, 2H). |
| 283 | 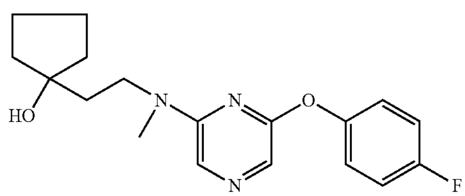 [SMILES: CN(CCC1(O)CCCC1)c1cncc(Oc2ccc(F)cc2)n1] | B | 2.40 | 1-(2-{[6-(4-Fluoro-phenoxy)-pyrazin-2-yl]-methyl-amino}-ethyl)-cyclopentanol | 1H NMR (400 MHz, DMSO-d6) ppm = 7.74 (s, 1H), 7.51 (s, 1H), 7.27-7.10 (m, 4H), 4.04 (s, 1H), 3.48-3.33 (m, 2H), 2.92 (s, 3H), 1.73-1.51 (m, 4H), 1.51-1.33 (m, 4H), 1.32-1.10 (m, 2H). |
| 284 | 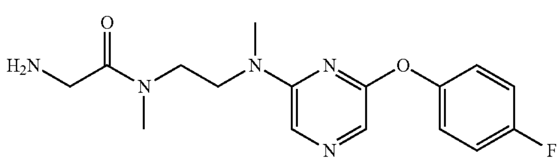 [SMILES: CN(CCN(C)c1cncc(Oc2ccc(F)cc2)n1)C(=O)CN] | C | 1.49 | 2-Amino-N-(2-{[6-(4-fluoro-phenoxy)-pyrazin-2-yl]-methyl-amino}-ethyl)-N-methyl-acetamide | 1H NMR (500 MHz, DMSO-d6) ppm = 8.14-7.97 (m, 3H), 7.83 (s, 1H), 7.58 (s, 1H), 7.31-7.19 (m, 4H), 3.75-3.62 (m, 2H), 3.54-3.41 (m, 2H), 3.41-3.23 (m, 2H), 2.96 (s, 3H), 2.76 (s, 3H). |
| 285 | 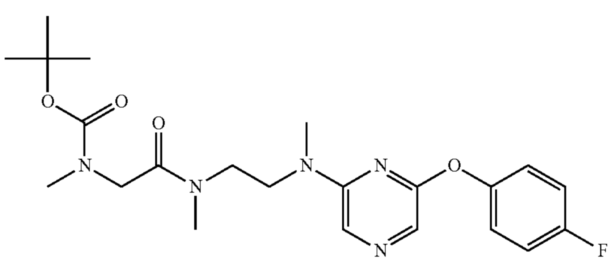 [SMILES: CN(CCN(C)c1cncc(Oc2ccc(F)cc2)n1)C(=O)CN(C)C(=O)OC(C)(C)C] | C | 2.38 | {[(2-{[6-(4-Fluoro-phenoxy)-pyrazin-2-yl]-methyl-amino}-ethyl)-methyl-carbamoyl]-methyl}-methyl-carbamic acid tert-butyl ester | 1H NMR (500 MHz, DMSO-d6) ppm = 7.82 (s, 1H), 7.54 (s, 1H), 7.33-7.16 (m, 4H), 3.84 (s, 2H), 3.50-3.40 (m, 2H), 3.38-3.29 (m, 2H), 2.94 (s, 3H), 2.72-2.61 (m, 6H), 1.38 (s, 9H). |
| 286 | 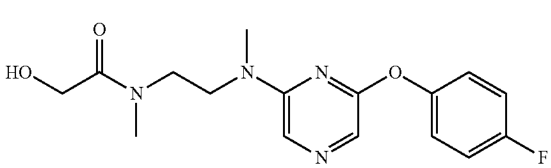 [SMILES: CN(CCN(C)c1cncc(Oc2ccc(F)cc2)n1)C(=O)CO] | A | 1.92 | N-(2-{[6-(4-Fluoro-phenoxy)-pyrazin-2-yl]-methyl-amino}-ethyl)-2-hydroxy-N-methyl-acetamide | 1H NMR (400 MHz, DMSO-d6) ppm = 7.79 (s, 1H), 7.55 (s, 1H), 7.28-7.17 (m, 4H), 4.31 (t, J = 5.4, 1H), 3.92 (d, J = 5.4, 2H), 3.45 (q, J = 6.3, 2H), 3.20 (t, J = 6.6, 2H), 2.94 (s, 3H), 2.65 (s, 3H). |

TABLE 1-continued

| No | Chemical Structure | IC$_{50}$ | HPLC/MS Rt [Min] | Chemical Name | NMR data |
|---|---|---|---|---|---|
| 287 | 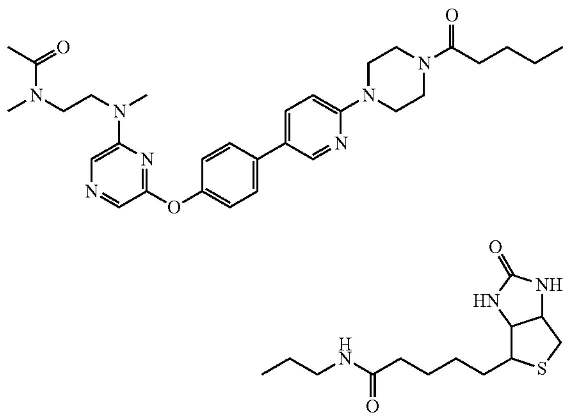 | A | 1.73 | 5-(2-Oxo-hexahydro-thieno[3,4-d]imidazol-6-yl)-pentanoic acid [6-(4-{5-[4-(6-{[2-(acetyl-methyl-amino)-ethyl]-methyl-amino}-pyrazin-2-yloxy)-phenyl]-pyridin-2-yl}-piperazin-1-yl)-6-oxo-hexyl]-amide | 1H NMR (500 MHz, DMSO-d6) ppm = 8.46 (t, J = 3.2, 1H), 7.90-7.86 (m, 1H), 7.81 (s, 1H), 7.70 (t, J = 5.6, 1H), 7.66 (d, J = 8.6, 2H), 7.56 (s, 1H), 7.23 (d, J = 8.6, 2H), 6.95 (s, 1H), 6.38 (s, 1H), 6.32 (s, 1H), 4.34-4.25 (m, 1H), 4.16-4.05 (m, 1H), 3.63-3.55 (m, 6H), 3.55-3.50 (m, 2H), 3.48-3.41 (m, 2H), 3.28 (s, 2H), 3.13-2.98 (m, 2H), 3.02 (s, 3H), 2.81 (dd, J = 12.4, 5.2, 1H), 2.58 (d, J = 12.5, 1H), 2.53 (s, 3H), 2.35 (t, J = 7.5, 2H), 2.04 (t, J = 7.4, 2H), 1.83 (s, 3H), 1.66-1.57 (m, 1H), 1.55-1.45 (m, 5H), 1.44-1.36 (m, 2H), 1.34-1.19 (m, 5H). |
| 288 | 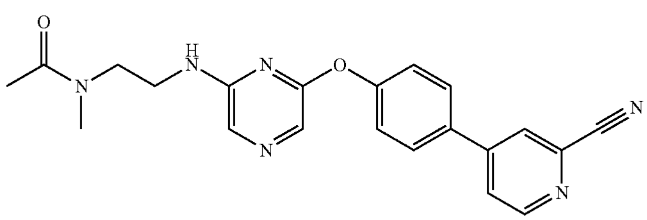 [SMILES: CC(=O)N(C)CCNc1cncc(Oc2ccc(-c3ccnc(C#N)c3)cc2)n1] | C | 1.99 | N-(2-{6-[4-(2-Cyano-pyridin-4-yl)-phenoxy]-pyrazin-2-ylamino}-ethyl)-N-methyl-acetamide | 1H NMR (400 MHz, DMSO-d6) ppm = 9.11 (dd, J = 2.4, 0.9, 1H), 8.36 (dd, J = 8.2, 2.4, 1H), 8.12 (ddd, J = 8.2, 1.7, 0.8, 1H), 7.90 (d, J = 8.7, 2H), 7.71 (s, 1H), 7.53 (s, 1H), 7.40 (s, 1H), 7.31 (d, J = 8.7, 2H), 3.29-3.12 (m, 4H), 2.60 (s, 3H), 1.75 (s, 3H). |
| 289 | 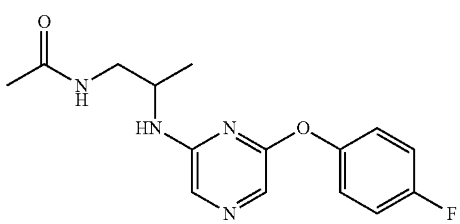 [SMILES: CC(=O)NCC(C)Nc1cncc(Oc2ccc(F)cc2)n1] | C | 1.88 | N-{2-[6-(4-Fluoro-phenoxy)-pyrazin-2-ylamino]-propyl}-acetamide | 1H NMR (400 MHz, DMSO-d6) ppm = 7.76 (t, J = 5.2, 1H), 7.63 (s, 1H), 7.36 (s, 1H), 7.26-7.14 (m, 4H), 6.95 (d, J = 7.4, 1H), 3.71-3.54 (m, 1H), 3.07 (t, J = 5.9, 2H), 1.78 (s, 3H), 1.00 (d, J = 6.6, 3H). |
| 290 | 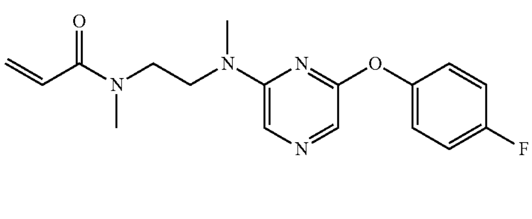 [SMILES: C=CC(=O)N(C)CCN(C)c1cncc(Oc2ccc(F)cc2)n1] | C | 2.10 | N-(2-{[6-(4-Fluoro-phenoxy)-pyrazin-2-yl]-methyl-amino}-ethyl)-N-methyl-acrylamide | 1H NMR (400 MHz, DMSO-d6) ppm = 7.75 (s, 1H), 7.59 (s, 1H), 7.31-7.13 (m, 4H), 6.44 (dd, J = 16.6, 10.4, 1H), 6.08-5.83 (m, 1H), 5.46 (dd, J = 10.4, 2.4, 1H), 3.52-3.43 (m, 2H), 3.43-3.38 (m, 2H), 2.94 (s, 3H), 2.68 (s, 3H). |

TABLE 1-continued

| No | Chemical Structure | IC$_{50}$ | HPLC/MS Rt [Min] | Chemical Name | NMR data |
|---|---|---|---|---|---|
| 291 | 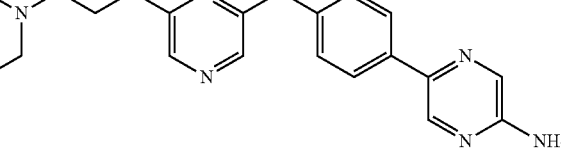 | A | 1.77 | 1-(2-{6-[4-(5-Amino-pyrazin-2-yl)-phenoxy]-pyrazin-2-ylamino}-ethyl)-piperidin-2-one | 1H NMR (500 MHz, DMSO-d6) ppm = 8.50 (d, J = 1.3, 1H), 8.01-7.88 (m, 3H), 7.62 (s, 1H), 7.46 (s, 1H), 7.34-7.26 (m, 1H), 7.19 (d, J = 8.7, 2H), 6.51 (s, 2H), 3.25-3.06 (m, 4H), 2.90 (t, J = 5.8, 2H), 2.09 (t, J = 6.5, 2H), 1.61-1.49 (m, 2H), 1.49-1.38 (m, 2H). |
| 292 | 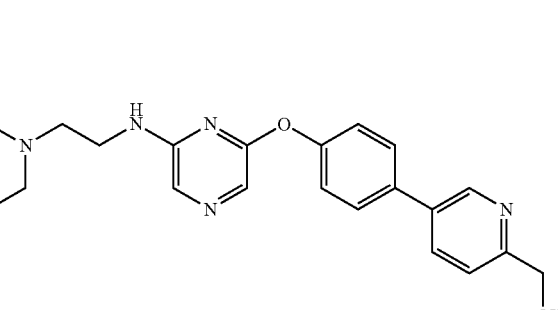 | A | 1.53 | 1-(2-{6-[4-(6-Hydroxy-methyl-pyridin-3-yl)-phenoxy]-pyrazin-2-ylamino}-ethyl)-piperidin-2-one | 1H NMR (400 MHz, DMSO-d6) ppm = 8.80 (d, J = 2.0, 1H), 8.09 (dd, J = 8.2, 2.4, 1H), 7.77 (d, J = 8.7, 2H), 7.64 (s, 1H), 7.54 (d, J = 8.1, 1H), 7.48 (s, 1H), 7.38-7.17 (m, 3H), 5.41 (t, J = 5.8, 1H), 4.61 (d, J = 5.8, 2H), 3.26-3.10 (m, 4H), 2.95 (t, J = 5.8, 2H), 2.10 (t, J = 6.6, 2H), 1.60-1.51 (m, 2H), 1.51-1.40 (m, 2H). |
| 293 | 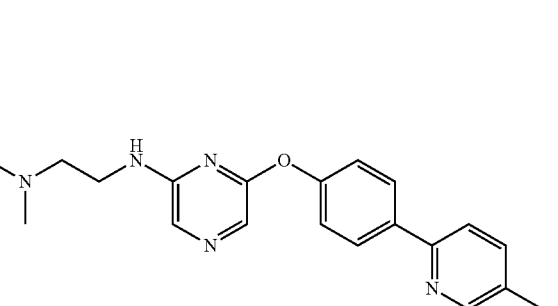 | B | 1.49 | N-(2-{6-[4-(5-Hydroxy-methyl-pyridin-2-yl)-phenoxy]-pyrazin-2-ylamino}-ethyl)-N-methyl-acetamide | 1H NMR (400 MHz, DMSO-d6) ppm = 8.59 (d, J = 1.6, 1H), 8.12 (d, J = 8.7, 2H), 7.92 (d, J = 8.2, 1H), 7.80 (dd, J = 8.2, 1.3, 1H), 7.69 (s, 1H), 7.51 (s, 1H), 7.41-7.16 (m, 3H), 5.33 (t, J = 5.2, 1H), 4.57 (d, J = 4.7, 2H), 3.31-3.13 (m, 4H), 2.58 (s, 3H), 1.74 (s, 3H). |
| 294 | 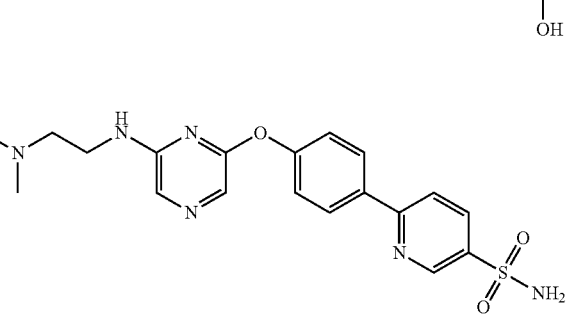 | C | 1.75 | N-Methyl-N-(2-{6-[4-(5-sulfamoyl-pyridin-2-yl)-phenoxy]-pyrazin-2-ylamino}-ethyl)-acetamide | 1H NMR (400 MHz, DMSO-d6) ppm = 9.02 (s, 1H), 8.28-8.12 (m, 4H), 7.71 (s, 1H), 7.60 (s, 2H), 7.54 (s, 1H), 7.41 (s, 1H), 7.28 (d, J = 8.8, 2H), 3.28-3.12 (m, 4H), 2.58 (s, 3H), 1.73 (s, 3H). |
| 295 | 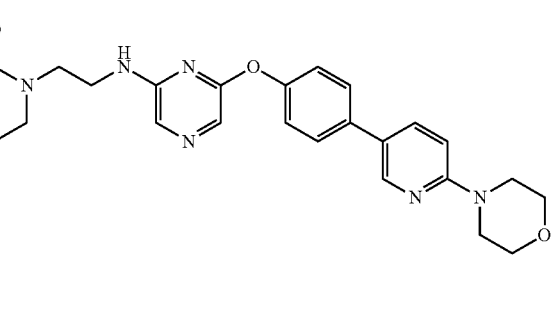 | A | 1.79 | 1-(2-{6-[4-(6-Morpholin-4-yl-pyridin-3-yl)-phenoxy]-pyrazin-2-ylamino}-ethyl)-piperidin-2-one | 1H NMR (400 MHz, DMSO-d6) ppm = 8.48 (d, J = 2.3, 1H), 7.89 (dd, J = 8.9, 2.6, 1H), 7.67 (d, J = 8.7, 2H), 7.63 (s, 1H), 7.46 (s, 1H), 7.34-7.25 (m, 1H), 7.21 (d, J = 8.7, 2H), 6.92 (d, J = 8.9, 1H), 3.78-3.64 (m, 4H), 3.53-3.46 (m, 4H), 3.45-3.34 (m, 2H), 3.29-3.13 (m, 2H), 2.95 (t, J = 5.8, 2H), 2.11 (t, J = 6.5, 2H), 1.62-1.41 (m, 4H). |

TABLE 1-continued

| No | Chemical Structure | IC$_{50}$ | HPLC/MS Rt [Min] | Chemical Name | NMR data |
|---|---|---|---|---|---|
| 296 | 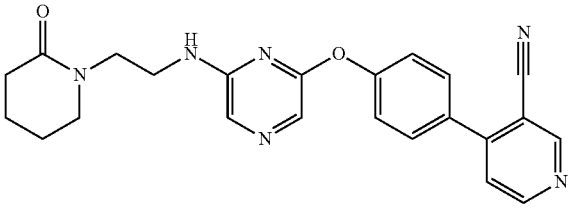 [SMILES: N#Cc1cnccc1-c1ccc(Oc2cncc(NCCN3CCCCC3=O)n2)cc1] | B | 1.98 | 4-(4-{6-[2-(2-Oxo-piperidin-1-yl)-ethylamino]-pyrazin-2-yloxy}-phenyl)-nicotinonitrile | |
| 298 | 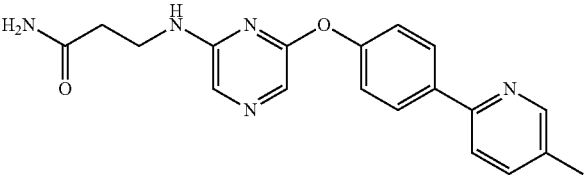 [SMILES: Cc1ccc(-c2ccc(Oc3cncc(NCCC(N)=O)n3)cc2)nc1] | B | 1.49 | 3-{6-[4-(5-Methyl-pyridin-2-yl)-phenoxy]-pyrazin-2-ylamino}-propionamide | $^1$H NMR (400 MHz, DMSO) δ 8.49 (d, J = 2.2 Hz, 1H), 8.11-8.06 (m, 2H), 7.84 (d, J = 8.1 Hz, 1H), 7.70-7.66 (m, 2H), 7.40 (s, 1H), 7.27-7.21 (m, 3H), 6.82-6.72 (m, 1H), 3.31 (t, J = 6.7 Hz, 2H), 2.33 (s, 3H), 2.26 (t, J = 6.8 Hz, 2H), one proton covered by water. |
| 299 | 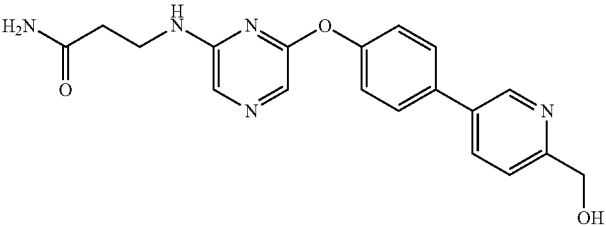 [SMILES: NC(=O)CCNc1cncc(Oc2ccc(-c3ccc(CO)nc3)cc2)n1] | C | 1.43 | 3-{6-[4-(6-Hydroxy-methyl-pyridin-3-yl)-phenoxy]-pyrazin-2-ylamino}-propionamide | |
| 300 | 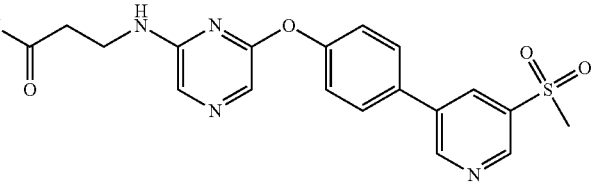 | D | 1.72 | 3-{6-[4-(5-Methane-sulfonyl-pyridin-3-yl)-phenoxy]-pyrazin-2-ylamino}-propionamide | |
| 301 | 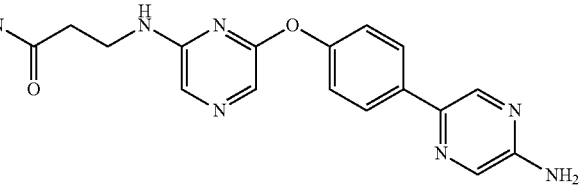 | C | 1.62 | 3-{6-[4-(5-Amino-pyrazin-2-yl)-phenoxy]-pyrazin-2-ylamino}-propionamide | |
| 302 | 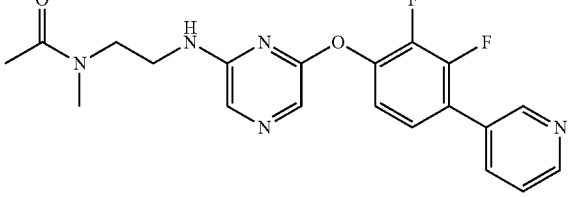 | C | 1.77 | N-{2-[6-(2,3-Difluoro-4-pyridin-3-yl-phenoxy)-pyrazin-2-ylamino]-ethyl}-N-methyl-acetamide | |

TABLE 1-continued

| No | Chemical Structure | IC$_{50}$ | HPLC/MS Rt [Min] | Chemical Name | NMR data |
|---|---|---|---|---|---|
| 303 | 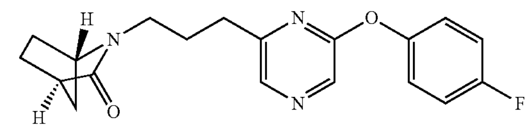 | B | 2.17 | (1S,4R)-2-{3-[6-(4-Fluoro-phenoxy)-pyrazin-2-yl]-propyl}-2-aza-bicyclo[2.2.1]heptan-3-one | |
| 304 | 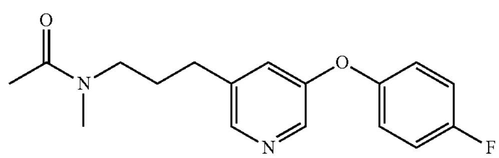 [SMILES: CC(=O)N(C)CCCc1cncc(Oc2ccc(F)cc2)c1] | B | 2.12 | N-{3-[5-(4-Fluoro-phenoxy)-pyridin-3-yl]-propyl}-N-methyl-acetamide | |
| 305 | 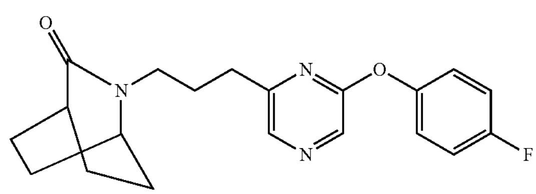 [SMILES: CCC1CCCN(CCCc2cncc(Oc3ccc(F)cc3)n2)C1=O] | C | 2.22 | 2-{3-[6-(4-Fluoro-phenoxy)-pyrazin-2-yl]-propyl}-2-aza-bicyclo[2.2.1]octan-3-one | $^1$H NMR (500 MHz, DMSO) δ 8.32 (s, 1H), 8.29 (s, 1H), 7.27 (s, 2H), 7.26 (s, 2H), 3.75 (s, 1H), 3.20-3.13 (m, 1H), 2.81-2.75 (m, 1H), 2.62-2.55 (m, 3H), 1.80-1.61 (m, 4H), 1.60-1.54 (m, 1H), 1.50-1.44 (m, 1H), 1.33-1.23 (m, 2H). |
| 306 | 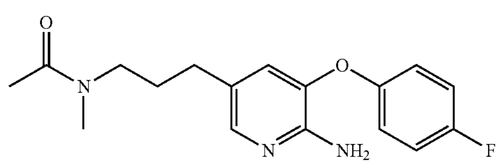 [SMILES: CC(=O)N(C)CCCc1cnc(N)c(Oc2ccc(F)cc2)c1] | C | 1.51 | N-{3-[6-Amino-5-(4-fluoro-phenoxy)-pyridin-3-yl]-propyl}-N-methyl-acetamide | |
| 307 | 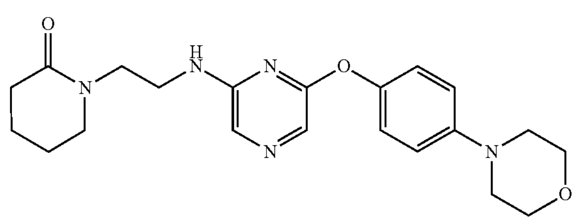 [SMILES: O=C1CCCCN1CCNc1cncc(Oc2ccc(N3CCOCC3)cc2)n1] | B | 1.89 | 1-{2-[6-(4-Morpholin-4-yl-phenoxy)-pyrazin-2-ylamino]-ethyl}-piperidin-2-one | $^1$H-NMR (400 MHz, DMSO) δ 7.56 (s, 1H), 7.33 (s, 1H), 7.20 (t, J = 5.4 Hz, 1H), 7.04-7.00 (m, 2H), 6.98-6.94 (m, 2H), 3.76-3.71 (m, 4H), 3.26-3.14 (m, 4H), 3.10-3.06 (m, 4H), 3.00-2.96 (m, 2H), 2.16-2.11 (m, 2H), 1.64-1.59 (m, 4H). |
| 308 | 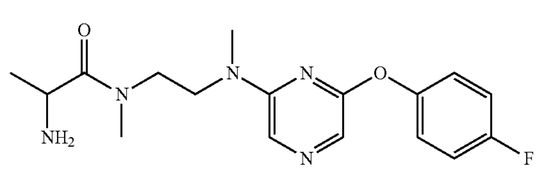 [SMILES: CC(N)C(=O)N(C)CCN(C)c1cncc(Oc2ccc(F)cc2)n1] | C | 1.54 | 2-Amino-N-(2-{[6-(4-fluoro-phenoxy)-pyrazin-2-yl]-methyl-amino}-ethyl)-N-methyl-propionamide | |
| 309 | 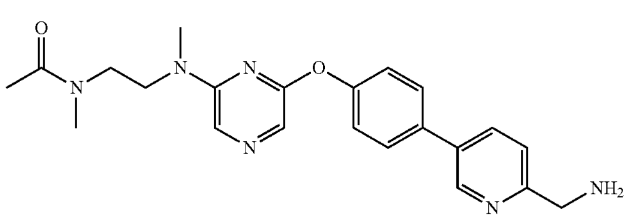 [SMILES: CC(=O)N(C)CCN(C)c1cncc(Oc2ccc(-c3ccc(CN)nc3)cc2)n1] | A | 1.45 | N-[2-({6-[4-(6-Amino-methyl-pyridin-3-yl)-pyrazin-2-yl]-methyl-amino)-ethyl]-N-methyl-acetamide | |

TABLE 1-continued

| No | Chemical Structure | IC$_{50}$ | HPLC/MS Rt [Min] | Chemical Name | NMR data |
|---|---|---|---|---|---|
| 310 | 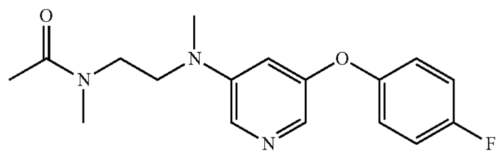 [SMILES: CC(=O)N(C)CCN(C)c1cncc(Oc2ccc(F)cc2)c1] | C | 1.50 | N-(2-{[5-(4-Fluoro-phenoxy)-pyridin-3-yl]-methyl-amino}-ethyl)-N-methyl-acetamide | |
| 311 | 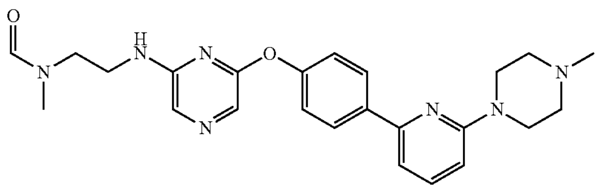 [SMILES: CN(C=O)CCNc1cncc(Oc2ccc(-c3cccc(N4CCN(C)CC4)n3)cc2)n1] | B | 1.56 | N-Methyl-N-[2-(6-{4-[6-(4-methyl-piperazin-1-yl)-pyridin-2-yl]-phenoxy}-pyrazin-2-ylamino)-ethyl]-formamide | |
| 312 | 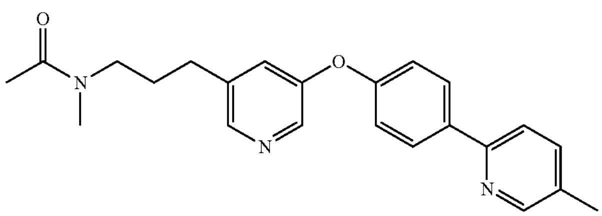 [SMILES: CC(=O)N(C)CCCc1cncc(Oc2ccc(-c3ccc(C)cn3)cc2)c1] | C | 1.65 | N-Methyl-N-(3-{5-[4-(5-methyl-pyridin-2-yl)-phenoxy]-pyridin-3-yl}-propyl)-acetamide | 1H NMR (500 MHz, DMSO-d6) δ 8.49-8.47 (m, 1H), 8.30 (dd, J = 13.3, 1.8 Hz, 1H), 8.25 (dd, J = 9.4, 2.7 Hz, 1H), 8.13-8.06 (m, 2H), 7.83 (d, J = 8.1 Hz, 1H), 7.71-7.66 (m, 1H), 7.47-7.66 (m, 1H), 7.15-7.09 (m, 2H), 3.32-3.25 (m, 5H), 2.66-2.60 (m, 1H), 2.60-2.54 (m, 1H), 2.33 (s, 3H), 1.94 (d, J = 4.6 Hz, 3H), 1.87-1.89 (m, 1H), 1.79-1.69 (m, 1H) |
| 313 | 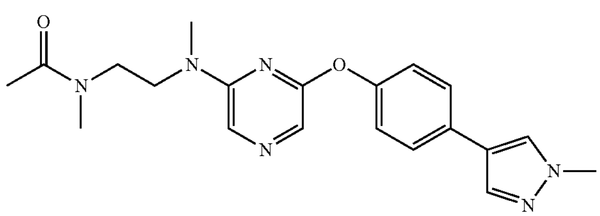 [SMILES: CC(=O)N(C)CCN(C)c1cncc(Oc2ccc(-c3cnn(C)c3)cc2)n1] | A | 1.87 | N-Methyl-N-[2-(methyl-{6-[4-(1-methyl-1H-pyrazol-4-yl)-phenoxy]-pyrazin-2-yl}-amino)-ethyl]-acetamide | |
| 314 | 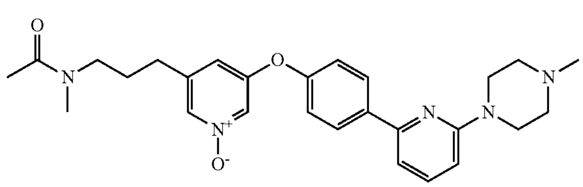 [SMILES: CC(=O)N(C)CCCc1cc(Oc2ccc(-c3cccc(N4CCN(C)CC4)n3)cc2)c[n+]([O-])c1] | C | 1.47 | N-Methyl-N-[3-(5-{4-[6-(4-methyl-piperazin-1-yl)-pyridin-2-yl]-phenoxy}-1-oxy-pyridin-3-yl)-propyl]-acetamide | |
| 315 | 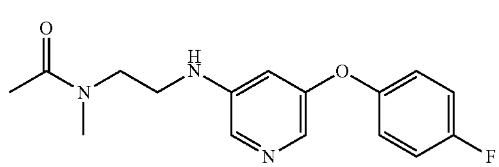 [SMILES: CC(=O)N(C)CCNc1cncc(Oc2ccc(F)cc2)c1] | D | 1.42 | N-{2-[5-(4-Fluoro-phenoxy)-pyridin-3-ylamino]-ethyl}-N-methyl-acetamide | |

TABLE 1-continued

| No | Chemical Structure | IC$_{50}$ | HPLC/MS Rt [Min] | Chemical Name | NMR data |
|---|---|---|---|---|---|
| 316 | 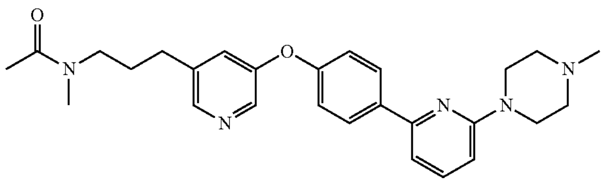 [SMILES: CC(=O)N(C)CCCc1cncc(Oc2ccc(-c3cccc(N4CCN(C)CC4)n3)cc2)c1] | C | 1.54 | N-Methyl-N-[3-(5-{4-[6-(4-methyl-piperazin-1-yl)-pyridin-2-yl]-phenoxy}-pyridin-3-yl)-propyl]-acetamide | |
| 317 | 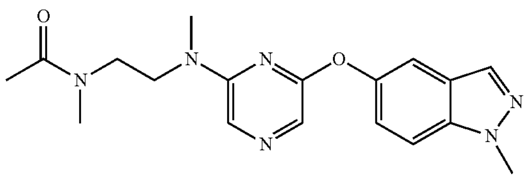 [SMILES: CC(=O)N(C)CCN(C)c1cncc(Oc2ccc3c(cnn3C)c2)n1] | A | 1.84 | N-Methyl-N-(2-{methyl-[6-(1-methyl-1H-indazol-5-yloxy)-pyrazin-2-yl]-amino}-ethyl)-acetamide | 1H NMR (500 MHz, DMSO-d6) δ 8.00 (d, J = 0.9 Hz, 1H), 7.77 (d, J = 7.3 Hz, 1H), 7.68-7.65 (m, 1H), 7.60 (s, 0.5H), 7.52 (d, J = 1.3 Hz, 1H), 7.50 (dd, J = 2.2, 0.7 Hz, 0.5H), 7.22 (ddd, J = 14.1, 9.0, 2.2 Hz, 1H), 4.06, 4.05 (2xs, 3H), 3.42-3.35 (m, 2H), 3.28-3.23 (m, 1H), 3.22-3.15 (m, 1H), 2.98, 2.91 (2xs, 3H), 2.57, 2.42 (2xs, 3H), 1.82, 1.63 (2xs, 3H). |
| 318 | 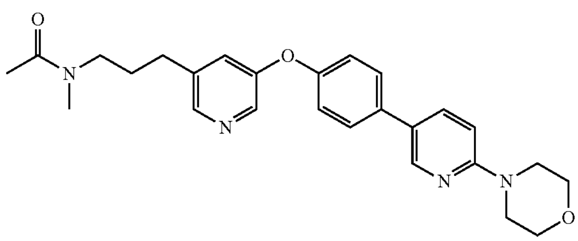 [SMILES: CC(=O)N(C)CCCc1cncc(Oc2ccc(-c3ccc(N4CCOCC4)nc3)cc2)c1] | B | 1.63 | N-Methyl-N-(3-{5-[4-(6-morpholin-4-yl-pyridin-3-yl)-phenoxy]-pyridin-3-yl}-propyl)-acetamide | |
| 319 | 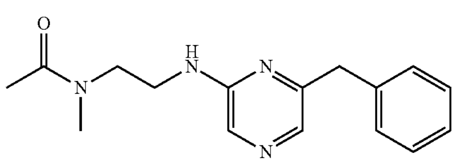 [SMILES: CC(=O)N(C)CCNc1cncc(Cc2ccccc2)n1] | B | 1.85 | N-[2-(6-Benzyl-pyrazin-2-ylamino)-ethyl]-N-methyl-acetamide | |
| 320 | 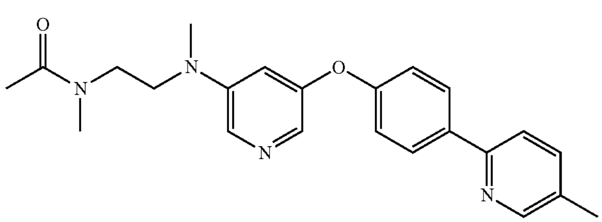 [SMILES: CC(=O)N(C)CCN(C)c1cncc(Oc2ccc(-c3ccc(C)cn3)cc2)c1] | B | 1.45 | N-Methyl-N-[2-(methyl-{5-[4-(5-methyl-pyridin-2-yl)-phenoxy]-pyridin-3-yl}-amino)-ethyl]-acetamide | |
| 321 | 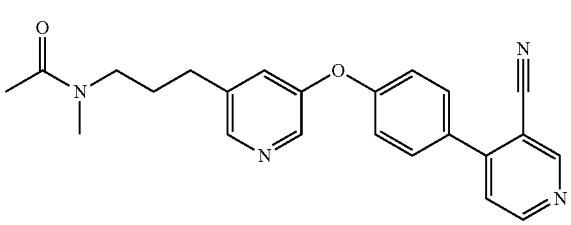 [SMILES: CC(=O)N(C)CCCc1cncc(Oc2ccc(-c3ccncc3C#N)cc2)c1] | A | 1.79 | N-(3-{5-[4-(3-Cyano-pyridin-4-yl)-phenoxy]-pyridin-3-yl}-propyl)-N-methyl-acetamide | |

TABLE 1-continued

| No | Chemical Structure | IC$_{50}$ | HPLC/MS Rt [Min] | Chemical Name | NMR data |
|---|---|---|---|---|---|
| 322 | 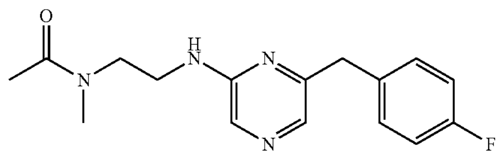 [SMILES: CC(=O)N(C)CCNc1cncc(Cc2ccc(F)cc2)n1] | C | 1.90 | N-{2-[6-(4-Fluoro-benzyl)-pyrazin-2-ylamino]-ethyl}-N-methyl-acetamide | |
| 323 | 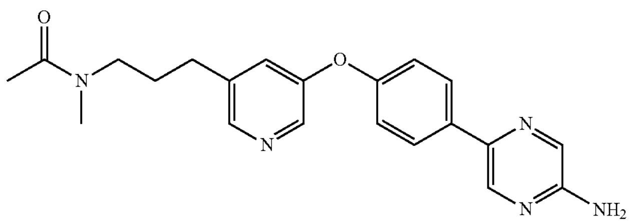 [SMILES: CC(=O)N(C)CCCc1cncc(Oc2ccc(-c3cnc(N)cn3)cc2)c1] | B | 1.57 | N-(3-{5-[4-(5-Amino-pyrazin-2-yl)-phenoxy]-pyridin-3-yl}-propyl)-N-methyl-acetamide | 1H NMR (500 MHz, DMSO-d6) δ 8.48 (s, 1H), 8.31-8.21 (m, 2H), 7.97-7.91 (m, 3H), 7.39 (dt, J = 20.3, 2.3 Hz, 1H), 7.11-7.07 (m, 2H), 6.51 (s, 2H), 3.29-3.23 (m, 2H), 2.91, 2.76 (2xs, 3H), 2.67-2.53 (m, 2H), 1.95, 1.93 (2xs, 3H), 1.88-1.79 (m, 1H), 1.77-1.70 (m, 1H). |

Compound numbers 1-3, 5, 6, 9-11, 13-16, 18, 20-24 and 26-28 were assigned to synthesis intermediates and, therefore, omitted from Table 1. Also omitted were compound numbers 42, 68, 297.

The invention claimed is:

1. A compound of Formula (I)

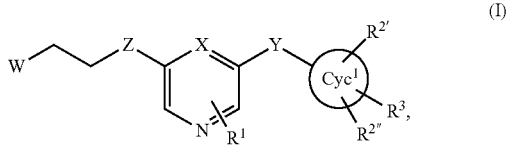

(I)

or its stereoisomers or tautomers, or pharmaceutically acceptable salts of each of the foregoing, including mixtures thereof in all ratios, wherein
  $R^1$ is H, LA, Hal, OH, CN, NO$_2$, NH$_2$, O(LA), NH(LA), N(LA)$_2$,
  $R^{2'}$, $R^{2''}$ are independently H, Hal, OH, CN, LA, O(LA),
  $R^3$ is H, LA, Hal, OH, SH, S(LA), CN, NO$_2$, NH$_2$, O(LA), (LA)OCO(LA), (LA)COO(LA), NH(LA), NHCOO(LA), N(LA)$_2$, (LA)NH$_2$, (LA)NH(LA), SO$_2$NH$_2$, SO$_2$(LA), or L-Cyc$^2$,
  $R^4$ is H, LA, (LA)OH, (LA)NH(R$^2$), O(LA), Cyc$^3$,
  $R^5$ is H, LA,
  $R^4$, $R^5$ together with the atoms they are attached to, can form a 4, 5, 6 or 7 membered heterocycle, having 1 or 2 heteroatoms, which is optionally substituted by $R^6$,
  $R^6$ is H, LA, Hal, OH, CN, NO$_2$, NH$_2$, O(LA), NH(LA), N(LA)$_2$,
  W is —NR$^5$COR$^4$ or —CON(R$^4$)(R$^5$),
  X is N,
  Y is O or CH$_2$,
  Z is NH, N(LA), S, CH$_2$, CH(LA), C(LA)$_2$,
  Cyc$^1$ is a mono- or binuclear, aliphatic or aromatic, 4, 5, 6, 7, 8, 9 or 10 membered homo- or heterocycle, having 0, 1, 2, 3 or 4 N, O and/or S atoms, which may be substituted by one or two oxo groups, and in which one N atom may be replaced by a N$^+$—O$^-$ group,
  Cyc$^2$ is a mono- or binuclear, aliphatic or aromatic, 4, 5, 6, 7, 8, 9 or 10 membered homo- or heterocycle, having 0, 1, 2, 3 or 4 N, O and/or S atoms, which may be mono-substituted by an oxo group, S(LA), SO$_2$(LA), N$_3$, NHCOH, NHCO(LA), NHCOO(LA), NHSO$_2$(LA), COO(LA), CONH$_2$, (LA)CONH$_2$, CONH(LA), L-Cyc$^3$ or A, or independently mono-, di-, tri- or tetra-substituted by LA, Hal, OH, CN, NO$_2$, NH$_2$, O(LA), NH(LA), N(LA)$_2$, CO(LA), and in which one N atom may be replaced by a N$^+$—O$^-$ group,
  Cyc$^3$ is a monocyclic, aliphatic or aromatic homo- or heterocycle having 0, 1, 2 or 3 N, N$^+$—O$^-$, O and/or S atoms and 5 or 6 skeleton atoms, which may be mono- or di-substituted by LA, Hal, OH, CN, NO$_2$, NH$_2$, O(LA), S(LA), NH(LA), N(LA)$_2$, and in which one N atom may be replaced by a N$^+$—O$^-$ group,
  L is a bond, or a unbranched alkyl or alkenyl linker having 1, 2 or 3 carbon atoms or alkenyl linker having 2 or 3 atoms, in which one CH$_2$ group may be replaced by a carbonyl group,
  LA is unbranched or branched alkyl having 1, 2, 3, 4 or 5 carbon atoms, alkenyl having 2, 3, 4 or 5 carbon atoms or alkynyl having 2, 3, 4 or 5 carbon atoms, wherein one, two or three H atoms may be replaced by Hal,
  A is a unbranched or branched alkyl or alkenyl chain having up to 25 non-hydrogen atoms, wherein 1, 2, 3, 4, 5 or 6 CH$_2$ groups may be replaced by O, S, NH, CO, N(LA), SO$_2$, and 1-7 H atoms may be replaced by Hal, and one CH$_3$ group may be replaced by OH, NH$_2$ or Cyc$^1$,
  Hal is F, Cl, Br or I.

2. The compound according to claim 1, wherein the compound is selected from the group consisting of:
  1-(2-{6-[4-(5-Methyl-pyridin-2-yl)-phenoxy]-pyrazin-2-ylamino }-ethyl)-piperidin-2-one,
  1-[2-(Methyl-{6-[4-(5-methyl-pyridin-2-yl)-phenoxy]-pyrazin-2-yl}-amino)-ethyl]-piperidin-2-one, N-[2-({6-[2-Fluoro-4-(5-fluoro-pyridin-2-yl)-phenoxy]-pyrazin-2-yl}-methyl-amino)-ethyl]-N-methyl-acetamide,
N-[2-({6-[2-Fluoro-4-(5-methyl-pyridin-2-yl)-phenoxy]-pyrazin-2-yl}-methyl-amino)-ethyl]-N-methyl-acetamide,
N-[2-({6-[2-Fluoro-4-(6-morpholin-4-yl-pyridin-3-yl)-phenoxy]-pyrazin-2-yl}-methyl-amino)-ethyl]-N-methyl-acetamide,
N-[2-({6-[4-(2-Amino-pyrimidin-4-yl)-phenoxy]-pyrazin-2-yl}-methyl-amino)-ethyl]-N-methyl-acetamide,
N-[2-({6-[4-(2-Cyano-pyridin-4-yl)-phenoxy]-pyrazin-2-yl}-methyl-amino)-ethyl]-N-methyl-acetamide,
N-[2-({6-[4-(2-Fluoro-pyridin-4-yl)-phenoxy]-pyrazin-2-yl}-methyl-amino)-ethyl]-N-methyl-acetamide,
N-[2-({6-[4-(3-Cyano-pyridin-4-yl)-2-fluoro-phenoxy]-pyrazin-2-yl}-methyl-amino)-ethyl]-N-methyl-acetamide,
N-[2-({6-[4-(3-Cyano-pyridin-4-yl)-phenoxy]-pyrazin-2-yl}-methyl-amino)-ethyl]-N-methyl-acetamide,
N-[2-({6-[4-(5-Amino-pyrazin-2-yl)-phenoxy]-pyrazin-2-yl}-methyl-amino)-ethyl]-N-methyl-acetamide,
N-[2-({6-[4-(5-Azido-pyridin-2-yl)-phenoxy]-pyrazin-2-yl}-methyl-amino)-ethyl]-N-methyl-acetamide,
N-[2-({6-[4-(5-Fluoro-pyridin-2-yl)-phenoxy]-pyrazin-2-yl}-methyl-amino)-ethyl]-N-methyl-acetamide,
N-[2-({6-[4-(5-Methoxy-pyridin-2-yl)-phenoxy]-pyrazin-2-yl}-methyl-amino)-ethyl]-N-methyl-acetamide,
N-[2-({6-[4-(6-Acetylamino-pyridin-2-yl)-phenoxy]-pyrazin-2-yl}-methyl-amino)-ethyl]-N-methyl-acetamide,
N-[2-({6-[4-(6-Acetylamino-pyridin-3-yl)-2-fluoro-phenoxy]-pyrazin-2-yl}-methyl-amino)-ethyl]-N-methyl-acetamide,
N-[2-({6-[4-(6-Amino-pyridin-2-yl)-phenoxy]-pyrazin-2-yl}-methyl-amino)-ethyl]-N-methyl-acetamide,
N-[2-({6-[4-(6-Cyano-pyridin-3-yl)-phenoxy]-pyrazin-2-yl}-methyl-amino)-ethyl]-N-methyl-acetamide,
N-[2-({6-[4-(6-Hydroxymethyl-pyridin-3-yl)-phenoxy]-pyrazin-2-yl}-methyl-amino)-ethyl]-N-methyl-acetamide,
N-[2-({6-[4-(6-Methanesulfonyl-pyridin-2-yl)-phenoxy]-pyrazin-2-yl}-methyl-amino)-ethyl]-N-methyl-acetamide,
N-{5-[4-(6-{[2-(Acetyl-methyl-amino)-ethyl]-methyl-amino}-pyrazin-2-yloxy)-phenyl]-pyridin-2-yl}-acetamide,
N-Ethyl-N-(2-{6-[4-(5-methyl-pyridin-2-yl)-phenoxy]-pyrazin-2-ylsulfanyl}-ethyl)-acetamide,
N-Isopropyl-N-(2-{6-[4-(5-methyl-pyridin-2-yl)-phenoxy]-pyrazin-2-ylsulfanyl}-ethyl)-acetamide,
N-Methyl-3-(methyl-{6-[4-(5-methyl-pyridin-2-yl)-phenoxy]-pyrazin-2-yl}-amino)-propionamide,
N-Methyl-N-(2-{6-[4-(5-methyl-pyridin-2-yl)-phenoxy]-pyrazin-2-ylsulfanyl}-ethyl)-acetamide,
N-Methyl-N-(2-{methyl-[6-(4-pyridin-2-yl-phenoxy)-pyrazin-2-yl]-amino}-ethyl)-acetamide,
N-Methyl-N-(2-{methyl-[6-(4-pyridin-4-yl-phenoxy)-pyrazin-2-yl]-amino}-ethyl)-acetamide,
N-Methyl-N-(2-{methyl-[6-(4-thiazol-2-yl-phenoxy)-pyrazin-2-yl]-amino}-ethyl)-acetamide,
N-Methyl-N-[2-(methyl-{6-[4 1H-pyrrolo [2,3-c]pyridin-5-yl)-phenoxy]-pyrazin-2-yl}-amino)-ethyl]-acetamide,
N-Methyl-N-[2-(methyl-{6-[4-(5-methyl-pyridin-2-yl)-phenoxy]-pyrazin-2-yl}-amino)-ethyl]-acetamide,
N-Methyl-N-[2-(methyl-{6-[4-(5-nitro-pyridin-2-yl)-phenoxy]-pyrazin-2-yl}-amino)-ethyl]-acetamide,
N-Methyl-N-[2-(methyl-{6-[4-(6-methylaminomethyl-pyridin-3-yl)-phenoxy]-pyrazin-2-yl}-amino)-ethyl]-acetamide,
N-Methyl-N-[2-(methyl-{6-[4-(6-methyl-pyridin-2-yl)-phenoxy]-pyrazin-2-yl}-amino)-ethyl]-acetamide,
N-Methyl-N-[2-(methyl-{6-[4-(6-methyl-pyridin-3-yl)-phenoxy]-pyrazin-2-yl}-amino)-ethyl]-acetamide,
N-Methyl-N-[2-(methyl-{6-[4-(6-morpholin-4-yl-pyridin-3-yl)-phenoxy]-pyrazin-2-yl}-amino)-ethyl]-acetamide,
N-Methyl-N-[2-(methyl-{6-[4-(7H-pyrrolo [2,3-d]pyrimidin-4-yl)-phenoxy]-pyrazin-2-yl}-amino)-ethyl]-acetamide,
N-Methyl-N-{2-[methyl-(6-{4-[6-(4-methyl-piperazin-1-yl)-pyridin-2-yl]-phenoxy}-pyrazin-2-yl)-amino]-ethyl}-acetamide,
or its stereoisomers or tautomers, or pharmaceutically acceptable salts of each of the foregoing, including mixtures thereof in all ratios.

3. A pharmaceutical composition comprising a compound according to claim 1, or its stereoisomers or tautomers, or pharmaceutically acceptable salts of each of the foregoing, including mixtures thereof in all ratios, as active ingredient, together with a pharmaceutically acceptable carrier.

4. The compound according to claim 1, or its stereoisomers or tautomers, or pharmaceutically acceptable salts of each of the foregoing, including mixtures thereof in all ratios, in which for Formula (I),
Z is $NCH_3$ or $CH_2$ or
Y is O.

5. The compound according to claim 1, or its stereoisomers or tautomers, or pharmaceutically acceptable salts of each of the foregoing, including mixtures thereof in all ratios, in which for Formula (I),
W is $-NR^5COR^4$.

6. The compound according to claim 1, or its stereoisomers or tautomers, or pharmaceutically acceptable salts of each of the foregoing, including mixtures thereof in all ratios, in which for Formula (I),
Z is $NCH_3$ or $CH_2$ and $R^4$, $R^5$ are methyl.

7. The compound according to claim 1, or its stereoisomers or tautomers, or pharmaceutically acceptable salts of each of the foregoing, including mixtures thereof in all ratios, in which for Formula (I):
W is $-NR^5COR^4$,
$R^4$, $R^5$ together with the atoms they are attached to, form piperidin-2-one or pyrrolidin-2-one, and
$R^6$ is H.

8. The compound according to claim 1, or its stereoisomers or tautomers, or pharmaceutically acceptable salts of each of the foregoing, including mixtures thereof in all ratios, in which for Formula (I):
W is $-CON(R^4)(R^5)$,
$R^4$ is methyl, and
$R^5$ is H.

9. The compound according to claim 1, or its stereoisomers or tautomers, or pharmaceutically acceptable salts of each of the foregoing, including mixtures thereof in all ratios, in which for Formula (I):
W is $-NR^5COR^4$,
$R^4$ is methyl, hydroxymethyl, tert-butyloxy or neopentyl, and
$R^5$ is H, methyl, ethyl, isopropyl or fluoromethyl.

10. The compound according to claim 1, or its stereoisomers or tautomers, or pharmaceutically acceptable salts of each of the foregoing, including mixtures thereof in all ratios, in which for Formula (I):
W is —$NR^5COR^4$, and
$R^4$, $R^5$ are methyl.

11. The compound according to claim 1, or its stereoisomers or tautomers, or pharmaceutically acceptable salts of each of the foregoing, including mixtures thereof in all ratios, in which for Formula (I):
X is N, and
$R^1$ is H.

12. The compound according to claim 1, or its stereoisomers or tautomers, or pharmaceutically acceptable salts of each of the foregoing, including mixtures thereof in all ratios, in which for Formula (I):
$Cyc^1$ is indanyl, indolyl, isoquinolinyl, benzoisoxazolyl or phenyl, and
$R^{2'}$, $R^{2''}$ and $R^3$ are independently H, F, Br, CN, O(LA) or LA.

13. The compound according to claim 1, or its stereoisomers or tautomers, or pharmaceutically acceptable salts of each of the foregoing, including mixtures thereof in all ratios, in which for Formula (I):
$Cyc^1$ is phenyl, which is substituted in 4-position by L-$Cyc^2$.

14. The compound according to claim 1, or its stereoisomers or tautomers, or pharmaceutically acceptable salts of each of the foregoing, including mixtures thereof in all ratios, in which for Formula (I):
$Cyc^1$ is phenyl,
$R^{2'}$, $R^{2''}$ are independently H or F and
$R^3$ is L-$Cyc^2$.

15. The compound according to claim 1, or its stereoisomers or tautomers, or pharmaceutically acceptable salts of each of the foregoing, including mixtures thereof in all ratios, in which for Formula (I):
X is N,
Y is O, and
Z is $NCH_3$ or $CH_2$.

16. The compound according to claim 1, or its stereoisomers or tautomers, or pharmaceutically acceptable salts of each of the foregoing, including mixtures thereof in all ratios, in which for Formula (I):
X is N,
Y is O,
Z is $NCH_3$ or $CH_2$, and
$R^1$ is H.

17. The compound according to claim 1, or its stereoisomers or tautomers, or pharmaceutically acceptable salts of each of the foregoing, including mixtures thereof in all ratios, in which for Formula (I):
W is —$NR^5COR^4$,
X is N,
Y is O,
Z is $NCH_3$ or $CH_2$,
$R^1$ is H, and
$Cyc^1$ is phenyl, and
$R^{2'}$, $R^{2''}$ and $R^3$ are independently H, F, Br, CN, O(LA) or LA.

18. The compound according to claim 1, or its stereoisomers or tautomers, or pharmaceutically acceptable salts of each of the foregoing, including mixtures thereof in all ratios, in which for Formula (I):
W is —$NR^5COR^4$,
X is N,
Y is O,
Z is $NCH_3$ or $CH_2$,
$R^1$ is H, and
$Cyc^1$ is phenyl, where
$R^{2'}$ is in the 1 position and is H or F,
$R^{2''}$ is in the 2 position and is H or F, and
$R^3$ is in the 4 position and is L-$Cyc^2$.

19. The compound according to claim 1, or its stereoisomers or tautomers, or pharmaceutically acceptable salts of each of the foregoing, including mixtures thereof in all ratios, in which for Formula (I):
W is —$NR^5COR^4$,
X is N,
Y is O,
Z is $NCH_3$ or $CH_2$,
$R^1$ is H, and
$Cyc^1$ is phenyl, where
$R^{2'}$ is F,
$R^{2''}$ is H or F, and
$R^3$ is in the 4 position and is L-$Cyc^2$.

20. The compound according to claim 1, or its stereoisomers or tautomers, or pharmaceutically acceptable salts of each of the foregoing, including mixtures thereof in all ratios, in which for Formula (I):
X is N,
Y is O,
Z is $NCH_3$, $CH_2$ or S,
$R^4$ is methyl,
$R^5$ is methyl, ethyl or isopropyl,
$R^1$ is H,
$Cyc^1$ is phenyl, where
$R^{2'}$ is in the 1 position and is H or F,
$R^{2''}$ is in the 2 position and is H or F,
$R^3$ is in the 4 position and is L-$Cyc^2$ and
$Cyc^2$ is pyridin-2, 3, or 4-yl, or pyrazin-2-yl, each of which is unsubstituted or substituted by HO(LA), LA, $NH_2$, CN.

21. The compound according to claim 1, or its stereoisomers or tautomers, or pharmaceutically acceptable salts of each of the foregoing, including mixtures thereof in all ratios, in which for Formula (I):
W is —$NR^5COR^4$,
X is N,
Y is O,
Z is $NCH_3$, $CH_2$ or S,
$R^4$, $R^5$ together with the atoms they are attached to, form piperidin-2-one
$R^1$ is H,
$Cyc^1$ is phenyl, and
$R^{2'}$, $R^{2''}$ are independently H, Hal, OH, CN, LA, O(LA),
$R^3$ is H, LA, Hal, OH, SH, S(LA), CN, $NO_{2-}$, $NH_2$, O(LA), (LA)OCO(LA), (LA)COO(LA),NH(LA), NHCOO(LA), N(LA)$_2$, (LA)NH$_2$, (LA)NH(LA), $SO_2NH_2$, $SO_2$(LA), or L-$Cyc^2$, and
$Cyc^2$ is pyridin-2, 3, or 4-yl, or pyrazin-2-yl, each of which is unsubstituted or substituted by O(LA), LA, $NH_2$ or CN.

22. The compound according to claim 1, or its stereoisomers or tautomers, or pharmaceutically acceptable salts of each of the foregoing, including mixtures thereof in all ratios, in which for Formula (I),
W is —CON($R^4$)($R^5$).

* * * * *